US010286052B2

(12) United States Patent
Rammensee et al.

(10) Patent No.: US 10,286,052 B2
(45) Date of Patent: May 14, 2019

(54) IMMUNOTHERAPY AGAINST SEVERAL TUMORS OF THE BLOOD, SUCH AS ACUTE MYELOID LEUKEMIA (AML)

(71) Applicant: Immatics Biotechnologies GmbH, Tübingen (DE)

(72) Inventors: Hans-Georg Rammensee, Unterjesingen (DE); Stefan Stevanovic, Tübingen (DE); Juliane Stickel, Tübingen (DE); Daniel Johannes Kowalewski, Tübingen (DE); Claudia Berlin, Tübingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/032,231

(22) Filed: Jul. 11, 2018

(65) Prior Publication Data
US 2018/0311330 A1    Nov. 1, 2018

Related U.S. Application Data

(63) Continuation of application No. 14/707,230, filed on May 8, 2015, now Pat. No. 10,064,924.

(60) Provisional application No. 61/990,980, filed on May 9, 2014.

(30) Foreign Application Priority Data

May 9, 2014 (GB) .................... 1408255.6

(51) Int. Cl.
| A61K 39/395 | (2006.01) |
| A61K 39/00 | (2006.01) |
| C07K 7/06 | (2006.01) |
| C07K 7/08 | (2006.01) |
| C07K 7/02 | (2006.01) |
| C07K 14/725 | (2006.01) |
| A61K 35/17 | (2015.01) |
| G01N 33/50 | (2006.01) |
| C12Q 1/6886 | (2018.01) |
| C07K 14/47 | (2006.01) |
| C12N 9/90 | (2006.01) |
| C12N 9/14 | (2006.01) |
| C12N 5/0783 | (2010.01) |

(52) U.S. Cl.
CPC .......... *A61K 39/0011* (2013.01); *A61K 35/17* (2013.01); *C07K 7/02* (2013.01); *C07K 7/06* (2013.01); *C07K 7/08* (2013.01); *C07K 14/47* (2013.01); *C07K 14/4748* (2013.01); *C07K 14/7051* (2013.01); *C12N 9/14* (2013.01); *C12N 9/90* (2013.01); *C12Q 1/6886* (2013.01); *C12Y 306/04004* (2013.01); *C12Y 599/01002* (2013.01); *G01N 33/505* (2013.01); *A61K 2039/5156* (2013.01); *A61K 2039/5158* (2013.01); *A61K 2039/572* (2013.01); *C07K 2319/70* (2013.01); *C12N 5/0638* (2013.01); *C12Q 2600/136* (2013.01)

(58) Field of Classification Search
None
See application file for complete search history.

(56) References Cited

U.S. PATENT DOCUMENTS

| 7,314,630 B2 | 1/2008 | Hu |
| 7,834,146 B2 | 11/2010 | Kovalic et al. |
| 2002/0061569 A1 | 5/2002 | Haselbeck et al. |
| 2005/0261190 A1 | 11/2005 | Lee et al. |
| 2008/0206216 A1 | 8/2008 | Dengjel |
| 2009/0136528 A1 | 5/2009 | Singh et al. |

FOREIGN PATENT DOCUMENTS

| KR | 20040101707 A | 3/2004 |
| WO | 0116174 A2 | 3/2001 |

OTHER PUBLICATIONS

Hinrichs et al, Nature Biotechnology vol. 31 p. 999 (2013) (Year: 2013).*
Baruch et al (Cancer vol. 123 p. 2154 (2017)) (Year: 2017).*
Search and Examination Report from corresponding GB 1408255.6, dated Feb. 10, 2015.
Berlin et al., "Mapping the HLA ligandome landscape of acute myeloid leukemia: a targeted approach toward peptide-based immunotherapy", Leukemia (2014), pp. 1-13.
Hassan, et al., "The Human Leukocyte Antigen-presented Ligandome of B Lymphocytes", The American Society for Biochemistry and Molecular Biology, Inc., Molecular & Cellular Proteomics 12.7, pp. 1829-1843, (2013).
JS Stickel, et al., HLA Class I Ligandome Analysis in Acute Myeloid Leukemia—Novel T-Cell Epitopes for Peptide-Based Immunotherapy, Blood Journal, Nov. 15, 2013, 2 pages.

(Continued)

*Primary Examiner* — Sheela J. Huff
(74) *Attorney, Agent, or Firm* — McBee Moore Woodward & Vanik IP, LLC; Susan McBee

(57) ABSTRACT

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to several novel peptide sequences and their variants derived from HLA class I and HLA class II molecules of human tumor cells that can be used in vaccine compositions for eliciting anti-tumor immune responses.

17 Claims, 6 Drawing Sheets
Specification includes a Sequence Listing.

(56) References Cited

OTHER PUBLICATIONS

Kowalewski et al. (Mapping the HLA Ligandome of Chronic Lymphocytic Leukemia—Towards Peptide Based Immunotherapy Blood 2013; 122(21):4123) describe a method to analyse the HLA class I peptidomes of 25 CLL patients and 35 healthy controls.
Berge et al., "Pharmaceutical Salts", J_Pharm. Sci. (1977) 66(1): 1-19.
International Search Report dated Dec. 11, 2015.
Norimitsu Kadowaki et al.; "Recent Advance in Antigen-Specific Immunotherapy for Acute Myeloid Leukemia"; Clinical and Developmental Immunology; vol. 163; No. 10; Jan. 1, 2011; pp. 5211-5217; XP055212173.
MarinaOstankovitch et al.; "Antileukemia HLA-restricted T-cell clones generated with naturally processed peptide eluted from acute myeloblastic leukemia blasts"; Blood; vol. 92; No. 1; Jul. 1, 1998; pp. 19-24; XP002744389.
Michael Schmitt et al.; "Peptide vaccines for patients with acute myeloid leukemia"; Expert Review of Vaccines; Oct. 2009; XP002744390.
Jochen Greiner et al.; "Cancer vaccines for patients with acute myeloid leukemia-definition of leukemia-associated antigens and current clinical protocols targeting these antigens"; Haematologica; vol. 91; No. 12; Dec. 2006; pp. 1653-1661; XP002744391.
Sebastian P. Haen et al.; "The repertoire of human tumor-associated epitopes—identification and selection of antigens and their application in clinical trials"; Current Opinion in Immunology; vol. 25; No. 2; Apr. 1, 2013; pp. 277-283; XP055212257.
Database UniProt; Oct. 16, 2013; Subname: Full=Uncharacterized protein; XP002744426; retrieved from EBI accession No. UNIPROT: S9YKJ2.
Database REFSEQ; Genbank; NCBI; Jul. 22, 2014; FAS-associated factor 1-like, partial (Galeopterus variegatus) KP002744356; accession No. XP008593192.
Engelhard, Current Opinion in Immunology vol. 6 p. 13 (1994).
Guo, et al Nature vol. 360 p. 384 (1992).
Rammensee et al, Immunogenetics vol. 41 p. 178 (1995).
Shastri et al J. Immunol. vol. 1995 vol. 155 p. 4339.

\* cited by examiner

SEQUENCE LISTING

```
<160> NUMBER OF SEQ ID NOS: 614

<210> SEQ ID NO 1
<211> LENGTH: 9
<212> TYPE: PRT
<213> ORGANISM: Homo sapiens

<400> SEQUENCE: 1

Ala Glu Gln Phe Arg Leu Glu Gln Ile
1               5

<210> SEQ ID NO 2
<211> LENGTH: 9
<212> TYPE: PRT
<213> ORGANISM: Homo sapiens

<400> SEQUENCE: 2

Phe Thr Ala Glu Phe Ser Ser Arg Tyr
1               5

<210> SEQ ID NO 3
<211> LENGTH: 11
<212> TYPE: PRT
<213> ORGANISM: Homo sapiens

<400> SEQUENCE: 3

His His Asp Glu Ser Val Leu Thr Asn Val Phe
1               5                   10

<210> SEQ ID NO 4
<211> LENGTH: 9
<212> TYPE: PRT
<213> ORGANISM: Homo sapiens

<400> SEQUENCE: 4

Arg Glu Gln Asp Glu Ala Tyr Arg Leu
1               5

<210> SEQ ID NO 5
<211> LENGTH: 9
<212> TYPE: PRT
<213> ORGANISM: Homo sapiens

<400> SEQUENCE: 5

Arg Pro Val Met Pro Ser Arg Gln Ile
1               5
```

```
<210> SEQ ID NO 6
<211> LENGTH: 9
<212> TYPE: PRT
<213> ORGANISM: Homo sapiens

<400> SEQUENCE: 6

Val Gln Arg Glu Tyr Asn Leu Asn Phe
1               5

<210> SEQ ID NO 7
<211> LENGTH: 9
<212> TYPE: PRT
<213> ORGANISM: Homo sapiens

<400> SEQUENCE: 7

Gly Gln Leu Pro Ile Thr Ile Gln Val
1               5

<210> SEQ ID NO 8
<211> LENGTH: 9
<212> TYPE: PRT
<213> ORGANISM: Homo sapiens

<400> SEQUENCE: 8

Arg Ala Tyr Ala Asp Glu Val Ala Val
1               5

<210> SEQ ID NO 9
<211> LENGTH: 9
<212> TYPE: PRT
<213> ORGANISM: Homo sapiens

<400> SEQUENCE: 9

Arg Glu Asp Lys Pro Pro Leu Ala Val
1               5

<210> SEQ ID NO 10
<211> LENGTH: 10
<212> TYPE: PRT
<213> ORGANISM: Homo sapiens

<400> SEQUENCE: 10

Arg Val Lys Asp Leu Asp Thr Glu Lys Tyr
1               5                   10

<210> SEQ ID NO 11
<211> LENGTH: 9
<212> TYPE: PRT
<213> ORGANISM: Homo sapiens

<400> SEQUENCE: 11

Ser Glu Gln Glu Met Asn Ala His Leu
1               5

<210> SEQ ID NO 12
<211> LENGTH: 9
<212> TYPE: PRT
<213> ORGANISM: Homo sapiens

<400> SEQUENCE: 12

Tyr Val Leu Pro Leu Val His Ser Leu
1               5
```

```
<210> SEQ ID NO 13
<211> LENGTH: 9
<212> TYPE: PRT
<213> ORGANISM: Homo sapiens

<400> SEQUENCE: 13

Leu Pro Leu Arg Phe Trp Val Asn Ile
1               5

<210> SEQ ID NO 14
<211> LENGTH: 9
<212> TYPE: PRT
<213> ORGANISM: Homo sapiens

<400> SEQUENCE: 14

Glu Val Ala Glu His Val Gln Tyr Met
1               5

<210> SEQ ID NO 15
<211> LENGTH: 9
<212> TYPE: PRT
<213> ORGANISM: Homo sapiens

<400> SEQUENCE: 15

Tyr Met Ala Glu Leu Ile Glu Arg Leu
1               5

<210> SEQ ID NO 16
<211> LENGTH: 9
<212> TYPE: PRT
<213> ORGANISM: Homo sapiens

<400> SEQUENCE: 16

Ala Leu Ala Ser Leu Ile Arg Ser Val
1               5

<210> SEQ ID NO 17
<211> LENGTH: 10
<212> TYPE: PRT
<213> ORGANISM: Homo sapiens

<400> SEQUENCE: 17

Thr Val Ala Glu Ile Thr Gly Ser Lys Tyr
1               5                   10

<210> SEQ ID NO 18
<211> LENGTH: 11
<212> TYPE: PRT
<213> ORGANISM: Homo sapiens

<400> SEQUENCE: 18

Glu Ile Ile Gly Lys Arg Gly Ile Ile Gly Tyr
1               5                   10

<210> SEQ ID NO 19
<211> LENGTH: 9
<212> TYPE: PRT
<213> ORGANISM: Homo sapiens

<400> SEQUENCE: 19

Asn Leu Val Glu Lys Thr Pro Ala Leu
1               5

<210> SEQ ID NO 20
<211> LENGTH: 9
```

```
<212> TYPE: PRT
<213> ORGANISM: Homo sapiens

<400> SEQUENCE: 20

Ile Glu Asp Lys Ala Gln Ile Leu Leu
1               5

<210> SEQ ID NO 21
<211> LENGTH: 10
<212> TYPE: PRT
<213> ORGANISM: Homo sapiens

<400> SEQUENCE: 21

Ser Ile Tyr Asp Asp Ser Tyr Leu Gly Tyr
1               5                   10

<210> SEQ ID NO 22
<211> LENGTH: 9
<212> TYPE: PRT
<213> ORGANISM: Homo sapiens

<400> SEQUENCE: 22

Thr Thr Asn His Pro Ile Asn Pro Lys
1               5

<210> SEQ ID NO 23
<211> LENGTH: 8
<212> TYPE: PRT
<213> ORGANISM: Homo sapiens

<400> SEQUENCE: 23

Asn Ala Ala Ile Leu Lys Lys Val
1               5

<210> SEQ ID NO 24
<211> LENGTH: 9
<212> TYPE: PRT
<213> ORGANISM: Homo sapiens

<400> SEQUENCE: 24

Asn Tyr Leu Asp Ile Lys Gly Leu Leu
1               5

<210> SEQ ID NO 25
<211> LENGTH: 10
<212> TYPE: PRT
<213> ORGANISM: Homo sapiens

<400> SEQUENCE: 25

Tyr Leu Asp Ile Lys Gly Leu Leu Asp Val
1               5                   10

<210> SEQ ID NO 26
<211> LENGTH: 10
<212> TYPE: PRT
<213> ORGANISM: Homo sapiens

<400> SEQUENCE: 26

Glu Glu Val Gly Asp Phe Ile Gln Arg Tyr
1               5                   10

<210> SEQ ID NO 27
<211> LENGTH: 9
<212> TYPE: PRT
<213> ORGANISM: Homo sapiens
```

<400> SEQUENCE: 27

Glu Val Gly Asp Phe Ile Gln Arg Tyr
1               5

<210> SEQ ID NO 28
<211> LENGTH: 10
<212> TYPE: PRT
<213> ORGANISM: Homo sapiens

<400> SEQUENCE: 28

Met Lys Asp Leu Ser Leu Gly Gly Val Leu
1               5                   10

<210> SEQ ID NO 29
<211> LENGTH: 9
<212> TYPE: PRT
<213> ORGANISM: Homo sapiens

<400> SEQUENCE: 29

Asp Glu Phe Ile Thr Val His Ser Met
1               5

<210> SEQ ID NO 30
<211> LENGTH: 9
<212> TYPE: PRT
<213> ORGANISM: Homo sapiens

<400> SEQUENCE: 30

Glu Phe Ile Thr Val His Ser Met Leu
1               5

<210> SEQ ID NO 31
<211> LENGTH: 9
<212> TYPE: PRT
<213> ORGANISM: Homo sapiens

<400> SEQUENCE: 31

Gly Gln Leu Asp Val Arg Glu Leu Ile
1               5

<210> SEQ ID NO 32
<211> LENGTH: 8
<212> TYPE: PRT
<213> ORGANISM: Homo sapiens

<400> SEQUENCE: 32

Thr Gln Tyr Ile Ile His Asn Tyr
1               5

<210> SEQ ID NO 33
<211> LENGTH: 9
<212> TYPE: PRT
<213> ORGANISM: Homo sapiens

<400> SEQUENCE: 33

Glu Val Val Asp Val Thr Trp Arg Tyr
1               5

<210> SEQ ID NO 34
<211> LENGTH: 9
<212> TYPE: PRT
<213> ORGANISM: Homo sapiens

<400> SEQUENCE: 34

Lys Glu Ala Leu Leu Arg Asp Thr Ile
1               5

<210> SEQ ID NO 35
<211> LENGTH: 9
<212> TYPE: PRT
<213> ORGANISM: Homo sapiens

<400> SEQUENCE: 35

His Gly Tyr Glu Asn Pro Thr Tyr Lys
1               5

<210> SEQ ID NO 36
<211> LENGTH: 9
<212> TYPE: PRT
<213> ORGANISM: Homo sapiens

<400> SEQUENCE: 36

Ser Leu Leu Tyr Lys Val Pro Tyr Val
1               5

<210> SEQ ID NO 37
<211> LENGTH: 8
<212> TYPE: PRT
<213> ORGANISM: Homo sapiens

<400> SEQUENCE: 37

Ala Glu Ile Pro Leu Arg Met Val
1               5

<210> SEQ ID NO 38
<211> LENGTH: 9
<212> TYPE: PRT
<213> ORGANISM: Homo sapiens

<400> SEQUENCE: 38

Glu Val Val Tyr Arg Phe Thr Ala Arg
1               5

<210> SEQ ID NO 39
<211> LENGTH: 8
<212> TYPE: PRT
<213> ORGANISM: Homo sapiens

<400> SEQUENCE: 39

Phe Pro Gly Leu Ala Ile Lys Ile
1               5

<210> SEQ ID NO 40
<211> LENGTH: 9
<212> TYPE: PRT
<213> ORGANISM: Homo sapiens

<400> SEQUENCE: 40

Ile Tyr Asn Gly Lys Leu Phe Asp Leu
1               5

<210> SEQ ID NO 41
<211> LENGTH: 10
<212> TYPE: PRT
<213> ORGANISM: Homo sapiens

<400> SEQUENCE: 41

Ile Tyr Asn Gly Lys Leu Phe Asp Leu Leu

```
<210> SEQ ID NO 42
<211> LENGTH: 8
<212> TYPE: PRT
<213> ORGANISM: Homo sapiens

<400> SEQUENCE: 42

Lys Glu Ile Asp Val Ile Ser Ile
1               5

<210> SEQ ID NO 43
<211> LENGTH: 9
<212> TYPE: PRT
<213> ORGANISM: Homo sapiens

<400> SEQUENCE: 43

Leu Glu Glu Gln Ala Ser Arg Gln Ile
1               5

<210> SEQ ID NO 44
<211> LENGTH: 9
<212> TYPE: PRT
<213> ORGANISM: Homo sapiens

<400> SEQUENCE: 44

Thr Arg Met Ser Thr Val Ser Glu Leu
1               5

<210> SEQ ID NO 45
<211> LENGTH: 9
<212> TYPE: PRT
<213> ORGANISM: Homo sapiens

<400> SEQUENCE: 45

Ser Glu Glu Thr Phe Arg Phe Glu Leu
1               5

<210> SEQ ID NO 46
<211> LENGTH: 9
<212> TYPE: PRT
<213> ORGANISM: Homo sapiens

<400> SEQUENCE: 46

Lys Leu Tyr Pro Thr Leu Val Ile Arg
1               5

<210> SEQ ID NO 47
<211> LENGTH: 11
<212> TYPE: PRT
<213> ORGANISM: Homo sapiens

<400> SEQUENCE: 47

Ala Leu Arg Asn Gln Ala Thr Met Val Gln Lys
1               5                   10

<210> SEQ ID NO 48
<211> LENGTH: 9
<212> TYPE: PRT
<213> ORGANISM: Homo sapiens

<400> SEQUENCE: 48

Leu Leu Asp His Ala Pro Pro Glu Ile
1               5
```

<210> SEQ ID NO 49
<211> LENGTH: 10
<212> TYPE: PRT
<213> ORGANISM: Homo sapiens

<400> SEQUENCE: 49

Gly Val Leu Gly Thr Val Val His Gly Lys
1               5                   10

<210> SEQ ID NO 50
<211> LENGTH: 10
<212> TYPE: PRT
<213> ORGANISM: Homo sapiens

<400> SEQUENCE: 50

Val Gln Phe Ile Gly Arg Glu Ser Lys Tyr
1               5                   10

<210> SEQ ID NO 51
<211> LENGTH: 8
<212> TYPE: PRT
<213> ORGANISM: Homo sapiens

<400> SEQUENCE: 51

Gly Gln Ser Leu Ile His Val Ile
1               5

<210> SEQ ID NO 52
<211> LENGTH: 9
<212> TYPE: PRT
<213> ORGANISM: Homo sapiens

<400> SEQUENCE: 52

Val His Ser Pro Ala Gly Met Ala Leu
1               5

<210> SEQ ID NO 53
<211> LENGTH: 10
<212> TYPE: PRT
<213> ORGANISM: Homo sapiens

<400> SEQUENCE: 53

Val Leu Tyr Glu Gly Ile Lys Val Gly Lys
1               5                   10

<210> SEQ ID NO 54
<211> LENGTH: 11
<212> TYPE: PRT
<213> ORGANISM: Homo sapiens

<400> SEQUENCE: 54

Ala Val Ile Glu Ala Glu Lys Ile Ala Gln Val
1               5                   10

<210> SEQ ID NO 55
<211> LENGTH: 9
<212> TYPE: PRT
<213> ORGANISM: Homo sapiens

<400> SEQUENCE: 55

Asp Arg Ile Glu Val Val Asn Met Leu
1               5

<210> SEQ ID NO 56

```
<211> LENGTH: 9
<212> TYPE: PRT
<213> ORGANISM: Homo sapiens

<400> SEQUENCE: 56

Ile Glu Ala Glu Lys Ile Ala Gln Val
1               5

<210> SEQ ID NO 57
<211> LENGTH: 9
<212> TYPE: PRT
<213> ORGANISM: Homo sapiens

<400> SEQUENCE: 57

Ile Glu Asp Leu Lys Ala Gln Ile Leu
1               5

<210> SEQ ID NO 58
<211> LENGTH: 9
<212> TYPE: PRT
<213> ORGANISM: Homo sapiens

<400> SEQUENCE: 58

Tyr Leu Leu Glu Ser Val Asn Lys Leu
1               5

<210> SEQ ID NO 59
<211> LENGTH: 9
<212> TYPE: PRT
<213> ORGANISM: Homo sapiens

<400> SEQUENCE: 59

His Arg Ile Tyr Val Pro Leu Met Leu
1               5

<210> SEQ ID NO 60
<211> LENGTH: 9
<212> TYPE: PRT
<213> ORGANISM: Homo sapiens

<400> SEQUENCE: 60

Lys Glu Tyr Ile Pro Pro Leu Ile Trp
1               5

<210> SEQ ID NO 61
<211> LENGTH: 8
<212> TYPE: PRT
<213> ORGANISM: Homo sapiens

<400> SEQUENCE: 61

Met Asp Lys Leu Val Val Glu Tyr
1               5

<210> SEQ ID NO 62
<211> LENGTH: 9
<212> TYPE: PRT
<213> ORGANISM: Homo sapiens

<400> SEQUENCE: 62

Ala Leu Leu Gly His Ile Leu Leu His
1               5

<210> SEQ ID NO 63
<211> LENGTH: 9
<212> TYPE: PRT
```

<213> ORGANISM: Homo sapiens

<400> SEQUENCE: 63

Ala Leu Leu Pro His Leu Tyr Thr Leu
1               5

<210> SEQ ID NO 64
<211> LENGTH: 9
<212> TYPE: PRT
<213> ORGANISM: Homo sapiens

<400> SEQUENCE: 64

His Val Ala Gly Glu Thr Val Ala Arg
1               5

<210> SEQ ID NO 65
<211> LENGTH: 9
<212> TYPE: PRT
<213> ORGANISM: Homo sapiens

<400> SEQUENCE: 65

Lys Val Trp Pro Gly Ser Thr Ala Phe
1               5

<210> SEQ ID NO 66
<211> LENGTH: 9
<212> TYPE: PRT
<213> ORGANISM: Homo sapiens

<400> SEQUENCE: 66

Glu Thr Ala Val Ala Ile Leu Arg Phe
1               5

<210> SEQ ID NO 67
<211> LENGTH: 11
<212> TYPE: PRT
<213> ORGANISM: Homo sapiens

<400> SEQUENCE: 67

Arg Val Tyr Asn Thr Asp Pro Leu Lys Glu Lys
1               5                   10

<210> SEQ ID NO 68
<211> LENGTH: 9
<212> TYPE: PRT
<213> ORGANISM: Homo sapiens

<400> SEQUENCE: 68

Ile Gly Val Glu His Val Val Val Tyr
1               5

<210> SEQ ID NO 69
<211> LENGTH: 9
<212> TYPE: PRT
<213> ORGANISM: Homo sapiens

<400> SEQUENCE: 69

Arg Gln Ile Gly Val Glu His Val Val
1               5

<210> SEQ ID NO 70
<211> LENGTH: 10
<212> TYPE: PRT
<213> ORGANISM: Homo sapiens

```
<400> SEQUENCE: 70

Asp Val Phe Glu Arg Pro Ser Ala Lys Lys
1               5                   10

<210> SEQ ID NO 71
<211> LENGTH: 9
<212> TYPE: PRT
<213> ORGANISM: Homo sapiens

<400> SEQUENCE: 71

Glu Glu Phe Gln Phe Ile Lys Lys Ala
1               5

<210> SEQ ID NO 72
<211> LENGTH: 11
<212> TYPE: PRT
<213> ORGANISM: Homo sapiens

<400> SEQUENCE: 72

Thr His Leu Val Asp Gln Asp Thr Thr Ser Phe
1               5                   10

<210> SEQ ID NO 73
<211> LENGTH: 9
<212> TYPE: PRT
<213> ORGANISM: Homo sapiens

<400> SEQUENCE: 73

Glu Ser Ala Asp Leu Ile Gln His Tyr
1               5

<210> SEQ ID NO 74
<211> LENGTH: 9
<212> TYPE: PRT
<213> ORGANISM: Homo sapiens

<400> SEQUENCE: 74

Glu Ile Ile Lys Glu Ile Ser Ile Met
1               5

<210> SEQ ID NO 75
<211> LENGTH: 9
<212> TYPE: PRT
<213> ORGANISM: Homo sapiens

<400> SEQUENCE: 75

Ser Val Ser Asp Ile Ile Arg Leu Arg
1               5

<210> SEQ ID NO 76
<211> LENGTH: 9
<212> TYPE: PRT
<213> ORGANISM: Homo sapiens

<400> SEQUENCE: 76

Ala Val Ser Leu Ile Arg Glu Glu Trp
1               5

<210> SEQ ID NO 77
<211> LENGTH: 9
<212> TYPE: PRT
<213> ORGANISM: Homo sapiens

<400> SEQUENCE: 77
```

```
Gly Glu Lys Ser Glu Ser Ile Ser Val
1               5
```

<210> SEQ ID NO 78
<211> LENGTH: 9
<212> TYPE: PRT
<213> ORGANISM: Homo sapiens

<400> SEQUENCE: 78

```
Phe Leu Thr Ile Leu Pro Glu Glu Leu
1               5
```

<210> SEQ ID NO 79
<211> LENGTH: 9
<212> TYPE: PRT
<213> ORGANISM: Homo sapiens

<400> SEQUENCE: 79

```
Ile Leu Trp Glu Thr Val Pro Ser Met
1               5
```

<210> SEQ ID NO 80
<211> LENGTH: 8
<212> TYPE: PRT
<213> ORGANISM: Homo sapiens

<400> SEQUENCE: 80

```
Leu Pro Val Arg Thr Leu Ser Ile
1               5
```

<210> SEQ ID NO 81
<211> LENGTH: 9
<212> TYPE: PRT
<213> ORGANISM: Homo sapiens

<400> SEQUENCE: 81

```
Arg Glu Ser Glu Tyr Lys Gln Val Tyr
1               5
```

<210> SEQ ID NO 82
<211> LENGTH: 9
<212> TYPE: PRT
<213> ORGANISM: Homo sapiens

<400> SEQUENCE: 82

```
Ser Glu Ser Leu Pro Val Arg Thr Leu
1               5
```

<210> SEQ ID NO 83
<211> LENGTH: 9
<212> TYPE: PRT
<213> ORGANISM: Homo sapiens

<400> SEQUENCE: 83

```
Arg Leu Leu Glu Ser Val Val Val Leu
1               5
```

<210> SEQ ID NO 84
<211> LENGTH: 9
<212> TYPE: PRT
<213> ORGANISM: Homo sapiens

<400> SEQUENCE: 84

```
Arg Pro Glu Glu Gly Lys Glu Ser Leu
1               5
```

```
<210> SEQ ID NO 85
<211> LENGTH: 9
<212> TYPE: PRT
<213> ORGANISM: Homo sapiens

<400> SEQUENCE: 85

Thr His Gly Lys Leu Val Ile Leu Phe
1               5

<210> SEQ ID NO 86
<211> LENGTH: 9
<212> TYPE: PRT
<213> ORGANISM: Homo sapiens

<400> SEQUENCE: 86

Lys Glu Leu Glu His Leu Ser His Ile
1               5

<210> SEQ ID NO 87
<211> LENGTH: 9
<212> TYPE: PRT
<213> ORGANISM: Homo sapiens

<400> SEQUENCE: 87

Arg Glu Met Glu Asn Tyr Glu Lys Ile
1               5

<210> SEQ ID NO 88
<211> LENGTH: 9
<212> TYPE: PRT
<213> ORGANISM: Homo sapiens

<400> SEQUENCE: 88

Val Leu Leu Ser Thr Ile His Glu Leu
1               5

<210> SEQ ID NO 89
<211> LENGTH: 10
<212> TYPE: PRT
<213> ORGANISM: Homo sapiens

<400> SEQUENCE: 89

Lys Thr Tyr Thr Lys Ser Ser His Leu Lys
1               5                   10

<210> SEQ ID NO 90
<211> LENGTH: 9
<212> TYPE: PRT
<213> ORGANISM: Homo sapiens

<400> SEQUENCE: 90

Glu Ile Ile Glu Lys Asn Phe Asp Tyr
1               5

<210> SEQ ID NO 91
<211> LENGTH: 10
<212> TYPE: PRT
<213> ORGANISM: Homo sapiens

<400> SEQUENCE: 91

Gly Thr Glu Glu Ala Pro Lys Val Phe Lys
1               5                   10
```

```
<210> SEQ ID NO 92
<211> LENGTH: 9
<212> TYPE: PRT
<213> ORGANISM: Homo sapiens

<400> SEQUENCE: 92

Lys Leu Met Ala Ile Pro Leu Val Phe
1               5

<210> SEQ ID NO 93
<211> LENGTH: 8
<212> TYPE: PRT
<213> ORGANISM: Homo sapiens

<400> SEQUENCE: 93

Asp Ile Lys Arg Gly Ile Pro Asn
1               5

<210> SEQ ID NO 94
<211> LENGTH: 9
<212> TYPE: PRT
<213> ORGANISM: Homo sapiens

<400> SEQUENCE: 94

Asp Ile Lys Arg Gly Ile Pro Asn Tyr
1               5

<210> SEQ ID NO 95
<211> LENGTH: 9
<212> TYPE: PRT
<213> ORGANISM: Homo sapiens

<400> SEQUENCE: 95

Phe Leu Asp Ile Thr Asn Pro Lys Ala
1               5

<210> SEQ ID NO 96
<211> LENGTH: 9
<212> TYPE: PRT
<213> ORGANISM: Homo sapiens

<400> SEQUENCE: 96

Ala Leu Tyr Ser Val Tyr Arg Gln Lys
1               5

<210> SEQ ID NO 97
<211> LENGTH: 9
<212> TYPE: PRT
<213> ORGANISM: Homo sapiens

<400> SEQUENCE: 97

Lys Val Leu Ala Leu Val Phe Gly Phe
1               5

<210> SEQ ID NO 98
<211> LENGTH: 9
<212> TYPE: PRT
<213> ORGANISM: Homo sapiens

<400> SEQUENCE: 98

Ser Phe Thr Asp Val Ile Gly His Tyr
1               5

<210> SEQ ID NO 99
<211> LENGTH: 11
```

```
<212> TYPE: PRT
<213> ORGANISM: Homo sapiens

<400> SEQUENCE: 99

Ala Ser Ala Ala Ala Ser Gly Gly Leu Leu Lys
1               5                   10

<210> SEQ ID NO 100
<211> LENGTH: 10
<212> TYPE: PRT
<213> ORGANISM: Homo sapiens

<400> SEQUENCE: 100

Ala Leu Leu Gly Val Thr Gly Ala Pro Lys
1               5                   10

<210> SEQ ID NO 101
<211> LENGTH: 9
<212> TYPE: PRT
<213> ORGANISM: Homo sapiens

<400> SEQUENCE: 101

Asp Glu Ile Lys Thr Leu Gln Arg Tyr
1               5

<210> SEQ ID NO 102
<211> LENGTH: 8
<212> TYPE: PRT
<213> ORGANISM: Homo sapiens

<400> SEQUENCE: 102

Glu Ala Tyr Val Gln Lys Met Val
1               5

<210> SEQ ID NO 103
<211> LENGTH: 10
<212> TYPE: PRT
<213> ORGANISM: Homo sapiens

<400> SEQUENCE: 103

Val Leu His Gln Asp Ser Gly Leu Gly Tyr
1               5                   10

<210> SEQ ID NO 104
<211> LENGTH: 9
<212> TYPE: PRT
<213> ORGANISM: Homo sapiens

<400> SEQUENCE: 104

Tyr Leu Gln Asn His Phe Val Gly Leu
1               5

<210> SEQ ID NO 105
<211> LENGTH: 9
<212> TYPE: PRT
<213> ORGANISM: Homo sapiens

<400> SEQUENCE: 105

Ala Glu Ile Glu Asp Ile Arg Val Leu
1               5

<210> SEQ ID NO 106
<211> LENGTH: 9
<212> TYPE: PRT
<213> ORGANISM: Homo sapiens
```

<400> SEQUENCE: 106

Gly Gln Ser Arg Leu Ile Phe Thr Tyr
1               5

<210> SEQ ID NO 107
<211> LENGTH: 9
<212> TYPE: PRT
<213> ORGANISM: Homo sapiens

<400> SEQUENCE: 107

Arg Glu Ala Asp Phe Lys Glu Thr Leu
1               5

<210> SEQ ID NO 108
<211> LENGTH: 10
<212> TYPE: PRT
<213> ORGANISM: Homo sapiens

<400> SEQUENCE: 108

Asp Thr Met Gly Pro Ser Gln His Val Tyr
1               5                   10

<210> SEQ ID NO 109
<211> LENGTH: 9
<212> TYPE: PRT
<213> ORGANISM: Homo sapiens

<400> SEQUENCE: 109

Glu Ser Arg Gly Pro Ala Leu Thr Arg
1               5

<210> SEQ ID NO 110
<211> LENGTH: 12
<212> TYPE: PRT
<213> ORGANISM: Homo sapiens

<400> SEQUENCE: 110

Phe Gln Leu Pro Gly Leu Gly Thr Pro Pro Ile Thr
1               5                   10

<210> SEQ ID NO 111
<211> LENGTH: 9
<212> TYPE: PRT
<213> ORGANISM: Homo sapiens

<400> SEQUENCE: 111

Arg Ile Gln Gly Tyr Val Val Ser Trp
1               5

<210> SEQ ID NO 112
<211> LENGTH: 9
<212> TYPE: PRT
<213> ORGANISM: Homo sapiens

<400> SEQUENCE: 112

Leu Leu Asp Pro Ser Val Phe His Val
1               5

<210> SEQ ID NO 113
<211> LENGTH: 9
<212> TYPE: PRT
<213> ORGANISM: Homo sapiens

<400> SEQUENCE: 113

```
Arg Phe Phe His Leu Ala Asp Leu Phe
1               5
```

```
<210> SEQ ID NO 114
<211> LENGTH: 9
<212> TYPE: PRT
<213> ORGANISM: Homo sapiens

<400> SEQUENCE: 114

Asp Ser Ile Ser Gly Asn Leu Gln Arg
1               5
```

```
<210> SEQ ID NO 115
<211> LENGTH: 9
<212> TYPE: PRT
<213> ORGANISM: Homo sapiens

<400> SEQUENCE: 115

Glu Thr Glu Gln Thr Ile Gln Lys Leu
1               5
```

```
<210> SEQ ID NO 116
<211> LENGTH: 9
<212> TYPE: PRT
<213> ORGANISM: Homo sapiens

<400> SEQUENCE: 116

Phe Leu Tyr Pro Phe Leu Ser His Leu
1               5
```

```
<210> SEQ ID NO 117
<211> LENGTH: 9
<212> TYPE: PRT
<213> ORGANISM: Homo sapiens

<400> SEQUENCE: 117

Thr Leu Asp Gln Lys Ile Glu Arg Val
1               5
```

```
<210> SEQ ID NO 118
<211> LENGTH: 9
<212> TYPE: PRT
<213> ORGANISM: Homo sapiens

<400> SEQUENCE: 118

Asp Ala Asp Ser Arg Ala Ala Thr Val
1               5
```

```
<210> SEQ ID NO 119
<211> LENGTH: 9
<212> TYPE: PRT
<213> ORGANISM: Homo sapiens

<400> SEQUENCE: 119

Asp His Glu Gly Phe Gly Phe Val Leu
1               5
```

```
<210> SEQ ID NO 120
<211> LENGTH: 9
<212> TYPE: PRT
<213> ORGANISM: Homo sapiens

<400> SEQUENCE: 120

Gly Glu Ala Val Lys Val Leu Ser Ile
```

```
1               5
```

<210> SEQ ID NO 121
<211> LENGTH: 9
<212> TYPE: PRT
<213> ORGANISM: Homo sapiens

<400> SEQUENCE: 121

```
Asn Ala Thr Asp Leu Leu Lys Val Leu
1               5
```

<210> SEQ ID NO 122
<211> LENGTH: 9
<212> TYPE: PRT
<213> ORGANISM: Homo sapiens

<400> SEQUENCE: 122

```
Lys Glu Ile Thr Glu Gly Lys Thr Val
1               5
```

<210> SEQ ID NO 123
<211> LENGTH: 9
<212> TYPE: PRT
<213> ORGANISM: Homo sapiens

<400> SEQUENCE: 123

```
Tyr Arg Gln Lys Gln Val Val Ile Leu
1               5
```

<210> SEQ ID NO 124
<211> LENGTH: 9
<212> TYPE: PRT
<213> ORGANISM: Homo sapiens

<400> SEQUENCE: 124

```
Val Ala Ile Asn Leu Ile Val Gln His
1               5
```

<210> SEQ ID NO 125
<211> LENGTH: 9
<212> TYPE: PRT
<213> ORGANISM: Homo sapiens

<400> SEQUENCE: 125

```
Ser Gln Asp Lys Lys Ile His Val Tyr
1               5
```

<210> SEQ ID NO 126
<211> LENGTH: 9
<212> TYPE: PRT
<213> ORGANISM: Homo sapiens

<400> SEQUENCE: 126

```
Tyr His Ala Asp Ile Tyr Asp Lys Val
1               5
```

<210> SEQ ID NO 127
<211> LENGTH: 9
<212> TYPE: PRT
<213> ORGANISM: Homo sapiens

<400> SEQUENCE: 127

```
Asp Ala Ile Lys Val Phe Val Arg Ile
1               5
```

<210> SEQ ID NO 128
<211> LENGTH: 8
<212> TYPE: PRT
<213> ORGANISM: Homo sapiens

<400> SEQUENCE: 128

Leu Glu Lys Ala Phe Ser Glu Ile
1               5

<210> SEQ ID NO 129
<211> LENGTH: 8
<212> TYPE: PRT
<213> ORGANISM: Homo sapiens

<400> SEQUENCE: 129

Met Glu Lys Ser Asp Lys Asn Gln
1               5

<210> SEQ ID NO 130
<211> LENGTH: 9
<212> TYPE: PRT
<213> ORGANISM: Homo sapiens

<400> SEQUENCE: 130

Gly Gln Thr Gly Ser Gly Lys Thr Phe
1               5

<210> SEQ ID NO 131
<211> LENGTH: 9
<212> TYPE: PRT
<213> ORGANISM: Homo sapiens

<400> SEQUENCE: 131

Asp Thr Ser Pro Asp Leu Ser Ser Arg
1               5

<210> SEQ ID NO 132
<211> LENGTH: 9
<212> TYPE: PRT
<213> ORGANISM: Homo sapiens

<400> SEQUENCE: 132

Lys Leu Asn Glu Val Ile Val Asn Lys
1               5

<210> SEQ ID NO 133
<211> LENGTH: 10
<212> TYPE: PRT
<213> ORGANISM: Homo sapiens

<400> SEQUENCE: 133

Phe Ala Gln Ile Ile Ser Val Ala Leu Ile
1               5                   10

<210> SEQ ID NO 134
<211> LENGTH: 9
<212> TYPE: PRT
<213> ORGANISM: Homo sapiens

<400> SEQUENCE: 134

Ile Ile Phe Asp Arg Pro Leu Leu Tyr
1               5

<210> SEQ ID NO 135

```
<211> LENGTH: 10
<212> TYPE: PRT
<213> ORGANISM: Homo sapiens

<400> SEQUENCE: 135

Asp Ala Val Asn Gln Asn Thr Lys Leu Leu
1               5                   10

<210> SEQ ID NO 136
<211> LENGTH: 9
<212> TYPE: PRT
<213> ORGANISM: Homo sapiens

<400> SEQUENCE: 136

His His Ile Leu Ala Asp Val Ser Leu
1               5

<210> SEQ ID NO 137
<211> LENGTH: 9
<212> TYPE: PRT
<213> ORGANISM: Homo sapiens

<400> SEQUENCE: 137

Tyr Pro Ser Glu Lys Arg Gly Glu Leu
1               5

<210> SEQ ID NO 138
<211> LENGTH: 9
<212> TYPE: PRT
<213> ORGANISM: Homo sapiens

<400> SEQUENCE: 138

Ser Val Val Asp Leu Ile Asn His Tyr
1               5

<210> SEQ ID NO 139
<211> LENGTH: 9
<212> TYPE: PRT
<213> ORGANISM: Homo sapiens

<400> SEQUENCE: 139

Glu Ile Ile Glu Lys Asp Thr Lys Tyr
1               5

<210> SEQ ID NO 140
<211> LENGTH: 9
<212> TYPE: PRT
<213> ORGANISM: Homo sapiens

<400> SEQUENCE: 140

Glu Asn Glu Glu Lys Leu Lys Glu Leu
1               5

<210> SEQ ID NO 141
<211> LENGTH: 11
<212> TYPE: PRT
<213> ORGANISM: Homo sapiens

<400> SEQUENCE: 141

Ile Leu Gly Gly Pro Gly Thr Val Gln Gly Val
1               5                   10

<210> SEQ ID NO 142
<211> LENGTH: 9
<212> TYPE: PRT
```

```
<213> ORGANISM: Homo sapiens

<400> SEQUENCE: 142

Glu Ser Ala Ala Leu Ile His His Tyr
1               5

<210> SEQ ID NO 143
<211> LENGTH: 8
<212> TYPE: PRT
<213> ORGANISM: Homo sapiens

<400> SEQUENCE: 143

Tyr Gln Arg Glu Thr Pro Gln Val
1               5

<210> SEQ ID NO 144
<211> LENGTH: 9
<212> TYPE: PRT
<213> ORGANISM: Homo sapiens

<400> SEQUENCE: 144

Ala Arg Ile Glu Ile Gly Leu His Tyr
1               5

<210> SEQ ID NO 145
<211> LENGTH: 9
<212> TYPE: PRT
<213> ORGANISM: Homo sapiens

<400> SEQUENCE: 145

Ile Pro Tyr Pro Arg Pro Ile His Leu
1               5

<210> SEQ ID NO 146
<211> LENGTH: 10
<212> TYPE: PRT
<213> ORGANISM: Homo sapiens

<400> SEQUENCE: 146

Asp Val Ser Gly Lys Thr Ala Leu Asn Gln
1               5                   10

<210> SEQ ID NO 147
<211> LENGTH: 8
<212> TYPE: PRT
<213> ORGANISM: Homo sapiens

<400> SEQUENCE: 147

Thr Glu Phe Arg Ser Leu Val Ile
1               5

<210> SEQ ID NO 148
<211> LENGTH: 10
<212> TYPE: PRT
<213> ORGANISM: Homo sapiens

<400> SEQUENCE: 148

Thr Leu Lys Ser Gly Asp Gly Ile Thr Phe
1               5                   10

<210> SEQ ID NO 149
<211> LENGTH: 9
<212> TYPE: PRT
<213> ORGANISM: Homo sapiens
```

```
<400> SEQUENCE: 149

His Glu Ala Asp Lys Thr Tyr Met Leu
1               5

<210> SEQ ID NO 150
<211> LENGTH: 9
<212> TYPE: PRT
<213> ORGANISM: Homo sapiens

<400> SEQUENCE: 150

Lys Phe Phe Glu Glu Val Leu Leu Phe
1               5

<210> SEQ ID NO 151
<211> LENGTH: 9
<212> TYPE: PRT
<213> ORGANISM: Homo sapiens

<400> SEQUENCE: 151

Arg Val Met Pro Ser Ser Phe Phe Leu
1               5

<210> SEQ ID NO 152
<211> LENGTH: 10
<212> TYPE: PRT
<213> ORGANISM: Homo sapiens

<400> SEQUENCE: 152

Tyr Glu Leu Asp Leu Arg Glu Pro Ala Leu
1               5                   10

<210> SEQ ID NO 153
<211> LENGTH: 9
<212> TYPE: PRT
<213> ORGANISM: Homo sapiens

<400> SEQUENCE: 153

Gly Ala Tyr Gly Lys Val Phe Leu Val
1               5

<210> SEQ ID NO 154
<211> LENGTH: 8
<212> TYPE: PRT
<213> ORGANISM: Homo sapiens

<400> SEQUENCE: 154

Asp His Asp Leu Leu Lys Asn Phe
1               5

<210> SEQ ID NO 155
<211> LENGTH: 9
<212> TYPE: PRT
<213> ORGANISM: Homo sapiens

<400> SEQUENCE: 155

Glu Glu Leu Gln Leu Ile Arg Gln Ala
1               5

<210> SEQ ID NO 156
<211> LENGTH: 9
<212> TYPE: PRT
<213> ORGANISM: Homo sapiens

<400> SEQUENCE: 156
```

Ala Ala Glu Leu Leu Lys His Pro Phe
1               5

<210> SEQ ID NO 157
<211> LENGTH: 10
<212> TYPE: PRT
<213> ORGANISM: Homo sapiens

<400> SEQUENCE: 157

Gly Arg Val Lys Leu Ser Asp Phe Gly Phe
1               5                   10

<210> SEQ ID NO 158
<211> LENGTH: 10
<212> TYPE: PRT
<213> ORGANISM: Homo sapiens

<400> SEQUENCE: 158

Lys Ser Asn Ser Ile Ile Val Ser Pro Arg
1               5                   10

<210> SEQ ID NO 159
<211> LENGTH: 9
<212> TYPE: PRT
<213> ORGANISM: Homo sapiens

<400> SEQUENCE: 159

Glu Thr Leu Glu Arg Leu Gln Glu Leu
1               5

<210> SEQ ID NO 160
<211> LENGTH: 8
<212> TYPE: PRT
<213> ORGANISM: Homo sapiens

<400> SEQUENCE: 160

Lys Asp Asp Glu Leu Ser Arg Gln
1               5

<210> SEQ ID NO 161
<211> LENGTH: 9
<212> TYPE: PRT
<213> ORGANISM: Homo sapiens

<400> SEQUENCE: 161

Leu Gln Gln Thr Asn Ser Glu Lys Ile
1               5

<210> SEQ ID NO 162
<211> LENGTH: 9
<212> TYPE: PRT
<213> ORGANISM: Homo sapiens

<400> SEQUENCE: 162

Gly Glu Phe Gly Lys Pro Tyr Phe Ile
1               5

<210> SEQ ID NO 163
<211> LENGTH: 8
<212> TYPE: PRT
<213> ORGANISM: Homo sapiens

<400> SEQUENCE: 163

Lys Asp Val Lys Val Val Ile Leu
1               5

<210> SEQ ID NO 164
<211> LENGTH: 9
<212> TYPE: PRT
<213> ORGANISM: Homo sapiens

<400> SEQUENCE: 164

Arg Pro Val Pro Pro Pro Pro Ser Leu
1               5

<210> SEQ ID NO 165
<211> LENGTH: 10
<212> TYPE: PRT
<213> ORGANISM: Homo sapiens

<400> SEQUENCE: 165

Lys Glu Asp Ile Pro Gly Arg His Ser Tyr
1               5                   10

<210> SEQ ID NO 166
<211> LENGTH: 9
<212> TYPE: PRT
<213> ORGANISM: Homo sapiens

<400> SEQUENCE: 166

Lys Glu Thr Lys Ala Val Thr Asn Phe
1               5

<210> SEQ ID NO 167
<211> LENGTH: 8
<212> TYPE: PRT
<213> ORGANISM: Homo sapiens

<400> SEQUENCE: 167

Tyr Glu Ile Leu Ile His Asp Leu
1               5

<210> SEQ ID NO 168
<211> LENGTH: 9
<212> TYPE: PRT
<213> ORGANISM: Homo sapiens

<400> SEQUENCE: 168

Phe Pro Arg Phe Val Asn Val Thr Val
1               5

<210> SEQ ID NO 169
<211> LENGTH: 9
<212> TYPE: PRT
<213> ORGANISM: Homo sapiens

<400> SEQUENCE: 169

Gln Val Ala Gly Trp Gly Ser Gln Arg
1               5

<210> SEQ ID NO 170
<211> LENGTH: 12
<212> TYPE: PRT
<213> ORGANISM: Homo sapiens

<400> SEQUENCE: 170

Trp Ile Asp Gly Val Leu Asn Asn Pro Gly Pro Gly
1               5                   10

-continued

<210> SEQ ID NO 171
<211> LENGTH: 8
<212> TYPE: PRT
<213> ORGANISM: Homo sapiens

<400> SEQUENCE: 171

Ser Phe Met Thr His Pro Glu Phe
1               5

<210> SEQ ID NO 172
<211> LENGTH: 9
<212> TYPE: PRT
<213> ORGANISM: Homo sapiens

<400> SEQUENCE: 172

His Tyr Thr Ile Val Phe Asn Thr Phe
1               5

<210> SEQ ID NO 173
<211> LENGTH: 10
<212> TYPE: PRT
<213> ORGANISM: Homo sapiens

<400> SEQUENCE: 173

Gly Thr Asn Asp Gly Pro Ala Leu Lys Lys
1               5                   10

<210> SEQ ID NO 174
<211> LENGTH: 9
<212> TYPE: PRT
<213> ORGANISM: Homo sapiens

<400> SEQUENCE: 174

Ile Glu Asp Pro Val Arg Pro Glu Val
1               5

<210> SEQ ID NO 175
<211> LENGTH: 9
<212> TYPE: PRT
<213> ORGANISM: Homo sapiens

<400> SEQUENCE: 175

Asn Thr Ala Ser Gly Gly Met Thr Arg
1               5

<210> SEQ ID NO 176
<211> LENGTH: 10
<212> TYPE: PRT
<213> ORGANISM: Homo sapiens

<400> SEQUENCE: 176

Glu Val Ile Glu Thr Glu Lys Thr Leu Tyr
1               5                   10

<210> SEQ ID NO 177
<211> LENGTH: 9
<212> TYPE: PRT
<213> ORGANISM: Homo sapiens

<400> SEQUENCE: 177

Met Lys Ile Leu Asn His Pro Asn Ile
1               5

<210> SEQ ID NO 178
<211> LENGTH: 9

```
<212> TYPE: PRT
<213> ORGANISM: Homo sapiens

<400> SEQUENCE: 178

His Glu Ile Asp Arg Tyr Thr Ala Ile
1               5

<210> SEQ ID NO 179
<211> LENGTH: 9
<212> TYPE: PRT
<213> ORGANISM: Homo sapiens

<400> SEQUENCE: 179

Val Phe Thr Leu Lys Pro Leu Glu Phe
1               5

<210> SEQ ID NO 180
<211> LENGTH: 8
<212> TYPE: PRT
<213> ORGANISM: Homo sapiens

<400> SEQUENCE: 180

Tyr Trp Val Pro Arg Asn Ala Leu
1               5

<210> SEQ ID NO 181
<211> LENGTH: 9
<212> TYPE: PRT
<213> ORGANISM: Homo sapiens

<400> SEQUENCE: 181

Glu Val Ser Pro Asn Leu Val Arg Tyr
1               5

<210> SEQ ID NO 182
<211> LENGTH: 10
<212> TYPE: PRT
<213> ORGANISM: Homo sapiens

<400> SEQUENCE: 182

Leu Ser Glu Ile Ala Gly Met Thr Leu Pro
1               5                   10

<210> SEQ ID NO 183
<211> LENGTH: 9
<212> TYPE: PRT
<213> ORGANISM: Homo sapiens

<400> SEQUENCE: 183

Phe Leu Ser Phe Met Asn Thr Glu Leu
1               5

<210> SEQ ID NO 184
<211> LENGTH: 9
<212> TYPE: PRT
<213> ORGANISM: Homo sapiens

<400> SEQUENCE: 184

Lys Ala Val Pro Ser Gln Lys Arg Thr
1               5

<210> SEQ ID NO 185
<211> LENGTH: 10
<212> TYPE: PRT
<213> ORGANISM: Homo sapiens
```

<400> SEQUENCE: 185

Leu Lys Ala Val Pro Ser Gln Lys Arg Thr
1               5                   10

<210> SEQ ID NO 186
<211> LENGTH: 9
<212> TYPE: PRT
<213> ORGANISM: Homo sapiens

<400> SEQUENCE: 186

Ser Leu Ile Ala Val Phe Gln Lys Tyr
1               5

<210> SEQ ID NO 187
<211> LENGTH: 9
<212> TYPE: PRT
<213> ORGANISM: Homo sapiens

<400> SEQUENCE: 187

Ile Ile Lys Glu Lys Thr Val Val Tyr
1               5

<210> SEQ ID NO 188
<211> LENGTH: 9
<212> TYPE: PRT
<213> ORGANISM: Homo sapiens

<400> SEQUENCE: 188

Leu Leu Glu Gln Lys Val Trp Glu Val
1               5

<210> SEQ ID NO 189
<211> LENGTH: 9
<212> TYPE: PRT
<213> ORGANISM: Homo sapiens

<400> SEQUENCE: 189

Ser Glu Ile Ala Glu Ser His Arg Phe
1               5

<210> SEQ ID NO 190
<211> LENGTH: 9
<212> TYPE: PRT
<213> ORGANISM: Homo sapiens

<400> SEQUENCE: 190

Tyr Leu Ala Ile Gly Ile His Glu Leu
1               5

<210> SEQ ID NO 191
<211> LENGTH: 9
<212> TYPE: PRT
<213> ORGANISM: Homo sapiens

<400> SEQUENCE: 191

Ile His Asp Glu Leu Gln Gln Ser Phe
1               5

<210> SEQ ID NO 192
<211> LENGTH: 9
<212> TYPE: PRT
<213> ORGANISM: Homo sapiens

<400> SEQUENCE: 192

Ala His Val Ile Asp Lys Phe Leu Leu
1               5

<210> SEQ ID NO 193
<211> LENGTH: 10
<212> TYPE: PRT
<213> ORGANISM: Homo sapiens

<400> SEQUENCE: 193

Lys Ala Gly Gly Glu Phe Leu Leu Arg Tyr
1               5                   10

<210> SEQ ID NO 194
<211> LENGTH: 9
<212> TYPE: PRT
<213> ORGANISM: Homo sapiens

<400> SEQUENCE: 194

Phe Glu Val Lys Asp Leu Leu Ser Leu
1               5

<210> SEQ ID NO 195
<211> LENGTH: 9
<212> TYPE: PRT
<213> ORGANISM: Homo sapiens

<400> SEQUENCE: 195

Phe Ser Lys Ala Lys Pro Ser Val Leu
1               5

<210> SEQ ID NO 196
<211> LENGTH: 8
<212> TYPE: PRT
<213> ORGANISM: Homo sapiens

<400> SEQUENCE: 196

Glu Ala Ile Lys Ala Leu Glu Val
1               5

<210> SEQ ID NO 197
<211> LENGTH: 11
<212> TYPE: PRT
<213> ORGANISM: Homo sapiens

<400> SEQUENCE: 197

Glu Val Ala Ser Ala Lys Gln Ser Val Lys Tyr
1               5                   10

<210> SEQ ID NO 198
<211> LENGTH: 9
<212> TYPE: PRT
<213> ORGANISM: Homo sapiens

<400> SEQUENCE: 198

Ile Glu Phe Thr Tyr Thr Ala Lys Leu
1               5

<210> SEQ ID NO 199
<211> LENGTH: 9
<212> TYPE: PRT
<213> ORGANISM: Homo sapiens

<400> SEQUENCE: 199

Leu Leu Ala Asp Ile Thr Ser Lys Tyr

```
1               5

<210> SEQ ID NO 200
<211> LENGTH: 9
<212> TYPE: PRT
<213> ORGANISM: Homo sapiens

<400> SEQUENCE: 200

Val Leu Val Asp Arg Thr Ile Tyr Ile
1               5

<210> SEQ ID NO 201
<211> LENGTH: 8
<212> TYPE: PRT
<213> ORGANISM: Homo sapiens

<400> SEQUENCE: 201

Ile Pro Val Val His Ala Ser Ile
1               5

<210> SEQ ID NO 202
<211> LENGTH: 11
<212> TYPE: PRT
<213> ORGANISM: Homo sapiens

<400> SEQUENCE: 202

Thr Val Ala Asp Gln Val Leu Val Gly Ser Tyr
1               5                   10

<210> SEQ ID NO 203
<211> LENGTH: 8
<212> TYPE: PRT
<213> ORGANISM: Homo sapiens

<400> SEQUENCE: 203

Val Ala Leu Val His Pro Asp Leu
1               5

<210> SEQ ID NO 204
<211> LENGTH: 9
<212> TYPE: PRT
<213> ORGANISM: Homo sapiens

<400> SEQUENCE: 204

Leu Pro Asp Asp Lys Val Thr Ala Leu
1               5

<210> SEQ ID NO 205
<211> LENGTH: 9
<212> TYPE: PRT
<213> ORGANISM: Homo sapiens

<400> SEQUENCE: 205

Lys Ile Ala Lys Gln Ile Val Gln Lys
1               5

<210> SEQ ID NO 206
<211> LENGTH: 9
<212> TYPE: PRT
<213> ORGANISM: Homo sapiens

<400> SEQUENCE: 206

Val Glu Lys Ile Leu Leu Ser Val Val
1               5
```

```
<210> SEQ ID NO 207
<211> LENGTH: 10
<212> TYPE: PRT
<213> ORGANISM: Homo sapiens

<400> SEQUENCE: 207

Ala Pro Ala Gly Ala Arg Gly Gly Pro Ala
1               5                   10

<210> SEQ ID NO 208
<211> LENGTH: 9
<212> TYPE: PRT
<213> ORGANISM: Homo sapiens

<400> SEQUENCE: 208

Glu His Leu Arg Lys Leu Glu Ala Glu
1               5

<210> SEQ ID NO 209
<211> LENGTH: 9
<212> TYPE: PRT
<213> ORGANISM: Homo sapiens

<400> SEQUENCE: 209

Arg Phe Ile Pro Glu Leu Ile Asn Phe
1               5

<210> SEQ ID NO 210
<211> LENGTH: 8
<212> TYPE: PRT
<213> ORGANISM: Homo sapiens

<400> SEQUENCE: 210

Thr Glu Lys Ile Ala Gln Leu Phe
1               5

<210> SEQ ID NO 211
<211> LENGTH: 9
<212> TYPE: PRT
<213> ORGANISM: Homo sapiens

<400> SEQUENCE: 211

Lys Leu His Asp Glu Thr Leu Thr Tyr
1               5

<210> SEQ ID NO 212
<211> LENGTH: 9
<212> TYPE: PRT
<213> ORGANISM: Homo sapiens

<400> SEQUENCE: 212

Leu His Asp Glu Thr Leu Thr Tyr Leu
1               5

<210> SEQ ID NO 213
<211> LENGTH: 11
<212> TYPE: PRT
<213> ORGANISM: Homo sapiens

<400> SEQUENCE: 213

Gly Pro Gln Glu Gly Asn Gly Pro Ser Leu Phe
1               5                   10

<210> SEQ ID NO 214
```

-continued

<210> SEQ ID NO 214
<211> LENGTH: 9
<212> TYPE: PRT
<213> ORGANISM: Homo sapiens

<400> SEQUENCE: 214

Tyr Leu Leu Gln Arg Ala Val Glu Val
1               5

<210> SEQ ID NO 215
<211> LENGTH: 9
<212> TYPE: PRT
<213> ORGANISM: Homo sapiens

<400> SEQUENCE: 215

Phe Ala Ala Leu His Gly Pro Ala Leu
1               5

<210> SEQ ID NO 216
<211> LENGTH: 10
<212> TYPE: PRT
<213> ORGANISM: Homo sapiens

<400> SEQUENCE: 216

Arg Met Ala Asn Leu Met Gly Ile Glu Phe
1               5                   10

<210> SEQ ID NO 217
<211> LENGTH: 10
<212> TYPE: PRT
<213> ORGANISM: Homo sapiens

<400> SEQUENCE: 217

Asp Thr Phe Pro Gly Pro Tyr Ala Val Leu
1               5                   10

<210> SEQ ID NO 218
<211> LENGTH: 9
<212> TYPE: PRT
<213> ORGANISM: Homo sapiens

<400> SEQUENCE: 218

Asp Thr Met Pro Gln Thr Tyr Lys Arg
1               5

<210> SEQ ID NO 219
<211> LENGTH: 9
<212> TYPE: PRT
<213> ORGANISM: Homo sapiens

<400> SEQUENCE: 219

Ile Glu His Val Phe Val Thr Asp Val
1               5

<210> SEQ ID NO 220
<211> LENGTH: 9
<212> TYPE: PRT
<213> ORGANISM: Homo sapiens

<400> SEQUENCE: 220

Lys Glu Ser Pro Thr Ser Val Gly Phe
1               5

<210> SEQ ID NO 221
<211> LENGTH: 9
<212> TYPE: PRT

<213> ORGANISM: Homo sapiens

<400> SEQUENCE: 221

Glu Ala Ile Thr Ala Ile Met Lys Tyr
1               5

<210> SEQ ID NO 222
<211> LENGTH: 9
<212> TYPE: PRT
<213> ORGANISM: Homo sapiens

<400> SEQUENCE: 222

Lys Glu Lys Pro Ala Glu Asn Thr Leu
1               5

<210> SEQ ID NO 223
<211> LENGTH: 9
<212> TYPE: PRT
<213> ORGANISM: Homo sapiens

<400> SEQUENCE: 223

Asn Glu Phe Gln Ser Gln Gln Asn Ile
1               5

<210> SEQ ID NO 224
<211> LENGTH: 11
<212> TYPE: PRT
<213> ORGANISM: Homo sapiens

<400> SEQUENCE: 224

Asn Val Ile Asp Tyr Gly His Ala Ser Lys Tyr
1               5                   10

<210> SEQ ID NO 225
<211> LENGTH: 9
<212> TYPE: PRT
<213> ORGANISM: Homo sapiens

<400> SEQUENCE: 225

Phe Ala Lys Ser Gln Ser Lys Thr Phe
1               5

<210> SEQ ID NO 226
<211> LENGTH: 8
<212> TYPE: PRT
<213> ORGANISM: Homo sapiens

<400> SEQUENCE: 226

Leu Pro Phe Ser Leu Ala His Leu
1               5

<210> SEQ ID NO 227
<211> LENGTH: 9
<212> TYPE: PRT
<213> ORGANISM: Homo sapiens

<400> SEQUENCE: 227

Ala Pro Asn Tyr Arg Leu Lys Ser Leu
1               5

<210> SEQ ID NO 228
<211> LENGTH: 10
<212> TYPE: PRT
<213> ORGANISM: Homo sapiens

<400> SEQUENCE: 228

Ile Leu Lys Asp Met Gly Ile Thr Glu Tyr
1               5                   10

<210> SEQ ID NO 229
<211> LENGTH: 9
<212> TYPE: PRT
<213> ORGANISM: Homo sapiens

<400> SEQUENCE: 229

Ala His Asp Asp Gly Arg Trp Ser Leu
1               5

<210> SEQ ID NO 230
<211> LENGTH: 10
<212> TYPE: PRT
<213> ORGANISM: Homo sapiens

<400> SEQUENCE: 230

Lys Tyr Leu Thr Ala Glu Ala Phe Gly Phe
1               5                   10

<210> SEQ ID NO 231
<211> LENGTH: 9
<212> TYPE: PRT
<213> ORGANISM: Homo sapiens

<400> SEQUENCE: 231

Glu Ser Ala Ala Leu Ile His His Tyr
1               5

<210> SEQ ID NO 232
<211> LENGTH: 8
<212> TYPE: PRT
<213> ORGANISM: Homo sapiens

<400> SEQUENCE: 232

Tyr Gln Arg Glu Thr Pro Gln Val
1               5

<210> SEQ ID NO 233
<211> LENGTH: 9
<212> TYPE: PRT
<213> ORGANISM: Homo sapiens

<400> SEQUENCE: 233

Glu Glu Leu Gln Arg Asn Ile Ser Leu
1               5

<210> SEQ ID NO 234
<211> LENGTH: 9
<212> TYPE: PRT
<213> ORGANISM: Homo sapiens

<400> SEQUENCE: 234

Arg Pro Ala Ala Leu Phe Leu Thr Leu
1               5

<210> SEQ ID NO 235
<211> LENGTH: 10
<212> TYPE: PRT
<213> ORGANISM: Homo sapiens

<400> SEQUENCE: 235

Ser Glu Glu Leu Gln Arg Asn Ile Ser Leu
1               5                   10

<210> SEQ ID NO 236
<211> LENGTH: 10
<212> TYPE: PRT
<213> ORGANISM: Homo sapiens

<400> SEQUENCE: 236

Glu Thr Ile Asp Ser Arg Val Gln Glu Tyr
1               5                   10

<210> SEQ ID NO 237
<211> LENGTH: 9
<212> TYPE: PRT
<213> ORGANISM: Homo sapiens

<400> SEQUENCE: 237

Glu Val Ser Glu Gln Ile Leu His Met
1               5

<210> SEQ ID NO 238
<211> LENGTH: 12
<212> TYPE: PRT
<213> ORGANISM: Homo sapiens

<400> SEQUENCE: 238

Gly Thr Leu Ser Gly Gly Ile Leu Ser Ser Gly Lys
1               5                   10

<210> SEQ ID NO 239
<211> LENGTH: 8
<212> TYPE: PRT
<213> ORGANISM: Homo sapiens

<400> SEQUENCE: 239

Gly Val Pro Ile Met Leu Ala Tyr
1               5

<210> SEQ ID NO 240
<211> LENGTH: 10
<212> TYPE: PRT
<213> ORGANISM: Homo sapiens

<400> SEQUENCE: 240

Glu Glu Val Lys Glu Glu Val Lys Lys Phe
1               5                   10

<210> SEQ ID NO 241
<211> LENGTH: 10
<212> TYPE: PRT
<213> ORGANISM: Homo sapiens

<400> SEQUENCE: 241

Lys Thr Ile Ala Phe Leu Leu Pro Met Phe
1               5                   10

<210> SEQ ID NO 242
<211> LENGTH: 9
<212> TYPE: PRT
<213> ORGANISM: Homo sapiens

<400> SEQUENCE: 242

Glu Val Thr Thr Asn Ile Pro Lys Met
1               5

<210> SEQ ID NO 243
<211> LENGTH: 10
<212> TYPE: PRT
<213> ORGANISM: Homo sapiens

<400> SEQUENCE: 243

Ile His Gly Asp Thr Val Gln Asn Gln Leu
1               5                   10

<210> SEQ ID NO 244
<211> LENGTH: 9
<212> TYPE: PRT
<213> ORGANISM: Homo sapiens

<400> SEQUENCE: 244

Arg Thr Met Val Lys Thr Leu Glu Tyr
1               5

<210> SEQ ID NO 245
<211> LENGTH: 10
<212> TYPE: PRT
<213> ORGANISM: Homo sapiens

<400> SEQUENCE: 245

Glu Thr Val Arg Thr Leu Asn Asn Leu Tyr
1               5                   10

<210> SEQ ID NO 246
<211> LENGTH: 9
<212> TYPE: PRT
<213> ORGANISM: Homo sapiens

<400> SEQUENCE: 246

His Ser Ile Asp Lys Val Thr Ser Arg
1               5

<210> SEQ ID NO 247
<211> LENGTH: 9
<212> TYPE: PRT
<213> ORGANISM: Homo sapiens

<400> SEQUENCE: 247

Val Ser Asn Pro Lys Ser Phe Glu Tyr
1               5

<210> SEQ ID NO 248
<211> LENGTH: 8
<212> TYPE: PRT
<213> ORGANISM: Homo sapiens

<400> SEQUENCE: 248

Gly Leu Gly Pro Thr Phe Lys Leu
1               5

<210> SEQ ID NO 249
<211> LENGTH: 10
<212> TYPE: PRT
<213> ORGANISM: Homo sapiens

<400> SEQUENCE: 249

Asn Lys Gly Ile Ser Asp Ile Ile Lys Val
1               5                   10

```
<210> SEQ ID NO 250
<211> LENGTH: 8
<212> TYPE: PRT
<213> ORGANISM: Homo sapiens

<400> SEQUENCE: 250

Thr Ser Thr Thr Arg Pro Val Leu
1               5

<210> SEQ ID NO 251
<211> LENGTH: 11
<212> TYPE: PRT
<213> ORGANISM: Homo sapiens

<400> SEQUENCE: 251

Val Leu Gly Gly Lys Ala Phe Leu Glu His Leu
1               5                   10

<210> SEQ ID NO 252
<211> LENGTH: 9
<212> TYPE: PRT
<213> ORGANISM: Homo sapiens

<400> SEQUENCE: 252

Tyr Glu Phe Glu Arg Thr Thr Ser Ile
1               5

<210> SEQ ID NO 253
<211> LENGTH: 9
<212> TYPE: PRT
<213> ORGANISM: Homo sapiens

<400> SEQUENCE: 253

Tyr Leu Asp Phe Thr Asn Pro Lys Val
1               5

<210> SEQ ID NO 254
<211> LENGTH: 10
<212> TYPE: PRT
<213> ORGANISM: Homo sapiens

<400> SEQUENCE: 254

Ile Pro Ala Val Ala Arg Thr Thr Thr Leu
1               5                   10

<210> SEQ ID NO 255
<211> LENGTH: 9
<212> TYPE: PRT
<213> ORGANISM: Homo sapiens

<400> SEQUENCE: 255

Lys Gln Gln Leu Glu Leu Asp Ser Ile
1               5

<210> SEQ ID NO 256
<211> LENGTH: 9
<212> TYPE: PRT
<213> ORGANISM: Homo sapiens

<400> SEQUENCE: 256

Lys Thr Thr Asp Thr Val Ser Ser Phe
1               5

<210> SEQ ID NO 257
<211> LENGTH: 10
```

```
<212> TYPE: PRT
<213> ORGANISM: Homo sapiens

<400> SEQUENCE: 257

Asp Tyr Leu Asp Gly Val His Thr Val Phe
1               5                   10

<210> SEQ ID NO 258
<211> LENGTH: 9
<212> TYPE: PRT
<213> ORGANISM: Homo sapiens

<400> SEQUENCE: 258

Tyr Leu Asp Gly Val His Thr Val Phe
1               5

<210> SEQ ID NO 259
<211> LENGTH: 9
<212> TYPE: PRT
<213> ORGANISM: Homo sapiens

<400> SEQUENCE: 259

Thr Tyr Val Ser Gly Met Leu Arg Phe
1               5

<210> SEQ ID NO 260
<211> LENGTH: 9
<212> TYPE: PRT
<213> ORGANISM: Homo sapiens

<400> SEQUENCE: 260

Asp Ala Ile Asp Gly Lys Gln Ala Arg
1               5

<210> SEQ ID NO 261
<211> LENGTH: 12
<212> TYPE: PRT
<213> ORGANISM: Homo sapiens

<400> SEQUENCE: 261

Asp Pro Met Ala Pro Gly Val Gln Gly Ser Leu Leu
1               5                   10

<210> SEQ ID NO 262
<211> LENGTH: 9
<212> TYPE: PRT
<213> ORGANISM: Homo sapiens

<400> SEQUENCE: 262

Gly Leu Asp Pro Ser Gln Arg Pro Lys
1               5

<210> SEQ ID NO 263
<211> LENGTH: 9
<212> TYPE: PRT
<213> ORGANISM: Homo sapiens

<400> SEQUENCE: 263

Ile Glu Asp Ser Arg Val Tyr Glu Leu
1               5

<210> SEQ ID NO 264
<211> LENGTH: 10
<212> TYPE: PRT
<213> ORGANISM: Homo sapiens
```

<400> SEQUENCE: 264

Tyr Val His Ser Phe Leu Ser Ser Gly Tyr
1               5                   10

<210> SEQ ID NO 265
<211> LENGTH: 9
<212> TYPE: PRT
<213> ORGANISM: Homo sapiens

<400> SEQUENCE: 265

His Glu Tyr Thr Thr Lys Glu Val Phe
1               5

<210> SEQ ID NO 266
<211> LENGTH: 9
<212> TYPE: PRT
<213> ORGANISM: Homo sapiens

<400> SEQUENCE: 266

Lys Leu Gln Glu Gln Leu Ala Gln Leu
1               5

<210> SEQ ID NO 267
<211> LENGTH: 9
<212> TYPE: PRT
<213> ORGANISM: Homo sapiens

<400> SEQUENCE: 267

Ser Ile Ala Ala Lys Ile Leu Ser Tyr
1               5

<210> SEQ ID NO 268
<211> LENGTH: 8
<212> TYPE: PRT
<213> ORGANISM: Homo sapiens

<400> SEQUENCE: 268

Lys Glu Leu Leu Ala Val Lys Leu
1               5

<210> SEQ ID NO 269
<211> LENGTH: 11
<212> TYPE: PRT
<213> ORGANISM: Homo sapiens

<400> SEQUENCE: 269

Lys Leu Lys Gln Thr Thr Ser Ala Leu Glu Lys
1               5                   10

<210> SEQ ID NO 270
<211> LENGTH: 10
<212> TYPE: PRT
<213> ORGANISM: Homo sapiens

<400> SEQUENCE: 270

Glu Val Gly Pro Arg Glu Ala Gly Leu Arg
1               5                   10

<210> SEQ ID NO 271
<211> LENGTH: 10
<212> TYPE: PRT
<213> ORGANISM: Homo sapiens

<400> SEQUENCE: 271

Ser Glu Ala Gln Glu Gly Leu Gln Lys Phe
1               5                   10

<210> SEQ ID NO 272
<211> LENGTH: 9
<212> TYPE: PRT
<213> ORGANISM: Homo sapiens

<400> SEQUENCE: 272

Asp Glu Ala Val Leu Phe Val Gln Val
1               5

<210> SEQ ID NO 273
<211> LENGTH: 9
<212> TYPE: PRT
<213> ORGANISM: Homo sapiens

<400> SEQUENCE: 273

Glu Val Ala Lys Phe Leu Ser Phe Tyr
1               5

<210> SEQ ID NO 274
<211> LENGTH: 9
<212> TYPE: PRT
<213> ORGANISM: Homo sapiens

<400> SEQUENCE: 274

Lys Leu Asp Gln Lys Leu Pro Glu Leu
1               5

<210> SEQ ID NO 275
<211> LENGTH: 9
<212> TYPE: PRT
<213> ORGANISM: Homo sapiens

<400> SEQUENCE: 275

Ser Val Phe Glu Lys Ser Val Gly Tyr
1               5

<210> SEQ ID NO 276
<211> LENGTH: 9
<212> TYPE: PRT
<213> ORGANISM: Homo sapiens

<400> SEQUENCE: 276

Asn Glu Gly Gln Thr Ala Leu His Tyr
1               5

<210> SEQ ID NO 277
<211> LENGTH: 9
<212> TYPE: PRT
<213> ORGANISM: Homo sapiens

<400> SEQUENCE: 277

Val Glu Phe Pro His Ser Pro Glu Ile
1               5

<210> SEQ ID NO 278
<211> LENGTH: 9
<212> TYPE: PRT
<213> ORGANISM: Homo sapiens

<400> SEQUENCE: 278

Arg Leu Gln Gly Glu Leu Gln Ala Val

```
1               5

<210> SEQ ID NO 279
<211> LENGTH: 9
<212> TYPE: PRT
<213> ORGANISM: Homo sapiens

<400> SEQUENCE: 279

Lys Glu Leu Arg Glu Leu Leu Ser Ile
1               5

<210> SEQ ID NO 280
<211> LENGTH: 9
<212> TYPE: PRT
<213> ORGANISM: Homo sapiens

<400> SEQUENCE: 280

Ser Leu Val Asp Gln Ser Ala Ala Leu
1               5

<210> SEQ ID NO 281
<211> LENGTH: 8
<212> TYPE: PRT
<213> ORGANISM: Homo sapiens

<400> SEQUENCE: 281

Leu Glu Leu Ile Met Ser Lys Tyr
1               5

<210> SEQ ID NO 282
<211> LENGTH: 9
<212> TYPE: PRT
<213> ORGANISM: Homo sapiens

<400> SEQUENCE: 282

Asp Ile Lys Pro Tyr Ile Ala Glu Tyr
1               5

<210> SEQ ID NO 283
<211> LENGTH: 9
<212> TYPE: PRT
<213> ORGANISM: Homo sapiens

<400> SEQUENCE: 283

Lys Leu Met Ala Met Phe Leu Glu Tyr
1               5

<210> SEQ ID NO 284
<211> LENGTH: 9
<212> TYPE: PRT
<213> ORGANISM: Homo sapiens

<400> SEQUENCE: 284

Tyr Thr Val Glu Lys Arg Glu Gly Tyr
1               5

<210> SEQ ID NO 285
<211> LENGTH: 9
<212> TYPE: PRT
<213> ORGANISM: Homo sapiens

<400> SEQUENCE: 285

Phe Glu Phe Asp Ile His Gln Val Ile
1               5
```

<210> SEQ ID NO 286
<211> LENGTH: 10
<212> TYPE: PRT
<213> ORGANISM: Homo sapiens

<400> SEQUENCE: 286

Ser Glu Asn Pro Ser Lys His Asp Ser Phe
1               5                   10

<210> SEQ ID NO 287
<211> LENGTH: 8
<212> TYPE: PRT
<213> ORGANISM: Homo sapiens

<400> SEQUENCE: 287

Asn Phe Leu Arg Ile Asn Thr Ile
1               5

<210> SEQ ID NO 288
<211> LENGTH: 9
<212> TYPE: PRT
<213> ORGANISM: Homo sapiens

<400> SEQUENCE: 288

Tyr Ser Gly Pro Thr Ser Val Ser Arg
1               5

<210> SEQ ID NO 289
<211> LENGTH: 10
<212> TYPE: PRT
<213> ORGANISM: Homo sapiens

<400> SEQUENCE: 289

Asp Ile Tyr Gly Gly Asp Tyr Glu Arg Phe
1               5                   10

<210> SEQ ID NO 290
<211> LENGTH: 9
<212> TYPE: PRT
<213> ORGANISM: Homo sapiens

<400> SEQUENCE: 290

Ser Ala Arg Leu Glu Lys Leu Gly Tyr
1               5

<210> SEQ ID NO 291
<211> LENGTH: 9
<212> TYPE: PRT
<213> ORGANISM: Homo sapiens

<400> SEQUENCE: 291

Tyr Val Phe Pro Gly Val Thr Arg Leu
1               5

<210> SEQ ID NO 292
<211> LENGTH: 9
<212> TYPE: PRT
<213> ORGANISM: Homo sapiens

<400> SEQUENCE: 292

Tyr Tyr Leu Asn Glu Ile Gln Ser Phe
1               5

<210> SEQ ID NO 293

```
<211> LENGTH: 9
<212> TYPE: PRT
<213> ORGANISM: Homo sapiens

<400> SEQUENCE: 293

Tyr His Ser Gln Asp Arg Tyr Glu Phe
1               5

<210> SEQ ID NO 294
<211> LENGTH: 9
<212> TYPE: PRT
<213> ORGANISM: Homo sapiens

<400> SEQUENCE: 294

Phe Pro Pro Gly Arg Gln Val Val Met
1               5

<210> SEQ ID NO 295
<211> LENGTH: 10
<212> TYPE: PRT
<213> ORGANISM: Homo sapiens

<400> SEQUENCE: 295

Ile Leu Asp Glu Ala His Glu Arg Thr Ile
1               5                   10

<210> SEQ ID NO 296
<211> LENGTH: 10
<212> TYPE: PRT
<213> ORGANISM: Homo sapiens

<400> SEQUENCE: 296

Val Ile Tyr Asn Glu Gln Met Ala Ser Lys
1               5                   10

<210> SEQ ID NO 297
<211> LENGTH: 9
<212> TYPE: PRT
<213> ORGANISM: Homo sapiens

<400> SEQUENCE: 297

Glu Ala Thr Ser Ile Lys Arg Val Arg
1               5

<210> SEQ ID NO 298
<211> LENGTH: 9
<212> TYPE: PRT
<213> ORGANISM: Homo sapiens

<400> SEQUENCE: 298

Leu Pro Glu Asp Lys Pro Arg Leu Ile
1               5

<210> SEQ ID NO 299
<211> LENGTH: 9
<212> TYPE: PRT
<213> ORGANISM: Homo sapiens

<400> SEQUENCE: 299

Lys Tyr Pro Leu Asn Leu Tyr Leu Leu
1               5

<210> SEQ ID NO 300
<211> LENGTH: 11
<212> TYPE: PRT
```

<213> ORGANISM: Homo sapiens

<400> SEQUENCE: 300

Val His Glu Ser Pro Ala Leu Ile Leu Leu Phe
1               5                   10

<210> SEQ ID NO 301
<211> LENGTH: 9
<212> TYPE: PRT
<213> ORGANISM: Homo sapiens

<400> SEQUENCE: 301

Glu Val Thr Gly His Ser Lys Gly Tyr
1               5

<210> SEQ ID NO 302
<211> LENGTH: 9
<212> TYPE: PRT
<213> ORGANISM: Homo sapiens

<400> SEQUENCE: 302

Arg Asp Ser Glu Glu Leu Leu Gln Ile
1               5

<210> SEQ ID NO 303
<211> LENGTH: 8
<212> TYPE: PRT
<213> ORGANISM: Homo sapiens

<400> SEQUENCE: 303

Ser Pro Ala Ser Lys Thr Thr Leu
1               5

<210> SEQ ID NO 304
<211> LENGTH: 8
<212> TYPE: PRT
<213> ORGANISM: Homo sapiens

<400> SEQUENCE: 304

Asp Ala Lys Thr Val Asn Val Ile
1               5

<210> SEQ ID NO 305
<211> LENGTH: 9
<212> TYPE: PRT
<213> ORGANISM: Homo sapiens

<400> SEQUENCE: 305

Asp Ser Asn Ala Thr Ala Ala Lys Met
1               5

<210> SEQ ID NO 306
<211> LENGTH: 10
<212> TYPE: PRT
<213> ORGANISM: Homo sapiens

<400> SEQUENCE: 306

Arg Thr Leu Asn Pro Gln Met Leu Gln Lys
1               5                   10

<210> SEQ ID NO 307
<211> LENGTH: 11
<212> TYPE: PRT
<213> ORGANISM: Homo sapiens

```
<400> SEQUENCE: 307

Arg Thr Leu Asn Pro Gln Met Leu Gln Lys Lys
1               5                   10

<210> SEQ ID NO 308
<211> LENGTH: 10
<212> TYPE: PRT
<213> ORGANISM: Homo sapiens

<400> SEQUENCE: 308

Leu Met Ala Glu Met Gly Val His Ser Val
1               5                   10

<210> SEQ ID NO 309
<211> LENGTH: 10
<212> TYPE: PRT
<213> ORGANISM: Homo sapiens

<400> SEQUENCE: 309

Arg Leu Leu Pro Pro Val Gly Thr Gly Arg
1               5                   10

<210> SEQ ID NO 310
<211> LENGTH: 12
<212> TYPE: PRT
<213> ORGANISM: Homo sapiens

<400> SEQUENCE: 310

Val Arg Ile Gly Thr Ile Leu Ile Gln Thr Asn Gln
1               5                   10

<210> SEQ ID NO 311
<211> LENGTH: 9
<212> TYPE: PRT
<213> ORGANISM: Homo sapiens

<400> SEQUENCE: 311

Lys Glu Leu Ser Val Leu Ser Leu Ile
1               5

<210> SEQ ID NO 312
<211> LENGTH: 9
<212> TYPE: PRT
<213> ORGANISM: Homo sapiens

<400> SEQUENCE: 312

Thr Gln Pro His Pro Asn Thr Val Tyr
1               5

<210> SEQ ID NO 313
<211> LENGTH: 9
<212> TYPE: PRT
<213> ORGANISM: Homo sapiens

<400> SEQUENCE: 313

Ala Leu Glu Glu Gln Leu Leu Lys Tyr
1               5

<210> SEQ ID NO 314
<211> LENGTH: 10
<212> TYPE: PRT
<213> ORGANISM: Homo sapiens

<400> SEQUENCE: 314
```

Asp His Phe Thr Gly Ala Ile Glu Lys Leu
1               5                   10

<210> SEQ ID NO 315
<211> LENGTH: 9
<212> TYPE: PRT
<213> ORGANISM: Homo sapiens

<400> SEQUENCE: 315

Lys Ile Leu Asp Leu Glu Thr Glu Leu
1               5

<210> SEQ ID NO 316
<211> LENGTH: 9
<212> TYPE: PRT
<213> ORGANISM: Homo sapiens

<400> SEQUENCE: 316

Ala Glu Asp Ile Pro Ser Leu Lys Leu
1               5

<210> SEQ ID NO 317
<211> LENGTH: 9
<212> TYPE: PRT
<213> ORGANISM: Homo sapiens

<400> SEQUENCE: 317

Asp Ile Pro Ser Leu Lys Leu Ala Leu
1               5

<210> SEQ ID NO 318
<211> LENGTH: 10
<212> TYPE: PRT
<213> ORGANISM: Homo sapiens

<400> SEQUENCE: 318

Gly Leu Asp Pro Asn Lys Pro Pro Glu Leu
1               5                   10

<210> SEQ ID NO 319
<211> LENGTH: 9
<212> TYPE: PRT
<213> ORGANISM: Homo sapiens

<400> SEQUENCE: 319

Phe Leu Arg Asp Pro Ala Glu Ala Leu
1               5

<210> SEQ ID NO 320
<211> LENGTH: 9
<212> TYPE: PRT
<213> ORGANISM: Homo sapiens

<400> SEQUENCE: 320

Gly Tyr Gly Ser Gln Gly Tyr Lys Tyr
1               5

<210> SEQ ID NO 321
<211> LENGTH: 9
<212> TYPE: PRT
<213> ORGANISM: Homo sapiens

<400> SEQUENCE: 321

Lys Leu Leu Ala Glu Val Thr Leu Lys
1               5

<210> SEQ ID NO 322
<211> LENGTH: 9
<212> TYPE: PRT
<213> ORGANISM: Homo sapiens

<400> SEQUENCE: 322

Ser Ala Ala Asp Gly Pro Arg Val Phe
1               5

<210> SEQ ID NO 323
<211> LENGTH: 10
<212> TYPE: PRT
<213> ORGANISM: Homo sapiens

<400> SEQUENCE: 323

Lys Leu Tyr Glu Leu His Val Phe Thr Phe
1               5                   10

<210> SEQ ID NO 324
<211> LENGTH: 8
<212> TYPE: PRT
<213> ORGANISM: Homo sapiens

<400> SEQUENCE: 324

Tyr Glu Leu His Val Phe Thr Phe
1               5

<210> SEQ ID NO 325
<211> LENGTH: 9
<212> TYPE: PRT
<213> ORGANISM: Homo sapiens

<400> SEQUENCE: 325

Tyr Leu Asn Lys Glu Ile Glu Glu Ala
1               5

<210> SEQ ID NO 326
<211> LENGTH: 9
<212> TYPE: PRT
<213> ORGANISM: Homo sapiens

<400> SEQUENCE: 326

Asp Glu Asn Glu His Gln Leu Ser Leu
1               5

<210> SEQ ID NO 327
<211> LENGTH: 9
<212> TYPE: PRT
<213> ORGANISM: Homo sapiens

<400> SEQUENCE: 327

Glu Ile Thr Pro Pro Val Val Leu Arg
1               5

<210> SEQ ID NO 328
<211> LENGTH: 11
<212> TYPE: PRT
<213> ORGANISM: Homo sapiens

<400> SEQUENCE: 328

Gly Phe Glu Ile Thr Pro Pro Val Val Leu Arg
1               5                   10

```
<210> SEQ ID NO 329
<211> LENGTH: 8
<212> TYPE: PRT
<213> ORGANISM: Homo sapiens

<400> SEQUENCE: 329

His Gln Leu Ser Leu Arg Thr Val
1               5

<210> SEQ ID NO 330
<211> LENGTH: 9
<212> TYPE: PRT
<213> ORGANISM: Homo sapiens

<400> SEQUENCE: 330

Met Ser Val Gln Pro Thr Val Ser Leu
1               5

<210> SEQ ID NO 331
<211> LENGTH: 9
<212> TYPE: PRT
<213> ORGANISM: Homo sapiens

<400> SEQUENCE: 331

Ser Ile Arg Asp Thr Pro Ala Lys Asn
1               5

<210> SEQ ID NO 332
<211> LENGTH: 12
<212> TYPE: PRT
<213> ORGANISM: Homo sapiens

<400> SEQUENCE: 332

Ser Ile Arg Asp Thr Pro Ala Lys Asn Ala Gln Lys
1               5                   10

<210> SEQ ID NO 333
<211> LENGTH: 10
<212> TYPE: PRT
<213> ORGANISM: Homo sapiens

<400> SEQUENCE: 333

Ser Pro Ile Lys Val Thr Leu Ala Thr Leu
1               5                   10

<210> SEQ ID NO 334
<211> LENGTH: 8
<212> TYPE: PRT
<213> ORGANISM: Homo sapiens

<400> SEQUENCE: 334

Thr Pro Pro Val Val Leu Arg Leu
1               5

<210> SEQ ID NO 335
<211> LENGTH: 8
<212> TYPE: PRT
<213> ORGANISM: Homo sapiens

<400> SEQUENCE: 335

Val Glu Ala Lys Phe Ile Asn Tyr
1               5

<210> SEQ ID NO 336
<211> LENGTH: 8
```

```
<212> TYPE: PRT
<213> ORGANISM: Homo sapiens

<400> SEQUENCE: 336

Tyr Glu Gly Ser Pro Ile Lys Val
1               5

<210> SEQ ID NO 337
<211> LENGTH: 10
<212> TYPE: PRT
<213> ORGANISM: Homo sapiens

<400> SEQUENCE: 337

Tyr Glu Gly Ser Pro Ile Lys Val Thr Leu
1               5                   10

<210> SEQ ID NO 338
<211> LENGTH: 9
<212> TYPE: PRT
<213> ORGANISM: Homo sapiens

<400> SEQUENCE: 338

Ser Glu Leu Lys Met Met Thr Gln Leu
1               5

<210> SEQ ID NO 339
<211> LENGTH: 9
<212> TYPE: PRT
<213> ORGANISM: Homo sapiens

<400> SEQUENCE: 339

Glu Lys Asp Pro Gln Pro Gln Gln Leu
1               5

<210> SEQ ID NO 340
<211> LENGTH: 8
<212> TYPE: PRT
<213> ORGANISM: Homo sapiens

<400> SEQUENCE: 340

Gly Tyr Val Pro Arg Thr Ala Leu
1               5

<210> SEQ ID NO 341
<211> LENGTH: 10
<212> TYPE: PRT
<213> ORGANISM: Homo sapiens

<400> SEQUENCE: 341

Lys Glu Lys Asp Pro Gln Pro Gln Gln Leu
1               5                   10

<210> SEQ ID NO 342
<211> LENGTH: 10
<212> TYPE: PRT
<213> ORGANISM: Homo sapiens

<400> SEQUENCE: 342

Leu Pro Lys Lys Pro Ser Lys Leu Glu Leu
1               5                   10

<210> SEQ ID NO 343
<211> LENGTH: 9
<212> TYPE: PRT
<213> ORGANISM: Homo sapiens
```

<400> SEQUENCE: 343

Arg Pro Ser Ala Ala Ser Ile Asp Leu
1               5

<210> SEQ ID NO 344
<211> LENGTH: 9
<212> TYPE: PRT
<213> ORGANISM: Homo sapiens

<400> SEQUENCE: 344

Ser Arg His Pro Leu Ser Pro Gly Phe
1               5

<210> SEQ ID NO 345
<211> LENGTH: 9
<212> TYPE: PRT
<213> ORGANISM: Homo sapiens

<400> SEQUENCE: 345

Thr Pro Arg Ser Pro Gln Pro Glu Leu
1               5

<210> SEQ ID NO 346
<211> LENGTH: 9
<212> TYPE: PRT
<213> ORGANISM: Homo sapiens

<400> SEQUENCE: 346

Gly Arg Ile Val Ala Phe Phe Glu Phe
1               5

<210> SEQ ID NO 347
<211> LENGTH: 9
<212> TYPE: PRT
<213> ORGANISM: Homo sapiens

<400> SEQUENCE: 347

His Thr Pro His Pro Ala Ala Ser Arg
1               5

<210> SEQ ID NO 348
<211> LENGTH: 9
<212> TYPE: PRT
<213> ORGANISM: Homo sapiens

<400> SEQUENCE: 348

Asn Pro Asp Glu Leu Lys Thr Thr Val
1               5

<210> SEQ ID NO 349
<211> LENGTH: 9
<212> TYPE: PRT
<213> ORGANISM: Homo sapiens

<400> SEQUENCE: 349

Pro Ser Lys Gln Leu Pro Asp Gln Ile
1               5

<210> SEQ ID NO 350
<211> LENGTH: 9
<212> TYPE: PRT
<213> ORGANISM: Homo sapiens

<400> SEQUENCE: 350

Val Tyr Val Glu Arg Ala Glu Val Leu
1               5

<210> SEQ ID NO 351
<211> LENGTH: 9
<212> TYPE: PRT
<213> ORGANISM: Homo sapiens

<400> SEQUENCE: 351

Asp Pro Phe Ile Ile Ile His Ser Ile
1               5

<210> SEQ ID NO 352
<211> LENGTH: 9
<212> TYPE: PRT
<213> ORGANISM: Homo sapiens

<400> SEQUENCE: 352

Glu His Ser Ile Ala Thr Leu Leu Leu
1               5

<210> SEQ ID NO 353
<211> LENGTH: 9
<212> TYPE: PRT
<213> ORGANISM: Homo sapiens

<400> SEQUENCE: 353

Phe Leu Asp Pro Arg Pro Leu Thr Val
1               5

<210> SEQ ID NO 354
<211> LENGTH: 9
<212> TYPE: PRT
<213> ORGANISM: Homo sapiens

<400> SEQUENCE: 354

Ser Ala Phe Ala Asp Arg Pro Ala Phe
1               5

<210> SEQ ID NO 355
<211> LENGTH: 9
<212> TYPE: PRT
<213> ORGANISM: Homo sapiens

<400> SEQUENCE: 355

Asp Thr Thr Leu Pro Ala Ser Ala Arg
1               5

<210> SEQ ID NO 356
<211> LENGTH: 9
<212> TYPE: PRT
<213> ORGANISM: Homo sapiens

<400> SEQUENCE: 356

Lys Leu Leu Glu Tyr Ile Glu Glu Ile
1               5

<210> SEQ ID NO 357
<211> LENGTH: 8
<212> TYPE: PRT
<213> ORGANISM: Homo sapiens

<400> SEQUENCE: 357

Leu Glu Lys Gln Leu Ile Glu Leu

-continued

```
1               5

<210> SEQ ID NO 358
<211> LENGTH: 9
<212> TYPE: PRT
<213> ORGANISM: Homo sapiens

<400> SEQUENCE: 358

Leu Met Ser Val Tyr Val Val Glu Leu
1               5

<210> SEQ ID NO 359
<211> LENGTH: 9
<212> TYPE: PRT
<213> ORGANISM: Homo sapiens

<400> SEQUENCE: 359

Glu Ser Ile Thr Asp Val Leu Val Arg
1               5

<210> SEQ ID NO 360
<211> LENGTH: 9
<212> TYPE: PRT
<213> ORGANISM: Homo sapiens

<400> SEQUENCE: 360

Glu Thr Ala Phe Gln Gly Met Leu Arg
1               5

<210> SEQ ID NO 361
<211> LENGTH: 12
<212> TYPE: PRT
<213> ORGANISM: Homo sapiens

<400> SEQUENCE: 361

Glu Val Pro Asp Val Thr Ala Thr Pro Ala Arg Leu
1               5                   10

<210> SEQ ID NO 362
<211> LENGTH: 9
<212> TYPE: PRT
<213> ORGANISM: Homo sapiens

<400> SEQUENCE: 362

Gly Arg Ile Val Thr Leu Ile Ser Phe
1               5

<210> SEQ ID NO 363
<211> LENGTH: 10
<212> TYPE: PRT
<213> ORGANISM: Homo sapiens

<400> SEQUENCE: 363

His Val Phe Ser Asp Gly Val Thr Asn Trp
1               5                   10

<210> SEQ ID NO 364
<211> LENGTH: 12
<212> TYPE: PRT
<213> ORGANISM: Homo sapiens

<400> SEQUENCE: 364

Arg Glu Ile Gly Gly Gly Glu Ala Gly Ala Val Ile
1               5                   10
```

-continued

```
<210> SEQ ID NO 365
<211> LENGTH: 9
<212> TYPE: PRT
<213> ORGANISM: Homo sapiens

<400> SEQUENCE: 365

Arg Gly Trp Asp Gly Phe Val Glu Phe
1               5

<210> SEQ ID NO 366
<211> LENGTH: 8
<212> TYPE: PRT
<213> ORGANISM: Homo sapiens

<400> SEQUENCE: 366

Arg Pro Ala Val Leu Pro Leu Leu
1               5

<210> SEQ ID NO 367
<211> LENGTH: 9
<212> TYPE: PRT
<213> ORGANISM: Homo sapiens

<400> SEQUENCE: 367

Val Glu Phe Phe His Val Glu Asp Leu
1               5

<210> SEQ ID NO 368
<211> LENGTH: 9
<212> TYPE: PRT
<213> ORGANISM: Homo sapiens

<400> SEQUENCE: 368

Val Gln Arg Asn His Glu Thr Ala Phe
1               5

<210> SEQ ID NO 369
<211> LENGTH: 8
<212> TYPE: PRT
<213> ORGANISM: Homo sapiens

<400> SEQUENCE: 369

Ala Glu Leu Glu Ala Ala Arg Leu
1               5

<210> SEQ ID NO 370
<211> LENGTH: 9
<212> TYPE: PRT
<213> ORGANISM: Homo sapiens

<400> SEQUENCE: 370

Ala Thr Gln Thr Pro Val Ser Asn Lys
1               5

<210> SEQ ID NO 371
<211> LENGTH: 9
<212> TYPE: PRT
<213> ORGANISM: Homo sapiens

<400> SEQUENCE: 371

Glu Ser Ile Asp Gln Tyr Ile Glu Arg
1               5

<210> SEQ ID NO 372
```

```
<211> LENGTH: 10
<212> TYPE: PRT
<213> ORGANISM: Homo sapiens

<400> SEQUENCE: 372

Phe Glu Glu His Asn Ser Met Asn Glu Leu
1               5                   10

<210> SEQ ID NO 373
<211> LENGTH: 10
<212> TYPE: PRT
<213> ORGANISM: Homo sapiens

<400> SEQUENCE: 373

Ser Val Ala Ser Thr Pro Ile Ser Gln Arg
1               5                   10

<210> SEQ ID NO 374
<211> LENGTH: 9
<212> TYPE: PRT
<213> ORGANISM: Homo sapiens

<400> SEQUENCE: 374

Val Ala Ser Thr Pro Ile Ser Gln Arg
1               5

<210> SEQ ID NO 375
<211> LENGTH: 9
<212> TYPE: PRT
<213> ORGANISM: Homo sapiens

<400> SEQUENCE: 375

Ala Glu Ile Val Gly Gly His Glu Ala
1               5

<210> SEQ ID NO 376
<211> LENGTH: 10
<212> TYPE: PRT
<213> ORGANISM: Homo sapiens

<400> SEQUENCE: 376

Arg Pro Pro Ser Pro Ala Leu Ala Ser Val
1               5                   10

<210> SEQ ID NO 377
<211> LENGTH: 10
<212> TYPE: PRT
<213> ORGANISM: Homo sapiens

<400> SEQUENCE: 377

Ser Val Ala Gln Val Phe Leu Asn Asn Tyr
1               5                   10

<210> SEQ ID NO 378
<211> LENGTH: 9
<212> TYPE: PRT
<213> ORGANISM: Homo sapiens

<400> SEQUENCE: 378

Thr Gln Glu Pro Thr Gln Gln His Phe
1               5

<210> SEQ ID NO 379
<211> LENGTH: 9
<212> TYPE: PRT
```

<213> ORGANISM: Homo sapiens

<400> SEQUENCE: 379

Lys Asp Ile Thr Met Lys Asn Leu Val
1               5

<210> SEQ ID NO 380
<211> LENGTH: 9
<212> TYPE: PRT
<213> ORGANISM: Homo sapiens

<400> SEQUENCE: 380

Met Ala Glu Lys Ala Lys Gln Ile Tyr
1               5

<210> SEQ ID NO 381
<211> LENGTH: 9
<212> TYPE: PRT
<213> ORGANISM: Homo sapiens

<400> SEQUENCE: 381

Lys Leu Asp Asn Gln Val Ser Lys Val
1               5

<210> SEQ ID NO 382
<211> LENGTH: 9
<212> TYPE: PRT
<213> ORGANISM: Homo sapiens

<400> SEQUENCE: 382

Ser Glu Asn Val Lys Leu Phe Ser Ala
1               5

<210> SEQ ID NO 383
<211> LENGTH: 8
<212> TYPE: PRT
<213> ORGANISM: Homo sapiens

<400> SEQUENCE: 383

Val Gln Lys Leu Gln Asn Ile Ile
1               5

<210> SEQ ID NO 384
<211> LENGTH: 10
<212> TYPE: PRT
<213> ORGANISM: Homo sapiens

<400> SEQUENCE: 384

Ala Phe Thr Val His Phe Ser Gly Gln Phe
1               5                   10

<210> SEQ ID NO 385
<211> LENGTH: 9
<212> TYPE: PRT
<213> ORGANISM: Homo sapiens

<400> SEQUENCE: 385

Gly Val Phe Arg Gly Ile Gln Asp Val
1               5

<210> SEQ ID NO 386
<211> LENGTH: 9
<212> TYPE: PRT
<213> ORGANISM: Homo sapiens

<400> SEQUENCE: 386

Gln Arg Asn Met Thr Lys Leu Gln Leu
1               5

<210> SEQ ID NO 387
<211> LENGTH: 9
<212> TYPE: PRT
<213> ORGANISM: Homo sapiens

<400> SEQUENCE: 387

Arg Met Phe Pro Asn Ala Pro Tyr Leu
1               5

<210> SEQ ID NO 388
<211> LENGTH: 9
<212> TYPE: PRT
<213> ORGANISM: Homo sapiens

<400> SEQUENCE: 388

Glu Ala Ala Glu Ala Lys Ala Arg
1               5

<210> SEQ ID NO 389
<211> LENGTH: 9
<212> TYPE: PRT
<213> ORGANISM: Homo sapiens

<400> SEQUENCE: 389

Ile Ile Lys Glu Tyr Thr Asp Val Tyr
1               5

<210> SEQ ID NO 390
<211> LENGTH: 9
<212> TYPE: PRT
<213> ORGANISM: Homo sapiens

<400> SEQUENCE: 390

Lys Glu Ile Asp Lys Asn Asp His Leu
1               5

<210> SEQ ID NO 391
<211> LENGTH: 10
<212> TYPE: PRT
<213> ORGANISM: Homo sapiens

<400> SEQUENCE: 391

Lys Val Ser Lys Ala Ser Gly Val Ser Lys
1               5                   10

<210> SEQ ID NO 392
<211> LENGTH: 9
<212> TYPE: PRT
<213> ORGANISM: Homo sapiens

<400> SEQUENCE: 392

Met Pro Ala Thr Glu Thr Lys Lys Val
1               5

<210> SEQ ID NO 393
<211> LENGTH: 9
<212> TYPE: PRT
<213> ORGANISM: Homo sapiens

<400> SEQUENCE: 393

Asn Ala Asp Pro Gln Ala Val Thr Met
1               5

<210> SEQ ID NO 394
<211> LENGTH: 9
<212> TYPE: PRT
<213> ORGANISM: Homo sapiens

<400> SEQUENCE: 394

Arg Ser Asp Met Leu Lys Asp Ile Ile
1               5

<210> SEQ ID NO 395
<211> LENGTH: 10
<212> TYPE: PRT
<213> ORGANISM: Homo sapiens

<400> SEQUENCE: 395

Ser Glu Ser Gly Ala Gly Leu Thr Arg Phe
1               5                   10

<210> SEQ ID NO 396
<211> LENGTH: 9
<212> TYPE: PRT
<213> ORGANISM: Homo sapiens

<400> SEQUENCE: 396

Ser Met Met Gln Thr Leu Leu Thr Val
1               5

<210> SEQ ID NO 397
<211> LENGTH: 9
<212> TYPE: PRT
<213> ORGANISM: Homo sapiens

<400> SEQUENCE: 397

Thr Glu Val Ser Lys Thr Pro Glu Ala
1               5

<210> SEQ ID NO 398
<211> LENGTH: 9
<212> TYPE: PRT
<213> ORGANISM: Homo sapiens

<400> SEQUENCE: 398

Val Glu Val Pro Glu Thr Pro Lys Ala
1               5

<210> SEQ ID NO 399
<211> LENGTH: 9
<212> TYPE: PRT
<213> ORGANISM: Homo sapiens

<400> SEQUENCE: 399

Asp Val Tyr Pro Glu Ile Ile Glu Arg
1               5

<210> SEQ ID NO 400
<211> LENGTH: 9
<212> TYPE: PRT
<213> ORGANISM: Homo sapiens

<400> SEQUENCE: 400

Arg Glu Val Glu Ile Gln Ser His Leu
1               5

<210> SEQ ID NO 401
<211> LENGTH: 8
<212> TYPE: PRT
<213> ORGANISM: Homo sapiens

<400> SEQUENCE: 401

Glu Pro Pro Ala Val Leu Leu Leu
1               5

<210> SEQ ID NO 402
<211> LENGTH: 9
<212> TYPE: PRT
<213> ORGANISM: Homo sapiens

<400> SEQUENCE: 402

Leu Glu Ala Asp Pro Phe Leu Lys Tyr
1               5

<210> SEQ ID NO 403
<211> LENGTH: 10
<212> TYPE: PRT
<213> ORGANISM: Homo sapiens

<400> SEQUENCE: 403

Thr Thr Gln Gly Gln Asp Val Thr Leu Ala
1               5                   10

<210> SEQ ID NO 404
<211> LENGTH: 10
<212> TYPE: PRT
<213> ORGANISM: Homo sapiens

<400> SEQUENCE: 404

Ala Glu Tyr Glu Asp Gly Phe Ser Ile Pro
1               5                   10

<210> SEQ ID NO 405
<211> LENGTH: 8
<212> TYPE: PRT
<213> ORGANISM: Homo sapiens

<400> SEQUENCE: 405

Ala Gln Ile Ser Leu Pro Arg Ile
1               5

<210> SEQ ID NO 406
<211> LENGTH: 9
<212> TYPE: PRT
<213> ORGANISM: Homo sapiens

<400> SEQUENCE: 406

Asp Phe Thr Pro Glu Pro Ala Ala Arg
1               5

<210> SEQ ID NO 407
<211> LENGTH: 10
<212> TYPE: PRT
<213> ORGANISM: Homo sapiens

<400> SEQUENCE: 407

Asp Asn Thr Gly Ile Thr Thr Val Ser Lys
1               5                   10

```
<210> SEQ ID NO 408
<211> LENGTH: 11
<212> TYPE: PRT
<213> ORGANISM: Homo sapiens

<400> SEQUENCE: 408

Glu Glu Ala Lys Gln Leu Val Asp Lys Ala Tyr
1               5                   10

<210> SEQ ID NO 409
<211> LENGTH: 8
<212> TYPE: PRT
<213> ORGANISM: Homo sapiens

<400> SEQUENCE: 409

Glu Arg Arg Glu Ser Ile Lys Gln
1               5

<210> SEQ ID NO 410
<211> LENGTH: 11
<212> TYPE: PRT
<213> ORGANISM: Homo sapiens

<400> SEQUENCE: 410

Glu Thr Val Gly Gln Leu Gly Thr Val Leu Arg
1               5                   10

<210> SEQ ID NO 411
<211> LENGTH: 9
<212> TYPE: PRT
<213> ORGANISM: Homo sapiens

<400> SEQUENCE: 411

Phe Glu Gln Val Met Arg Ile Gly Leu
1               5

<210> SEQ ID NO 412
<211> LENGTH: 9
<212> TYPE: PRT
<213> ORGANISM: Homo sapiens

<400> SEQUENCE: 412

Phe Ser Met Gln Gln Arg Gln Ala Leu
1               5

<210> SEQ ID NO 413
<211> LENGTH: 9
<212> TYPE: PRT
<213> ORGANISM: Homo sapiens

<400> SEQUENCE: 413

Gly Val Pro Phe Phe Ser Ser Leu Arg
1               5

<210> SEQ ID NO 414
<211> LENGTH: 9
<212> TYPE: PRT
<213> ORGANISM: Homo sapiens

<400> SEQUENCE: 414

Ile Val Arg Phe Pro Thr Asp Gln Leu
1               5

<210> SEQ ID NO 415
<211> LENGTH: 11
```

```
<212> TYPE: PRT
<213> ORGANISM: Homo sapiens

<400> SEQUENCE: 415

Lys Gln Pro Val Ala Ala Thr Arg Thr Ala Val
1               5                   10

<210> SEQ ID NO 416
<211> LENGTH: 9
<212> TYPE: PRT
<213> ORGANISM: Homo sapiens

<400> SEQUENCE: 416

Leu Gly Ala Ser Asn Arg Ala Phe Val
1               5

<210> SEQ ID NO 417
<211> LENGTH: 9
<212> TYPE: PRT
<213> ORGANISM: Homo sapiens

<400> SEQUENCE: 417

Asn Pro Arg Trp Asp Gly Glu Arg Leu
1               5

<210> SEQ ID NO 418
<211> LENGTH: 9
<212> TYPE: PRT
<213> ORGANISM: Homo sapiens

<400> SEQUENCE: 418

Asn Val Phe Thr Asn Ala Phe Arg Tyr
1               5

<210> SEQ ID NO 419
<211> LENGTH: 11
<212> TYPE: PRT
<213> ORGANISM: Homo sapiens

<400> SEQUENCE: 419

Gln Pro Met Glu Pro Asn Pro Arg Val Pro Leu
1               5                   10

<210> SEQ ID NO 420
<211> LENGTH: 10
<212> TYPE: PRT
<213> ORGANISM: Homo sapiens

<400> SEQUENCE: 420

Gln Pro Val Ala Ala Thr Arg Thr Ala Val
1               5                   10

<210> SEQ ID NO 421
<211> LENGTH: 9
<212> TYPE: PRT
<213> ORGANISM: Homo sapiens

<400> SEQUENCE: 421

Arg Leu Phe Glu Gln Val Met Arg Ile
1               5

<210> SEQ ID NO 422
<211> LENGTH: 9
<212> TYPE: PRT
<213> ORGANISM: Homo sapiens
```

```
<400> SEQUENCE: 422

Ser Glu Glu Pro Leu Ala Arg Asn Leu
1               5

<210> SEQ ID NO 423
<211> LENGTH: 9
<212> TYPE: PRT
<213> ORGANISM: Homo sapiens

<400> SEQUENCE: 423

Thr Ile Arg Asn Gln Ile Asn Ala Leu
1               5

<210> SEQ ID NO 424
<211> LENGTH: 9
<212> TYPE: PRT
<213> ORGANISM: Homo sapiens

<400> SEQUENCE: 424

Val Leu Gly Pro Thr Ala Met Arg Lys
1               5

<210> SEQ ID NO 425
<211> LENGTH: 9
<212> TYPE: PRT
<213> ORGANISM: Homo sapiens

<400> SEQUENCE: 425

Ala Glu Leu Arg Asn Ala Thr Ala Ala
1               5

<210> SEQ ID NO 426
<211> LENGTH: 11
<212> TYPE: PRT
<213> ORGANISM: Homo sapiens

<400> SEQUENCE: 426

Asp Val Pro Asp Gly Thr Leu Val Thr Val Met
1               5                   10

<210> SEQ ID NO 427
<211> LENGTH: 8
<212> TYPE: PRT
<213> ORGANISM: Homo sapiens

<400> SEQUENCE: 427

Leu Pro Ile Ala Phe Lys Val Val
1               5

<210> SEQ ID NO 428
<211> LENGTH: 9
<212> TYPE: PRT
<213> ORGANISM: Homo sapiens

<400> SEQUENCE: 428

Ser Ala Met Gly Ser Ala Thr Arg Tyr
1               5

<210> SEQ ID NO 429
<211> LENGTH: 8
<212> TYPE: PRT
<213> ORGANISM: Homo sapiens

<400> SEQUENCE: 429
```

Ala Glu Lys Gln Gly His Gln Trp
1               5

<210> SEQ ID NO 430
<211> LENGTH: 9
<212> TYPE: PRT
<213> ORGANISM: Homo sapiens

<400> SEQUENCE: 430

Gly Glu Gln Lys Pro Thr Gly Thr Phe
1               5

<210> SEQ ID NO 431
<211> LENGTH: 9
<212> TYPE: PRT
<213> ORGANISM: Homo sapiens

<400> SEQUENCE: 431

Gly Gln Phe Ser Lys Pro Phe Ser Phe
1               5

<210> SEQ ID NO 432
<211> LENGTH: 9
<212> TYPE: PRT
<213> ORGANISM: Homo sapiens

<400> SEQUENCE: 432

Ile Ala Phe Phe Asp Val Arg Thr Phe
1               5

<210> SEQ ID NO 433
<211> LENGTH: 10
<212> TYPE: PRT
<213> ORGANISM: Homo sapiens

<400> SEQUENCE: 433

Leu Ser Ala Gly Lys Thr Ser Phe Ser Phe
1               5                   10

<210> SEQ ID NO 434
<211> LENGTH: 9
<212> TYPE: PRT
<213> ORGANISM: Homo sapiens

<400> SEQUENCE: 434

Val Ser Asn Lys Tyr Gly Leu Val Phe
1               5

<210> SEQ ID NO 435
<211> LENGTH: 10
<212> TYPE: PRT
<213> ORGANISM: Homo sapiens

<400> SEQUENCE: 435

Gly Glu Val Asp Val Glu Gln His Thr Leu
1               5                   10

<210> SEQ ID NO 436
<211> LENGTH: 8
<212> TYPE: PRT
<213> ORGANISM: Homo sapiens

<400> SEQUENCE: 436

Val Asp Val Glu Gln His Thr Leu

```
1               5

<210> SEQ ID NO 437
<211> LENGTH: 11
<212> TYPE: PRT
<213> ORGANISM: Homo sapiens

<400> SEQUENCE: 437

Asp Ala Ala Asp Glu Leu Ser Val Gly Arg Tyr
1               5                   10

<210> SEQ ID NO 438
<211> LENGTH: 8
<212> TYPE: PRT
<213> ORGANISM: Homo sapiens

<400> SEQUENCE: 438

Leu Ser Glu Ala Asp Val Arg Ala
1               5

<210> SEQ ID NO 439
<211> LENGTH: 9
<212> TYPE: PRT
<213> ORGANISM: Homo sapiens

<400> SEQUENCE: 439

Glu Leu Thr Leu Gly Glu Phe Leu Lys
1               5

<210> SEQ ID NO 440
<211> LENGTH: 10
<212> TYPE: PRT
<213> ORGANISM: Homo sapiens

<400> SEQUENCE: 440

Glu Leu Thr Leu Gly Glu Phe Leu Lys Leu
1               5                   10

<210> SEQ ID NO 441
<211> LENGTH: 8
<212> TYPE: PRT
<213> ORGANISM: Homo sapiens

<400> SEQUENCE: 441

Leu Thr Leu Gly Glu Phe Leu Lys
1               5

<210> SEQ ID NO 442
<211> LENGTH: 9
<212> TYPE: PRT
<213> ORGANISM: Homo sapiens

<400> SEQUENCE: 442

Leu Thr Leu Gly Glu Phe Leu Lys Leu
1               5

<210> SEQ ID NO 443
<211> LENGTH: 8
<212> TYPE: PRT
<213> ORGANISM: Homo sapiens

<400> SEQUENCE: 443

Thr Leu Gly Glu Phe Leu Lys Leu
1               5
```

```
<210> SEQ ID NO 444
<211> LENGTH: 10
<212> TYPE: PRT
<213> ORGANISM: Homo sapiens

<400> SEQUENCE: 444

Lys Thr Tyr Thr Lys Ser Ser His Leu Lys
1               5                   10

<210> SEQ ID NO 445
<211> LENGTH: 9
<212> TYPE: PRT
<213> ORGANISM: Homo sapiens

<400> SEQUENCE: 445

Ser Gln Leu Thr Thr Leu Ser Phe Tyr
1               5

<210> SEQ ID NO 446
<211> LENGTH: 9
<212> TYPE: PRT
<213> ORGANISM: Homo sapiens

<400> SEQUENCE: 446

Lys Met Gln Glu Lys Lys Lys Leu Gln
1               5

<210> SEQ ID NO 447
<211> LENGTH: 9
<212> TYPE: PRT
<213> ORGANISM: Homo sapiens

<400> SEQUENCE: 447

Leu Leu Gly His Leu Pro Ala Glu Ile
1               5

<210> SEQ ID NO 448
<211> LENGTH: 16
<212> TYPE: PRT
<213> ORGANISM: Homo sapiens

<400> SEQUENCE: 448

Ala Pro Val Glu Leu Ile Leu Ser Asp Glu Thr Leu Pro Ala Pro Glu
1               5                   10                  15

<210> SEQ ID NO 449
<211> LENGTH: 17
<212> TYPE: PRT
<213> ORGANISM: Homo sapiens

<400> SEQUENCE: 449

Glu Thr Pro Asp Phe Gln Leu Phe Lys Asn Gly Val Ala Gln Glu Pro
1               5                   10                  15

Val

<210> SEQ ID NO 450
<211> LENGTH: 15
<212> TYPE: PRT
<213> ORGANISM: Homo sapiens

<400> SEQUENCE: 450

Leu Ala Pro Leu Glu Gly Ala Arg Phe Ala Leu Val Arg Glu Asp
1               5                   10                  15
```

```
<210> SEQ ID NO 451
<211> LENGTH: 16
<212> TYPE: PRT
<213> ORGANISM: Homo sapiens

<400> SEQUENCE: 451

Ser Pro Asp Arg Ile Phe Phe His Leu Asn Ala Val Ala Leu Gly Asp
1               5                   10                  15

<210> SEQ ID NO 452
<211> LENGTH: 17
<212> TYPE: PRT
<213> ORGANISM: Homo sapiens

<400> SEQUENCE: 452

Ser Pro Asp Arg Ile Phe Phe His Leu Asn Ala Val Ala Leu Gly Asp
1               5                   10                  15

Gly

<210> SEQ ID NO 453
<211> LENGTH: 16
<212> TYPE: PRT
<213> ORGANISM: Homo sapiens

<400> SEQUENCE: 453

Glu Glu Met Arg Lys Leu Gln Ala Thr Val Gln Glu Leu Gln Lys Arg
1               5                   10                  15

<210> SEQ ID NO 454
<211> LENGTH: 14
<212> TYPE: PRT
<213> ORGANISM: Homo sapiens

<400> SEQUENCE: 454

Glu Glu Pro Leu Ser Leu Gln Glu Leu Asp Thr Ser Ser Gly
1               5                   10

<210> SEQ ID NO 455
<211> LENGTH: 15
<212> TYPE: PRT
<213> ORGANISM: Homo sapiens

<400> SEQUENCE: 455

Glu Met Arg Lys Leu Gln Ala Thr Val Gln Glu Leu Gln Lys Arg
1               5                   10                  15

<210> SEQ ID NO 456
<211> LENGTH: 16
<212> TYPE: PRT
<213> ORGANISM: Homo sapiens

<400> SEQUENCE: 456

His Leu Glu Glu Pro Leu Ser Leu Gln Glu Leu Asp Thr Ser Ser Gly
1               5                   10                  15

<210> SEQ ID NO 457
<211> LENGTH: 15
<212> TYPE: PRT
<213> ORGANISM: Homo sapiens

<400> SEQUENCE: 457

Leu Glu Glu Pro Leu Ser Leu Gln Glu Leu Asp Thr Ser Ser Gly
1               5                   10                  15
```

<210> SEQ ID NO 458
<211> LENGTH: 15
<212> TYPE: PRT
<213> ORGANISM: Homo sapiens

<400> SEQUENCE: 458

Ala Gly Thr Val Arg Arg Gln Ala Val Asp Val Ser Pro Leu Arg
1               5                   10                  15

<210> SEQ ID NO 459
<211> LENGTH: 18
<212> TYPE: PRT
<213> ORGANISM: Homo sapiens

<400> SEQUENCE: 459

Ile Gly Arg Ala Gly Thr Val Arg Arg Gln Ala Val Asp Val Ser Pro
1               5                   10                  15

Leu Arg

<210> SEQ ID NO 460
<211> LENGTH: 16
<212> TYPE: PRT
<213> ORGANISM: Homo sapiens

<400> SEQUENCE: 460

Arg Ala Gly Thr Val Arg Arg Gln Ala Val Asp Val Ser Pro Leu Arg
1               5                   10                  15

<210> SEQ ID NO 461
<211> LENGTH: 13
<212> TYPE: PRT
<213> ORGANISM: Homo sapiens

<400> SEQUENCE: 461

Thr Val Arg Arg Gln Ala Val Asp Val Ser Pro Leu Arg
1               5                   10

<210> SEQ ID NO 462
<211> LENGTH: 15
<212> TYPE: PRT
<213> ORGANISM: Homo sapiens

<400> SEQUENCE: 462

Gly Val Val His Ser Phe Ser His Asn Val Gly Pro Gly Asp Lys
1               5                   10                  15

<210> SEQ ID NO 463
<211> LENGTH: 16
<212> TYPE: PRT
<213> ORGANISM: Homo sapiens

<400> SEQUENCE: 463

Gly Val Val His Ser Phe Ser His Asn Val Gly Pro Gly Asp Lys Tyr
1               5                   10                  15

<210> SEQ ID NO 464
<211> LENGTH: 17
<212> TYPE: PRT
<213> ORGANISM: Homo sapiens

<400> SEQUENCE: 464

Gly Val Val His Ser Phe Ser His Asn Val Gly Pro Gly Asp Lys Tyr
1               5                   10                  15

Thr

<210> SEQ ID NO 465
<211> LENGTH: 16
<212> TYPE: PRT
<213> ORGANISM: Homo sapiens

<400> SEQUENCE: 465

Lys Thr Glu Glu Phe Glu Val Thr Lys Thr Ala Val Ala His Arg Pro
1               5                   10                  15

<210> SEQ ID NO 466
<211> LENGTH: 17
<212> TYPE: PRT
<213> ORGANISM: Homo sapiens

<400> SEQUENCE: 466

Lys Thr Glu Glu Phe Glu Val Thr Lys Thr Ala Val Ala His Arg Pro
1               5                   10                  15

Gly

<210> SEQ ID NO 467
<211> LENGTH: 19
<212> TYPE: PRT
<213> ORGANISM: Homo sapiens

<400> SEQUENCE: 467

Val Arg Pro Gly Gly Val Val His Ser Phe Ser His Asn Val Gly Pro
1               5                   10                  15

Gly Asp Lys

<210> SEQ ID NO 468
<211> LENGTH: 21
<212> TYPE: PRT
<213> ORGANISM: Homo sapiens

<400> SEQUENCE: 468

Val Arg Pro Gly Gly Val Val His Ser Phe Ser His Asn Val Gly Pro
1               5                   10                  15

Gly Asp Lys Tyr Thr
            20

<210> SEQ ID NO 469
<211> LENGTH: 17
<212> TYPE: PRT
<213> ORGANISM: Homo sapiens

<400> SEQUENCE: 469

Ala Glu Lys Gly Val Arg Thr Leu Thr Ala Ala Val Ser Gly Ala
1               5                   10                  15

Gln

<210> SEQ ID NO 470
<211> LENGTH: 17
<212> TYPE: PRT
<213> ORGANISM: Homo sapiens

<400> SEQUENCE: 470

Ala Gln Pro Ile Leu Ser Lys Leu Glu Pro Gln Ile Ala Ser Ala Ser
1               5                   10                  15

Glu

```
<210> SEQ ID NO 471
<211> LENGTH: 16
<212> TYPE: PRT
<213> ORGANISM: Homo sapiens

<400> SEQUENCE: 471

Glu Lys Gly Val Arg Thr Leu Thr Ala Ala Ala Val Ser Gly Ala Gln
1               5                   10                  15

<210> SEQ ID NO 472
<211> LENGTH: 17
<212> TYPE: PRT
<213> ORGANISM: Homo sapiens

<400> SEQUENCE: 472

Glu Lys Gly Val Arg Thr Leu Thr Ala Ala Ala Val Ser Gly Ala Gln
1               5                   10                  15

Pro

<210> SEQ ID NO 473
<211> LENGTH: 14
<212> TYPE: PRT
<213> ORGANISM: Homo sapiens

<400> SEQUENCE: 473

Gly Val Arg Thr Leu Thr Ala Ala Ala Val Ser Gly Ala Gln
1               5                   10

<210> SEQ ID NO 474
<211> LENGTH: 15
<212> TYPE: PRT
<213> ORGANISM: Homo sapiens

<400> SEQUENCE: 474

Lys Gly Val Arg Thr Leu Thr Ala Ala Ala Val Ser Gly Ala Gln
1               5                   10                  15

<210> SEQ ID NO 475
<211> LENGTH: 15
<212> TYPE: PRT
<213> ORGANISM: Homo sapiens

<400> SEQUENCE: 475

Asp Val Asn Glu Tyr Ala Pro Val Phe Lys Glu Lys Ser Tyr Lys
1               5                   10                  15

<210> SEQ ID NO 476
<211> LENGTH: 13
<212> TYPE: PRT
<213> ORGANISM: Homo sapiens

<400> SEQUENCE: 476

His Arg Ser Phe Val Asp Leu Ser Gly His Asn Leu Ala
1               5                   10

<210> SEQ ID NO 477
<211> LENGTH: 16
<212> TYPE: PRT
<213> ORGANISM: Homo sapiens

<400> SEQUENCE: 477

His Arg Ser Phe Val Asp Leu Ser Gly His Asn Leu Ala Asn Pro His
1               5                   10                  15
```

```
<210> SEQ ID NO 478
<211> LENGTH: 17
<212> TYPE: PRT
<213> ORGANISM: Homo sapiens

<400> SEQUENCE: 478

His Arg Ser Phe Val Asp Leu Ser Gly His Asn Leu Ala Asn Pro His
1               5                   10                  15

Pro

<210> SEQ ID NO 479
<211> LENGTH: 17
<212> TYPE: PRT
<213> ORGANISM: Homo sapiens

<400> SEQUENCE: 479

Ala Leu Pro Glu Phe Asp Gly Lys Arg Phe Gln Asn Val Ala Lys Glu
1               5                   10                  15

Gly

<210> SEQ ID NO 480
<211> LENGTH: 13
<212> TYPE: PRT
<213> ORGANISM: Homo sapiens

<400> SEQUENCE: 480

Asp Ser Asn Glu Phe Ser Val Ile Ala Asp Pro Arg Gly
1               5                   10

<210> SEQ ID NO 481
<211> LENGTH: 14
<212> TYPE: PRT
<213> ORGANISM: Homo sapiens

<400> SEQUENCE: 481

Asp Ser Asn Glu Phe Ser Val Ile Ala Asp Pro Arg Gly Asn
1               5                   10

<210> SEQ ID NO 482
<211> LENGTH: 15
<212> TYPE: PRT
<213> ORGANISM: Homo sapiens

<400> SEQUENCE: 482

Asp Ser Asn Glu Phe Ser Val Ile Ala Asp Pro Arg Gly Asn Thr
1               5                   10                  15

<210> SEQ ID NO 483
<211> LENGTH: 16
<212> TYPE: PRT
<213> ORGANISM: Homo sapiens

<400> SEQUENCE: 483

Asp Ser Asn Glu Phe Ser Val Ile Ala Asp Pro Arg Gly Asn Thr Leu
1               5                   10                  15

<210> SEQ ID NO 484
<211> LENGTH: 17
<212> TYPE: PRT
<213> ORGANISM: Homo sapiens

<400> SEQUENCE: 484

Asp Ser Asn Glu Phe Ser Val Ile Ala Asp Pro Arg Gly Asn Thr Leu
1               5                   10                  15
```

Gly

<210> SEQ ID NO 485
<211> LENGTH: 13
<212> TYPE: PRT
<213> ORGANISM: Homo sapiens

<400> SEQUENCE: 485

Pro Glu Phe Asp Gly Lys Arg Phe Gln Asn Val Ala Lys
1               5                   10

<210> SEQ ID NO 486
<211> LENGTH: 18
<212> TYPE: PRT
<213> ORGANISM: Homo sapiens

<400> SEQUENCE: 486

Ser Asp Ser Asn Glu Phe Ser Val Ile Ala Asp Pro Arg Gly Asn Thr
1               5                   10                  15

Leu Gly

<210> SEQ ID NO 487
<211> LENGTH: 16
<212> TYPE: PRT
<213> ORGANISM: Homo sapiens

<400> SEQUENCE: 487

Ser Gln Lys Lys Thr Phe Glu Ile Asn Pro Arg His Pro Leu Ile Arg
1               5                   10                  15

<210> SEQ ID NO 488
<211> LENGTH: 17
<212> TYPE: PRT
<213> ORGANISM: Homo sapiens

<400> SEQUENCE: 488

Ala Leu Pro Glu Phe Asp Gly Lys Arg Phe Gln Asn Val Ala Lys Glu
1               5                   10                  15

Gly

<210> SEQ ID NO 489
<211> LENGTH: 13
<212> TYPE: PRT
<213> ORGANISM: Homo sapiens

<400> SEQUENCE: 489

Pro Glu Phe Asp Gly Lys Arg Phe Gln Asn Val Ala Lys
1               5                   10

<210> SEQ ID NO 490
<211> LENGTH: 14
<212> TYPE: PRT
<213> ORGANISM: Homo sapiens

<400> SEQUENCE: 490

Pro Glu Phe Asp Gly Lys Arg Phe Gln Asn Val Ala Lys Glu
1               5                   10

<210> SEQ ID NO 491
<211> LENGTH: 15
<212> TYPE: PRT
<213> ORGANISM: Homo sapiens

<400> SEQUENCE: 491

Leu Asn Ser Leu Thr Tyr Gln Val Leu Asp Val Gln Arg Tyr Pro
1               5                   10                  15

<210> SEQ ID NO 492
<211> LENGTH: 13
<212> TYPE: PRT
<213> ORGANISM: Homo sapiens

<400> SEQUENCE: 492

Leu Pro Gln Leu Val Gly Val Ser Thr Pro Leu Gln Gly
1               5                   10

<210> SEQ ID NO 493
<211> LENGTH: 14
<212> TYPE: PRT
<213> ORGANISM: Homo sapiens

<400> SEQUENCE: 493

Leu Pro Gln Leu Val Gly Val Ser Thr Pro Leu Gln Gly Gly
1               5                   10

<210> SEQ ID NO 494
<211> LENGTH: 15
<212> TYPE: PRT
<213> ORGANISM: Homo sapiens

<400> SEQUENCE: 494

Leu Pro Gln Leu Val Gly Val Ser Thr Pro Leu Gln Gly Gly Ser
1               5                   10                  15

<210> SEQ ID NO 495
<211> LENGTH: 16
<212> TYPE: PRT
<213> ORGANISM: Homo sapiens

<400> SEQUENCE: 495

Arg Leu Pro Gln Leu Val Gly Val Ser Thr Pro Leu Gln Gly Gly Ser
1               5                   10                  15

<210> SEQ ID NO 496
<211> LENGTH: 15
<212> TYPE: PRT
<213> ORGANISM: Homo sapiens

<400> SEQUENCE: 496

Ser Asp Val Asp Leu Ile Pro Met Asn Asp His Asn Ala Tyr Arg
1               5                   10                  15

<210> SEQ ID NO 497
<211> LENGTH: 16
<212> TYPE: PRT
<213> ORGANISM: Homo sapiens

<400> SEQUENCE: 497

Gly Arg Arg Lys Ser Arg Gln Gly Ser Leu Ala Met Glu Glu Leu Lys
1               5                   10                  15

<210> SEQ ID NO 498
<211> LENGTH: 14
<212> TYPE: PRT
<213> ORGANISM: Homo sapiens

<400> SEQUENCE: 498

Arg Lys Ser Arg Gln Gly Ser Leu Ala Met Glu Glu Leu Lys
1               5                   10

<210> SEQ ID NO 499
<211> LENGTH: 21
<212> TYPE: PRT
<213> ORGANISM: Homo sapiens

<400> SEQUENCE: 499

Ser Gly Pro Ser Leu Lys Gly Glu Glu Glu Pro Leu Val Ala Ser Glu
1               5                   10                  15

Asp Gly Ala Val Asp
            20

<210> SEQ ID NO 500
<211> LENGTH: 23
<212> TYPE: PRT
<213> ORGANISM: Homo sapiens

<400> SEQUENCE: 500

Ser Gly Ser Gly Pro Ser Leu Lys Gly Glu Glu Glu Pro Leu Val Ala
1               5                   10                  15

Ser Glu Asp Gly Ala Val Asp
            20

<210> SEQ ID NO 501
<211> LENGTH: 15
<212> TYPE: PRT
<213> ORGANISM: Homo sapiens

<400> SEQUENCE: 501

Ile Lys Pro Gly Val Thr Thr Glu Glu Ile Asp His Ala Val His
1               5                   10                  15

<210> SEQ ID NO 502
<211> LENGTH: 14
<212> TYPE: PRT
<213> ORGANISM: Homo sapiens

<400> SEQUENCE: 502

Lys Pro Gly Val Thr Thr Glu Glu Ile Asp His Ala Val His
1               5                   10

<210> SEQ ID NO 503
<211> LENGTH: 12
<212> TYPE: PRT
<213> ORGANISM: Homo sapiens

<400> SEQUENCE: 503

Asp Gly Val Leu Arg Ile Gln Asn Leu Asp Gln Ser
1               5                   10

<210> SEQ ID NO 504
<211> LENGTH: 14
<212> TYPE: PRT
<213> ORGANISM: Homo sapiens

<400> SEQUENCE: 504

Gly Ala Tyr Phe His Asp Asp Gly Phe Leu Ala Phe Pro Gly
1               5                   10

<210> SEQ ID NO 505
<211> LENGTH: 16

```
<212> TYPE: PRT
<213> ORGANISM: Homo sapiens

<400> SEQUENCE: 505

Thr Pro Tyr Ser Phe Leu Pro Leu Pro Thr Ile Lys Asp Ala Tyr Arg
1               5                   10                  15

<210> SEQ ID NO 506
<211> LENGTH: 17
<212> TYPE: PRT
<213> ORGANISM: Homo sapiens

<400> SEQUENCE: 506

Tyr Pro Thr Pro Asp Ile Ser Trp Ser Lys Leu Asp Gly Ser Leu Pro
1               5                   10                  15

Pro

<210> SEQ ID NO 507
<211> LENGTH: 18
<212> TYPE: PRT
<213> ORGANISM: Homo sapiens

<400> SEQUENCE: 507

Tyr Pro Thr Pro Asp Ile Ser Trp Ser Lys Leu Asp Gly Ser Leu Pro
1               5                   10                  15

Pro Asp

<210> SEQ ID NO 508
<211> LENGTH: 14
<212> TYPE: PRT
<213> ORGANISM: Homo sapiens

<400> SEQUENCE: 508

Ala Ser His Phe Glu Gln Met Ala Ala Ala Ser Met His Arg
1               5                   10

<210> SEQ ID NO 509
<211> LENGTH: 15
<212> TYPE: PRT
<213> ORGANISM: Homo sapiens

<400> SEQUENCE: 509

Gly Gly Gln Val Ile Val Ala Ile Pro Lys Leu Gln Thr Gln Gln
1               5                   10                  15

<210> SEQ ID NO 510
<211> LENGTH: 13
<212> TYPE: PRT
<213> ORGANISM: Homo sapiens

<400> SEQUENCE: 510

Gly Gln Val Ile Val Ala Ile Pro Lys Leu Gln Thr Gln
1               5                   10

<210> SEQ ID NO 511
<211> LENGTH: 14
<212> TYPE: PRT
<213> ORGANISM: Homo sapiens

<400> SEQUENCE: 511

Gly Gln Val Ile Val Ala Ile Pro Lys Leu Gln Thr Gln Gln
1               5                   10
```

```
<210> SEQ ID NO 512
<211> LENGTH: 14
<212> TYPE: PRT
<213> ORGANISM: Homo sapiens

<400> SEQUENCE: 512

Ile Glu Ser Thr Phe Asp Val Val Ser Ser Lys Pro Val Gly
1               5                   10

<210> SEQ ID NO 513
<211> LENGTH: 16
<212> TYPE: PRT
<213> ORGANISM: Homo sapiens

<400> SEQUENCE: 513

Asp Trp Gly Ala Leu Ala Thr Ile Ser Thr Leu Glu Ala Val Arg Gly
1               5                   10                  15

<210> SEQ ID NO 514
<211> LENGTH: 16
<212> TYPE: PRT
<213> ORGANISM: Homo sapiens

<400> SEQUENCE: 514

Gly Arg Pro Phe Ala Asp Val Leu Ser Leu Ser Asp Gly Pro Pro Gly
1               5                   10                  15

<210> SEQ ID NO 515
<211> LENGTH: 14
<212> TYPE: PRT
<213> ORGANISM: Homo sapiens

<400> SEQUENCE: 515

Trp Gly Ala Leu Ala Thr Ile Ser Thr Leu Glu Ala Val Arg
1               5                   10

<210> SEQ ID NO 516
<211> LENGTH: 15
<212> TYPE: PRT
<213> ORGANISM: Homo sapiens

<400> SEQUENCE: 516

Trp Gly Ala Leu Ala Thr Ile Ser Thr Leu Glu Ala Val Arg Gly
1               5                   10                  15

<210> SEQ ID NO 517
<211> LENGTH: 13
<212> TYPE: PRT
<213> ORGANISM: Homo sapiens

<400> SEQUENCE: 517

Ala Asp Glu Leu Ala Leu Val Asp Val Ile Glu Asp Lys
1               5                   10

<210> SEQ ID NO 518
<211> LENGTH: 15
<212> TYPE: PRT
<213> ORGANISM: Homo sapiens

<400> SEQUENCE: 518

Gly Val Ser Leu Lys Thr Leu His Pro Asp Leu Gly Thr Asp Lys
1               5                   10                  15

<210> SEQ ID NO 519
<211> LENGTH: 15
```

```
<212> TYPE: PRT
<213> ORGANISM: Homo sapiens

<400> SEQUENCE: 519

Ile Val Ser Gly Lys Asp Tyr Asn Val Thr Ala Asn Ser Lys Leu
1               5                   10                  15

<210> SEQ ID NO 520
<211> LENGTH: 13
<212> TYPE: PRT
<213> ORGANISM: Homo sapiens

<400> SEQUENCE: 520

Asp Asp Asn Ile Lys Thr Tyr Ser Asp His Pro Glu Lys
1               5                   10

<210> SEQ ID NO 521
<211> LENGTH: 15
<212> TYPE: PRT
<213> ORGANISM: Homo sapiens

<400> SEQUENCE: 521

Asp Lys Val Tyr Val His Leu Lys Asn Leu Ala Ser Arg Pro Tyr
1               5                   10                  15

<210> SEQ ID NO 522
<211> LENGTH: 16
<212> TYPE: PRT
<213> ORGANISM: Homo sapiens

<400> SEQUENCE: 522

Gly Asp Lys Val Tyr Val His Leu Lys Asn Leu Ala Ser Arg Pro Tyr
1               5                   10                  15

<210> SEQ ID NO 523
<211> LENGTH: 14
<212> TYPE: PRT
<213> ORGANISM: Homo sapiens

<400> SEQUENCE: 523

Leu Asp Asp Asn Ile Lys Thr Tyr Ser Asp His Pro Glu Lys
1               5                   10

<210> SEQ ID NO 524
<211> LENGTH: 17
<212> TYPE: PRT
<213> ORGANISM: Homo sapiens

<400> SEQUENCE: 524

Thr Gly Asp Lys Val Tyr Val His Leu Lys Asn Leu Ala Ser Arg Pro
1               5                   10                  15
Tyr

<210> SEQ ID NO 525
<211> LENGTH: 13
<212> TYPE: PRT
<213> ORGANISM: Homo sapiens

<400> SEQUENCE: 525

Val Tyr Val His Leu Lys Asn Leu Ala Ser Arg Pro Tyr
1               5                   10

<210> SEQ ID NO 526
<211> LENGTH: 19
```

<212> TYPE: PRT
<213> ORGANISM: Homo sapiens

<400> SEQUENCE: 526

Lys Thr Ser Arg Leu Pro Ile Ile Asp Val Ala Pro Leu Asp Val Gly
1               5                   10                  15

Ala Pro Asp

<210> SEQ ID NO 527
<211> LENGTH: 21
<212> TYPE: PRT
<213> ORGANISM: Homo sapiens

<400> SEQUENCE: 527

Lys Thr Ser Arg Leu Pro Ile Ile Asp Val Ala Pro Leu Asp Val Gly
1               5                   10                  15

Ala Pro Asp Gln Glu
            20

<210> SEQ ID NO 528
<211> LENGTH: 15
<212> TYPE: PRT
<213> ORGANISM: Homo sapiens

<400> SEQUENCE: 528

Leu Pro Ile Ile Asp Val Ala Pro Leu Asp Val Gly Ala Pro Asp
1               5                   10                  15

<210> SEQ ID NO 529
<211> LENGTH: 16
<212> TYPE: PRT
<213> ORGANISM: Homo sapiens

<400> SEQUENCE: 529

Arg Leu Pro Ile Ile Asp Val Ala Pro Leu Asp Val Gly Ala Pro Asp
1               5                   10                  15

<210> SEQ ID NO 530
<211> LENGTH: 18
<212> TYPE: PRT
<213> ORGANISM: Homo sapiens

<400> SEQUENCE: 530

Arg Leu Pro Ile Ile Asp Val Ala Pro Leu Asp Val Gly Ala Pro Asp
1               5                   10                  15

Gln Glu

<210> SEQ ID NO 531
<211> LENGTH: 17
<212> TYPE: PRT
<213> ORGANISM: Homo sapiens

<400> SEQUENCE: 531

Ser Arg Leu Pro Ile Ile Asp Val Ala Pro Leu Asp Val Gly Ala Pro
1               5                   10                  15

Asp

<210> SEQ ID NO 532
<211> LENGTH: 19
<212> TYPE: PRT
<213> ORGANISM: Homo sapiens

<400> SEQUENCE: 532

```
Ser Arg Leu Pro Ile Ile Asp Val Ala Pro Leu Asp Val Gly Ala Pro
1               5                   10                  15

Asp Gln Glu

<210> SEQ ID NO 533
<211> LENGTH: 18
<212> TYPE: PRT
<213> ORGANISM: Homo sapiens

<400> SEQUENCE: 533

Thr Ser Arg Leu Pro Ile Ile Asp Val Ala Pro Leu Asp Val Gly Ala
1               5                   10                  15

Pro Asp

<210> SEQ ID NO 534
<211> LENGTH: 20
<212> TYPE: PRT
<213> ORGANISM: Homo sapiens

<400> SEQUENCE: 534

Thr Ser Arg Leu Pro Ile Ile Asp Val Ala Pro Leu Asp Val Gly Ala
1               5                   10                  15

Pro Asp Gln Glu
            20

<210> SEQ ID NO 535
<211> LENGTH: 12
<212> TYPE: PRT
<213> ORGANISM: Homo sapiens

<400> SEQUENCE: 535

Asp Thr Ser Tyr Val Ser Leu Lys Ala Pro Leu Thr
1               5                   10

<210> SEQ ID NO 536
<211> LENGTH: 14
<212> TYPE: PRT
<213> ORGANISM: Homo sapiens

<400> SEQUENCE: 536

Asp Thr Ser Tyr Val Ser Leu Lys Ala Pro Leu Thr Lys Pro
1               5                   10

<210> SEQ ID NO 537
<211> LENGTH: 15
<212> TYPE: PRT
<213> ORGANISM: Homo sapiens

<400> SEQUENCE: 537

Asp Thr Ser Tyr Val Ser Leu Lys Ala Pro Leu Thr Lys Pro Leu
1               5                   10                  15

<210> SEQ ID NO 538
<211> LENGTH: 14
<212> TYPE: PRT
<213> ORGANISM: Homo sapiens

<400> SEQUENCE: 538

Glu Ser Asp Thr Ser Tyr Val Ser Leu Lys Ala Pro Leu Thr
1               5                   10

<210> SEQ ID NO 539
```

```
<211> LENGTH: 17
<212> TYPE: PRT
<213> ORGANISM: Homo sapiens

<400> SEQUENCE: 539

Glu Ser Asp Thr Ser Tyr Val Ser Leu Lys Ala Pro Leu Thr Lys Pro
1               5                   10                  15

Leu

<210> SEQ ID NO 540
<211> LENGTH: 13
<212> TYPE: PRT
<213> ORGANISM: Homo sapiens

<400> SEQUENCE: 540

Ser Asp Thr Ser Tyr Val Ser Leu Lys Ala Pro Leu Thr
1               5                   10

<210> SEQ ID NO 541
<211> LENGTH: 15
<212> TYPE: PRT
<213> ORGANISM: Homo sapiens

<400> SEQUENCE: 541

Ser Asp Thr Ser Tyr Val Ser Leu Lys Ala Pro Leu Thr Lys Pro
1               5                   10                  15

<210> SEQ ID NO 542
<211> LENGTH: 16
<212> TYPE: PRT
<213> ORGANISM: Homo sapiens

<400> SEQUENCE: 542

Ser Asp Thr Ser Tyr Val Ser Leu Lys Ala Pro Leu Thr Lys Pro Leu
1               5                   10                  15

<210> SEQ ID NO 543
<211> LENGTH: 15
<212> TYPE: PRT
<213> ORGANISM: Homo sapiens

<400> SEQUENCE: 543

Asp Pro Ala Ser Phe Arg Ala Ala Ile Gly Leu Leu Ala Arg His
1               5                   10                  15

<210> SEQ ID NO 544
<211> LENGTH: 16
<212> TYPE: PRT
<213> ORGANISM: Homo sapiens

<400> SEQUENCE: 544

Thr Glu Gly Gln Phe Val Asp Leu Thr Gly Asn Arg Leu Thr Tyr Thr
1               5                   10                  15

<210> SEQ ID NO 545
<211> LENGTH: 14
<212> TYPE: PRT
<213> ORGANISM: Homo sapiens

<400> SEQUENCE: 545

Ala Leu Asp Phe Phe Gly Asn Gly Pro Pro Val Asn Tyr Lys
1               5                   10

<210> SEQ ID NO 546
```

```
<211> LENGTH: 16
<212> TYPE: PRT
<213> ORGANISM: Homo sapiens

<400> SEQUENCE: 546

Ala Leu Asp Phe Phe Gly Asn Gly Pro Pro Val Asn Tyr Lys Thr Gly
1               5                   10                  15

<210> SEQ ID NO 547
<211> LENGTH: 14
<212> TYPE: PRT
<213> ORGANISM: Homo sapiens

<400> SEQUENCE: 547

Asp Phe Phe Gly Asn Gly Pro Pro Val Asn Tyr Lys Thr Gly
1               5                   10

<210> SEQ ID NO 548
<211> LENGTH: 13
<212> TYPE: PRT
<213> ORGANISM: Homo sapiens

<400> SEQUENCE: 548

Leu Asp Phe Phe Gly Asn Gly Pro Pro Val Asn Tyr Lys
1               5                   10

<210> SEQ ID NO 549
<211> LENGTH: 15
<212> TYPE: PRT
<213> ORGANISM: Homo sapiens

<400> SEQUENCE: 549

Leu Asp Phe Phe Gly Asn Gly Pro Pro Val Asn Tyr Lys Thr Gly
1               5                   10                  15

<210> SEQ ID NO 550
<211> LENGTH: 17
<212> TYPE: PRT
<213> ORGANISM: Homo sapiens

<400> SEQUENCE: 550

Gln Ala Leu Asp Phe Phe Gly Asn Gly Pro Pro Val Asn Tyr Lys Thr
1               5                   10                  15

Gly

<210> SEQ ID NO 551
<211> LENGTH: 15
<212> TYPE: PRT
<213> ORGANISM: Homo sapiens

<400> SEQUENCE: 551

Ala Ile Ser Asp Tyr Val Phe Asn Thr Ala Ser Leu Val Tyr His
1               5                   10                  15

<210> SEQ ID NO 552
<211> LENGTH: 17
<212> TYPE: PRT
<213> ORGANISM: Homo sapiens

<400> SEQUENCE: 552

Ala Ile Ser Asp Tyr Val Phe Asn Thr Ala Ser Leu Val Tyr His Glu
1               5                   10                  15

Glu
```

<210> SEQ ID NO 553
<211> LENGTH: 14
<212> TYPE: PRT
<213> ORGANISM: Homo sapiens

<400> SEQUENCE: 553

Ile Ser Asp Tyr Val Phe Asn Thr Ala Ser Leu Val Tyr His
1               5                   10

<210> SEQ ID NO 554
<211> LENGTH: 16
<212> TYPE: PRT
<213> ORGANISM: Homo sapiens

<400> SEQUENCE: 554

Ile Ser Asp Tyr Val Phe Asn Thr Ala Ser Leu Val Tyr His Glu Glu
1               5                   10                  15

<210> SEQ ID NO 555
<211> LENGTH: 13
<212> TYPE: PRT
<213> ORGANISM: Homo sapiens

<400> SEQUENCE: 555

Tyr Val Phe Asn Thr Ala Ser Leu Val Tyr His Glu Glu
1               5                   10

<210> SEQ ID NO 556
<211> LENGTH: 13
<212> TYPE: PRT
<213> ORGANISM: Homo sapiens

<400> SEQUENCE: 556

Ile Val Ile Ala Leu Ser Gly Asn Lys Ala Asp Leu Ala
1               5                   10

<210> SEQ ID NO 557
<211> LENGTH: 15
<212> TYPE: PRT
<213> ORGANISM: Homo sapiens

<400> SEQUENCE: 557

Ser Pro Asn Ile Val Ile Ala Leu Ser Gly Asn Lys Ala Asp Leu
1               5                   10                  15

<210> SEQ ID NO 558
<211> LENGTH: 16
<212> TYPE: PRT
<213> ORGANISM: Homo sapiens

<400> SEQUENCE: 558

Ser Pro Asn Ile Val Ile Ala Leu Ser Gly Asn Lys Ala Asp Leu Ala
1               5                   10                  15

<210> SEQ ID NO 559
<211> LENGTH: 14
<212> TYPE: PRT
<213> ORGANISM: Homo sapiens

<400> SEQUENCE: 559

Thr Pro Pro Arg Leu Val Ala Pro Arg Phe Leu Glu Val Glu
1               5                   10

<210> SEQ ID NO 560

```
<211> LENGTH: 15
<212> TYPE: PRT
<213> ORGANISM: Homo sapiens

<400> SEQUENCE: 560

Thr Pro Pro Arg Leu Val Ala Pro Arg Phe Leu Glu Val Glu Thr
1               5                   10                  15

<210> SEQ ID NO 561
<211> LENGTH: 16
<212> TYPE: PRT
<213> ORGANISM: Homo sapiens

<400> SEQUENCE: 561

Thr Pro Pro Arg Leu Val Ala Pro Arg Phe Leu Glu Val Glu Thr Ser
1               5                   10                  15

<210> SEQ ID NO 562
<211> LENGTH: 17
<212> TYPE: PRT
<213> ORGANISM: Homo sapiens

<400> SEQUENCE: 562

Glu Ile Gln Arg Asp Ile Leu Leu Glu Lys Lys Lys Val Ala Gln Asp
1               5                   10                  15

Gln

<210> SEQ ID NO 563
<211> LENGTH: 12
<212> TYPE: PRT
<213> ORGANISM: Homo sapiens

<400> SEQUENCE: 563

Phe Gly Ala Ile Phe Phe Leu Pro Asp Ser Ser Lys
1               5                   10

<210> SEQ ID NO 564
<211> LENGTH: 14
<212> TYPE: PRT
<213> ORGANISM: Homo sapiens

<400> SEQUENCE: 564

Ile Gln Arg Asp Ile Leu Leu Glu Lys Lys Lys Val Ala Gln
1               5                   10

<210> SEQ ID NO 565
<211> LENGTH: 15
<212> TYPE: PRT
<213> ORGANISM: Homo sapiens

<400> SEQUENCE: 565

Ile Gln Arg Asp Ile Leu Leu Glu Lys Lys Lys Val Ala Gln Asp
1               5                   10                  15

<210> SEQ ID NO 566
<211> LENGTH: 16
<212> TYPE: PRT
<213> ORGANISM: Homo sapiens

<400> SEQUENCE: 566

Ile Gln Arg Asp Ile Leu Leu Glu Lys Lys Lys Val Ala Gln Asp Gln
1               5                   10                  15

<210> SEQ ID NO 567
```

```
<211> LENGTH: 15
<212> TYPE: PRT
<213> ORGANISM: Homo sapiens

<400> SEQUENCE: 567

Leu Ser Gly Val Leu Phe His Ser Ser Pro Ala Leu Gln Pro Ala
1               5                   10                  15

<210> SEQ ID NO 568
<211> LENGTH: 14
<212> TYPE: PRT
<213> ORGANISM: Homo sapiens

<400> SEQUENCE: 568

Arg Asp Ile Leu Leu Glu Lys Lys Lys Val Ala Gln Asp Gln
1               5                   10

<210> SEQ ID NO 569
<211> LENGTH: 15
<212> TYPE: PRT
<213> ORGANISM: Homo sapiens

<400> SEQUENCE: 569

Ser Ser Lys Leu Leu Ser Gly Val Leu Phe His Ser Ser Pro Ala
1               5                   10                  15

<210> SEQ ID NO 570
<211> LENGTH: 16
<212> TYPE: PRT
<213> ORGANISM: Homo sapiens

<400> SEQUENCE: 570

Ser Ser Pro Ala Leu Gln Pro Ala Ala Asp His Lys Pro Gly Pro Gly
1               5                   10                  15

<210> SEQ ID NO 571
<211> LENGTH: 14
<212> TYPE: PRT
<213> ORGANISM: Homo sapiens

<400> SEQUENCE: 571

Ala Pro Pro Thr Arg Gly Pro Pro Pro Ser Tyr Gly Gly Ser
1               5                   10

<210> SEQ ID NO 572
<211> LENGTH: 22
<212> TYPE: PRT
<213> ORGANISM: Homo sapiens

<400> SEQUENCE: 572

Gly Asn Ser Arg Ser Ala Pro Pro Thr Arg Gly Pro Pro Pro Ser Tyr
1               5                   10                  15

Gly Gly Ser Ser Arg Tyr
            20

<210> SEQ ID NO 573
<211> LENGTH: 14
<212> TYPE: PRT
<213> ORGANISM: Homo sapiens

<400> SEQUENCE: 573

Arg Asp Tyr Gly His Ser Ser Ser Arg Asp Asp Tyr Pro Ser
1               5                   10
```

```
<210> SEQ ID NO 574
<211> LENGTH: 13
<212> TYPE: PRT
<213> ORGANISM: Homo sapiens

<400> SEQUENCE: 574

Ser Pro Arg Asp Asp Gly Tyr Ser Thr Lys Asp Ser Tyr
1               5                   10

<210> SEQ ID NO 575
<211> LENGTH: 15
<212> TYPE: PRT
<213> ORGANISM: Homo sapiens

<400> SEQUENCE: 575

Gly Gly Ser Ala Ala Ala Ala Ala Ala Ala Ala Ser Gly Gly
1               5                   10                  15

<210> SEQ ID NO 576
<211> LENGTH: 14
<212> TYPE: PRT
<213> ORGANISM: Homo sapiens

<400> SEQUENCE: 576

Asp Asn Met Leu Leu Ala Glu Gly Val Ser Gly Pro Glu Lys
1               5                   10

<210> SEQ ID NO 577
<211> LENGTH: 17
<212> TYPE: PRT
<213> ORGANISM: Homo sapiens

<400> SEQUENCE: 577

Ala Asp Ser Leu Tyr Val Glu Lys Ile Asp Val Gly Glu Ala Glu Pro
1               5                   10                  15

Arg

<210> SEQ ID NO 578
<211> LENGTH: 15
<212> TYPE: PRT
<213> ORGANISM: Homo sapiens

<400> SEQUENCE: 578

Arg Ile Gln Leu Val Glu Glu Glu Leu Asp Arg Ala Gln Glu Arg
1               5                   10                  15

<210> SEQ ID NO 579
<211> LENGTH: 16
<212> TYPE: PRT
<213> ORGANISM: Homo sapiens

<400> SEQUENCE: 579

Arg Arg Ile Gln Leu Val Glu Glu Glu Leu Asp Arg Ala Gln Glu Arg
1               5                   10                  15

<210> SEQ ID NO 580
<211> LENGTH: 17
<212> TYPE: PRT
<213> ORGANISM: Homo sapiens

<400> SEQUENCE: 580

His Gln Pro His Lys Val Thr Gln Tyr Lys Lys Gly Lys Asp Ser Leu
1               5                   10                  15

Tyr
```

<210> SEQ ID NO 581
<211> LENGTH: 12
<212> TYPE: PRT
<213> ORGANISM: Homo sapiens

<400> SEQUENCE: 581

Arg Lys Lys Ala Lys Thr Thr Lys Lys Ile Val Leu
1               5                   10

<210> SEQ ID NO 582
<211> LENGTH: 17
<212> TYPE: PRT
<213> ORGANISM: Homo sapiens

<400> SEQUENCE: 582

Asp Val Phe Arg Gln Tyr Ala Ser Leu Thr Gly Thr Gln Ala Leu Pro
1               5                   10                  15

Pro

<210> SEQ ID NO 583
<211> LENGTH: 14
<212> TYPE: PRT
<213> ORGANISM: Homo sapiens

<400> SEQUENCE: 583

Gly Thr Ala Gln Gly Glu Leu Phe Leu Asp Asp Gly His Thr
1               5                   10

<210> SEQ ID NO 584
<211> LENGTH: 16
<212> TYPE: PRT
<213> ORGANISM: Homo sapiens

<400> SEQUENCE: 584

Val Phe Arg Gln Tyr Ala Ser Leu Thr Gly Thr Gln Ala Leu Pro Pro
1               5                   10                  15

<210> SEQ ID NO 585
<211> LENGTH: 13
<212> TYPE: PRT
<213> ORGANISM: Homo sapiens

<400> SEQUENCE: 585

Pro Glu Phe Asp Gly Lys Arg Phe Gln Asn Val Ala Lys
1               5                   10

<210> SEQ ID NO 586
<211> LENGTH: 14
<212> TYPE: PRT
<213> ORGANISM: Homo sapiens

<400> SEQUENCE: 586

Pro Glu Phe Asp Gly Lys Arg Phe Gln Asn Val Ala Lys Glu
1               5                   10

<210> SEQ ID NO 587
<211> LENGTH: 17
<212> TYPE: PRT
<213> ORGANISM: Homo sapiens

<400> SEQUENCE: 587

Ala Leu Pro Glu Phe Asp Gly Lys Arg Phe Gln Asn Val Ala Lys Glu
1               5                   10                  15

Gly

<210> SEQ ID NO 588
<211> LENGTH: 23
<212> TYPE: PRT
<213> ORGANISM: Homo sapiens

<400> SEQUENCE: 588

Ala Ser Pro Ser Glu Ser Glu Ala Arg Phe Arg Ile Asp Ser Val Ser
1               5                   10                  15

Glu Gly Asn Ala Gly Pro Tyr
            20

<210> SEQ ID NO 589
<211> LENGTH: 16
<212> TYPE: PRT
<213> ORGANISM: Homo sapiens

<400> SEQUENCE: 589

Glu Ala Arg Phe Arg Ile Asp Ser Val Ser Glu Gly Asn Ala Gly Pro
1               5                   10                  15

<210> SEQ ID NO 590
<211> LENGTH: 18
<212> TYPE: PRT
<213> ORGANISM: Homo sapiens

<400> SEQUENCE: 590

Glu Ser Glu Ala Arg Phe Arg Ile Asp Ser Val Ser Glu Gly Asn Ala
1               5                   10                  15

Gly Pro

<210> SEQ ID NO 591
<211> LENGTH: 19
<212> TYPE: PRT
<213> ORGANISM: Homo sapiens

<400> SEQUENCE: 591

Glu Ser Glu Ala Arg Phe Arg Ile Asp Ser Val Ser Glu Gly Asn Ala
1               5                   10                  15

Gly Pro Tyr

<210> SEQ ID NO 592
<211> LENGTH: 13
<212> TYPE: PRT
<213> ORGANISM: Homo sapiens

<400> SEQUENCE: 592

Phe Arg Ile Asp Ser Val Ser Glu Gly Asn Ala Gly Pro
1               5                   10

<210> SEQ ID NO 593
<211> LENGTH: 14
<212> TYPE: PRT
<213> ORGANISM: Homo sapiens

<400> SEQUENCE: 593

Phe Arg Ile Asp Ser Val Ser Glu Gly Asn Ala Gly Pro Tyr
1               5                   10

<210> SEQ ID NO 594
<211> LENGTH: 18

```
<212> TYPE: PRT
<213> ORGANISM: Homo sapiens

<400> SEQUENCE: 594

Ser Glu Ala Arg Phe Arg Ile Asp Ser Val Ser Glu Gly Asn Ala Gly
1               5                   10                  15

Pro Tyr

<210> SEQ ID NO 595
<211> LENGTH: 22
<212> TYPE: PRT
<213> ORGANISM: Homo sapiens

<400> SEQUENCE: 595

Ser Pro Ser Glu Ser Glu Ala Arg Phe Arg Ile Asp Ser Val Ser Glu
1               5                   10                  15

Gly Asn Ala Gly Pro Tyr
            20

<210> SEQ ID NO 596
<211> LENGTH: 13
<212> TYPE: PRT
<213> ORGANISM: Homo sapiens

<400> SEQUENCE: 596

Gly Asn Gln Leu Phe Arg Ile Asn Glu Ala Asn Gln Leu
1               5                   10

<210> SEQ ID NO 597
<211> LENGTH: 15
<212> TYPE: PRT
<213> ORGANISM: Homo sapiens

<400> SEQUENCE: 597

Gly Asn Gln Leu Phe Arg Ile Asn Glu Ala Asn Gln Leu Met Gln
1               5                   10                  15

<210> SEQ ID NO 598
<211> LENGTH: 14
<212> TYPE: PRT
<213> ORGANISM: Homo sapiens

<400> SEQUENCE: 598

Ser Pro Ala Met Ala Gly Gly Leu Phe Ala Ile Glu Arg Glu
1               5                   10

<210> SEQ ID NO 599
<211> LENGTH: 15
<212> TYPE: PRT
<213> ORGANISM: Homo sapiens

<400> SEQUENCE: 599

Phe Ile Gly Asn Ile Ala Val Asn His Ala Pro Val Ser Pro Arg
1               5                   10                  15

<210> SEQ ID NO 600
<211> LENGTH: 17
<212> TYPE: PRT
<213> ORGANISM: Homo sapiens

<400> SEQUENCE: 600

Phe Ile Gly Asn Ile Ala Val Asn His Ala Pro Val Ser Pro Arg Pro
1               5                   10                  15
```

Gly

<210> SEQ ID NO 601
<211> LENGTH: 15
<212> TYPE: PRT
<213> ORGANISM: Homo sapiens

<400> SEQUENCE: 601

Ile Gly Asn Ile Ala Val Asn His Ala Pro Val Ser Pro Arg Pro
1               5                   10                  15

<210> SEQ ID NO 602
<211> LENGTH: 16
<212> TYPE: PRT
<213> ORGANISM: Homo sapiens

<400> SEQUENCE: 602

Ile Gly Asn Ile Ala Val Asn His Ala Pro Val Ser Pro Arg Pro Gly
1               5                   10                  15

<210> SEQ ID NO 603
<211> LENGTH: 15
<212> TYPE: PRT
<213> ORGANISM: Homo sapiens

<400> SEQUENCE: 603

Phe Glu Gly Gln Phe Ser Ile Asn Lys Val Pro Gly Asn Phe His
1               5                   10                  15

<210> SEQ ID NO 604
<211> LENGTH: 17
<212> TYPE: PRT
<213> ORGANISM: Homo sapiens

<400> SEQUENCE: 604

Phe Glu Gly Gln Phe Ser Ile Asn Lys Val Pro Gly Asn Phe His Val
1               5                   10                  15

Ser

<210> SEQ ID NO 605
<211> LENGTH: 16
<212> TYPE: PRT
<213> ORGANISM: Homo sapiens

<400> SEQUENCE: 605

Arg Phe Glu Gly Gln Phe Ser Ile Asn Lys Val Pro Gly Asn Phe His
1               5                   10                  15

<210> SEQ ID NO 606
<211> LENGTH: 10
<212> TYPE: PRT
<213> ORGANISM: Homo sapiens

<400> SEQUENCE: 606

Glu Leu Ala Gly Ile Gly Ile Leu Thr Val
1               5                   10

<210> SEQ ID NO 607
<211> LENGTH: 9
<212> TYPE: PRT
<213> ORGANISM: Homo sapiens

<400> SEQUENCE: 607

Tyr Leu Leu Pro Ala Ile Val His Ile

```
<210> SEQ ID NO 608
<211> LENGTH: 10
<212> TYPE: PRT
<213> ORGANISM: Homo sapiens

<400> SEQUENCE: 608

Ser Tyr Asn Pro Ala Thr Ala Lys Glu Ile
1               5                   10

<210> SEQ ID NO 609
<211> LENGTH: 11
<212> TYPE: PRT
<213> ORGANISM: Homo sapiens

<400> SEQUENCE: 609

Ser Tyr Asn Pro Ala Thr Ala Lys Glu Ile Ile
1               5                   10

<210> SEQ ID NO 610
<211> LENGTH: 10
<212> TYPE: PRT
<213> ORGANISM: Homo sapiens

<400> SEQUENCE: 610

Ile Leu Ser Lys Leu Thr Asp Ile Gln Tyr
1               5                   10

<210> SEQ ID NO 611
<211> LENGTH: 9
<212> TYPE: PRT
<213> ORGANISM: Homo sapiens

<400> SEQUENCE: 611

Leu Ser Lys Leu Thr Asp Ile Gln Tyr
1               5

<210> SEQ ID NO 612
<211> LENGTH: 13
<212> TYPE: PRT
<213> ORGANISM: Homo sapiens

<400> SEQUENCE: 612

Ser Val Ser Tyr Asn Pro Ala Thr Ala Lys Glu Ile Ile
1               5                   10

<210> SEQ ID NO 613
<211> LENGTH: 14
<212> TYPE: PRT
<213> ORGANISM: Homo sapiens

<400> SEQUENCE: 613

Ile Leu Ser Lys Leu Thr Asp Ile Gln Tyr Gly Arg Glu Glu
1               5                   10

<210> SEQ ID NO 614
<211> LENGTH: 16
<212> TYPE: PRT
<213> ORGANISM: Homo sapiens

<400> SEQUENCE: 614

Tyr Val Gly Glu Ile Ile Gly Lys Arg Gly Ile Ile Gly Tyr Asp Val
1               5                   10                  15
```

IMMUNOTHERAPY AGAINST SEVERAL TUMORS OF THE BLOOD, SUCH AS ACUTE MYELOID LEUKEMIA (AML)

CROSS REFERENCE TO RELATED APPLICATIONS

This application is continuation of U.S. patent application Ser. No. 14/707,230, filed 8 May 2015, which claims priority to U.S. Provisional Application No. 61/990,980, filed 9 May 2014 and British Patent Application No. 1408255.6, filed 9 May 2014. The contents of each of the aforementioned applications are incorporated herein by reference in their entireties.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-033002_ST25.txt" created on 6 Jul. 2018, and 101,542 bytes in size) is submitted concurrently with the instant application, and the entire contents of the Sequence Listing are incorporated herein by reference.

BACKGROUND

Field of the Invention

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to several novel peptide sequences and their variants derived from HLA class I and HLA class II molecules of human tumor cells that can be used in vaccine compositions for eliciting anti-tumor immune responses.

Description of Related Art

Acute myeloid leukemia (AML), also known as acute myelogenous leukemia or acute nonlymphocytic leukemia (ANLL), is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for approximately 1.2% of cancer deaths in the United States, its incidence is expected to increase as the population ages.

The symptoms of AML are caused by replacement of normal bone marrow with leukemic cells, which causes a drop in red blood cells, platelets, and normal white blood cells. These symptoms include fatigue, shortness of breath, easy bruising and bleeding, and increased risk of infection. Several risk factors and chromosomal abnormalities have been identified, but the specific cause is not clear. As an acute leukemia, AML progresses rapidly and is typically fatal within weeks or months if left untreated.

AML has several subtypes; treatment and prognosis varies among subtypes. Five-year survival varies from 15-70%, and relapse rate varies from 33-78%, depending on the subtype. AML is treated initially with chemotherapy aimed at inducing a remission; patients may go on to receive additional chemotherapy or a hematopoietic stem cell transplant.

US 2005/0261190 A1 discloses polypeptide fragments of Fas associated Factor 1, which bind to Hsc70/Hsp70, ubiquinated protein or valosin containing protein. Some of the fragments include SEQ ID NO: 5 as disclosed herein.

Similarly, KR100692416 discloses a fragment of FAF-1 (Fas-associated Factor 1) as having inhibitory effects on angiogenesis and cell proliferation. Therefore, it is proposed as an anticancer agent, e.g. a tumor metastasis inhibitory agent. The fraction having inhibitory effect on tumor metastasis is composed of 290-345 amino acids of FAF1.

Hassan et al. (The human leukocyte antigen-presented ligandome of B lymphocytes. Mol Cell Proteomics. 2013 July; 12(7):1829-43) disclose the identification and relative quantification of 14,500 peptide ligands constituting the HLA ligandome of B cells as a starting point for solving a wealth of specific immunological questions.

Kowalewski et al. (Mapping The HLA Ligandome Of Chronic Lymphocytic Leukemia—Towards Peptide Based Immunotherapy Blood 2013; 122(21):4123) describe a method to analyse the HLA class I peptidomes of 25 CLL patients and 35 healthy controls.

Despite the above, there remains a need for new efficacious and safe treatment option for cancers such as blood cancer, in particular acute myeloid leukemia (AML) and other cancers of the blood of different phenotypes which improve the well-being of the patients by not using excessive chemotherapeutic agents or other agents that may lead to severe side effects.

The present invention employs peptides that stimulate the immune system of the patient and act as anti-tumor-agents in a non-invasive fashion.

SUMMARY

In a first aspect of the present invention, the present invention relates to a peptide comprising an amino acid sequence selected from the group of SEQ ID NO: 1 to SEQ ID NO: 325, SEQ ID NO: 326 to SEQ ID NO: 447 or SEQ ID NO: 448 to SEQ ID NO: 605 or a variant sequence thereof which is at least 80%, preferably at least 90%, homologous (preferably at least 80% or at least 90% identical) to SEQ ID NO: 1 to SEQ ID NO: 325 or SEQ ID NO: 448 to SEQ ID NO: 605, wherein said variant induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group SEQ ID NO: 1 to SEQ ID NO: 325, SEQ ID NO: 326 to SEQ ID NO: 447 or SEQ ID NO: 448 to SEQ ID NO: 605 or a variant thereof, which is at least 80%, preferably at least 90%, homologous (preferably at least 80% or at least 90% identical) to SEQ ID NO: 1 to SEQ ID NO: 325 or SEQ ID NO: 448 to SEQ ID NO: 605, wherein said peptide or variant thereof has an overall length for SEQ ID NO: 1 to SEQ ID NO: 325 of between 8 and 100, preferably between 8 and 30, and most preferred of between 8 and 14 amino acids, and for SEQ ID NO: SEQ ID NO: 448 to SEQ ID NO: 605 of between 12 and 100, preferably between 12 and 30, and most preferred of between 12 to 18 amino acids.

DETAILED DESCRIPTION OF A PREFERRED EMBODIMENT

The following tables show the peptides according to the present invention, their respective SEQ ID NO, and the prospective source protein(s) for these peptides. All peptides in Table 1 bind to HLA A HLA B or HLA C alleles, peptides in Table 2 were identified as derived from AML-related antigens, and the peptides in Table 3 bind to HLA-DR (MHC class II) alleles. The class II peptides in Table 3 are further useful in the diagnosis and/or treatment of AML, Chronic lymphatic leukemia (CLL) and other hematological malignancies, which involve an over-expression or over-presentation of the respective underlying polypeptide.

Thus, the present invention relates in particular to a peptide of the present invention comprising a sequence according to SEQ ID NO: 448 to SEQ ID NO: 605 or a variant thereof, which is at least 80%, preferably at least 90%, homologous (preferably at least 80% or at least 90% identical) to SEQ ID NO: 448 to SEQ ID NO: 605, wherein said peptide or variant thereof has an overall length of between 12 and 100, preferably between 12 and 30, and most preferred of between 12 to 18 amino acids. The present invention relates in particular to a peptide of the present invention consisting of the sequence according to SEQ ID NO: 448 to SEQ ID NO: 605.

TABLE 1

Peptides according to the present invention, underlying polypeptides in bold

| SEQ ID | Protein/Peptides | Number of positive AMLs [rep. frequency] | HLA |
|---|---|---|---|
| | FAF1 Fas (TNFRSF6) associated factor 1 | 8 [53.3%] | |
| 1 | AEQFRLEQI | 1 | B*44 |
| 2 | FTAEFSSRY | 2 | A*03 |
| 3 | HHDESVLTNVF | 3 | B*38:01 |
| 4 | REQDEAYRL | 1 | B*44:25 |
| 5 | RPVMPSRQI | 1 | B*07 |
| 6 | VQREYNLNF | 1 | B*15 |
| | PLXND1 plexin D1 | 7 [46.7%] | |
| 7 | GQLPITIQV | 1 | B*13:02 |
| 8 | RAYADEVAV | 1 | B*51:01 |
| 9 | REDKPPLAV | 1 | B*49:01 |
| 10 | RVKDLDTEKY | 2 | B*15 |
| 11 | SEQEMNAHL | 1 | B*44:25 |
| 12 | YVLPLVHSL | 1 | A*02 |
| 13 | LPLRFWVNI | 1 | B*51:01 |
| | GMNN geminin, DNA replication inhibitor | 6 [40.0%] | |
| 14 | EVAEHVQYM | 3 | A*26:01 |
| 15 | YMAELIERL | 3 | A*02 |
| | CPQ carboxypeptidase Q | 6 [40.0%] | |
| 16 | ALASLIRSV | 5 | A*02 |
| 17 | TVAEITGSKY | 1 | A*26:01 |
| | ATP5L ATP synthase, H+ transporting, mitochondrial Fo complex, subunit G | 5 [33.3%] | |
| 18 | EIIGKRGIIGY | 4 | A*26, A*03:01 |
| 19 | NLVEKTPAL | 1 | A*02 |
| | ITGA5 integrin, alpha 5 | 5 [33.3%] | |

TABLE 1-continued

Peptides according to the present invention, underlying polypeptides in bold

| SEQ ID | Protein/Peptides | Number of positive AMLs [rep. frequency] | HLA |
|---|---|---|---|
| 20 | IEDKAQILL | 3 | B*49:01/B*40 |
| 21 | SIYDDSYLGY | 1 | A*26:01 |
| 22 | TTNHPINPK |  | A*11 |
|  | SKP1 S-phase kinase-associated protein 1 | 5 [33.3%] |  |
| 23 | NAAILKKV | 2 | B*51:01 |
| 24 | NYLDIKGLL | 1 | A*24 |
| 25 | YLDIKGLLDV | 2 | A*02 |
|  | CHD1L chromodomain helicase DNA binding protein 1-like | 5 [33.3%] |  |
| 26 | EEVGDFIQRY | 1 | B*44:03 |
| 27 | EVGDFIQRY | 4 | A*26:01, A*03 |
| 28 | MKDLSLGGVL | 1 | n.a. |
|  | TGFBRAP1 transforming growth factor, beta receptor associated protein 1 | 5 [33.3%] |  |
| 29 | DEFITVHSM | 1 | B*18:01 |
| 30 | EFITVHSML | 2 | A*23:01 |
| 31 | GQLDVRELI | 1 | B*13:02 |
| 32 | TQYIIHNY | 1 | B*15 |
|  | NGLY1 N-glycanase 1 | 5 [33.3%] |  |
| 33 | EVVDVTWRY | 4 | A*26, A*03:01 |
| 34 | KEALLRDTI | 1 | B*49:01 |
|  | APLP2 amyloid beta (A4) precursor-like protein 2 | 5 [33.3%] |  |
| 35 | HGYENPTYK | 4 | A*03 |
| 36 | SLLYKVPYV | 1 | A*02 |
|  | KIF2C kinesin family member 2C | 5 [33.3%] |  |
| 37 | AEIPLRMV | 1 | B*49:01 |
| 38 | EVVYRFTAR | 1 | A*66 |
| 39 | FPGLAIKI | 2 | B*51:01 |
| 40 | IYNGKLFDL | 1 | A*24 |
| 41 | IYNGKLFDLL | 1 | A*24 |
| 42 | KEIDVISI | 1 | B*49:01 |
| 43 | LEEQASRQI | 1 | B*49:01 |
| 44 | TRMSTVSEL | 1 | B*39:01 |
|  | ELP3 elongator acetyltransferase complex subunit 3 | 5 [33.3%] |  |
| 45 | SEETFRFEL | 1 | B*40 |

TABLE 1-continued

Peptides according to the present invention, underlying polypeptides in bold

| SEQ ID | Protein/Peptides | Number of positive AMLs [rep. frequency] | HLA |
|---|---|---|---|
| 46 | KLYPTLVIR | 4 | A*03 |
| | DGKZ diacylglycerol kinase, zeta | 5 [33.3%] | |
| 47 | ALRNQATMVQK | 23 | A*03:01 |
| 48 | LLDHAPPEI | 3 | A*02 |
| | MTCH2 mitochondrial carrier 2 | 5 [33.3%] | |
| 49 | GVLGTVVHGK | 4 | A*03:01 |
| 50 | VQFIGRESKY | 1 | B*15 |
| | SLC31A2 solute carrier family 31 (copper transporter), member 2 | 4 [26.7%] | |
| 51 | GQSLIHVI | 1 | B*52:15 |
| 52 | VHSPAGMAL | 1 | B*38:01 |
| 53 | VLYEGIKVGK | 4 | A*03 |
| | ERLIN1 ER lipid raft associated 1 | 4 [26.7%] | |
| 54 | AVIEAEKIAQV | 2 | A*02 |
| 55 | DRIEVVNML | 1 | B*39:01 |
| 56 | IEAEKIAQV | 1 | B*49:01 |
| | SERPINB2 serpin peptidase inhibitor, clade B (ovalbumin), member 2 | 4 [26.7%] | |
| 57 | IEDLKAQIL | 1 | B*49:01 |
| 58 | YLLESVNKL | 3 | A*02 |
| | ABHD2 abhydrolase domain containing 2 | 4 [26.7%] | |
| 59 | HRIYVPLML | 1 | B*39:01 |
| 60 | KEYIPPLIW | 1 | B*4403 |
| 61 | MDKLVVEY | 2 | B*15 |
| | GAA glucosidase, alpha; acid | 4 [26.7%] | |
| 62 | ALLGHILLH | 1 | A*03:01 |
| 63 | ALLPHLYTL | 2 | A*02 |
| 64 | HVAGETVAR | 1 | A*66 |
| 65 | KVWPGSTAF | 1 | A*32 |
| | OPRL1 opiate receptor like 1 | 4 [26.7%] | |
| 66 | ETAVAILRF | 4 | A*26, A*03:01 |
| | WDR45B WD repeat domain 45B | 4 [26.7%] | |
| 67 | RVYNTDPLKEK | 4 | A*03 |
| | TUFM Tu translation elongation factor, mitochondrial | 4 [26.7%] | |
| 68 | IGVEHVVVY | 4 | C*12:03 |

TABLE 1-continued

Peptides according to the present invention, underlying polypeptides in bold

| SEQ ID | Protein/Peptides | Number of positive AMLs [rep. frequency] | HLA |
|---|---|---|---|
| 69 | RQIGVEHVV | 1 | B*15 |
| | MFAP1 microfibrillar-associated protein 1 | 4 [26.7%] | |
| 70 | DVFERPSAKK | 1 | A*66 |
| 71 | EEFQFIKKA | 2 | B*40:02, B*50 |
| 72 | THLVDQDTTSF | 1 | B*38 |
| | ZNF543 zinc finger protein 543 | 4 [26.7%] | |
| 73 | ESADLIQHY | 4 | A*26, A*03:01 |
| | STK4 serine/threonine kinase 4 | 4 [26.7%] | |
| 74 | EIIKEISIM | 3 | A*26 |
| 75 | SVSDIIRLR | 1 | A*66 |
| | ZKSCAN8 zinc finger with KRAB and SCAN domains 8 | 4 [26.7%] | |
| 76 | AVSLIREEW | 2 | A*32 |
| 77 | GEKSESISV | 1 | B*49:01 |
| 78 | FLTILPEEL | 1 | A*02:01 |
| | FNDC3B fibronectin type III domain containing 3B | 4 [26.7%] | |
| 79 | ILWETVPSM | 1 | A*02:01 |
| 80 | LPVRTLSI | 1 | B*51:01 |
| 81 | RESEYKQVY | 1 | B*44:03 |
| 82 | SESLPVRTL | 1 | B*40 |
| | TMEM164 transmembrane protein 164 | 4 [26.7%] | |
| 83 | RLLESVVVL | 1 | A*02:01 |
| 84 | RPEEGKESL | 1 | B*07 |
| 85 | THGKLVILF | 2 | B*38 |
| | THOC7 THO complex 7 homolog | 4 [26.7%] | |
| 86 | KELEHLSHI | 1 | B*49:01 |
| 87 | REMENYEKI | 2 | B*49:01 B*44:25 |
| 88 | VLLSTIHEL | 2 | A*02 |
| | KLF2 Kruppel-like factor 2 | 4 [26.7%] | |
| 89 | KTYTKSSHLK | 4 | A*03 |
| | TMEM126B transmembrane protein 126B | 4 [26.7%] | |
| 90 | EIIEKNFDY | 3 | A*26 |
| 91 | GTEEAPKVFK | 1 | A*11 |

TABLE 1-continued

Peptides according to the present invention, underlying polypeptides in bold

| SEQ ID | Protein/Peptides | Number of positive AMLs [rep. frequency] | HLA |
|---|---|---|---|
| 92 | KLMAIPLVF | 1 | B*15 |
| | UFD1L ubiquitin fusion degradation 1 like | 4 [26.7%] | |
| 93 | DIKRGIPN | 1 | Fragment of Seq 94 |
| 94 | DIKRGIPNY | 1 | A*26 |
| 95 | FLDITNPKA | 2 | A*02 |
| | MUL1 mitochondrial E3 ubiquitin protein ligase 1 | 4 [26.7%] | |
| 96 | ALYSVYRQK | 2 | A*03 |
| 97 | KVLALVFGF | 1 | B*15 |
| 98 | SFTDVIGHY | 1 | A*29 |
| | VCPIP1 valosin containing protein (p97)/p47 complex interacting protein 1 | 4 [26.7%] | |
| 99 | ASAAASGGLLK | 3 | A*03:01 |
| 100 | ALLGVTGAPK | 1 | A*03 |
| | FAM46A family with sequence similarity 46, member A | 4 [26.7%] | |
| 101 | DEIKTLQRY | 1 | B*18:01 |
| 102 | EAYVQKMV | 1 | B*51:01 |
| 103 | VLHQDSGLGY | 1 | B*15 |
| 104 | YLQNHFVGL | 1 | A*02 |
| | KIF20B kinesin family member 20B | 4 [26.7%] | |
| 105 | AEIEDIRVL | 1 | B*44:25 |
| 106 | GQSRLIFTY | 1 | B*15 |
| 107 | READFKETL | 2 | B*49:01, B*40 |
| | CSF3R colony stimulating factor 3 receptor (granulocyte) | 4 [26.7%] | |
| 108 | DTMGPSQHVY | 1 | A*26 |
| 109 | ESRGPALTR | 1 | A*66 |
| 110 | FQLPGLGTPPIT | 1 | C*12:03 |
| 111 | RIQGYVVSW | 1 | A*32 |
| | NOC4L nucleolar complex associated 4 homolog | 4 [26.7%] | |
| 112 | LLDPSVFHV | 3 | A*02 |
| 113 | RFFHLADLF | 1 | A*23:01 |
| | EMILIN2 elastin microfibril interfacer 2 | 4 [26.7%] | |
| 114 | DSISGNLQR | 1 | A*66 |
| 115 | ETEQTIQKL | 1 | n.a. |
| 116 | FLYPFLSHL | 1 | A*02 |

TABLE 1-continued

Peptides according to the present invention, underlying polypeptides in bold

| SEQ ID | Protein/Peptides | Number of positive AMLs [rep. frequency] | HLA |
|---|---|---|---|
| 117 | TLDQKIERV | 3 | A*02:01 |
| | SHANK3 SH3 and multiple ankyrin repeat domains 3 | 4 [26.7%] | |
| 118 | DADSRAATV | 1 | B*51:01 |
| 119 | DHEGFGFVL | 1 | B*38:01 |
| 120 | GEAVKVLSI | 1 | B*49:01 |
| 121 | NATDLLKVL | 2 | C*12:03 |
| | UCK2 uridine-cytidine kinase 2 | 4 [26.7%] | |
| 122 | KEITEGKTV | 1 | B*40:02 |
| 123 | YRQKQVVIL | 2 | C*07 |
| 124 | VAINLIVQH | 1 | A*03:01 |
| | PHPT1 phosphohistidine phosphatase 1 | 4 [26.7%] | |
| 125 | SQDKKIHVY | 1 | B*15 |
| 126 | YHADIYDKV | 3 | B*38, B*39:01 |
| | KIF15 kinesin family member 15 | 4 [26.7%] | |
| 127 | DAIKVFVRI | 1 | B*51:01 |
| 128 | LEKAFSEI | 1 | B*49:01 |
| 129 | MEKSDKNQ | 1 | n.a. |
| 130 | GQTGSGKTF | 1 | B*15 |
| | SLC12A6 solute carrier family 12 (potassium/chloride transporter), member 6 | 4 [26.7%] | |
| 131 | DTSPDLSSR | 1 | A*66 |
| 132 | KLNEVIVNK | 3 | A*03 |
| | DOLK dolichol kinase | 4 [26.7%] | |
| 133 | FAQIISVALI | 1 | A*02 |
| 134 | IIFDRPLLY | 3 | A*03:01, A*29 |
| | EEF2K eukaryotic elongation factor-2 kinase | 3 [20.0%] | |
| 135 | DAVNQNTKLL | 1 | A*02 |
| 136 | HHILADVSL | 1 | B*38:01 |
| 137 | YPSEKRGEL | 1 | B*07 |
| | PIK3R2 phosphoinositide-3-kinase, regulatory subunit 2 (beta) | 3 [20.0%] | |
| 138 | SVVDLINHY | 3 | A*26 |
| | TMEM194A transmembrane protein 194A | 3 [20.0%] | |
| 139 | EIIEKDTKY | 2 | A*26 |

TABLE 1-continued

Peptides according to the present invention, underlying polypeptides in bold

| SEQ ID | Protein/Peptides | Number of positive AMLs [rep. frequency] | HLA |
|---|---|---|---|
| 140 | ENEEKLKEL | 1 | n.a. |
| | CCS copper chaperone for superoxide dismutase | 3 [20.0%] | |
| 141 | ILGGPGTVQGV | 3 | A*02 |
| | ZNF264 zinc finger protein 264 | 3 [20.0%] | |
| 142 | ESAALIHHY | 2 | A*26 |
| 143 | YQRETPQV | 1 | B*52:15 |
| | LYRM1 LYR motif containing 1 | 3 [20.0%] | |
| 144 | ARIEIGLHY | 1 | B*27:05 |
| 145 | IPYPRPIHL | 2 | B*07, B*51:01 |
| | NBN nibrin | 3 [20.0%] | |
| 146 | DVSGKTALNQ | 1 | n.a. |
| 147 | TEFRSLVI | 1 | B*49:01 |
| 148 | TLKSGDGITF | 1 | B*15 |
| | TIPRL TIP41, TOR signaling pathway regulator-like | 3 [20.0%] | |
| 149 | HEADKTYML | 1 | B*40 |
| 150 | KFFEEVLLF | 1 | A*23:01 |
| 151 | RVMPSSFFL | 1 | A*02:01 |
| | RPS6KA4 ribosomal protein S6 kinase, 90 kDa, polypeptide 4 | 3 [20.0%] | |
| 152 | YELDLREPAL | 2 | B*40 |
| 153 | GAYGKVFLV | 1 | A*02:01 |
| | RCBTB2 regulator of chromosome condensation (RCC1) and BTB (POZ) domain containing protein 2 | 3 [20.0%] | |
| 154 | DHDLLKNF | 2 | B*38 |
| 155 | EELQLIRQA | 1 | B*44 |
| | PAK4 p21 protein (Cdc42/Rac)-activated kinase 4 | 3 [20.0%] | |
| 156 | AAELLKHPF | 2 | A*32 |
| 157 | GRVKLSDFGF | 1 | B*27:01 |
| | ERCC1 excision repair cross-complementing rodent repair deficiency, complementation group 1 (includes overlapping antisense sequence) | 3 [20.0%] | |
| 158 | KSNSIIVSPR | 3 | A*03 |
| | DMD dystrophin | 3 [20.0%] | |
| 159 | ETLERLQEL | 1 | A*02:01 |
| 160 | KDDELSRQ | 1 | n.a. |
| 161 | LQQTNSEKI | 1 | B*13:02 |
| | UNG uracil-DNA glycosylase | 3 [20.0%] | |

TABLE 1-continued

Peptides according to the present invention, underlying polypeptides in bold

| SEQ ID | Protein/Peptides | Number of positive AMLs [rep. frequency] | HLA |
|---|---|---|---|
| 162 | GEFGKPYFI | 1 | B*49:01 |
| 163 | KDVKVVIL | 1 | B*40:02 |
| 164 | RPVPPPPSL | 1 | B*07 |
|  | CPA3 carboxypeptidase A3 | 3 [20.0%] |  |
| 165 | KEDIPGRHSY | 1 | B*44:02 |
| 166 | KETKAVTNF | 1 | B*44:03 |
| 167 | YEILIHDL | 3 | B*44:02, B*44:03, B*18:01 |
|  | AZU1 azurocidin 1 | 3 [20.0%] |  |
| 168 | FPRFVNVTV | 1 | B*51:01 |
| 169 | QVAGWGSQR | 1 | A*66 |
| 170 | WIDGVLNNPGPG | 1 | n.a. |
|  | ATP2B4 ATPase, Ca++ transporting, plasma membrane 4 | 3 [20.0%] |  |
| 171 | SFMTHPEF | 1 | A*29 |
| 172 | HYTIVFNTF | 1 | A*23:01 |
| 173 | GTNDGPALKK | 1 | A*11 |
| 174 | IEDPVRPEV | 1 | B*49:01 |
|  | MARK3 MAP/microtubule affinity-regulating kinase 3 | 3 [20.0%] |  |
| 175 | NTASGGMTR | 1 | A*66 |
| 176 | EVIETEKTLY | 1 | A*26:01 |
| 177 | MKILNHPNI | 1 | B*15 |
|  | HLA-DMA major histocompatibility complex, class II, DM alpha | 3 [20.0%] |  |
| 178 | HEIDRYTAI | 1 | B*49:01 |
| 179 | VFTLKPLEF | 1 | A*24 |
| 180 | YWVPRNAL | 1 | C*05 |
|  | NDUFS1 NADH dehydrogenase (ubiquinone) Fe-S protein 1, 75 kDa | 3 [20.0%] |  |
| 181 | EVSPNLVRY | 2 | A*26 |
| 182 | LSEIAGMTLP | 1 | n.a. |
|  | S100A11 S100 calcium binding protein A11 | 3 [20.0%] |  |
| 183 | FLSFMNTEL | 1 | A*02:01 |
| 184 | KAVPSQKRT | 1 | n.a. |
| 185 | LKAVPSQKRT | 1 | n.a. |

TABLE 1-continued

Peptides according to the present invention, underlying polypeptides in bold

| SEQ ID | Protein/Peptides | Number of positive AMLs [rep. frequency] | HLA |
|---|---|---|---|
| 186 | SLIAVFQKY | 1 | B*15 |
| | HAL histidine ammonia-lyase | 3 [20.0%] | |
| 187 | IIKEKTVVY | 1 | B*15 |
| 188 | LLEQKVWEV | 1 | A*02 |
| 189 | SEIAESHRF | 2 | B*44:25 |
| 190 | YLAIGIHEL | 1 | A*02 |
| | PRIM1 primase, DNA, polypeptide 1 (49 kDa) | 3 [20.0%] | |
| 191 | IHDELQQSF | 3 | B*38 |
| | RENBP renin binding protein | 3 [20.0%] | |
| 192 | AHVIDKFLL | 2 | B*38 |
| 193 | KAGGEFLLRY | 1 | A*32 |
| | CCNG1 cyclin G1 | 3 [20.0%] | |
| 194 | FEVKDLLSL | 1 | B*49:01 |
| 195 | FSKAKPSVL | 2 | A*02, B*51 |
| | ZNF131 zinc finger protein 131 | 3 [20.0%] | |
| 196 | EAIKALEV | 1 | A*02:01 |
| 197 | EVASAKQSVKY | 1 | A*26 |
| 198 | IEFTYTAKL | 1 | B*49:01 |
| 199 | LLADITSKY | 1 | B*15 |
| | HRSP12 heat-responsive protein 12 | 3 [20.0%] | |
| 200 | VLVDRTIYI | 3 | A*02 |
| | EIF6 eukaryotic translation initiation factor 6 | 3 [20.0%] | |
| 201 | IPVVHASI | 1 | B*51:01 |
| 202 | TVADQVLVGSY | 1 | A*26:01 |
| 203 | VALVHPDL | 1 | n.a. |
| | TMPRSS3 transmembrane protease, serine 3 | 3 [20.0%] | |
| 204 | LPDDKVTAL | 3 | C*03, C*12:41 |
| | UBE2G2 ubiquitin-conjugating enzyme E2G 2 | 3 [20.0%] | |
| 205 | KIAKQIVQK | 1 | A*03 |
| 206 | VEKILLSVV | 2 | B*49:01 |
| | NOP14 NOP14 nucleolar protein | 3 [20.0%] | |
| 207 | APAGARGGPA | 1 | B*07 |
| 208 | EHLRKLEAE | 1 | n.a. |

TABLE 1-continued

Peptides according to the present invention, underlying polypeptides in bold

| SEQ ID | Protein/Peptides | Number of positive AMLs [rep. frequency] | HLA |
|---|---|---|---|
| 209 | RFIPELINF | 1 | A*23:01 |
|  | TFCP2 transcription factor CP2 | 3 [20.0%] |  |
| 210 | TEKIAQLF | 1 | B*18:01 |
| 211 | KLHDETLTY | 1 | A*03 |
| 212 | LHDETLTYL | 1 | B*38:01 |
|  | TARBP1 TAR (HIV-1) RNA binding protein 1 | 3 [20.0%] |  |
| 213 | GPQEGNGPSLF | 1 | B*35:01 |
| 214 | YLLQRAVEV | 2 | A*02 |
|  | TTLL12 tubulin tyrosine ligase-like family, member 12 | 3 [20.0%] |  |
| 215 | FAALHGPAL | 2 | A*02 |
| 216 | RMANLMGIEF | 1 | B*15 |
|  | HLX H2.0-like homeobox | 3 [20.0%] |  |
| 217 | DTFPGPYAVL | 2 | A*26 |
| 218 | DTMPQTYKR | 1 | A*66 |
|  | CBX2 chromobox homolog 2 | 3 [20.0%] |  |
| 219 | IEHVFVTDV | 2 | B*49:01 |
| 220 | KESPTSVGF | 1 | B*40 |
|  | ZNF638 zinc finger protein 638 | 3 [20.0%] |  |
| 221 | EAITAIMKY | 1 | A*26 |
| 222 | KEKPAENTL | 1 | B*44:03 |
| 223 | NEFQSQQNI | 1 | B*49:01 |
| 224 | NVIDYGHASKY | 1 | A*32 |
|  | C3AR1 complement component 3a receptor 1 | 3 [20.0%] |  |
| 225 | FAKSQSKTF | 2 | A*03, A*32 |
| 226 | LPFSLAHL | 1 | B*51:01 |
|  | TAF9 TAF9 RNA polymerase II, TATA box binding protein (TBP)-associated factor | 3 [20.0%] |  |
| 227 | APNYRLKSL | 1 | B*07 |
| 228 | ILKDMGITEY | 2 | A*66, A*32 |
|  | FSCN1 fascin homolog 1, actin-bundling protein | 3 [20.0%] |  |
| 229 | AHDDGRWSL | 1 | B*38 |
| 230 | KYLTAEAFGF | 2 | A*23:01 |
|  | ZNF805 zinc finger protein 805 | 3 [20.0%] |  |
| 231 | ESAALIHHY | 2 | A*26 |

TABLE 1-continued

Peptides according to the present invention, underlying polypeptides in bold

| SEQ ID | Protein/Peptides | Number of positive AMLs [rep. frequency] | HLA |
|---|---|---|---|
| 232 | YQRETPQV | 1 | B*52:15 |
| | CLEC12A C-type lectin domain family 12, member A | 3 [20.0%] | |
| 233 | EELQRNISL | 1 | B*44:25 |
| 234 | RPAALFLTL | 1 | B*07 |
| 235 | SEELQRNISL | 1 | B*40 |
| | SLX4IP SLX4 interacting protein | 3 [20.0%] | |
| 236 | ETIDSRVQEY | 3 | A*26 |
| | RLTPR RGD motif, leucine rich repeats, tropomodulin domain and proline-rich containing | 3 [20.0%] | |
| 237 | EVSEQILHM | 3 | A*26 |
| | RNF19B ring finger protein 19B | 3 [20.0%] | |
| 238 | GTLSGGILSSGK | 1 | A*03 |
| 239 | GVPIMLAY | 2 | n.a. |
| | DDX46 DEAD (Asp-Glu-Ala-Asp) box polypeptide 46 | 3 [20.0%] | |
| 240 | EEVKEEVKKF | 2 | B*44:25, B*44:03 |
| 241 | KTIAFLLPMF | 1 | A*32 |
| | LRRC8D leucine rich repeat containing 8 family, member D | 3 [20.0%] | |
| 242 | EVTTNIPKM | 3 | A*26 |
| | C16orf62 chromosome 16 open reading frame 62 | 3 [20.0%] | |
| 243 | IHGDTVQNL | 2 | B*38:01 |
| 244 | RTMVKTLEY | 1 | A*03:01 |
| | GOLGA7 golgin A7 | 3 [20.0%] | |
| 245 | ETVRTLNNLY | 3 | A*26 |
| | RHOT1 ras homolog family member T1 | 3 [20.0%] | |
| 246 | HSIDKVTSR | 2 | A*66 |
| 247 | VSNPKSFEY | 1 | A*32 |
| | BBS1 Bardet-Biedl syndrome 1 | 3 [20.0%] | |
| 248 | GLGPTFKL | 1 | A*02:01 |
| 249 | NKGISDIIKV | 1 | n.a. |
| 250 | TSTTRPVL | 1 | A*32 |
| | CEP76 centrosomal protein 76 kDa | 3 [20.0%] | |
| 251 | VLGGKAFLEHL | 1 | A*02 |
| 252 | YEFERTTSI | 2 | B*49:01 |
| | GANC glucosidase, alpha; neutral C | 3 [20.0%] | |

TABLE 1-continued

Peptides according to the present invention, underlying polypeptides in bold

| SEQ ID | Protein/Peptides | Number of positive AMLs [rep. frequency] | HLA |
|---|---|---|---|
| 253 | YLDFTNPKV | 3 | A*02 |
| | ATP8B4 ATPase, class I, type 8B, member 4 | 3 [20.0%] | |
| 254 | IPAVARTTTL | 1 | B*07 |
| 255 | KQQLELDSI | 1 | B*15 |
| 256 | KTTDTVSSF | 1 | A*32 |
| | PPIL4 peptidylprolyl isomerase (cyclophilin)-like 4 | 3 [20.0%] | |
| 257 | DYLDGVHTVF | 2 | A*23:01 |
| 258 | YLDGVHTVF | 1 | B*15:01 |
| | HPT1 choline phosphotransferase 1 | 3 [20.0%] | |
| 259 | TYVSGMLRF | 1 | A*23:01 |
| 260 | DAIDGKQAR | 2 | A*66 |
| | CHTF18 CTF18, chromosome transmission fidelity factor 18 homolog | 3 [20.0%] | |
| 261 | DPMAPGVQGSLL | 1 | A*26:01 |
| 262 | GLDPSQRPK | 2 | A*03 |
| | DGCR8 DGCR8 microprocessor complex subunit | 3 [20.0%] | |
| 263 | IEDSRVYEL | 3 | B*49:01, B*40 |
| | ANKS1A ankyrin repeat and sterile alpha motif domain containing 1A | 3 [20.0%] | |
| 264 | YVHSFLSSGY | 3 | A*26, A*03:01 |
| | TOP1MT topoisomerase (DNA) I, mitochondrial | 3 [20.0%] | |
| 265 | HEYTTKEVF | 1 | B*18:01 |
| 266 | KLQEQLAQL | 1 | A*02:01 |
| 267 | SIAAKILSY | 1 | A*03:01 |
| | PHACTR3 phosphatase and actin regulator 3 | 3 [20.0%] | |
| 268 | KELLAVKL | 1 | B*49:01 |
| 269 | KLKQTTSALEK | 2 | A*03 |
| | CCDC115 coiled-coil domain containing 115 | 3 [20.0%] | |
| 270 | EVGPREAGLR | 2 | A*66 |
| 271 | SEAQEGLQKF | 1 | B*44:25 |
| | SORCS2 sortilin-related VPS10 domain containing receptor 2 | 3 [20.0%] | |
| 272 | DEAVLFVQV | 3 | B*18:01, B*40 |
| | ACCS 1-aminocyclopropane-1-carboxylate synthase homolog | 3 [20.0%] | |
| 273 | EVAKFLSFY | 2 | A*26 |

TABLE 1-continued

Peptides according to the present invention, underlying polypeptides in bold

| SEQ ID | Protein/Peptides | Number of positive AMLs [rep. frequency] | HLA |
|---|---|---|---|
| 274 | KLDQKLPEL | 1 | A*02:01 |
| 275 | SVFEKSVGY | 1 | A*26:01 |
|  | ACBD6 acyl-CoA binding domain containing 6 | 3 [20.0%] |  |
| 276 | NEGQTALHY | 1 | B*44:03 |
| 277 | VEFPHSPEI | 2 | B*49:01 |
|  | ORAI3 ORAI calcium release-activated calcium modulator 3 | 3 [20.0%] |  |
| 278 | RLQGELQAV | 3 | A*02 |
|  | SIKE1 suppressor of IKBKE 1 | 3 [20.0%] |  |
| 279 | KELRELLSI | 1 | B*49:01 |
| 280 | SLVDQSAAL | 1 | A*02:01 |
| 281 | LELIMSKY | 1 | B*18:01 |
|  | C9orf156 chromosome 9 open reading frame 156 | 3 [20.0%] |  |
| 282 | DIKPYIAEY | 3 | A*26 |
|  | EDEM2 ER degradation enhancer, mannosidase alpha-like 2 | 3 [20.0%] |  |
| 283 | KLMAMFLEY | 1 | A*03:01 |
| 284 | YTVEKREGY | 2 | A*26 |
|  | NUP85 nucleoporin 85 kDa | 3 [20.0%] |  |
| 285 | FEFDIHQVI | 2 | B*49:01 |
| 286 | SENPSKHDSF | 1 | B*44:25 |
|  | PANK2 pantothenate kinase 2 | 3 [20.0%] |  |
| 287 | NFLRINTI | 1 | C*02 |
| 288 | YSGPTSVSR | 1 | A*66 |
| 289 | DIYGGDYERF | 1 | A*26:01 |
|  | SPATC1L spermatogenesis and centriole associated 1-like | 3 [20.0%] |  |
| 290 | SARLEKLGY | 1 | B*15 |
| 291 | YVFPGVTRL | 1 | A*02 |
| 292 | YYLNEIQSF | 1 | A*23:01 |
|  | IKZF4 IKAROS family zinc finger 4 | 3 [20.0%] |  |
| 293 | YHSQDRYEF | 3 | B*39:01 |
|  | DHX33 DEAH (Asp-Glu-Ala-His) box polypeptide 33 | 3 [20.0%] |  |
| 294 | FPPGRQVVM | 2 | C*12:03 |
| 295 | ILDEAHERTI | 1 | A*02 |
|  | METTL7A methyltransferase like 7A | 3 [20.0%] |  |

TABLE 1-continued

Peptides according to the present invention, underlying polypeptides in bold

| SEQ ID | Protein/Peptides | Number of positive AMLs [rep. frequency] | HLA |
|---|---|---|---|
| 296 | VIYNEQMASK | 3 | A*03 |
| | QTRTD1 queuine tRNA-ribosyltransferase domain containing 1 | 3 [20.0%] | |
| 297 | EATSIKRVR | 2 | A*66 |
| 298 | LPEDKPRLI | 1 | B*51:01 |
| | TMBIM4 transmembrane BAX inhibitor motif containing 4 | 3 [20.0%] | |
| 299 | KYPLNLYLL | 2 | A*23:01, A*24 |
| 300 | VHESPALILLF | 1 | B*38 |
| | RAVER2 ribonucleoprotein, PTB-binding 2 | 3 [20.0%] | |
| 301 | EVTGHSKGY | 2 | A*26 |
| 302 | RDSEELLQI | 1 | B*40 |
| 303 | SPASKTTL | 1 | B*07 |
| | SDAD1 SDA1 domain containing 1 | 3 [20.0%] | |
| 304 | DAKTVNVI | 1 | B*51:01 |
| 305 | DSNATAAKM | 1 | n.a. |
| 306 | RTLNPQMLQK | 1 | A*03 |
| 307 | RTLNPQMLQKK | 1 | A*03 |
| | UCKL1 uridine-cytidine kinase 1-like 1 | 3 [20.0%] | |
| 308 | LMAEMGVHSV | 1 | A*02 |
| 309 | RLLPPVGTGR | 1 | A*03 |
| 310 | VRIGTILIQTNQ | 1 | n.a. |
| | STMN3 stathmin-like 3 | 3 [20.0%] | |
| 311 | KELSVLSLI | 1 | B*49:01 |
| 312 | TQPHPNTVY | 2 | B*15 |
| | CHIC2 cysteine-rich hydrophobic domain 2 | 3 [20.0%] | |
| 313 | ALEEQLLKY | 3 | A*26:01, A*03:01 |
| | ODF2L outer dense fiber of sperm tails 2-like | 3 [20.0%] | |
| 314 | DHFTGAIEKL | 2 | B*38 |
| 315 | KILDLETEL | 1 | A*02:01 |
| | PRR12 proline rich 12 | 3 [20.0%] | |
| 316 | AEDIPSLKL | 2 | B*40, B*44:25 |
| 317 | DIPSLKLAL | 1 | A*26 |
| 318 | GLDPNKPPEL | 1 | A*02 |
| | FARSA phenylalanyl-tRNA synthetase, alpha subunit | 3 [20.0%] | |

TABLE 1-continued

Peptides according to the present invention, underlying polypeptides in bold

| SEQ ID | Protein/Peptides | Number of positive AMLs [rep. frequency] | HLA |
|---|---|---|---|
| 319 | FLRDPAEAL | 1 | A*02 |
| 320 | GYGSQGYKY | 1 | A*29 |
| 321 | KLLAEVTLK | 1 | A*03:01 |
| 322 | SAADGPRVF | 1 | A*32 |
| | CTDP1 CTD (carboxy-terminal domain, RNA polymerase II, polypeptide A) phosphatase, subunit 1 | 3 [20.0%] | |
| 323 | KLYELHVFTF | 1 | B*15 |
| 324 | YELHVFTF | 1 | B*18:01 |
| 325 | YLNKEIEEA | 1 | A*02 |

The table shows HLA class I ligandome-derived tumor associated antigens (LiTAAs) with representation frequencies ≥20% in AML patients (n = 15) and representing HLA ligands (LiTAPs) annotated with respective HLA restriction. Abbreviations: rep., representation; n.a., not assigned

TABLE 2

Additional peptides according to the present invention related to underlying antigens described as related with AML

| SEQ ID NO | Proteins, Peptides | Number of positive healthy donors (PBMC/BMNC) [rep. frequency %] | Number of positive AMLs [rep. frequency %] | HLA |
|---|---|---|---|---|
| | NPM1 nucleophosmin | 17 [56.7]/1 [20.0] | 9 [60.0] | |
| 326 | DENEHQLSL | 1/0 | 3 | B*18, B*40, B*44, B*44:25 |
| 327 | EITPPVVLR | 5/1 | 0 | A*68, A*28, A*32 |
| 328 | GFEITPPVVLR | 4/1 | 0 | A*68, A*28 |
| 329 | HQLSLRTV | 2/0 | 0 | B*13, B*52 |
| 330 | MSVQPTVSL | 0/0 | 1 | C*03 |
| 331 | SIRDTPAKN | 0/0 | 1 | n.a. |
| 332 | SIRDTPAKNAQK | 1/0 | 1 | A*11 |
| 333 | SPIKVTLATL | 3/0 | 0 | B*07 |
| 334 | TPPVVLRL | 6/0 | 2 | B*51 |
| 335 | VEAKFINY | 0/0 | 1 | B*18:01 |
| 336 | YEGSPIKV | 0/0 | 1 | B*49:01 |
| 337 | YEGSPIKVTL | 3/0 | 3 | B*40:01 |
| | FLT3, fms-related tyrosine kinase 3 | 0 [0.0]/0 0.0 | 1 [6.7] | |

TABLE 2-continued

Additional peptides according to the present invention related to underlying antigens described as related with AML

| SEQ ID NO | Proteins, Peptides | Number of positive healthy donors (PBMC/BMNC) [rep. frequency %] | Number of positive AMLs [rep. frequency %] | HLA |
|---|---|---|---|---|
| 338 | SELKMMTQL | 0/0 | 1 | B*40 |
| | PRAM1 PML-RARA regulated adaptor molecule 1 | 4 [13.3]/1 [20.0] | 3 [20.0] | |
| 339 | EKDPQPQQL | 1/0 | 0 | n.a. |
| 340 | GYVPRTAL | 1/0 | 0 | A*24 |
| 341 | KEKDPQPQQL | 0/0 | 1 | B*44:25 |
| 342 | LPKKPSKLEL | 1/0 | 1 | B*07 |
| 343 | RPSAASIDL | 0/1 | 1 | B*07 |
| 344 | SRHPLSPGF | 0/0 | 1 | B*27:05 |
| | BCL2 B-cell CLL/lymphoma 2 | 1 [3.3]/1 [20.0] | 2 [13.3] | |
| 345 | TPRSPQPEL | 0/1 | 1 | B*07 |
| 346 | GRIVAFFEF | 0/0 | 1 | B*27:05 |
| 347 | HTPHPAASR | 1/0 | 0 | A*33 |
| | BRAP BRCA1 associated protein | 1 [3.3]/1 [20.0] | 4 [26.7] | |
| 348 | NPDELKTTV | 1/0 | 0 | n.a. |
| 349 | PSKQLPDQI | 0/1 | 0 | n.a. |
| 350 | VYVERAEVL | 3/0 | 1 | A*24 |
| | NUDCD1 NudC domain containing 1 | 6 [20.0]/0 [0.0] | 4 [26.7] | |
| 351 | DPFIIIHSI | 5/0 | 2 | B*51 |
| 352 | EHSIATLLL | 1/0 | 2 | B*38, B*39 |
| | CYP1B1 cytochrome P450, family 1, subfamily B, polypeptide 1 | 6 [20.0]/1 [20.0] | 1 [6.7] | |
| 353 | FLDPRPLTV | 6/1 | 1 | A*02 |
| 354 | SAFADRPAF | 1/0 | 0 | n.a. |
| | HMMR hyaluronan-mediated motility receptor (RHAMM) | 1 [3.3]/0 [0.0] | 2 [13.3] | |
| 355 | DTTLPASAR | 0/0 | 1 | A*66 |
| 356 | KLLEYIEEI | 0/0 | 1 | A*02 |
| 357 | LEKQLIEL | 1/0 | 0 | n. a. |
| | TERT telomerase reverse transcriptase | 2 [6.6]/0 [0.0] | 0 [0.0] | |

TABLE 2-continued

Additional peptides according to the present invention related to underlying antigens described as related with AML

| SEQ ID NO | Proteins, Peptides | Number of positive healthy donors (PBMC/BMNC) [rep. frequency %] | Number of positive AMLs [rep. frequency %] | HLA |
|---|---|---|---|---|
| 358 | LMSVYVVEL | 2/0 | | A*02 |
| | MCL1 myeloid cell leukemia sequence 1 | 15 [50]/0 [0.0] | 5 [33.3] | |
| 359 | ESITDVLVR | 3/0 | 2 | A*66 |
| 360 | ETAFQGMLR | 0/0 | 1 | A*66 |
| 361 | EVPDVTATPARL | 1/0 | 0 | n.a. |
| 362 | GRIVTLISF | 3/0 | 1 | B*27 |
| 363 | HVFSDGVTNW | 2/0 | 0 | A*25 |
| 364 | REIGGGEAGAVI | 1/0 | 0 | B*49 |
| 365 | RGWDGFVEF | 0/0 | 1 | A*32 |
| 366 | RPAVLPLL | 1/0 | 0 | B*07 |
| 367 | VEFFHVEDL | 3/0 | 2 | B*40, B*52, B*60 |
| 368 | VQRNHETAF | 3/0 | 2 | B*15, B*62 |
| | DNAJC2 DnaJ (Hsp40) homolog, subfamily C, member 2 | 1 [3.3]/0 [0.0] | 0 [0.0] | |
| 369 | AELEAARL | 1/0 | 0 | B*44 |
| | NUSAP1 nucleolar and spindle associated protein 1 | 2 [6.6]/2 [40.0] | 5 [33.3] | |
| 370 | ATQTPVSNK | 0/1 | 1 | A*11 |
| 371 | ESIDQYIER | 1/1 | 2 | A*33, A*66, A*68 |
| 372 | FEEHNSMNEL | 1/0 | 1 | B*40 |
| 373 | SVASTPISQR | 0/1 | 1 | A*68 |
| 374 | VASTPISQR | 0/1 | 0 | A*68 |
| | PRTN3 proteinase 3 | 2 [6.6]/4 [80.0] | 2 [13.3] | |
| 375 | AEIVGGHEA | 2/2 | 1 | B*50, B*49 |
| 376 | RPPSPALASV | 0/1 | 0 | B*07 |
| 377 | SVAQVFLNNY | 0/1 | 0 | A*03 |
| 378 | TQEPTQQHF | 0/1 | 1 | B*15 |
| | RGS5 regulator of G-protein signaling 5 | 1 [3.3]/0 [0.0] | 2 [13.3] | |
| 379 | KDITmKNLV | 1/0 | 0 | n.a. |

TABLE 2-continued

Additional peptides according to the present invention related to underlying antigens described as related with AML

| SEQ ID NO | Proteins, Peptides | Number of positive healthy donors (PBMC/BMNC) [rep. frequency %] | Number of positive AMLs [rep. frequency %] | HLA |
| --- | --- | --- | --- | --- |
| 380 | mAEKAKQIY | 0/0 | 2 | n.a. |
| | SSX2IP synovial sarcoma, X breakpoint 2 interacting protein | 8 [26.7]/0 [0.0] | 0 [0.0] | |
| 381 | KLDNQVSKV | 6/0 | 0 | A*02 |
| 382 | SENVKLFSA | 1/0 | 0 | n.a. |
| 383 | VQKLQNII | 1/0 | 0 | B*13 |
| | WT1 Wilms tumor 1 | 10 [33.3]/0 [0.0] | 3 [20.0] | |
| 384 | AFTVHFSGQF | 0/0 | 2 | A*23 |
| 385 | GVFRGIQDV | 0/0 | 1 | A*02:01 |
| 386 | QRNMTKLQL | 1/0 | 0 | n.a. |
| 387 | RmFPNAPYL | 9/0 | 1 | A*02:01, E |
| | MAGED1 melanoma antigen family D, 1 | 15 [50.0]/3 [60.0] | 6 [40.0] | |
| 388 | EAAAEAKAR | 1/0 | 1 | A*66 |
| 389 | IIKEYTDVY | 1/0 | 0 | B*15:01 |
| 390 | KEIDKNDHL | 1/0 | 0 | B*40:01 |
| 391 | KVSKASGVSK | 2/0 | 1 | A*03 |
| 392 | MPATETKKV | 1/0 | 0 | B*07 |
| 393 | NADPQAVTm | 5/0 | 0 | A*02 |
| 394 | RSDmLKDII | 0/0 | 1 | n.a. |
| 395 | SESGAGLTRF | 0/0 | 1 | B*44:25 |
| 396 | SMMQTLLTV | 1/0 | 0 | A*02 |
| 397 | TEVSKTPEA | 4/2 | 3 | B*49:01 |
| 398 | VEVPETPKA | 2/1 | 1 | B*50 |
| 399 | DVYPEIIER | 6/1 | 2 | A*66, A*68 |
| | AURKA aurora kinase A | 0 [0.0]/0 [0.0] | 1 [6.7] | |
| 400 | REVEIQSHL | 0/0 | 1 | B*49:01 |
| | CCNA1 cyclin A1 | 0 [0.0]/0 [0.0] | 2 [13.3] | |
| 401 | EPPAVLLL | 0/0 | 1 | B*51:01 |
| 402 | LEADPFLKY | 0/0 | 1 | B*18:01 |
| | MUC1 mucin 1, cell surface associated | 1 [3.3]/0 [0.0] | 0 [0.0] | |
| 403 | TTQGQDVTLA | 1/0 | 0 | n.a. |
| | MPO myeloperoxidase | 0 [0.0]/3 [60.0] | 6 [40.0] | |

TABLE 2-continued

Additional peptides according to the present invention related to underlying antigens described as related with AML

| SEQ ID NO | Proteins, Peptides | Number of positive healthy donors (PBMC/BMNC) [rep. frequency %] | Number of positive AMLs [rep. frequency %] | HLA |
|---|---|---|---|---|
| 404 | AEYEDGFSIP | 0/1 | 0 | B*50 |
| 405 | AQISLPRI | 0/1 | 0 | B*13 |
| 406 | DFTPEPAAR | 0/0 | 2 | A*66 |
| 407 | DNTGITTVSK | 0/1 | 0 | A*68 |
| 408 | EEAKQLVDKAY | 0/0 | 1 | B*44 |
| 409 | ERRESIKQ | 0/0 | 1 | n.a. |
| 410 | ETVGQLGTVLR | 0/1 | 1 | A*66, A*68 |
| 411 | FEQVMRIGL | 0/0 | 1 | B*40 |
| 412 | FSMQQRQAL | 0/0 | 1 | C*03 |
| 413 | GVPFFSSLR | 0/1 | 1 | A*66, A*68 |
| 414 | IVRFPTDQL | 0/1 | 1 | A*02 |
| 415 | KQPVAATRTAV | 0/0 | 1 | B*15 |
| 416 | LGASNRAFV | 0/1 | 0 | n.a. |
| 417 | NPRWDGERL | 0/0 | 1 | B*07 |
| 418 | NVFTNAFRY | 0/0 | 1 | A*29 |
| 419 | QPMEPNPRVPL | 0/0 | 1 | B*07 |
| 420 | QPVAATRTAV | 0/1 | 0 | B*07 |
| 421 | RLFEQVMRI | 0/0 | 2 | A*02 |
| 422 | SEEPLARNL | 0/0 | 1 | B*40 |
| 423 | TIRNQINAL | 0/0 | 1 | A*02 |
| 424 | VLGPTAMRK | 0/1 | 0 | A*03 |
| | RUNX1 runt-related transcription factor 1 | 2 [6.6]/0 [0.0] | 4 [26.7] | |
| 425 | AELRNATAA | 1/0 | 0 | n.a. |
| 426 | DVPDGTLVTVm | 1/0 | 3 | A*26 |
| 427 | LPIAFKVV | 1/0 | 1 | B*51 |
| 428 | SAMGSATRY | 0/0 | 1 | A*32 |
| | NUP214 nucleoporin 214 kDa | 2 [6.6]/0 [0.0] | 3 [20.0] | |
| 429 | AEKQGHQW | 1/0 | 0 | B*44 |
| 430 | GEQKPTGTF | 0/0 | 1 | B*44:25 |
| 431 | GQFSKPFSF | 1/0 | 0 | B*15:01 |
| 432 | IAFFDVRTF | 0/0 | 1 | C*12:03 |
| 433 | LSAGKTSFSF | 0/0 | 1 | C*03 |

TABLE 2-continued

Additional peptides according to the present invention related to underlying antigens described as related with AML

| SEQ ID NO | Proteins, Peptides | Number of positive healthy donors (PBMC/BMNC) [rep. frequency %] | Number of positive AMLs [rep. frequency %] | HLA |
|---|---|---|---|---|
| 434 | VSNKYGLVF | 1/0 | 0 | B*58 |
| | CCNB1 Cyclin B1 | 2 [6.6]/0 [0.0] | 3 [20.0] | |
| 435 | GEVDVEQHTL | 2/0 | 2 | B*40:01 |
| 436 | VDVEQHTL | 0/0 | 1 | B*40:01 |
| | HOXA9 Homeobox A9 | 0 [0.0]/0 [0.0] | 1 [6.6] | |
| 437 | DAADELSVGRY | 0/0 | 1 | A*26:01 |
| | MSLN mesothelin | 0 [0.0]/0 [0.0] | 1 [6.6] | |
| 438 | LSEADVRA | 0/0 | 1 | n.a. |
| | BIRC5 survivin | 2 [6.6]/0 [0.0] | 3 [20.0] | |
| 439 | ELTLGEFLK | 2/0 | 2 | A*68 |
| 440 | ELTLGEFLKL | 1/0 | 2 | A*02 |
| 441 | LTLGEFLK | 1/0 | 1 | n.a. |
| 442 | LTLGEFLKL | 1/0 | 1 | A*02 |
| 443 | TLGEFLKL | 1/0 | 2 | A*02 |
| | KLF2 kruppel like factor 2 | 5 [16.7]/0 [0.0] | 4 [26.7] | |
| 444 | KTYTKSSHLK | 5/0 | 4 | A*03 |
| | PRAME preferentially expressed antigen in melanoma | 1 [3.3]/0 [0.0] | 0 [0.0] | |
| 445 | SQLTTLSFY | 1/0 | 0 | B*15 |
| | PASD1 pas domain containing 1 | 0 [0.0]/0 [0.0] | 2 [13.3] | |
| 446 | KMQEKKKLQ | 0/0 | 1 | n.a. |
| 447 | LLGHLPAEI | 0/0 | 1 | B*51 |

The table shows presented HLA ligands derived from established AML-associated antigens annotated with sample of origin, representation frequencies in different tissue (15 AML samples, 30 PBMC samples, 5 BMNC samples) and corresponding HLA restriction. Abbreviations: rep., representation; n.a., not assigned.

The peptides in the following Table 3 are further useful in the diagnosis and/or treatment of hematological malignancies, AML and/or chronic lymphatic leukemia (CLL) cells, but preferably AML.

TABLE 3

MHC class II peptides according to the present invention

| SEQ ID NO | Protein/Peptides | Number of positive AMLs [rep. frequency] |
|---|---|---|
| | A1BG alpha-1-B glycoprotein | 6 [50%] |
| 448 | APVELILSDETLPAPE | 3 |

TABLE 3-continued

MHC class II peptides according to the present invention

| SEQ ID NO | Protein/Peptides | Number of positive AMLs [rep. frequency] |
|---|---|---|
| 449 | ETPDFQLFKNGVAQEPV | 1 |
| 450 | LAPLEGARFALVRED | 2 |
| 451 | SPDRIFFHLNAVALGD | 1 |
| 452 | SPDRIFFHLNAVALGDG | 2 |
|  | CORO1A coronin, actin binding protein, 1A | 5 [41.7%] |
| 453 | EEMRKLQATVQELQKR | 1 |
| 454 | EEPLSLQELDTSSG | 4 |
| 455 | EMRKLQATVQELQKR | 1 |
| 456 | HLEEPLSLQELDTSSG | 1 |
| 457 | LEEPLSLQELDTSSG | 2 |
|  | RPS5 ribosomal protein S5 | 5 [41.7%] |
| 458 | AGTVRRQAVDVSPLR | 5 |
| 459 | IGRAGTVRRQAVDVSPLR | 1 |
| 460 | RAGTVRRQAVDVSPLR | 4 |
| 461 | TVRRQAVDVSPLR | 1 |
|  | C19orf10 chromosome 19 open reading frame 10 | 5 [41.7%] |
| 462 | GVVHSFSHNVGPGDK | 2 |
| 463 | GVVHSFSHNVGPGDKY | 1 |
| 464 | GVVHSFSHNVGPGDKYT | 1 |
| 465 | KTEEFEVTKTAVAHRP | 1 |
| 466 | KTEEFEVTKTAVAHRPG | 3 |
| 467 | VRPGGVVHSFSHNVGPGDK | 1 |
| 468 | VRPGGVVHSFSHNVGPGDKYT | 1 |
|  | PLIN3 perilipin 3 | 4 [33.3%] |
| 469 | AEKGVRTLTAAAVSGAQ | 1 |
| 470 | AQPILSKLEPQIASASE | 1 |
| 471 | EKGVRTLTAAAVSGAQ | 3 |
| 472 | EKGVRTLTAAAVSGAQP | 1 |
| 473 | GVRTLTAAAVSGAQ | 1 |
| 474 | KGVRTLTAAAVSGAQ | 1 |
|  | CLSTN1 calsyntenin 1 | 4 [33.3%] |
| 475 | DVNEYAPVFKEKSYK | 1 |
| 476 | HRSFVDLSGHNLA | 1 |
| 477 | HRSFVDLSGHNLANPH | 1 |

TABLE 3-continued

MHC class II peptides according to the present invention

| SEQ ID NO | Protein/Peptides | Number of positive AMLs [rep. frequency] |
|---|---|---|
| 478 | HRSFVDLSGHNLANPHP | 3 |
| | HSP90B1 heat shock protein 90 kDa beta (Grp94), member 1 | 4 [33.3%] |
| 479 | ALPEFDGKRFQNVAKEG | 1 |
| 480 | DSNEFSVIADPRG | 1 |
| 481 | DSNEFSVIADPRGN | 1 |
| 482 | DSNEFSVIADPRGNT | 1 |
| 483 | DSNEFSVIADPRGNTL | 1 |
| 484 | DSNEFSVIADPRGNTLG | 1 |
| 485 | PEFDGKRFQNVAK | 1 |
| 486 | SDSNEFSVIADPRGNTLG | 1 |
| 487 | SQKKTFEINPRHPLIR | 1 |
| 488 | ALPEFDGKRFQNVAKEG | 1 |
| 489 | PEFDGKRFQNVAK | 2 |
| 490 | PEFDGKRFQNVAKE | 1 |
| | B4GALT1 UDP-Gal:betaGlcNAc beta 1,4-galactosyltransferase, polypeptide 1 | 4 [33.3%] |
| 491 | LNSLTYQVLDVQRYP | 1 |
| 492 | LPQLVGVSTPLQG | 2 |
| 493 | LPQLVGVSTPLQGG | 1 |
| 494 | LPQLVGVSTPLQGGS | 3 |
| 495 | RLPQLVGVSTPLQGGS | 1 |
| 496 | SDVDLIPMNDHNAYR | 1 |
| | SPN sialophorin | 4 [33.3%] |
| 497 | GRRKSRQGSLAMEELK | 1 |
| 498 | RKSRQGSLAMEELK | 3 |
| 499 | SGPSLKGEEEPLVASEDGAVD | 1 |
| 500 | SGSGPSLKGEEEPLVASEDGAVD | 1 |
| | METAP1 methionyl aminopeptidase 1 | 4 [33.3%] |
| 501 | IKPGVTTEEIDHAVH | 4 |
| 502 | KPGVTTEEIDHAVH | 3 |
| | HSPG2 heparan sulfate proteoglycan 2 | 4 [33.3%] |
| 503 | DGVLRIQNLDQS | 4 |
| 504 | GAYFHDDGFLAFPG | 1 |
| 505 | TPYSFLPLPTIKDAYR | 1 |
| 506 | YPTPDISWSKLDGSLPP | 1 |

TABLE 3-continued

MHC class II peptides according to the present invention

| SEQ ID NO | Protein/Peptides | Number of positive AMLs [rep. frequency] |
|---|---|---|
| 507 | YPTPDISWSKLDGSLPPD | 1 |
| | QSOX1 quiescin Q6 sulfhydryl oxidase 1 | 3 [25.0%] |
| 508 | ASHFEQMAAASMHR | 3 |
| | MANBA mannosidase, beta A, lysosomal | 3 [25.0%] |
| 509 | GGQVIVAIPKLQTQQ | 1 |
| 510 | GQVIVAIPKLQTQ | 1 |
| 511 | GQVIVAIPKLQTQQ | 1 |
| 512 | IESTFDVVSSKPVG | 2 |
| | CREG1 cellular repressor of E1A-stimulated genes 1 | 3 [25.0%] |
| 513 | DWGALATISTLEAVRG | 1 |
| 514 | GRPFADVLSLSDGPPG | 1 |
| 515 | WGALATISTLEAVR | 2 |
| 516 | WGALATISTLEAVRG | 2 |
| | LDHA lactate dehydrogenase A | 3 [25.0%] |
| 517 | ADELALVDVIEDK | 1 |
| 518 | GVSLKTLHPDLGTDK | 2 |
| 519 | IVSGKDYNVTANSKL | 1 |
| | CP ceruloplasmin (ferroxidase) | 3 [25.0%] |
| 520 | DDNIKTYSDHPEK | 1 |
| 521 | DKVYVHLKNLASRPY | 1 |
| 522 | GDKVYVHLKNLASRPY | 1 |
| 523 | LDDNIKTYSDHPEK | 1 |
| 524 | TGDKVYVHLKNLASRPY | 1 |
| 525 | VYVHLKNLASRPY | 1 |
| | COL1A1 collagen, type I, alpha 1 | 3 [25.0%] |
| 526 | KTSRLPIIDVAPLDVGAPD | 1 |
| 527 | KTSRLPIIDVAPLDVGAPDQE | 1 |
| 528 | LPIIDVAPLDVGAPD | 1 |
| 529 | RLPIIDVAPLDVGAPD | 3 |
| 530 | RLPIIDVAPLDVGAPDQE | 2 |
| 531 | SRLPIIDVAPLDVGAPD | 1 |
| 532 | SRLPIIDVAPLDVGAPDQE | 1 |
| 533 | TSRLPIIDVAPLDVGAPD | 1 |
| 534 | TSRLPIIDVAPLDVGAPDQE | 1 |
| | CRP C-reactive protein, pentraxin-related | 3 [25.0%] |

TABLE 3-continued

MHC class II peptides according to the present invention

| SEQ ID NO | Protein/Peptides | Number of positive AMLs [rep. frequency] |
|---|---|---|
| 535 | DTSYVSLKAPLT | 2 |
| 536 | DTSYVSLKAPLTKP | 1 |
| 537 | DTSYVSLKAPLTKPL | 1 |
| 538 | ESDTSYVSLKAPLT | 2 |
| 539 | ESDTSYVSLKAPLTKPL | 1 |
| 540 | SDTSYVSLKAPLT | 3 |
| 541 | SDTSYVSLKAPLTKP | 2 |
| 542 | SDTSYVSLKAPLTKPL | 2 |
| | APRT adenine phosphoribosyltransferase | 3 [25.0%] |
| 543 | DPASFRAAIGLLARH | 3 |
| | MBL2 mannose-binding lectin 2 | 3 [25.0%] |
| 544 | TEGQFVDLTGNRLTYT | 3 |
| | IFI30 interferon, gamma-inducible protein 30 | 3 [25.0%] |
| 545 | ALDFFGNGPPVNYK | 1 |
| 546 | ALDFFGNGPPVNYKTG | 1 |
| 547 | DFFGNGPPVNYKTG | 2 |
| 548 | LDFFGNGPPVNYK | 1 |
| 549 | LDFFGNGPPVNYKTG | 1 |
| 550 | QALDFFGNGPPVNYKTG | 1 |
| | LBP lipopolysaccharide binding protein | 3 [25.0%] |
| 551 | AISDYVFNTASLVYH | 1 |
| 552 | AISDYVFNTASLVYHEE | 2 |
| 553 | ISDYVFNTASLVYH | 1 |
| 554 | ISDYVFNTASLVYHEE | 3 |
| 555 | YVFNTASLVYHEE | 1 |
| | RAB5A RAB5A, member RAS oncogene family | 3 [25.0%] |
| 556 | IVIALSGNKADLA | 1 |
| 557 | SPNIVIALSGNKADL | 1 |
| 558 | SPNIVIALSGNKADLA | 3 |
| | ICAM3 intercellular adhesion molecule 3 | 3 [25.0%] |
| 559 | TPPRLVAPRFLEVE | 1 |
| 560 | TPPRLVAPRFLEVET | 1 |
| 561 | TPPRLVAPRFLEVETS | 3 |
| | MAN1A1 mannosidase, alpha, class 1A, member 1 | 3 [25.0%] |
| 562 | EIQRDILLEKKKVAQDQ | 1 |
| 563 | FGAIFFLPDSSK | 1 |

TABLE 3-continued

MHC class II peptides according to the present invention

| SEQ ID NO | Protein/Peptides | Number of positive AMLs [rep. frequency] |
|---|---|---|
| 564 | IQRDILLEKKKVAQ | 1 |
| 565 | IQRDILLEKKKVAQD | 1 |
| 566 | IQRDILLEKKKVAQDQ | 1 |
| 567 | LSGVLFHSSPALQPA | 1 |
| 568 | RDILLEKKKVAQDQ | 1 |
| 569 | SSKLLSGVLFHSSPA | 1 |
| 570 | SSPALQPAADHKPGPG | 1 |
|  | RBMX RNA binding motif protein, X-linked | 3 [25.0%] |
| 571 | APPTRGPPPSYGGS | 1 |
| 572 | GNSRSAPPTRGPPPSYGGSSRY | 1 |
| 573 | RDYGHSSSRDDYPS | 1 |
| 574 | SPRDDGYSTKDSY | 1 |
|  | PBX2 pre-B-cell leukemia homeobox 2 | 3 [25.0%] |
| 575 | GGSAAAAAAAAASGG | 1 |
| 576 | DNMLLAEGVSGPEK | 2 |
|  | YARS tyrosyl-tRNA synthetase | 3 [25.0%] |
| 577 | ADSLYVEKIDVGEAEPR | 3 |
|  | TPM4 tropomyosin 4 | 3 [25.0%] |
| 578 | RIQLVEEELDRAQER | 2 |
| 579 | RRIQLVEEELDRAQER | 1 |
|  | RPL36A ribosomal protein L36a | 3 [25.0%] |
| 580 | HQPHKVTQYKKGKDSLY | 2 |
| 581 | RKKAKTTKKIVL | 1 |
|  | GANAB glucosidase, alpha; neutral AB | 3 [25.0%] |
| 582 | DVFRQYASLTGTQALPP | 1 |
| 583 | GTAQGELFLDDGHT | 1 |
| 584 | VFRQYASLTGTQALPP | 1 |
|  | HSP90B2P heat shock protein 90 kDa beta (Grp94), member 2, pseudogene | 3 [25.0%] |
| 585 | PEFDGKRFQNVAK | 1 |
| 586 | PEFDGKRFQNVAKE | 2 |
| 587 | ALPEFDGKRFQNVAKEG | 1 |
|  | LAIR1 leukocyte-associated immunoglobulin-like receptor 1 | 3 [25.0%] |
| 588 | ASPSESEARFRIDSVSEGNAGPY | 1 |
| 589 | EARFRIDSVSEGNAGP | 1 |
| 590 | ESEARFRIDSVSEGNAGP | 1 |

TABLE 3-continued

MHC class II peptides according to the present invention

| SEQ ID NO | Protein/Peptides | Number of positive AMLs [rep. frequency] |
|---|---|---|
| 591 | ESEARFRIDSVSEGNAGPY | 1 |
| 592 | FRIDSVSEGNAGP | 1 |
| 593 | PRIDSVSEGNAGPY | 1 |
| 594 | SEARFRIDSVSEGNAGPY | 3 |
| 595 | SPSESEARFRIDSVSEGNAGPY | 1 |
| | GALNT7 UDP-N-acetyl-alpha-D-galactosamine:polypeptide N-acetylgalactosaminyltransferase 7 (GalNAc-T7) | 3 [25.0%] |
| 596 | GNQLFRINEANQL | 1 |
| 597 | GNQLFRINEANQLMQ | 2 |
| 598 | SPAMAGGLFAIERE | 1 |
| | ARRDC1 arrestin domain containing 1 | 3 [25.0%] |
| 599 | FIGNIAVNHAPVSPR | 1 |
| 600 | FIGNIAVNHAPVSPRPG | 1 |
| 601 | IGNIAVNHAPVSPRP | 3 |
| 602 | IGNIAVNHAPVSPRPG | 1 |
| | ERGIC1 endoplasmic reticulum-golgi intermediate compartment (ERGIC) 1 | 3 [25.0%] |
| 603 | FEGQFSINKVPGNFH | 3 |
| 604 | FEGQFSINKVPGNFHVS | 2 |
| 605 | RFEGQFSINKVPGNFH | 2 |

The table shows HLA class II ligandome-derived tumor-associated antigens (LiTAAs) with representation frequencies >20% in AML patients (n = 12) and representing HLA ligands (LiTAPs). Abbreviations: rep., representation.

The peptides in the following Table 4 are both useful in the diagnosis and/or treatment of AML and/or CLL, and preferably AML.

TABLE 4

Peptides according to the present invention that can be used both for the treatment of AML and CLL

| SEQ ID NO: | Sequence |
|---|---|
| 448 | APVELILSDETLPAPE |
| 520 | DDNIKTYSDHPEK |
| 471 | EKGVRTLTAAAVSGAQ |
| 472 | EKGVRTLTAAAVSGAQP |
| 439 | ELTLGEFLK |
| 353 | FLDPRPLTV |
| 522 | GDKVYVHLKNLASRPY |
| 318 | GLDPNKPPEL |
| 178 | HEIDRYTAI |
| 68 | IGVEHVVVY |
| 201 | IPVVHASI |
| 474 | KGVRTLTAAAVSGAQ |
| 381 | KLDNQVSKV |
| 323 | KLYELHVFTF |
| 46 | KLYPTLVIR |
| 241 | KTIAFLLPMF |
| 450 | LAPLEGARFALVRED |
| 357 | LEKQLIEL |

TABLE 4-continued

Peptides according to the present invention that can be used both for the treatment of AML and CLL

| SEQ ID NO: | Sequence |
| --- | --- |
| 491 | LNSLTYQVLDVQRYP |
| 492 | LPQLVGVSTPLQG |
| 493 | LPQLVGVSTPLQGG |
| 494 | LPQLVGVSTPLQGGS |
| 441 | LTLGEFLK |
| 442 | LTLGEFLKL |
| 498 | RKSRQGSLAMEELK |
| 495 | RLPQLVGVSTPLQGGS |
| 354 | SAFADRPAF |
| 45 | SEETFRFEL |
| 382 | SENVKLFSA |
| 445 | SQLTTLSFY |
| 443 | TLGEFLKL |
| 202 | TVADQVLVGSY |
| 179 | VFTLKPLEF |
| 296 | VIYNEQMASK |
| 383 | VQKLQNII |
| 525 | VYVHLKNLASRPY |
| 325 | YLNKEIEEA |
| 180 | YWVPRNAL |

Thus, particularly preferred is at least one peptide according to the present invention selected from the group consisting of SEQ ID NO: 448, 520, 471, 472, 439, 353, 522, 318, 178, 68, 201, 474, 381, 323, 46, 241, 450, 357, 491, 492, 493, 494, 441, 442, 498, 495, 354, 45, 382, 445, 443, 202, 179, 296, 383, 525, 325, and 180, and the use thereof in the treatment of AML and/or CLL as described herein.

The present invention furthermore relates to the peptides according to the present invention for use in the treatment of proliferative diseases other than AML, such as, for example, CLL. Nevertheless, as shown in the following table 5, many of the peptides according to the present invention can also be used in other indications.

TABLE 5

Peptides according to the present invention and their specific uses in other proliferative diseases, optionally in other organs.

| Seq. ID | Sequence | Proliferative disease and location thereof |
| --- | --- | --- |
| 1 | AEQFRLEQI | colon or rectum, lung, small cell carcinoma |
| 2 | FTAEFSSRY | colon or rectum, lung, small cell carcinoma |
| 3 | HHDESVLTNVF | colon or rectum, lung, small cell carcinoma |
| 4 | REQDEAYRL | colon or rectum, lung, small cell carcinoma |
| 5 | RPVMPSRQI | colon or rectum, lung, small cell carcinoma |
| 6 | VQREYNLNF | colon or rectum, lung, small cell carcinoma |
| 7 | GQLPITIQV | kidney, clear cell renal cell carcinoma, bone, non-ossifying fibroma |
| 8 | RAYADEVAV | kidney, clear cell renal cell carcinoma, bone, non-ossifying fibroma |
| 9 | REDKPPLAV | kidney, clear cell renal cell carcinoma, bone, non-ossifying fibroma |
| 10 | RVKDLDTEKY | kidney, clear cell renal cell carcinoma, bone, non-ossifying fibroma |
| 11 | SEQEMNAHL | kidney, clear cell renal cell carcinoma, bone, non-ossifying fibroma |
| 12 | YVLPLVHSL | kidney, clear cell renal cell carcinoma, bone, non-ossifying fibroma |
| 13 | LPLRFWVNI | liver, hepatocellular carcinoma, cancer, pancreas, adenocarcinoma |

TABLE 5-continued

Peptides according to the present invention and their specific uses in other proliferative diseases, optionally in other organs.

| Seq. ID | Sequence | Proliferative disease and location thereof |
|---|---|---|
| 14 | EVAEHVQYM | colon or rectum, prostate, benign nodular hyperplasia |
| 15 | YMAELIERL | colon or rectum, prostate, benign nodular hyperplasia |
| 16 | ALASLIRSV | thyroid gland, nodular hyperplasia |
| 17 | TVAEITGSKY | thyroid gland, nodular hyperplasia |
| 18 | EIIGKRGIIGY | colon or rectum, kidney, carcinoma |
| 19 | NLVEKTPAL | colon or rectum, kidney, carcinoma |
| 20 | IEDKAQILL | malignant fibrous histiocytoma |
| 21 | SIYDDSYLGY | malignant fibrous histiocytoma |
| 22 | TTNHPINPK | malignant fibrous histiocytoma |
| 23 | NAAILKKV | brain, glioblastoma, thyroid gland, nodular hyperplasia |
| 24 | NYLDIKGLL | brain, glioblastoma, thyroid gland, nodular hyperplasia |
| 25 | YLDIKGLLDV | brain, glioblastoma, thyroid gland, nodular hyperplasia |
| 26 | EEVGDFIQRY | lung, non-small cell lung carcinoma, |
| 27 | EVGDFIQRY | lung, non-small cell lung carcinoma, |
| 28 | MKDLSLGGVL | lung, non-small cell lung carcinoma, |
| 29 | DEFITVHSM | stomach, skin, basal cell carcinoma |
| 30 | EFITVHSML | stomach, skin, basal cell carcinoma |
| 31 | GQLDVRELI | stomach, skin, basal cell carcinoma |
| 32 | TQYIIHNY | stomach, skin, basal cell carcinoma |
| 33 | EVVDVTWRY | colon or rectum, lymph node, non-Hodgkin's lymphoma |
| 34 | KEALLRDTI | colon or rectum, lymph node, non-Hodgkin's lymphoma |
| 35 | HGYENPTYK | lung, non-small cell lung carcinoma, kidney, carcinoma |
| 36 | SLLYKVPYV | lung, non-small cell lung carcinoma, kidney, carcinoma |
| 37 | AEIPLRMV | stomach, metastatic, adenocarcinoma |
| 38 | EVVYRFTAR | stomach, metastatic, adenocarcinoma |
| 39 | FPGLAIKI | stomach, metastatic, adenocarcinoma |
| 40 | IYNGKLFDL | stomach, metastatic, adenocarcinoma |
| 41 | IYNGKLFDLL | stomach, metastatic, adenocarcinoma |
| 42 | KEIDVISI | stomach, metastatic, adenocarcinoma |
| 43 | LEEQASRQI | stomach, metastatic, adenocarcinoma |
| 44 | TRMSTVSEL | stomach, metastatic, adenocarcinoma |

TABLE 5-continued

Peptides according to the present invention and their specific uses in other proliferative diseases, optionally in other organs.

| Seq. ID | Sequence | Proliferative disease and location thereof |
|---|---|---|
| 45 | SEETFRFEL | stomach, adenocarcinoma, endometrium, adenocarcinoma |
| 46 | KLYPTLVIR | stomach, adenocarcinoma, endometrium, adenocarcinoma |
| 47 | ALRNQATMVQK | stomach, adenocarcinoma, non-Hodgkin's lymphoma, mycosis fungoides |
| 48 | LLDHAPPEI | stomach, adenocarcinoma, non-Hodgkin's lymphoma, mycosis fungoides |
| 49 | GVLGTVVHGK | colon or rectum, liver, focal nodular hyperplasia |
| 50 | VQFIGRESKY | colon or rectum, liver, focal nodular hyperplasia |
| 51 | GQSLIHVI | parathyroid gland, adenoma |
| 52 | VHSPAGMAL | parathyroid gland, adenoma |
| 53 | VLYEGIKVGK | parathyroid gland, adenoma |
| 54 | AVIEAEKIAQV | ovary, granulosa cell tumor, |
| 55 | DRIEVVNML | ovary, granulosa cell tumor, |
| 56 | IEAEKIAQV | ovary, granulosa cell tumor, |
| 57 | IEDLKAQIL | uterine cervix, squamous cell carcinoma, |
| 58 | YLLESVNKL | uterine cervix, squamous cell carcinoma, |
| 59 | HRIYVPLML | stomach, diffuse subtype adenocarcinoma, pancreas, adenocarcinoma |
| 60 | KEYIPPLIW | stomach, adenocarcinoma, pancreas, adenocarcinoma |
| 61 | MDKLVVEY | stomach, adenocarcinoma, pancreas, adenocarcinoma |
| 62 | ALLGHILLH | kidney, renal cell carcinoma, non-clear cell type, |
| 63 | ALLPHLYTL | kidney, renal cell carcinoma, non-clear cell type, |
| 64 | HVAGETVAR | kidney, renal cell carcinoma, non-clear cell type, |
| 65 | KVWPGSTAF | kidney, renal cell carcinoma, non-clear cell type, |
| 66 | ETAVAILRF | metastatic infiltrating lobular carcinoma of breast |
| 67 | RVYNTDPLKEK | endometrium, adenocarcinoma, |
| 68 | IGVEHVVVY | brain, cancer, kidney, oncocytoma |
| 69 | RQIGVEHVV | brain, cancer, kidney, oncocytoma |
| 70 | DVFERPSAKK | kidney, clear cell renal cell carcinoma, synovial sarcoma |
| 71 | EEFQFIKKA | kidney, clear cell renal cell carcinoma, synovial sarcoma |
| 72 | THLVDQDTTSF | kidney, clear cell renal cell carcinoma, synovial sarcoma |

TABLE 5-continued

Peptides according to the present invention and their specific uses in other proliferative diseases, optionally in other organs.

| Seq. ID | Sequence | Proliferative disease and location thereof |
|---|---|---|
| 73 | ESADLIQHY | pancreas, adenocarcinoma, kidney, renal cell carcinoma |
| 74 | EIIKEISIM | pancreas, adenocarcinoma, lymph node, Hodgkin's disease |
| 75 | SVSDIIRLR | pancreas, adenocarcinoma, lymph node, Hodgkin's disease |
| 76 | AVSLIREEW | stomach, adenocarcinoma, white blood cells, chronic lymphocytic leukemia |
| 77 | GEKSESISV | stomach, adenocarcinoma, white blood cells, chronic lymphocytic leukemia |
| 78 | FLTILPEEL | pancreas, adenocarcinoma, lung, adenocarcinoma |
| 79 | ILWETVPSM | colon or rectum, metastatic renal cell carcinoma |
| 80 | LPVRTLSI | colon or rectum, metastatic renal cell carcinoma |
| 81 | RESEYKQVY | colon or rectum, metastatic renal cell carcinoma |
| 82 | SESLPVRTL | colon or rectum, metastatic renal cell carcinoma |
| 83 | RLLESVVVL | lung, non-small cell lung carcinoma, spleen, chronic myeloid leukemia |
| 84 | RPEEGKESL | lung, non-small cell lung carcinoma, spleen, chronic myeloid leukemia |
| 85 | THGKLVILF | lung, non-small cell lung carcinoma, spleen, chronic myeloid leukemia |
| 86 | KELEHLSHI | stomach, adenocarcinoma, |
| 87 | REMENYEKI | stomach, adenocarcinoma, |
| 88 | VLLSTIHEL | stomach, adenocarcinoma, |
| 89 | KTYTKSSHLK | stomach, adenocarcinoma, brain, meningioma, |
| 90 | EIIEKNFDY | stomach, adenocarcinoma, |
| 91 | GTEEAPKVFK | stomach, adenocarcinoma, |
| 92 | KLMAIPLVF | stomach, adenocarcinoma, |
| 93 | DIKRGIPN | stomach, adenocarcinoma, lung, small cell carcinoma |
| 94 | DIKRGIPNY | stomach, adenocarcinoma, lung, small cell carcinoma |
| 95 | FLDITNPKA | stomach, differentiated subtype adenocarcinoma, lung, small cell carcinoma |
| 96 | ALYSVYRQK | kidney, angiomyolipoma |
| 97 | KVLALVFGF | kidney, angiomyolipoma |
| 98 | SFTDVIGHY | kidney, angiomyolipoma |
| 99 | ASAAASGGLLK | colon or rectum, spleen, extramedullary hematopoiesis |

TABLE 5-continued

Peptides according to the present invention and their specific uses in other proliferative diseases, optionally in other organs.

| Seq. ID | Sequence | Proliferative disease and location thereof |
|---|---|---|
| 100 | ALLGVTGAPK | colon or rectum, spleen, extramedullary hematopoiesis |
| 101 | DEIKTLQRY | stomach, adenocarcinoma, liver, carcinoid tumor, metastatic |
| 102 | EAYVQKMV | stomach, adenocarcinoma, liver, carcinoid tumor, metastatic |
| 103 | VLHQDSGLGY | stomach, adenocarcinoma, liver, carcinoid tumor, metastatic |
| 104 | YLQNHFVGL | stomach, adenocarcinoma, liver, carcinoid tumor, metastatic |
| 105 | AEIEDIRVL | stomach, metastatic, duodenum, adenocarcinoma |
| 106 | GQSRLIFTY | stomach, metastatic, duodenum, adenocarcinoma |
| 107 | READFKETL | stomach, metastatic, duodenum, adenocarcinoma |
| 108 | DTMGPSQHVY | lung, non-small cell lung carcinoma, spleen, extramedullary hematopoiesis |
| 109 | ESRGPALTR | lung, non-small cell lung carcinoma, spleen, extramedullary hematopoiesis |
| 110 | FQLPGLGTPPIT | lung, non-small cell lung carcinoma, spleen, extramedullary hematopoiesis |
| 111 | RIQGYVVSW | lung, non-small cell lung carcinoma, spleen, extramedullary hematopoiesis |
| 112 | LLDPSVFHV | stomach, adenocarcinoma, testis, seminoma |
| 113 | RFFHLADLF | stomach, adenocarcinoma, testis, seminoma |
| 114 | DSISGNLQR | stomach, metastatic, bone, non-ossifying fibroma |
| 115 | ETEQTIQKL | stomach, metastatic, bone, non-ossifying fibroma |
| 116 | FLYPFLSHL | stomach, metastatic, bone, non-ossifying fibroma |
| 117 | TLDQKIERV | stomach, metastatic, bone, non-ossifying fibroma |
| 118 | DADSRAATV | liver, hepatocellular carcinoma, kidney, renal cell carcinoma |
| 119 | DHEGFGFVL | liver, hepatocellular carcinoma, kidney, renal cell carcinoma |
| 120 | GEAVKVLSI | liver, hepatocellular carcinoma, kidney, renal cell carcinoma |
| 121 | NATDLLKVL | liver, hepatocellular carcinoma, kidney, renal cell carcinoma |
| 122 | KEITEGKTV | stomach, metastatic, rectum, adenocarcinoma |
| 123 | YRQKQVVIL | stomach, metastatic, rectum, adenocarcinoma |
| 124 | VAINLIVQH | stomach, metastatic, rectum, adenocarcinoma |
| 127 | DAIKVFVRI | stomach, adenocarcinoma, kidney, Warn's tumor |

TABLE 5-continued

Peptides according to the
present invention and their specific uses in other
proliferative diseases, optionally in other organs.

| Seq. ID | Sequence | Proliferative disease and location thereof |
|---|---|---|
| 128 | LEKAFSEI | stomach, adenocarcinoma, kidney, Warn's tumor |
| 129 | MEKSDKNQ | stomach, adenocarcinoma, kidney, Warn's tumor |
| 130 | GQTGSGKTF | stomach, adenocarcinoma, rectum, adenocarcinoma |
| 131 | DTSPDLSSR | lung, non-small cell lung carcinoma, testis, seminoma |
| 132 | KLNEVIVNK | lung, non-small cell lung carcinoma, testis, seminoma |
| 133 | FAQIISVALI | stomach, adenocarcinoma, parathyroid gland, adenoma |
| 134 | IIFDRPLLY | stomach, adenocarcinoma, parathyroid gland, adenoma |
| 135 | DAVNQNTKLL | ovary, adenocarcinoma, clear cell type, |
| 136 | HHILADVSL | ovary, adenocarcinoma, clear cell type, |
| 137 | YPSEKRGEL | ovary, adenocarcinoma, clear cell type, |
| 138 | SVVDLINHY | brain, glioblastoma, bone, non-ossifying fibroma |
| 139 | EIIEKDTKY | stomach, metastatic, lung, large cell carcinoma |
| 140 | ENEEKLKEL | stomach, metastatic, lung, large cell carcinoma |
| 141 | ILGGPGTVQGV | liver, hepatocellular carcinoma, cancer, vulva, squamous cell carcinoma |
| 142 | ESAALIHHY | liver, hepatocellular carcinoma, fibromatosis |
| 143 | YQRETPQV | liver, hepatocellular carcinoma, fibromatosis |
| 144 | ARIEIGLHY | liver, focal nodular hyperplasia |
| 145 | IPYPRPIHL | liver, focal nodular hyperplasia |
| 146 | DVSGKTALNQ | kidney, clear cell renal cell carcinoma, stomach, gastrointestinal stromal tumor (GIST) |
| 147 | TEFRSLVI | kidney, clear cell renal cell carcinoma, stomach, gastrointestinal stromal tumor (GIST) |
| 148 | TLKSGDGITF | kidney, clear cell renal cell carcinoma, stomach, gastrointestinal stromal tumor (GIST) |
| 149 | HEADKTYML | stomach, adenocarcinoma, |
| 150 | KFFEEVLLF | stomach, adenocarcinoma, |
| 151 | RVMPSSFFL | stomach, adenocarcinoma, |
| 152 | YELDLREPAL | lung, non-small cell lung carcinoma, lung, adenocarcinoma |
| 153 | GAYGKVFLV | liver, hepatocellular carcinoma, kidney, angiomyolipoma |
| 154 | DHDLLKNF | kidney, clear cell renal cell carcinoma, kidney, polycystic kidney disease |

TABLE 5-continued

Peptides according to the
present invention and their specific uses in other
proliferative diseases, optionally in other organs.

| Seq. ID | Sequence | Proliferative disease and location thereof |
|---|---|---|
| 155 | EELQLIRQA | kidney, clear cell renal cell carcinoma, kidney, polycystic kidney disease |
| 156 | AAELLKHPF | prostate, adenocarcinoma |
| 157 | GRVKLSDFGF | prostate, adenocarcinoma |
| 158 | KSNSIIVSPR | brain, glioblastoma, brain, meningioma |
| 159 | ETLERLQEL | liver, hepatocellular carcinoma, cancer, parotid gland, pleomorphic adenoma |
| 160 | KDDELSRQ | liver, hepatocellular carcinoma, cancer, parotid gland, pleomorphic adenoma |
| 161 | LQQTNSEKI | kidney, clear cell renal cell carcinoma, parotid gland, pleomorphic adenoma |
| 162 | GEFGKPYFI | colon or rectum, testis, seminoma |
| 163 | KDVKVVIL | colon or rectum, testis, seminoma |
| 164 | RPVPPPPSL | colon or rectum, testis, seminoma |
| 165 | KEDIPGRHSY | stomach, adenocarcinoma, spleen, chronic myeloid leukemia |
| 166 | KETKAVTNF | stomach, adenocarcinoma, spleen, chronic myeloid leukemia |
| 167 | YEILIHDL | stomach, adenocarcinoma, spleen, chronic myeloid leukemia |
| 168 | FPRFVNVTV | spleen, chronic myeloid leukemia |
| 169 | QVAGWGSQR | spleen, chronic myeloid leukemia |
| 170 | WIDGVLNNPGPG | spleen, chronic myeloid leukemia |
| 171 | SFMTHPEF | stomach, adenocarcinoma, myometrium, leiomyoma |
| 172 | HYTIVFNTF | colon or rectum, myometrium, leiomyoma |
| 173 | GTNDGPALKK | colon or rectum, liver, hepatocellular carcinoma |
| 174 | IEDPVRPEV | colon or rectum, liver, hepatocellular carcinoma |
| 175 | NTASGGMTR | brain, glioblastoma, skin, squamous cell carcinoma |
| 176 | EVIETEKTLY | colon or rectum, breast, mucinous carcinoma |
| 177 | MKILNHPNI | colon or rectum, lung, squamous cell carcinoma |
| 178 | HEIDRYTAI | kidney, clear cell renal cell carcinoma, non-Hodgkin's lymphoma |
| 179 | VFTLKPLEF | kidney, clear cell renal cell carcinoma, non-Hodgkin's lymphoma |
| 180 | YWVPRNAL | kidney, clear cell renal cell carcinoma, non-Hodgkin's lymphoma |
| 181 | EVSPNLVRY | stomach, metastatic, pancreas, adenocarcinoma |
| 182 | LSEIAGMTLP | stomach, metastatic, pancreas, adenocarcinoma |

TABLE 5-continued

Peptides according to the present invention and their specific uses in other proliferative diseases, optionally in other organs.

| Seq. ID | Sequence | Proliferative disease and location thereof |
|---|---|---|
| 183 | FLSFMNTEL | lung, non-small cell lung carcinoma, stomach, adenocarcinoma |
| 184 | KAVPSQKRT | lung, non-small cell lung carcinoma, stomach, adenocarcinoma |
| 185 | LKAVPSQKRT | lung, non-small cell lung carcinoma, stomach, adenocarcinoma |
| 186 | SLIAVFQKY | lung, non-small cell lung carcinoma, stomach, adenocarcinoma |
| 187 | IIKEKTVVY | liver, hepatocellular carcinoma, cancer, liver, hepatocellular carcinoma |
| 188 | LLEQKVWEV | liver, hepatocellular carcinoma, cancer, liver, hepatocellular carcinoma |
| 189 | SEIAESHRF | liver, hepatocellular carcinoma, cancer, liver, hepatocellular carcinoma |
| 190 | YLAIGIHEL | liver, hepatocellular carcinoma, cancer, liver, hepatocellular carcinoma |
| 191 | IHDELQQSF | colon or rectum, spleen, chronic myeloid leukemia |
| 192 | AHVIDKFLL | kidney, renal cell carcinoma, |
| 193 | KAGGEFLLRY | kidney, renal cell carcinoma, |
| 194 | FENKDLLSL | kidney, clear cell renal cell carcinoma, brain, meningioma |
| 195 | FSKAKPSVL | liver, hepatocellular carcinoma, breast, infiltrating lobular carcinoma |
| 196 | EAIKALEV | stomach, metastatic, lung, neuroendocrine carcinoma |
| 197 | EVASAKQSVKY | stomach, metastatic, lung, neuroendocrine carcinoma |
| 198 | IEFTYTAKL | stomach, metastatic, lung, neuroendocrine carcinoma |
| 199 | LLADITSKY | stomach, metastatic, lung, neuroendocrine carcinoma |
| 200 | VLVDRTIYI | liver, hepatocellular carcinoma, liver, focal nodular hyperplasia |
| 201 | IPVVHASI | stomach, adenocarcinoma, colon, adenocarcinoma |
| 202 | TVADQVLVGSY | stomach, adenocarcinoma, colon, adenocarcinoma |
| 203 | VALVHPDL | stomach, adenocarcinoma, colon, adenocarcinoma |
| 204 | LPDDKVTAL | stomach, metastatic, stomach, adenocarcinoma |
| 205 | KIAKQIVQK | lung, non-small cell lung carcinoma, lung, neuroendocrine carcinoma |
| 206 | VEKILLSVV | lung, non-small cell lung carcinoma, lung, neuroendocrine carcinoma |
| 207 | APAGARGGPA | colon or rectum, rectum, adenocarcinoma |

TABLE 5-continued

Peptides according to the present invention and their specific uses in other proliferative diseases, optionally in other organs.

| Seq. ID | Sequence | Proliferative disease and location thereof |
|---|---|---|
| 208 | EHLRKLEAE | colon or rectum, rectum, adenocarcinoma |
| 209 | RFIPELINF | colon or rectum, rectum, adenocarcinoma |
| 210 | TEKIAQLF | stomach, adenocarcinoma, ovary, adenocarcinoma |
| 211 | KLHDETLTY | stomach, adenocarcinoma, ovary, adenocarcinoma |
| 212 | LHDETLTYL | stomach, adenocarcinoma, ovary, adenocarcinoma |
| 213 | GPQEGNGPSLF | colon or rectum, synovial sarcoma |
| 214 | YLLQRAVEV | colon or rectum, synovial sarcoma |
| 215 | FAALHGPAL | squamous cell carcinoma, |
| 216 | RMANLMGIEF | squamous cell carcinoma, |
| 217 | DTFPGPYAVL | liposarcoma |
| 218 | DTMPQTYKR | liposarcoma |
| 219 | IEHVFVTDV | colon or rectum, lymph node, infiltrating ductal carcinoma of breast |
| 220 | KESPTSVGF | colon or rectum, lymph node, infiltrating ductal carcinoma of breast |
| 221 | EAITAIMKY | kidney, clear cell renal cell carcinoma, spleen, non-Hodgkin's lymphoma |
| 222 | KEKPAENTL | kidney, clear cell renal cell carcinoma, spleen, non-Hodgkin's lymphoma |
| 223 | NEFQSQQNI | kidney, clear cell renal cell carcinoma, spleen, non-Hodgkin's lymphoma |
| 224 | NVIDYGHASKY | kidney, clear cell renal cell carcinoma, spleen, non-Hodgkin's lymphoma |
| 225 | FAKSQSKTF | atypical lipoma |
| 226 | LPFSLAHL | atypical lipoma |
| 227 | APNYRLKSL | stomach, adenocarcinoma, metastatic renal cell carcinoma |
| 228 | ILKDMGITEY | stomach, adenocarcinoma, metastatic renal cell carcinoma |
| 229 | AHDDGRWSL | stomach, metastatic, lung, squamous cell carcinoma |
| 230 | KYLTAEAFGF | stomach, metastatic, lung, squamous cell carcinoma |
| 231 | ESAALIHHY | liver, hepatocellular carcinoma, fibromatosis |
| 232 | YQRETPQV | liver, hepatocellular carcinoma, fibromatosis |
| 233 | EELQRNISL | kidney, clear cell renal cell carcinoma, ovary, adenocarcinoma |
| 234 | RPAALFLTL | kidney, clear cell renal cell carcinoma, ovary, adenocarcinoma |
| 235 | SEELQRNISL | kidney, clear cell renal cell carcinoma, ovary, adenocarcinoma |
| 236 | ETIDSRVQEY | colon or rectum, ovary, teratoma |

TABLE 5-continued

Peptides according to the present invention and their specific uses in other proliferative diseases, optionally in other organs.

| Seq. ID | Sequence | Proliferative disease and location thereof |
|---|---|---|
| 237 | EVSEQILHM | stomach, metastatic, lymph node, non-Hodgkin's lymphoma |
| 238 | GTLSGGILSSGK | stomach, differentiated subtype adenocarcinoma, uterine, cervix, squamous cell carcinoma |
| 239 | GVPIMLAY | brain, glioblastoma, uterine cervix, squamous cell carcinoma |
| 240 | EEVKEEVKKF | lung, non-small cell lung carcinoma, thymus, thymoma |
| 241 | KTIAFLLPMF | lung, non-small cell lung carcinoma, thymus, thymoma |
| 242 | EVTTNIPKM | liver, hepatocellular carcinoma, cancer, adenoid cystic carcinoma |
| 243 | IHGDTVQNQL | colon or rectum, adrenal gland, adrenal cortical carcinoma |
| 244 | RTMVKTLEY | colon or rectum, adrenal gland, adrenal cortical carcinoma |
| 245 | ETVRTLNNLY | brain, glioblastoma, omentum, leiomyosarcoma, metastatic |
| 246 | HSIDKVTSR | colon or rectum, parathyroid gland, adenoma |
| 247 | VSNPKSFEY | colon or rectum, parathyroid gland, adenoma |
| 248 | GLGPTFKL | lung, non-small cell lung carcinoma, stomach, adenocarcinoma |
| 249 | NKGISDIIKV | lung, non-small cell lung carcinoma, stomach, adenocarcinoma |
| 250 | TSTTRPVL | lung, non-small cell lung carcinoma, stomach, adenocarcinoma |
| 251 | VLGGKAFLEHL | stomach, endometrium, adenocarcinoma |
| 252 | YEFERTTSI | stomach, endometrium, adenocarcinoma |
| 253 | YLDFTNPKV | liver, hepatocellular carcinoma, uterine cervix, squamous cell carcinoma |
| 254 | IPAVARTTTL | pancreas, adenocarcinoma, myometrium, leiomyoma |
| 255 | KQQLELDSI | pancreas, adenocarcinoma, myometrium, leiomyoma |
| 256 | KTTDTVSSF | pancreas, adenocarcinoma, myometrium, leiomyoma |
| 257 | DYLDGVHTVF | colon or rectum, fibromatosis |
| 258 | YLDGVHTVF | colon or rectum, fibromatosis |
| 259 | TYVSGMLRF | brain, glioblastoma, breast, carcinoma |
| 260 | DAIDGKQAR | brain, glioblastoma, liver, focal nodular hyperplasia |
| 261 | DPMAPGVQGSLL | lung, non-small cell lung carcinoma, uterine cervix, squamous cell carcinoma |
| 262 | GLDPSQRPK | lung, non-small cell lung carcinoma, uterine cervix, squamous cell carcinoma |

TABLE 5-continued

Peptides according to the present invention and their specific uses in other proliferative diseases, optionally in other organs.

| Seq. ID | Sequence | Proliferative disease and location thereof |
|---|---|---|
| 263 | IEDSRVYEL | stomach, metastatic, non-Hodgkin's lymphoma |
| 264 | YVHSFLSSGY | small Intestine, gastrointestinal stromal tumor |
| 265 | HEYTTKEVF | liver, hepatocellular carcinoma, cancer, colon, adenocarcinoma |
| 266 | KLQEQLAQL | liver, hepatocellular carcinoma, cancer, colon, adenocarcinoma |
| 267 | SIAAKILSY | liver, hepatocellular carcinoma, cancer, colon, adenocarcinoma |
| 268 | KELLAVKL | pancreas, adenocarcinoma, lung, adenocarcinoma |
| 269 | KLKQTTSALEK | pancreas, adenocarcinoma, lung, adenocarcinoma |
| 270 | EVGPREAGLR | kidney, clear cell renal cell carcinoma, kidney, transitional cell carcinoma |
| 271 | SEAQEGLQKF | kidney, clear cell renal cell carcinoma, kidney, transitional cell carcinoma |
| 272 | DEAVLFVQV | pancreas, adenocarcinoma, ovary, mucinous cystadenocarcinoma |
| 273 | EVAKFLSFY | kidney, clear cell renal cell carcinoma, kidney, angiomyolipoma |
| 274 | KLDQKLPEL | kidney, clear cell renal cell carcinoma, kidney, angiomyolipoma |
| 275 | SVFEKSVGY | kidney, clear cell renal cell carcinoma, kidney, angiomyolipoma |
| 276 | NEGQTALHY | colon or rectum, endometrium, Mullerian mixed tumor |
| 277 | VEFPHSPEI | colon or rectum, endometrium, Mullerian mixed tumor |
| 278 | RLQGELQAV | kidney, clear cell renal cell carcinoma, kidney, renal cell carcinoma |
| 279 | KELRELLSI | colon or rectum, fibromatosis |
| 280 | SLVDQSAAL | colon or rectum, fibromatosis |
| 281 | LELIMSKY | colon or rectum, ovary, thecoma-fibroma |
| 282 | DIKPYIAEY | pancreas, adenocarcinoma, thymus, thymoma |
| 283 | KLMAMFLEY | lung, adenocarcinoma, |
| 284 | YTVEKREGY | lung, adenocarcinoma, |
| 285 | FEFDIHQVI | stomach, metastatic, breast, carcinoma |
| 286 | SENPSKHDSF | stomach, metastatic, breast, carcinoma |
| 287 | NFLRINTI | colon or rectum, stomach, adenocarcinoma |
| 288 | YSGPTSVSR | colon or rectum, stomach, adenocarcinoma |
| 289 | DIYGGDYERF | colon or rectum, adrenal gland, adrenal cortical carcinoma |
| 290 | SARLEKLGY | stomach, metastatic, prostate, benign nodular hyperplasia |

TABLE 5-continued

Peptides according to the present invention and their specific uses in other proliferative diseases, optionally in other organs.

| Seq. ID | Sequence | Proliferative disease and location thereof |
|---|---|---|
| 291 | YVFPGVTRL | stomach, metastatic, prostate, benign nodular hyperplasia |
| 292 | YYLNEIQSF | stomach, metastatic, prostate, benign nodular hyperplasia |
| 293 | YHSQDRYEF | stomach, metastatic, non-Hodgkin's lymphoma |
| 294 | FPPGRQVVM | brain, cancer, lymph node, malignant melanoma |
| 295 | ILDEAHERTI | brain, cancer, lymph node, malignant melanoma |
| 296 | VIYNEQMASK | liver, hepatocellular carcinoma, cancer, liver, focal nodular hyperplasia |
| 297 | EATSIKRVR | colon or rectum, adenocarcinoma |
| 298 | LPEDKPRLI | colon or rectum, adenocarcinoma |
| 299 | KYPLNLYLL | kidney, clear cell renal cell carcinoma, lipoma |
| 300 | VHESPALILLF | kidney, clear cell renal cell carcinoma, lipoma |
| 301 | EVTGHSKGY | stomach, adenocarcinoma, rectum, adenocarcinoma |
| 302 | RDSEELLQI | stomach, adenocarcinoma, rectum, adenocarcinoma |
| 303 | SPASKTTL | stomach, adenocarcinoma, rectum, adenocarcinoma |
| 304 | DAKTVNVI | colon or rectum, testis, seminoma |
| 305 | DSNATAAKM | colon or rectum, testis, seminoma |
| 306 | RTLNPQMLQK | colon or rectum, testis, seminoma |
| 307 | RTLNPQMLQKK | colon or rectum, testis, seminoma |
| 308 | LMAEMGVHSV | stomach, metastatic, breast, carcinoma |
| 309 | RLLPPVGTGR | stomach, metastatic, breast, carcinoma |
| 310 | VRIGTILIQTNQ | stomach, metastatic, breast, carcinoma |
| 311 | KELSVLSLI | stomach, metastatic, lung, neuroendocrine carcinoma |
| 312 | TQPHPNTVY | stomach, metastatic, lung, neuroendocrine carcinoma |
| 313 | ALEEQLLKY | stomach, adenocarcinoma, malignant fibrous histiocytoma |
| 314 | DHFTGAIEKL | stomach, metastatic, breast, carcinoma |
| 315 | KILDLETEL | stomach, metastatic, breast, carcinoma |
| 316 | AEDIPSLKL | breast, carcinoma |
| 317 | DIPSLKLAL | breast, carcinoma |
| 318 | GLDPNKPPEL | breast, carcinoma |
| 319 | FLRDPAEAL | breast, carcinoma |
| 320 | GYGSQGYKY | breast, carcinoma |
| 321 | KLLAEVTLK | breast, carcinoma |

TABLE 5-continued

Peptides according to the present invention and their specific uses in other proliferative diseases, optionally in other organs.

| Seq. ID | Sequence | Proliferative disease and location thereof |
|---|---|---|
| 322 | SAADGPRVF | breast, carcinoma |
| 323 | KLYELHVFTF | colon, adenoma |
| 324 | YELHVFTF | colon, adenoma |
| 325 | YLNKEIEEA | colon, adenoma |
| 326 | DENEHQLSL | stomach, adenocarcinoma, colon, non-Hodgkin's lymphoma |
| 327 | EITPPVVLR | stomach, adenocarcinoma, colon, non-Hodgkin's lymphoma |
| 328 | GFEITPPVVLR | stomach, adenocarcinoma, colon, non-Hodgkin's lymphoma |
| 329 | HQLSLRTV | stomach, adenocarcinoma, colon, non-Hodgkin's lymphoma |
| 330 | MSVQPTVSL | stomach, adenocarcinoma, lymph node, non-Hodgkin's lymphoma |
| 331 | SIRDTPAKN | stomach, adenocarcinoma, lymph node, non-Hodgkin's lymphoma |
| 332 | SIRDTPAKNAQK | stomach, adenocarcinoma, lymph node, non-Hodgkin's lymphoma |
| 333 | SPIKVTLATL | stomach, adenocarcinoma, lymph node, non-Hodgkin's lymphoma |
| 334 | TPPVVLRL | stomach, adenocarcinoma, colon, non-Hodgkin's lymphoma |
| 335 | VEAKFINY | stomach, adenocarcinoma, colon, non-Hodgkin's lymphoma |
| 336 | YEGSPIKV | stomach, adenocarcinoma, colon, non-Hodgkin's lymphoma |
| 337 | YEGSPIKVTL | stomach, adenocarcinoma, colon, non-Hodgkin's lymphoma |
| 338 | SELKMMTQL | lymph node, non-Hodgkin's lymphoma |
| 339 | EKDPQPQQL | lung, non-small cell lung carcinoma, schwannoma |
| 340 | GYVPRTAL | lung, non-small cell lung carcinoma, schwannoma |
| 341 | KEKDPQPQQL | lung, non-small cell lung carcinoma, schwannoma |
| 342 | LPKKPSKLEL | lung, non-small cell lung carcinoma, schwannoma |
| 343 | RPSAASIDL | lung, non-small cell lung carcinoma, schwannoma |
| 344 | SRHPLSPGF | lung, non-small cell lung carcinoma, schwannoma |
| 345 | TPRSPQPEL | lung, non-small cell lung carcinoma, schwannoma |
| 346 | GRIVAFFEF | kidney, clear cell renal cell carcinoma, thyroid gland, nodular hyperplasia |
| 347 | HTPHPAASR | kidney, clear cell renal cell carcinoma, thyroid gland, nodular hyperplasia |

TABLE 5-continued

Peptides according to the present invention and their specific uses in other proliferative diseases, optionally in other organs.

| Seq. ID | Sequence | Proliferative disease and location thereof |
|---|---|---|
| 348 | NPDELKTTV | lung, non-small cell lung carcinoma, testis, seminoma |
| 349 | PSKQLPDQI | lung, non-small cell lung carcinoma, testis, seminoma |
| 350 | VYVERAEVL | lung, non-small cell lung carcinoma, testis, seminoma |
| 351 | DPFIIIHSI | colon or rectum, uterine cervix, squamous cell carcinoma |
| 352 | EHSIATLLL | colon or rectum, uterine cervix, squamous cell carcinoma |
| 353 | FLDPRPLTV | pancreas, adenocarcinoma, myometrium, leiomyoma |
| 354 | SAFADRPAF | pancreas, adenocarcinoma, myometrium, leiomyoma |
| 355 | DTTLPASAR | stomach, adenocarcinoma, rectum, adenocarcinoma |
| 356 | KLLEYIEEI | stomach, adenocarcinoma, rectum, adenocarcinoma |
| 357 | LEKQLIEL | stomach, adenocarcinoma, rectum, adenocarcinoma |
| 358 | LMSVYVVEL | liver, hepatocellular carcinoma, cancer |
| 359 | ESITDVLVR | pancreas, adenocarcinoma, stomach, adenocarcinoma |
| 360 | ETAFQGMLR | pancreas, adenocarcinoma, stomach, adenocarcinoma, |
| 361 | EVPDVTATPARL | pancreas, adenocarcinoma, stomach, adenocarcinoma, |
| 362 | GRIVTLISF | pancreas, adenocarcinoma, stomach, adenocarcinoma, |
| 363 | HVFSDGVTNW | pancreas, adenocarcinoma, stomach, adenocarcinoma, |
| 364 | REIGGGEAGAVI | pancreas, adenocarcinoma, stomach, adenocarcinoma, |
| 365 | RGWDGFVEF | pancreas, adenocarcinoma, stomach, adenocarcinoma, |
| 366 | RPAVLPLL | pancreas, adenocarcinoma, stomach, adenocarcinoma, |
| 367 | VEFFHVEDL | pancreas, adenocarcinoma, stomach, adenocarcinoma, |
| 368 | VQRNHETAF | pancreas, adenocarcinoma, stomach, adenocarcinoma, |
| 369 | AELEAARL | lung, non-small cell lung carcinoma, testis, seminoma |
| 370 | ATQTPVSNK | colon or rectum, rectum, adenocarcinoma |
| 371 | ESIDQYIER | colon or rectum, rectum, adenocarcinoma |
| 372 | FEEHNSMNEL | colon or rectum, rectum, adenocarcinoma |
| 373 | SVASTPISQR | colon or rectum, rectum, adenocarcinoma |

TABLE 5-continued

Peptides according to the present invention and their specific uses in other proliferative diseases, optionally in other organs.

| Seq. ID | Sequence | Proliferative disease and location thereof |
|---|---|---|
| 374 | VASTPISQR | colon or rectum, rectum, adenocarcinoma |
| 375 | AEIVGGHEA | spleen, extramedullary hematopoiesis |
| 376 | RPPSPALASV | spleen, extramedullary hematopoiesis |
| 377 | SVAQVFLNNY | spleen, extramedullary hematopoiesis |
| 378 | TQEPTQQHF | spleen, extramedullary hematopoiesis |
| 379 | KDITMKNLV | kidney, clear cell renal cell carcinoma, colon, non-Hodgkin's lymphoma |
| 380 | MAEKAKQIY | kidney, clear cell renal cell carcinoma, colon, non-Hodgkin's lymphoma |
| 381 | KLDNQVSKV | colon or rectum, prostate, benign nodular hyperplasia |
| 382 | SENVKLFSA | colon or rectum, prostate, benign nodular hyperplasia |
| 383 | VQKLQNII | colon or rectum, prostate, benign nodular hyperplasia |
| 384 | AFTVHFSGQF | omentum, adenocarcinoma |
| 385 | GVFRGIQDV | omentum, adenocarcinoma |
| 386 | QRNMTKLQL | omentum, adenocarcinoma |
| 387 | RMFPNAPYL | omentum, adenocarcinoma |
| 388 | EAAAEAKAR | lymph node, carcinoma of breast |
| 389 | IIKEYTDVY | lymph node, carcinoma of breast |
| 390 | KEIDKNDHL | lymph node, carcinoma of breast |
| 391 | KVSKASGVSK | lymph node, carcinoma of breast |
| 392 | MPATETKKV | lymph node, carcinoma of breast |
| 393 | NADPQAVTM | lymph node, carcinoma of breast |
| 394 | RSDMLKDII | lymph node, carcinoma of breast |
| 395 | SESGAGLTRF | lymph node, carcinoma of breast |
| 396 | SMMQTLLTV | lymph node, carcinoma of breast |
| 397 | TEVSKTPEA | lymph node, carcinoma of breast |
| 398 | VEVPETPKA | lymph node, carcinoma of breast |
| 399 | DVYPEIIER | brain, glioblastoma, lymph node, carcinoma of breast |
| 400 | REVEIQSHL | stomach, adenocarcinoma, stomach, adenocarcinoma |
| 401 | EPPAVLLL | lung, non-small cell lung carcinoma, omentum, adenocarcinoma |
| 402 | LEADPFLKY | lung, non-small cell lung carcinoma, omentum, adenocarcinoma |
| 403 | TTQGQDVTLA | stomach, adenocarcinoma, lung, adenocarcinoma |
| 404 | AEYEDGFSIP | pancreas, adenocarcinoma, bone, osteosarcoma |

TABLE 5-continued

Peptides according to the present invention and their specific uses in other proliferative diseases, optionally in other organs.

| Seq. ID | Sequence | Proliferative disease and location thereof |
|---|---|---|
| 405 | AQISLPRI | spleen, chronic myeloid leukemia |
| 406 | DFTPEPAAR | spleen, chronic myeloid leukemia |
| 407 | DNTGITTVSK | spleen, chronic myeloid leukemia |
| 408 | EEAKQLVDKAY | spleen, chronic myeloid leukemia |
| 409 | ERRESIKQ | spleen, chronic myeloid leukemia |
| 410 | ETVGQLGTVLR | spleen, chronic myeloid leukemia |
| 411 | FEQVMRIGL | spleen, chronic myeloid leukemia |
| 412 | FSMQQRQAL | spleen, chronic myeloid leukemia |
| 413 | GVPFFSSLR | spleen, chronic myeloid leukemia |
| 414 | IVRFPTDQL | spleen, chronic myeloid leukemia |
| 415 | KQPVAATRTAV | spleen, chronic myeloid leukemia |
| 416 | LGASNRAFV | spleen, chronic myeloid leukemia |
| 417 | NPRWDGERL | spleen, chronic myeloid leukemia |
| 418 | NVFTNAFRY | spleen, chronic myeloid leukemia |
| 419 | QPMEPNPRVPL | spleen, chronic myeloid leukemia |
| 420 | QPVAATRTAV | spleen, chronic myeloid leukemia |
| 421 | RLFEQVMRI | spleen, chronic myeloid leukemia |
| 422 | SEEPLARNL | spleen, chronic myeloid leukemia |
| 423 | TIRNQINAL | spleen, chronic myeloid leukemia |
| 424 | VLGPTAMRK | spleen, chronic myeloid leukemia |
| 425 | AELRNATAA | pancreas, adenocarcinoma, breast, carcinoma |
| 426 | DVPDGTLVTVM | pancreas, adenocarcinoma, breast, carcinoma |
| 427 | LPIAFKVV | pancreas, adenocarcinoma, breast, carcinoma |
| 428 | SAMGSATRY | pancreas, adenocarcinoma, breast, carcinoma |
| 429 | AEKQGHQW | stomach, metastatic, ovary, granulosa cell tumor |
| 430 | GEQKPTGTF | stomach, metastatic, ovary, granulosa cell tumor |
| 431 | GQFSKPFSF | stomach, metastatic, ovary, granulosa cell tumor |
| 432 | IAFFDVRTF | stomach, metastatic, ovary, granulosa cell tumor |
| 433 | LSAGKTSFSF | stomach, metastatic, ovary, granulosa cell tumor |
| 434 | VSNKYGLVF | stomach, metastatic, ovary, granulosa cell tumor |
| 435 | GEVDVEQHTL | colon or rectum, colon, adenocarcinoma |
| 436 | VDVEQHTL | colon or rectum, colon, adenocarcinoma |
| 437 | DAADELSVGRY | kidney, clear cell renal cell carcinoma, colon, adenoma |

TABLE 5-continued

Peptides according to the present invention and their specific uses in other proliferative diseases, optionally in other organs.

| Seq. ID | Sequence | Proliferative disease and location thereof |
| --- | --- | --- |
| 438 | LSEADVRA | stomach, adenocarcinoma, lung, adenocarcinoma |
| 439 | ELTLGEFLK | stomach, metastatic, ovary, Mullerian mixed tumor |
| 440 | ELTLGEFLKL | stomach, metastatic, ovary, Mullerian mixed tumor |
| 441 | LTLGEFLK | stomach, metastatic, ovary, Mullerian mixed tumor |
| 442 | LTLGEFLKL | stomach, metastatic, ovary, Mullerian mixed tumor |
| 443 | TLGEFLKL | stomach, metastatic, ovary, Mullerian mixed tumor |
| 444 | KTYTKSSHLK | stomach, adenocarcinoma, brain, meningioma |
| 445 | SQLTTLSFY | lung, non-small cell lung carcinoma, omentum, adenocarcinoma |
| 446 | KMQEKKKLQ | liver, hepatocellular carcinoma, lung, large cell carcinoma |
| 447 | LLGHLPAEI | liver, hepatocellular carcinoma, lung, large cell carcinoma |
| 448 | APVELILSDETLPAPE | liver, hepatocellular carcinoma, cancer |
| 449 | ETPDFQLFKNGVAQEPV | liver, hepatocellular carcinoma, cancer |
| 450 | LAPLEGARFALVRED | liver, hepatocellular carcinoma, cancer |
| 451 | SPDRIFFHLNAVALGD | liver, hepatocellular carcinoma, cancer |
| 452 | SPDRIFFHLNAVALGDG | liver, hepatocellular carcinoma, cancer |
| 453 | EEMRKLQATVQELQKR | lymph node, non-Hodgkin's lymphoma |
| 454 | EEPLSLQELDTSSG | lymph node, non-Hodgkin's lymphoma |
| 455 | EMRKLQATVQELQKR | lymph node, non-Hodgkin's lymphoma |
| 456 | HLEEPLSLQELDTSSG | lymph node, non-Hodgkin's lymphoma |
| 457 | LEEPLSLQELDTSSG | lymph node, non-Hodgkin's lymphoma |
| 462 | GVVHSFSHNVGPGDK | liver, hepatocellular carcinoma, cancer, lung, adenocarcinoma |
| 463 | GVVHSFSHNVGPGDKY | liver, hepatocellular carcinoma, cancer, lung, adenocarcinoma |
| 464 | GVVHSFSHNVGPGDKYT | liver, hepatocellular carcinoma, cancer, lung, adenocarcinoma |
| 465 | KTEEFEVTKTAVAHRP | liver, hepatocellular carcinoma, cancer, lung, adenocarcinoma |
| 466 | KTEEFEVTKTAVAHRPG | liver, hepatocellular carcinoma, cancer, lung, adenocarcinoma |
| 467 | VRPGGVVHSFSHNVGPGDK | liver, hepatocellular carcinoma, cancer, lung, adenocarcinoma |
| 468 | VRPGGVVHSFSHNVGPGDKYT | liver, hepatocellular carcinoma, cancer, lung, adenocarcinoma |
| 469 | AEKGVRTLTAAAVSGAQ | pancreas, adenocarcinoma, bone, giant cell tumor of bone |

TABLE 5-continued

Peptides according to the present invention and their specific uses in other proliferative diseases, optionally in other organs.

| Seq. ID | Sequence | Proliferative disease and location thereof |
|---|---|---|
| 470 | AQPILSKLEPQIASASE | pancreas, adenocarcinoma, bone, giant cell tumor of bone |
| 471 | EKGVRTLTAAAVSGAQ | pancreas, adenocarcinoma, bone, giant cell tumor of bone |
| 472 | EKGVRTLTAAAVSGAQP | pancreas, adenocarcinoma, bone, giant cell tumor of bone |
| 473 | GVRTLTAAAVSGAQ | pancreas, adenocarcinoma, bone, giant cell tumor of bone |
| 474 | KGVRTLTAAAVSGAQ | pancreas, adenocarcinoma, bone, giant cell tumor of bone |
| 475 | DVNEYAPVFKEKSYK | brain, glioblastoma, parotid gland, pleomorphic adenoma |
| 476 | HRSFVDLSGHNLA | brain, glioblastoma, parotid gland, pleomorphic adenoma |
| 477 | HRSFVDLSGHNLANPH | brain, glioblastoma, parotid gland, pleomorphic adenoma |
| 478 | HRSFVDLSGHNLANPHP | brain, glioblastoma, parotid gland, pleomorphic adenoma |
| 479 | ALPEFDGKRFQNVAKEG | liver, hepatocellular carcinoma, cancer, thyroid gland, nodular hyperplasia |
| 480 | DSNEFSVIADPRG | liver, hepatocellular carcinoma, cancer, thyroid gland, nodular hyperplasia |
| 481 | DSNEFSVIADPRGN | liver, hepatocellular carcinoma, cancer, thyroid gland, nodular hyperplasia |
| 482 | DSNEFSVIADPRGNT | liver, hepatocellular carcinoma, cancer, thyroid gland, nodular hyperplasia |
| 483 | DSNEFSVIADPRGNTL | liver, hepatocellular carcinoma, cancer, thyroid gland, nodular hyperplasia |
| 484 | DSNEFSVIADPRGNTLG | liver, hepatocellular carcinoma, cancer, thyroid gland, nodular hyperplasia |
| 485 | PEFDGKRFQNVAK | liver, hepatocellular carcinoma, cancer, thyroid gland, nodular hyperplasia |
| 486 | SDSNEFSVIADPRGNTLG | liver, hepatocellular carcinoma, cancer, thyroid gland, nodular hyperplasia |
| 487 | SQKKTFEINPRHPLIR | liver, hepatocellular carcinoma, cancer, thyroid gland, nodular hyperplasia |
| 488 | ALPEFDGKRFQNVAKEG | liver, hepatocellular carcinoma, cancer, thyroid gland, nodular hyperplasia |
| 489 | PEFDGKRFQNVAK | liver, hepatocellular carcinoma, cancer, thyroid gland, nodular hyperplasia |
| 490 | PEFDGKRFQNVAKE | liver, hepatocellular carcinoma, cancer, thyroid gland, nodular hyperplasia |
| 491 | LNSLTYQVLDVQRYP | kidney, clear cell renal cell carcinoma, endometrium, adenocarcinoma |
| 492 | LPQLVGVSTPLQG | kidney, clear cell renal cell carcinoma, endometrium, adenocarcinoma |
| 493 | LPQLVGVSTPLQGG | kidney, clear cell renal cell carcinoma, endometrium, adenocarcinoma |

TABLE 5-continued

Peptides according to the present invention and their specific uses in other proliferative diseases, optionally in other organs.

| Seq. ID | Sequence | Proliferative disease and location thereof |
|---|---|---|
| 494 | LPQLVGVSTPLQGGS | kidney, clear cell renal cell carcinoma, endometrium, adenocarcinoma |
| 495 | RLPQLVGVSTPLQGGS | kidney, clear cell renal cell carcinoma, endometrium, adenocarcinoma |
| 496 | SDVDLIPMNDHNAYR | kidney, clear cell renal cell carcinoma, endometrium, adenocarcinoma |
| 497 | GRRKSRQGSLAMEELK | rectum, adenocarcinoma |
| 498 | RKSRQGSLAMEELK | rectum, adenocarcinoma |
| 499 | SGPSLKGEEEPLVASEDGAVD | rectum, adenocarcinoma |
| 500 | SGSGPSLKGEEEPLVASEDGAVD | rectum, adenocarcinoma |
| 501 | IKPGVTTEEIDHAVH | endometrium, adenocarcinoma |
| 502 | KPGVTTEEIDHAVH | endometrium, adenocarcinoma |
| 503 | DGVLRIQNLDQS | pancreas, adenocarcinoma, myometrium, leiomyoma |
| 504 | GAYFHDDGFLAFPG | pancreas, adenocarcinoma, myometrium, leiomyoma |
| 505 | TPYSFLPLPTIKDAYR | pancreas, adenocarcinoma, myometrium, leiomyoma |
| 506 | YPTPDISWSKLDGSLPP | pancreas, adenocarcinoma, myometrium, leiomyoma |
| 507 | YPTPDISWSKLDGSLPPD | pancreas, adenocarcinoma, myometrium, leiomyoma |
| 508 | ASHFEQMAAASMHR | metastatic renal cell carcinoma |
| 509 | GGQVIVAIPKLQTQQ | parathyroid gland, adenoma |
| 510 | GQVIVAIPKLQTQ | parathyroid gland, adenoma |
| 511 | GQVIVAIPKLQTQQ | parathyroid gland, adenoma |
| 512 | IESTFDVVSSKPVG | parathyroid gland, adenoma |
| 513 | DWGALATISTLEAVRG | lung, non-small cell lung carcinoma, liver, hepatocellular carcinoma |
| 514 | GRPFADVLSLSDGPPG | lung, non-small cell lung carcinoma, liver, hepatocellular carcinoma |
| 515 | WGALATISTLEAVR | lung, non-small cell lung carcinoma, liver, hepatocellular carcinoma |
| 516 | WGALATISTLEAVRG | lung, non-small cell lung carcinoma, liver, hepatocellular carcinoma |
| 517 | ADELALVDVIEDK | kidney, clear cell renal cell carcinoma, kidney, renal cell carcinoma |
| 518 | GVSLKTLHPDLGTDK | kidney, clear cell renal cell carcinoma, kidney, renal cell carcinoma |
| 519 | IVSGKDYNVTANSKL | kidney, clear cell renal cell carcinoma, kidney, renal cell carcinoma |
| 520 | DDNIKTYSDHPEK | kidney, clear cell renal cell carcinoma, liver, hepatocellular carcinoma |
| 521 | DKVYVHLKNLASRPY | kidney, clear cell renal cell carcinoma, liver, hepatocellular carcinoma |

TABLE 5-continued

Peptides according to the present invention and their specific uses in other proliferative diseases, optionally in other organs.

| Seq. ID | Sequence | Proliferative disease and location thereof |
|---|---|---|
| 522 | GDKVYVHLKNLASRPY | kidney, clear cell renal cell carcinoma, liver, hepatocellular carcinoma |
| 523 | LDDNIKTYSDHPEK | kidney, clear cell renal cell carcinoma, liver, hepatocellular carcinoma |
| 524 | TGDKVYVHLKNLASRPY | kidney, clear cell renal cell carcinoma, liver, hepatocellular carcinoma |
| 525 | VYVHLKNLASRPY | kidney, clear cell renal cell carcinoma, liver, hepatocellular carcinoma |
| 526 | KTSRLPIIDVAPLDVGAPD | pancreas, adenocarcinoma, chondrosarcoma |
| 527 | KTSRLPIIDVAPLDVGAPDQE | pancreas, adenocarcinoma, chondrosarcoma |
| 528 | LPIIDVAPLDVGAPD | pancreas, adenocarcinoma, chondrosarcoma |
| 529 | RLPIIDVAPLDVGAPD | pancreas, adenocarcinoma, chondrosarcoma |
| 530 | RLPIIDVAPLDVGAPDQE | pancreas, adenocarcinoma, chondrosarcoma |
| 531 | SRLPIIDVAPLDVGAPD | pancreas, adenocarcinoma, chondrosarcoma |
| 532 | SRLPIIDVAPLDVGAPDQE | pancreas, adenocarcinoma, chondrosarcoma |
| 533 | TSRLPIIDVAPLDVGAPD | pancreas, adenocarcinoma, chondrosarcoma |
| 534 | TSRLPIIDVAPLDVGAPDQE | pancreas, adenocarcinoma, chondrosarcoma |
| 535 | DTSYVSLKAPLT | liver, hepatocellular carcinoma, cancer |
| 536 | DTSYVSLKAPLTKP | liver, hepatocellular carcinoma, cancer |
| 537 | DTSYVSLKAPLTKPL | liver, hepatocellular carcinoma, cancer |
| 538 | ESDTSYVSLKAPLT | liver, hepatocellular carcinoma, cancer |
| 539 | ESDTSYVSLKAPLTKPL | liver, hepatocellular carcinoma, cancer |
| 540 | SDTSYVSLKAPLT | liver, hepatocellular carcinoma, cancer |
| 541 | SDTSYVSLKAPLTKP | liver, hepatocellular carcinoma, cancer |
| 542 | SDTSYVSLKAPLTKPL | liver, hepatocellular carcinoma, cancer |
| 543 | DPASFRAAIGLLARH | kidney, clear cell renal cell carcinoma, colon, adenocarcinoma |
| 544 | TEGQFVDLTGNRLTYT | liver, hepatocellular carcinoma, cancer, liver, focal nodular hyperplasia |
| 545 | ALDFFGNGPPVNYK | lung, non-small cell lung carcinoma, |
| 546 | ALDFFGNGPPVNYKTG | lung, non-small cell lung carcinoma, bone, non-ossifying fibroma |
| 547 | DFFGNGPPVNYKTG | lung, non-small cell lung carcinoma, bone, non-ossifying fibroma |
| 548 | LDFFGNGPPVNYK | lung, non-small cell lung carcinoma, bone, non-ossifying fibroma |
| 549 | LDFFGNGPPVNYKTG | lung, non-small cell lung carcinoma, bone, non-ossifying fibroma |
| 550 | QALDFFGNGPPVNYKTG | lung, non-small cell lung carcinoma, bone, non-ossifying fibroma |
| 551 | AISDYVFNTASLVYH | liver, hepatocellular carcinoma, cancer |
| 552 | AISDYVFNTASLVYHEE | liver, hepatocellular carcinoma, cancer |

TABLE 5-continued

Peptides according to the present invention and their specific uses in other proliferative diseases, optionally in other organs.

| Seq. ID | Sequence | Proliferative disease and location thereof |
|---|---|---|
| 553 | ISDYVFNTASLVYH | liver, hepatocellular carcinoma, cancer |
| 554 | ISDYVFNTASLVYHEE | liver, hepatocellular carcinoma, cancer |
| 555 | YVFNTASLVYHEE | liver, hepatocellular carcinoma, cancer |
| 556 | IVIALSGNKADLA | brain, glioblastoma, endometrium, adenocarcinoma |
| 557 | SPNIVIALSGNKADL | brain, glioblastoma, endometrium, adenocarcinoma |
| 558 | SPNIVIALSGNKADLA | brain, glioblastoma, endometrium, adenocarcinoma |
| 559 | TPPRLVAPRFLEVE | stomach, metastatic, non-Hodgkin's lymphoma |
| 560 | TPPRLVAPRFLEVET | stomach, metastatic, non-Hodgkin's lymphoma |
| 561 | TPPRLVAPRFLEVETS | stomach, metastatic, non-Hodgkin's lymphoma |
| 562 | EIQRDILLEKKKVAQDQ | stomach, metastatic, liver, hepatic adenoma |
| 563 | FGAIFFLPDSSK | stomach, metastatic, liver, hepatic adenoma |
| 564 | IQRDILLEKKKVAQ | stomach, metastatic, liver, hepatic adenoma |
| 565 | IQRDILLEKKKVAQD | stomach, metastatic, liver, hepatic adenoma |
| 566 | IQRDILLEKKKVAQDQ | stomach, metastatic, liver, hepatic adenoma |
| 567 | LSGVLFHSSPALQPA | stomach, metastatic, liver, hepatic adenoma |
| 568 | RDILLEKKKVAQDQ | stomach, metastatic, liver, hepatic adenoma |
| 569 | SSKLLSGVLFHSSPA | stomach, metastatic, liver, hepatic adenoma |
| 570 | SSPALQPAADHKPGPG | stomach, metastatic, liver, hepatic adenoma |
| 571 | APPTRGPPPSYGGS | colon or rectum, thymus, thymoma, |
| 572 | GNSRSAPPTRGPPPSYGGSSRY | colon or rectum, thymus, thymoma, |
| 573 | RDYGHSSSRDDYPS | colon or rectum, thymus, thymoma, |
| 574 | SPRDDGYSTKDSY | colon or rectum, thymus, thymoma, |
| 575 | GGSAAAAAAAAASGG | liver, hepatocellular carcinoma, myometrium, leiomyoma |
| 576 | DNMLLAEGVSGPEK | liver, hepatocellular carcinoma, adrenal gland, adrenal cortical adenoma |
| 577 | ADSLYVEKIDVGEAEPR | esophagus, adenocarcinoma |
| 578 | RIQLVEEELDRAQER | pancreas, adenocarcinoma, intramuscular lipoma |
| 579 | RRIQLVEEELDRAQER | pancreas, adenocarcinoma, intramuscular lipoma |
| 580 | HQPHKVTQYKKGKDSLY | liposarcoma |
| 581 | RKKAKTTKKIVL | liposarcoma |
| 582 | DVFRQYASLTGTQALPP | liver, hepatocellular carcinoma, cancer, small intestine, gastrointestinal stromal tumor |
| 583 | GTAQGELFLDDGHT | liver, hepatocellular carcinoma, cancer, small intestine, gastrointestinal stromal tumor |

TABLE 5-continued

Peptides according to the present invention and their specific uses in other proliferative diseases, optionally in other organs.

| Seq. ID | Sequence | Proliferative disease and location thereof |
|---|---|---|
| 584 | VFRQYASLTGTQALPP | liver, hepatocellular carcinoma, cancer, small intestine, gastrointestinal stromal tumor |
| 585 | PEFDGKRFQNVAK | liver, hepatocellular carcinoma, cancer, thyroid gland, nodular hyperplasia |
| 586 | PEFDGKRFQNVAKE | liver, hepatocellular carcinoma, cancer, thyroid gland, nodular hyperplasia |
| 587 | ALPEFDGKRFQNVAKEG | liver, hepatocellular carcinoma, cancer, thyroid gland, nodular hyperplasia |
| 588 | ASPSESEARFRIDSVSEGNAGPY | pancreas, adenocarcinoma, lipoma |
| 589 | EARFRIDSVSEGNAGP | pancreas, adenocarcinoma, lipoma |
| 590 | ESEARFRIDSVSEGNAGP | pancreas, adenocarcinoma, lipoma |
| 591 | ESEARFRIDSVSEGNAGPY | pancreas, adenocarcinoma, lipoma |
| 592 | PRIDSVSEGNAGP | pancreas, adenocarcinoma, lipoma |
| 593 | PRIDSVSEGNAGPY | pancreas, adenocarcinoma, lipoma |
| 594 | SEARFRIDSVSEGNAGPY | pancreas, adenocarcinoma, lipoma |
| 595 | SPSESEARFRIDSVSEGNAGPY | pancreas, adenocarcinoma, lipoma |
| 596 | GNQLFRINEANQL | stomach, adenocarcinoma, prostate, adenocarcinoma |
| 597 | GNQLFRINEANQLMQ | stomach, adenocarcinoma, prostate, adenocarcinoma |
| 598 | SPAMAGGLFAIERE | stomach, adenocarcinoma, prostate, adenocarcinoma |
| 599 | FIGNIAVNHAPVSPR | stomach, adenocarcinoma, metastatic carcinoma of breast |
| 600 | FIGNIAVNHAPVSPRPG | stomach, adenocarcinoma, metastatic carcinoma of breast |
| 601 | IGNIAVNHAPVSPRP | stomach, adenocarcinoma, metastatic carcinoma of breast |
| 602 | IGNIAVNHAPVSPRPG | stomach, adenocarcinoma, metastatic carcinoma of breast |
| 603 | FEGQFSINKVPGNFH | kidney, clear cell renal cell carcinoma, prostate, adenocarcinoma |
| 604 | FEGQFSINKVPGNFHVS | kidney, clear cell renal cell carcinoma, prostate, adenocarcinoma |
| 605 | RFEGQFSINKVPGNFH | kidney, clear cell renal cell carcinoma, prostate, adenocarcinoma |

Thus, another aspect of the present invention relates to the use of the peptides according to the present invention for the—preferably combined—treatment of a proliferative disease selected from the group of atypical lipoma;

brain cancer and a proliferative disease selected from kidney oncocytoma and lymph node malignant melanoma; glioblastoma, and a proliferative disease selected from bone non-ossifying fibroma, meningioma, breast carcinoma, endometrial adenocarcinoma, omentum leiomyosarcoma, parotid gland pleomorphic adenoma, skin squamous cell carcinoma, thyroid gland nodular hyperplasia, and uterine cervix squamous cell carcinoma;

breast lobular carcinoma;

breast intraductal carcinoma;

colon or rectal cancer, and a proliferative disease selected from adenocarcinoma, adrenal cortical carcinoma, breast mucinous carcinoma, adenocarcinoma, endometrium Mullerian mixed tumor, fibromatosis, kidney carcinoma, liver focal nodular hyperplasia, liver hepatocellular carcinoma, lung small cell carcinoma, lung squamous cell carcinoma, carcinoma of breast, lymph node non-Hodgkin's lymphoma, metastatic renal cell carcinoma, myometrium leiomyoma, ovary teratoma, ovary thecoma-fibroma, parathyroid gland adenoma, prostate benign nodular hyperplasia, rectum adenocarcinoma, spleen chronic myeloid leukemia, spleen extramedullary hematopoiesis, stomach adenocarcinoma, synovial sarcoma, testis seminoma, thymus thymoma, and uterine cervix squamous cell carcinoma; colon adenoma;
  endometrium adenocarcinoma;
  esophagus, adenocarcinoma;
  kidney angiomyolipoma;
  kidney clear cell renal cell carcinoma and a proliferative disease selected from bone non-ossifying fibroma, brain meningioma, colon adenocarcinoma, colon adenoma, colon non-Hodgkin's lymphoma;
  kidney clear cell renal cell carcinoma and a proliferative disease selected from endometrium adenocarcinoma, kidney angiomyolipoma, kidney polycystic kidney disease, kidney transitional cell carcinoma, lipoma non-Hodgkin's lymphoma, ovary adenocarcinoma, parotid gland pleomorphic adenoma, prostate adenocarcinoma, spleen non-Hodgkin's lymphoma, stomach gastrointestinal stromal tumor (GIST), synovial sarcoma, and thyroid gland nodular hyperplasia;
  kidney, renal cell carcinoma; e.g. of the non-clear cell type;
  liposarcoma;
  liver focal nodular hyperplasia;
  liver, hepatocellular carcinoma and a proliferative disease selected from adrenal gland adrenal cortical adenoma, breast carcinoma, adenoid cystic carcinoma, colon adenocarcinoma, liver focal nodular hyperplasia, liver hepatocellular carcinoma, lung adenocarcinoma, pancreas adenocarcinoma, parotid gland pleomorphic adenoma, small intestine gastrointestinal stromal tumor, thyroid gland nodular hyperplasia, fibromatosis, kidney angiomyolipoma, kidney renal cell carcinoma, liver focal nodular hyperplasia, lung large cell carcinoma, myometrium leiomyoma, and uterine cervix squamous cell carcinoma; lung adenocarcinoma;
  lung non-small cell lung carcinoma and a proliferative disease selected from bone non-ossifying fibroma, kidney carcinoma, liver hepatocellular carcinoma, lung adenocarcinoma, lung neuroendocrine carcinoma, omentum, adenocarcinoma, schwannoma, spleen chronic myeloid leukemia, spleen extramedullary hematopoiesis, stomach adenocarcinoma, testis seminoma, thymus thymoma, and uterine cervix squamous cell carcinoma;
  lymph node infiltrating carcinoma of breast;
  lymph node non-Hodgkin's lymphoma;
  malignant fibrous histiocytoma;
  metastatic infiltrating carcinoma of breast;
  metastatic renal cell carcinoma;
  omentum adenocarcinoma;
  ovary adenocarcinoma clear cell type;
  ovary granulosa cell tumor;
  pancreas adenocarcinoma and a proliferative disease selected from bone giant cell tumor of bone, bone osteosarcoma, breast carcinoma, chondrosarcoma, intramuscular lipoma, lipoma, lung adenocarcinoma, lymph node Hodgkin's disease, myometrium, leiomyoma, ovary mucinous cystadenocarcinoma, stomach adenocarcinoma, and thymus thymoma;
  parathyroid gland adenoma;
  prostate adenocarcinoma;
  rectum adenocarcinoma;
  small intestine gastrointestinal stromal tumor;
  spleen chronic myeloid leukemia;
  spleen extramedullary hematopoiesis;
  squamous cell carcinoma;
  stomach adenocarcinoma and a proliferative disease selected from, brain meningioma, liver carcinoid tumor metastatic, prostate adenocarcinoma, and spleen chronic myeloid leukemia;
  stomach differentiated subtype adenocarcinoma and a proliferative disease selected from colon adenocarcinoma, colon non-Hodgkin's lymphoma, endometrium adenocarcinoma, kidney Wilm's tumor, lung adenocarcinoma, lung small cell carcinoma, lymph node non-Hodgkin's lymphoma, malignant fibrous histiocytoma, metastatic infiltrating lobular carcinoma of breast, parathyroid gland adenoma, rectum adenocarcinoma, stomach adenocarcinoma, testis seminoma, and uterine cervix squamous cell carcinoma;
  stomach adenocarcinoma, and a proliferative disease selected from lung adenocarcinoma, metastatic renal cell carcinoma, myometrium leiomyoma, non-Hodgkin's lymphoma, mycosis fungoides, ovary adenocarcinoma, pancreas adenocarcinoma, and white blood cells chronic lymphocytic leukemia;
  stomach endometrium, adenocarcinoma;
  metastatic stomach cancer, and a proliferative disease selected from adenocarcinoma, bone non-ossifying fibroma, breast carcinoma, duodenum adenocarcinoma, liver hepatic adenoma, lung large cell carcinoma, lung neuroendocrine carcinoma, lung squamous cell carcinoma, lymph node non-Hodgkin's lymphoma, ovary granulosa cell tumor, ovary Mullerian mixed tumor, pancreas adenocarcinoma, prostate benign nodular hyperplasia, rectum adenocarcinoma, and basal cell carcinoma;
  thyroid gland nodular hyperplasia;
  and uterine cervix squamous cell carcinoma.

ACBD6 encodes a modular protein that carries an acyl-CoA binding domain at its N terminus and two ankyrin motifs at its C terminus. ACBD6 expression is restricted to tissues and progenitor cells with functions in blood and vessel development. ACBD6 was detected in bone marrow, spleen, placenta, cord blood, circulating CD34+ progenitors, and embryonic-like stem cells derived from placenta (Soupene et al., 2008).

BRAP encodes the BRCA1 associated protein, which was identified by its ability to bind to the nuclear localization signal of BRCA1 and other proteins. It is a cytoplasmic protein which may regulate nuclear targeting by retaining proteins with a nuclear localization signal in the cytoplasm (RefSeq, 2002). BRAP has been described as leukemia-associated antigen (Greiner et al., 2003).

CDCA7L encodes the protein cell division cycle associated 7-like, which interacts with the oncogene c-Myc and potentiates its transforming activity (Huang et al., 2005). CDCA7L is strongly up-regulated in hepatocellular carcinoma and ectopic over-expression of CDCA7L promotes hepatocellular carcinoma cell proliferation and colony formation (Tian et al., 2013).

CHTF18 encodes a protein which together with CHTF8 and DCC1 is a component of an alternative replication factor C complex that loads PCNA onto DNA during S phase of the cell cycle (RefSeq, 2002). CHTF18 together with the other genes of the replication factor C complex can induce synthetic lethal genetic interactions that decrease somatic cell proliferation in Caenorhabditis elegans. Due to this fact CHTF18 was identified as a candidate cancer drug target (McLellan et al., 2009). The co-occurrence of somatic mutations in ESCO1 and CHTF18 was statistically significant in non-endometrioid endometrial tumors (Price et al., 2014).

KIF15 encodes kinesin family member 15, a protein involved in the assembly and the stabilization of the mitotic spindle (Vanneste et al., 2009). In breast cancer, KIF15 was shown to be over-expressed and to be immunogenic, as anti-KIF15 antibodies could be isolated from breast cancer patients (Scanlan et al., 2001). Furthermore, KIF15 appears to be implicated in lung adenocarcinoma (Bidkhori et al., 2013).

NOP14 encodes a protein that plays a role in pre-18s rRNA processing and small ribosomal subunit assembly (RefSeq, 2002). Mutations within the NOP14 gene and abnormal expression has been detected in pancreatic cancer. In pancreatic cancer cells, NOP14 over-expression promotes migration, proliferation and colony formation (Zhou et al., 2012b; Zhou et al., 2012a). Down-regulation of NOP14 expression in whole blood samples of ovarian cancer patients correlated with poor prognosis (Isaksson et al., 2014).

NUDCD1 encodes NudC domain containing 1 known as well as ovarian cancer-associated antigen 66 (OVA66) (RefSeq, 2002). In human cancer cells, NUDCD1 influences tumorigenesis by regulating the type I insulin-like growth factor receptor (IGF-1R) signaling pathway (Rao et al., 2014a). NUDCD1 induces oncogenic transformation of NIH3T3, the mouse embryonic fibroblast cell line (Rao et al., 2014b).

PRIM1 encodes a protein which is the small 49 kDa primase subunit. Primase and DNA polymerase alpha are the two key enzymatic components for DNA replication in eukaryotic cells (RefSeq, 2002). PRIM1 was found to be amplified in 41% of 22 pediatric osteosarcoma samples. PRIM1 is co-amplified with the core 12q13 amplicon genes CDK4, SAS, and OS9, and was physically mapped very close to them (Yotov et al., 1999). The up-regulation of SIX1 expression in cervical cancer results in the up-regulation of multiple genes related to the initiation of DNA replication including PRIM1 (Liu et al., 2014).

QTRTD1 encodes a subunit of tRNA-guanine transglycosylase which plays a critical role in tRNA modification by synthesizing the 7-deazaguanosine queuosine. The encoded protein may play a role in the queuosine 5'-monophosphate salvage pathway (RefSeq, 2002).

SDAD1 encodes a poorly characterized protein, which might be involved in rRNA processing. Single nucleotide polymorphisms within the SDAD1 gene were shown to be associated with seasonal allergic rhinitis (Babbio et al., 2004; Zhang et al., 2005).

TARBP1 encodes the TAR (HIV-1) RNA binding protein 1 a double stranded RNA binding protein, which might disengage RNA polymerase II from HIV-1 TAR during transcriptional elongation (RefSeq, 2002). TARBP1 expression was shown to be significantly up-regulated in basal cell carcinoma and squamous cell carcinoma of the skin (Sand et al., 2012).

VCPIP1 (also known as VCIP135) and p47 are shown to function in Golgi and ER assembly (Uchiyama et al., 2002). VCPIP1 is down-regulated in breast cancer (Kuznetsova et al., 2007). VCPIP1 is one of the de-ubiquitinating enzymes, being part of the ovarian tumor family (OTU) (Enesa and Evans, 2014).

ZNF131 encodes the zinc finger protein 131, a poorly characterized transcriptional regulator, which might act as repressor of estrogen receptor alpha (Oh and Chung, 2012).

The present invention furthermore relates to the peptides according to the present invention that have the ability to bind to a molecule of the human major histocompatibility complex (MHC) class-I or -II.

The present invention further relates to the peptides according to the present invention wherein said peptides (each) consist or consist essentially of an amino acid sequence according to SEQ ID NO: 1 to SEQ ID NO: 325, SEQ ID NO: 326 to SEQ ID NO: 447 or SEQ ID NO: 448 to SEQ ID NO: 605.

A peptide consisting essentially of the amino acid sequence as indicated can have one or two non-anchor amino acids (see below regarding the anchor motif) exchanged without that the ability to bind to a molecule of the human major histocompatibility complex (MHC) class-I or -II is substantially changed or is negatively affected, compared to the non-modified peptide. I In another peptide consisting essentially of the amino acid sequence, one or two amino acids are exchanged with their conservative exchange partners (see herein below as well) without that the ability to bind to a molecule of the human major histocompatibility complex (MHC) class-I or -II is substantially changed or is negatively affected, compared to the non-modified peptide.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention.

The present invention further relates to the nucleic acid according to the present invention that is DNA, cDNA, PNA, RNA or combinations thereof.

The present invention further relates to an expression vector capable of expressing or expressing a nucleic acid according to the present invention.

The present invention further relates to a peptide according to the present invention, a nucleic acid according to the present invention or an expression vector according to the present invention for use in medicine.

The present invention further relates to antibodies according to the present invention, and methods of making them.

The present invention further relates to T-cell receptors (TCR), in particular soluble TCR (sTCRs), according to the present invention, and methods of making them.

The present invention further relates to a host cell comprising a nucleic acid according to the present invention or an expression vector as described before.

The present invention further relates to the host cell according to the present invention that is an antigen presenting cell.

The present invention further relates to the host cell according to the present invention wherein the antigen presenting cell is a dendritic cell.

The present invention further relates to a method of producing a peptide according to the present invention, the method comprising culturing the host cell according to the present invention, and isolating the peptide from the host cell or its culture medium.

The present invention further relates to an in vitro method for producing activated cytotoxic T lymphocytes (CTL), the method comprising contacting in vitro CTL with antigen loaded human class I or II MHC molecules expressed on the surface of a suitable antigen-presenting cell for a period of time sufficient to activate said CTL in an antigen specific manner, wherein said antigen is any peptide according to the present invention.

The present invention further relates to the method according to the present invention, wherein the antigen is loaded onto class I or II MHC molecules expressed on the surface of a suitable antigen-presenting cell by contacting a sufficient amount of the antigen with an antigen-presenting cell.

The present invention further relates to the method according to the present invention, wherein the antigen-presenting cell comprises an expression vector capable of expressing said peptide containing SEQ ID NO: 1 to SEQ ID NO: 325, SEQ ID NO: 326 to SEQ ID NO: 447 or SEQ ID NO: 448 to SEQ ID NO: 605, or said variant amino acid sequence.

The present invention further relates to activated cytotoxic T lymphocytes (CTL), produced by the method according to the present invention, which selectively recognize a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of cytotoxic T lymphocytes (CTL) as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament.

The present invention further relates to a use according to the present invention, wherein said medicament is a vaccine.

The present invention further relates to a use according to the present invention, wherein the medicament is active against cancer.

The present invention further relates to a use according to the present invention, wherein said cancer cells are cells of hematological malignancies, AML or chronic lymphatic leukemia (CLL) cells.

The present invention further relates to particular marker proteins and biomarkers based on the peptides according to the present invention that can be used in the diagnosis and/or prognosis of hematological malignancies, AML or chronic lymphatic leukemia (CLL) cells, preferably AML.

Further, the present invention relates to the use of these novel targets for cancer treatment.

Further, the present invention relates to a method for producing a personalized anti-cancer vaccine for an individual patient using a warehouse (database) of prescreened tumor associated peptides.

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defences against cancer. CD8-positive T-cells in particular, which recognize Class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

There are two classes of MHC-molecules: MHC class I molecules that can be found on most cells having a nucleus. MHC molecules are composed of an alpha heavy chain and beta-2-microglobulin (MHC class I receptors) or an alpha and a beta chain (MHC class II receptors), respectively. Their three-dimensional conformation results in a binding groove, which is used for non-covalent interaction with peptides. MHC class I present peptides that result from proteolytic cleavage of predominantly endogenous proteins, DRIPs and larger peptides. MHC class II molecules can be found predominantly on professional antigen presenting cells (APCs), and primarily present peptides of exogenous or transmembrane proteins that are taken up by APCs during the course of endocytosis, and are subsequently processed. Complexes of peptide and MHC class I molecules are recognized by CD8-positive cytotoxic T-lymphocytes bearing the appropriate TCR (T-cell receptor), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses; Gnjatic S, et al. Survey of naturally occurring CD4+ T cell responses against NY-ESO-1 in cancer patients: correlation with antibody responses. Proc Natl Acad Sci USA. 2003 Jul. 22; 100(15):8862-7). At the tumor site, T helper cells, support a CTL friendly cytokine milieu (Mortara L, et al. CIITA-induced MHC class II expression in mammary adenocarcinoma leads to a Th1 polarization of the tumor microenvironment, tumor rejection, and specific antitumor memory. Clin Cancer Res. 2006 Jun. 1; 12(11 Pt 1):3435-43) and attract effector cells, e.g. CTLs, NK cells, macrophages, granulocytes (Hwang M L, et al. Cognate memory CD4+ T cells generated with dendritic cell priming influence the expansion, trafficking, and differentiation of secondary CD8+ T cells and enhance tumor control. J Immunol. 2007 Nov. 1; 179(9):5829-38).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have surprisingly been found to express MHC class II molecules (Dengjel J, et al. Unexpected abundance of HLA class II presented peptides in primary renal cell carcinomas. Clin Cancer Res. 2006 Jul. 15; 12(14 Pt 1):4163-70).

It was shown in mammalian animal models, e.g., mice, that even in the absence of CTL effector cells (i.e., CD8-positive T lymphocytes), CD4-positive T cells are sufficient for inhibiting manifestation of tumors via inhibition of angiogenesis by secretion of interferon-gamma (IFNγ).

Additionally, it was shown that CD4-positive T cells recognizing peptides from tumor-associated antigens presented by HLA class II molecules can counteract tumor progression via the induction of antibody (Ab) responses.

In contrast to tumor-associated peptides binding to HLA class I molecules, only a small number of class II ligands of tumor associated antigens (TAA) have been described to date.

Since the constitutive expression of HLA class II molecules is usually limited to cells of the immune system, the possibility of isolating class II peptides directly from primary tumors was not considered possible. However, Dengjel et al. were successful in identifying a number of MHC Class II epitopes directly from tumors (WO 2007/028574, EP 1 760 088 B1; (Dengjel et al., 2006).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

Since both types of response, CD8 and CD4 dependent, contribute jointly and synergistically to the anti-tumor effect, the identification and characterization of tumor-associated antigens recognized by either CD8+ CTLs (ligand: MHC class I molecule+peptide epitope) or by CD4-positive T-helper cells (ligand: MHC class II molecule+peptide epitope) is important in the development of tumor vaccines.

The present invention also relates to two new and very useful MHC class II peptides (according to SEQ ID NO: 448 to SEQ ID NO: 605). These peptides are particularly useful in the diagnosis and/or treatment of AML and other cancers over-expressing and/or over—presenting the antigens the peptides are derived from respectively.

The present invention also relates to so-called length variants of the inventive MHC class II peptides according to SEQ ID NO: 448 to SEQ ID NO: 605.

The length variants are generally N- and/or C-terminally extended (between 1 and 5, preferably 1 to 10 amino acids) or N- and/or C-terminally shortened (between 1 and 5 amino acids) peptides, which still can bind to MHC, and elicit a cellular immune response as described herein. As is known in the state of the art, peptides binding to class II proteins are not constrained in size and can vary from 11 to 30 amino acids in length. The peptide binding groove in the MHC class II molecules is open at both ends, which enables binding of peptides with relatively longer length. Though the "core" nine residues long segment contributes the most to the recognition of the peptide, the flanking regions are also important for the specificity of the peptide to the class II allele (see, for example, Meydan C, et al., Prediction of peptides binding to MHC class I and II alleles by temporal motif mining BMC Bioinformatics. 2013; 14 Suppl 2: S13). Using the many software tools as available (e.g. as described above), the person of skill in the art will be able to identify the binding motif, and thus identify the possibilities for extensions and/or deletions of the MHC class II peptides according to Table 3, in order to create length variants.

For a peptide to trigger (elicit) a cellular immune response, it must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules being expressed by tumor cells, they also have to be recognized by T cells bearing specific T cell receptors (TCR).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

The current classification of tumor associated antigens comprises the following major groups: a) Cancer-testis antigens: The first tumor associated antigens (TAAs) ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

b) Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their overexpression in tumor cells can trigger an anticancer response by breaking previously established tolerance. Prominent examples for this class of TAAs are Her-2/neu, Survivin, Telomerase or WT1.

d) Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens, and to be used in a therapy, particular prerequisites must be fulfilled. The antigen should be expressed mainly by tumor cells and not or in comparably small amounts by normal healthy tissues or in another preferred embodiment the peptide should be over-presented by tumor cells as compared to normal healthy tissues. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or suppression of apoptosis. Additionally, downstream targets of the proteins directly causative for a transformation may be upregulated and thus may be indirectly tumor-associated. Such indirect tumor-associated antigens may also be targets of a vaccination approach (Singh-Jasuja et al. The Tübingen approach: identification, selection, and validation of tumor-associated HLA peptides for cancer therapy. Cancer Immunol Immunother. 2004 March; 53(3):187-95). In both cases it is essential that epitopes are present in the amino acid sequence of the antigen, since such a peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues.

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of TCRs and antibodies according to the invention the immunogenicity of the underlying peptides is secondary. For TCRs and antibodies according to the invention the presentation is the determining factor.

T-helper cells play an important role in orchestrating the effector function of CTLs in anti-tumor immunity. T-helper cell epitopes that trigger a T-helper cell response of the $T_{H1}$ type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

Uses against additional cancers are disclosed in the following more detailed description of the peptides according to the invention.

DETAILED DESCRIPTION OF THE INVENTION

As used herein and except as noted otherwise all terms are defined as given below.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14, and in case of MHC class II peptides they can be as long as 15, 16, 17, 18, 19 or 20 amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts.

The term "peptide" shall include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "the peptides of the present invention" shall include the peptides consisting of or comprising a peptide as defined above according to SEQ ID NO: 1 to SEQ ID NO: 325, SEQ ID NO: 326 to SEQ ID NO: 447 or SEQ ID NO: 448 to SEQ ID NO: 605.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 6

Expression frequencies F of HLA*A02 and the most frequent HLA-DR serotypes. Frequencies are deduced from haplotype frequencies $G_f$ within the American population adapted from Mori et al. (Mori M, et al. HLA gene and haplotype frequencies in the North American population: the National Marrow Donor Program Donor Registry. Transplantation. 1997 Oct 15; 64(7): 1017-27) employing the Hardy-Weinberg formula $F = 1 - (1 - G_f)^2$. Combinations of A*02 with certain HLA-DR alleles might be enriched or less frequent than expected from their single frequencies due to linkage disequilibrium. For details refer to Chanock et al. (S. J. Chanock, et al (2004) HLA-A, -B, -Cw, -DQA1 and DRB1 in an African American population from Bethesda, USA Human Immunology, 65: 1223-1235)..

| HLA Allele | Expression frequencies of HLA*02 and HLA-DR serotypes within North American subpopulations | | | |
|---|---|---|---|---|
| | Caucasian American | African American | Asian American | Latin American |
| A*02 | 49.1% | 34.1% | 43.2% | 48.3% |
| DR1 | 19.4% | 13.2% | 6.8% | 15.3% |
| DR2 | 28.2% | 29.8% | 33.8% | 21.2% |
| DR3 | 20.6% | 24.8% | 9.2% | 15.2% |
| DR4 | 30.7% | 11.1% | 28.6% | 36.8% |
| DR5 | 23.3% | 31.1% | 30.0% | 20.0% |
| DR6 | 26.7% | 33.7% | 25.1% | 31.1% |
| DR7 | 24.8% | 19.2% | 13.4% | 20.2% |
| DR8 | 5.7% | 12.1% | 12.7% | 18.6% |
| DR9 | 2.1% | 5.8% | 18.6% | 2.1% |

Therefore, for therapeutic and diagnostic purposes a peptide that binds with appropriate affinity to several different HLA class II receptors is highly desirable. A peptide binding to several different HLA class II molecules is called a promiscuous binder.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene which either naturally or normally codes for the expression product of that gene in its natural genomic environment, i.e., the region coding in vivo for the native expression product of the gene.

The coding region can be from a non-mutated ("normal"), mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding (or encoding) for a peptide" refers to a nucleotide sequence coding for the peptide including artificial (man-made) start and stop codons compatible for the biological system the sequence is going to be expressed by.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

$$\text{Percent Identity} = 100[1 - (C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the Percent Identity as calculated above is about equal to or greater than a specified minimum Percent Identity then the Compared Sequence has the specified minimum Percent Identity to the Reference Sequence even though alignments may exist in which the herein above calculated Percent Identity is less than the specified Percent Identity.

The original (unmodified) peptides as disclosed herein can be modified by the substitution of one or more residues at different, possibly selective, sites within the peptide chain, if not otherwise stated. Preferably, these substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

The peptides of the invention can be elongated by up to four amino acids, that is 1, 2, 3 or 4 amino acids can be added to either end in any combination between 4:0 and 0:4.

Combinations of the elongations according to the invention can be depicted from the following Table 7:

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation can be the peptides of the original sequence of the protein or any other amino acid. The elongation can be used to enhance the stability or solubility of the peptides.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

Preferably, when the CTLs specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by CTLs from more than one individual, at least two, and more preferably three individuals.

Thus, the epitopes of the present invention may be identical to naturally occurring tumor-associated or tumor-specific epitopes or may include epitopes that differ by no more than 4 residues from the reference peptide, as long as they have substantially identical antigenic activity.

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defences against cancer. CD8-positive T-cells in particular, which recognize class I molecules of the major histocompatibility complex (MHC)-bearing peptides of usually 8 to 12 residues derived from proteins or defect ribosomal products (DRIPS) located in the cytosols, play an important role in this response. The MHC-molecules of the human are also designated as human leukocyte-antigens (HLA).

MHC class I molecules can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature.

Since both types of response, CD8 and CD4 dependent, contribute jointly and synergistically to the anti-tumor effect, the identification and characterization of tumor-associated antigens recognized by either CD8-positive CTLs (MHC class I molecule) or by CD4-positive CTLs (MHC class II molecule) is important in the development of tumor vaccines. It is therefore an object of the present invention, to provide compositions of peptides that contain peptides binding to MHC complexes of either class.

Considering the severe side-effects and expense associated with treating cancer better prognosis and diagnostic methods are desperately needed. Therefore, there is a need to identify other factors representing biomarkers for cancer in general and lung cancer in particular. Furthermore, there is a need to identify factors that can be used in the treatment of cancer in general and AML in particular.

The present invention provides peptides that are useful in treating cancers/tumors, preferably lung cancers, even more preferably AML and other cancers (see table 5) that over- or exclusively present the peptides of the invention. These peptides were shown by mass spectrometry to be naturally presented by HLA molecules on primary human AML samples.

The source gene/protein (also designated "full-length protein" or "underlying protein") from which the peptides are derived were shown to be highly overexpressed in tumor tissue compared with normal tissues (see example 1, and FIG. 2 for AML) demonstrating a high degree of tumor association of the source genes. Moreover, the peptides themselves are strongly over-presented on tumor tissue but not on normal tissues (see example 1 and FIG. 3).

HLA-bound peptides can be recognized by the immune system, specifically T lymphocytes/T cells. T cells can destroy the cells presenting the recognized HLA/peptide complex, e.g. lung cancer cells presenting the derived peptides.

The peptides of the present invention have been shown to be capable of stimulating T cell responses and/or are over-presented and thus can be used for the production of antibodies and/or TCRs, in particular sTCRs, according to the present invention (see example 1 and FIG. 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH$_2$ group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine, or the like.

In an especially preferred embodiment, the pharmaceutical compositions comprise the peptides as salts of acetic acid (acetates), trifluoro acetates or hydrochloric acid (chlorides).

In addition to being useful for treating cancer, the peptides of the present invention are also useful as diagnostics. Since the peptides were generated from lung cancer cells and since it was determined that these peptides are not or at lower levels present in normal tissues, these peptides can be used to diagnose the presence of a cancer.

The presence of claimed peptides on tissue biopsies can assist a pathologist in diagnosis of cancer. Detection of certain peptides by means of antibodies, mass spectrometry or other methods known in the art can tell the pathologist that the tissue is malignant or inflamed or generally diseased. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Yet another aspect of the present invention then relates to a method of producing said antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically bindable to said human major histocompatibility complex (MHC) class I or II being complexed with said HLA-restricted antigen. Respective methods for producing such antibodies and single chain class I major histocompatibility complexes, as well as other tools for the production of these antibodies are disclosed in WO 03/068201, WO 2004/084798, WO 01/72768, WO 03/070752, and Cohen C J, et al. Recombinant antibodies with MHC-restricted, peptide-specific, T-cell receptor-like specificity: new tools to study antigen presentation and TCR-peptide-MHC interactions. J Mol Recognit. 2003 September-October; 16(5):324-32.; Denkberg G, et al. Selective targeting of melanoma and APCs using a recombinant antibody with TCR-like specificity directed toward a melanoma differentiation antigen. J Immunol. 2003 Sep. 1; 171(5):2197-207; and Cohen C J, et al. Direct phenotypic analysis of human MHC class I antigen presentation: visualization, quantitation, and in situ detection of human viral epitopes using peptide-specific, MHC-restricted human recombinant antibodies. J Immunol. 2003 Apr. 15; 170(8): 4349-61, which for the purposes of the present invention are all explicitly incorporated by reference in their entireties.

Preferably, the antibody is binding with a binding affinity of below 20 nanomolar, preferably of below 10 nanomolar, to the complex, which is regarded as "specific" in the context of the present invention.

It is a further aspect of the invention to provide a method for producing a soluble T-cell receptor recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, Liddy N, et al. Monoclonal TCR-redirected tumor cell killing. *Nat Med* 2012 June; 18(6):980-987). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (see Boulter J M, et al. Stable, soluble T-cell receptor molecules for crystallization and therapeutics. Protein Eng 2003 September; 16(9):707-711.; Card K F, et al. A soluble single-chain T-cell receptor IL-2 fusion protein retains MHC-restricted peptide specificity and IL-2 bioactivity. Cancer Immunol Immunother 2004 April; 53(4):345-357; and Willcox B E, et al. Production of soluble alphabeta T-cell receptor heterodimers suitable for biophysical analysis of ligand binding. Protein Sci 1999 November; 8 (11):2418-2423). The T-cell receptor can be linked to toxins, drugs, cytokines (see US 2013/0115191), domains recruiting effector cells such as an anti-CD3 domain, etc., in order to execute particular functions on target cells. Moreover, it could be expressed in T cells used for adoptive transfer.

Further information can be found in WO 2004/033685A1 and WO 2004/074322A1. A combination of sTCRs is described in WO 2012/056407A1. Further methods for the production are disclosed in WO 2013/057586A1.

In addition, they can be used to verify a pathologist's diagnosis of a cancer based on a biopsied sample.

To select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (J. Pinheiro, et al. The nlme Package: Linear and Nonlinear Mixed Effects Models. 2007) adjusting for multiple testing by False Discovery Rate (Y. Benjamini and Y. Hochberg. Controlling the False Discovery Rate: A Practical and Powerful Approach to Multiple Testing. Journal of the Royal Statistical Society. Series B (Methodological), Vol. 57 (No. 1):289-300, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from AML samples with the fragmentation patterns of corresponding synthetic reference peptides of identical sequences. Since the peptides were directly identified as ligands of HLA molecules of primary tumors, these results provide direct evidence for the natural processing and presentation of the identified peptides on primary tumor tissue obtained from AML patients.

The discovery pipeline XPRESIDENT® v 2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

In the context of the present invention, HLA-peptide complexes from 50 shock-frozen AML tumor tissue samples were purified and HLA-associated peptides were isolated and analyzed by LC-MS (see examples). All TUMAPs contained in the present application were identified with this approach on primary AML tumor samples confirming their presentation on primary AML.

TUMAPs identified on multiple AML tumor and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

The present invention therefore relates to a peptide comprising a sequence that is selected from the group consisting of SEQ ID NO: 1 to SEQ ID NO: 325, SEQ ID NO: 326 to SEQ ID NO: 447 or SEQ ID NO: 448 to SEQ ID NO: 605 or a variant thereof which is at least 90% homologous (preferably identical) to SEQ ID NO: 1 to SEQ ID NO: 325, SEQ ID NO: 326 to SEQ ID NO: 447 or SEQ ID NO: 448 to SEQ ID NO: 605 or a variant thereof that induces T cells cross-reacting with said peptide, wherein said peptide is not a full-length polypeptide.

The present invention further relates to a peptide comprising a sequence that is selected from the group consisting of SEQ ID NO: 1 to SEQ ID NO: 325, SEQ ID NO: 326 to SEQ ID NO: 447 or SEQ ID NO: 448 to SEQ ID NO: 605 or a variant thereof which is at least 90% homologous (preferably identical) to SEQ ID NO: 1 to SEQ ID NO: 325, SEQ ID NO: 326 to SEQ ID NO: 447 or SEQ ID NO: 448 to SEQ ID NO: 605, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 325, SEQ ID NO: 326 to SEQ ID NO: 447 or SEQ ID NO: 448 to SEQ ID NO: 605.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the full human protein.

The present invention further relates to the nucleic acid according to the invention that is DNA, cDNA, PNA, RNA or combinations thereof.

The present invention further relates to an expression vector capable of expressing a nucleic acid according to the invention.

The present invention further relates to a peptide according to the invention, a nucleic acid according to the invention or an expression vector according to the invention for use in medicine.

The present invention further relates to a host cell comprising a nucleic acid according to the invention or an expression vector according to the invention.

The present invention further relates to the host cell according to the invention that is an antigen presenting cell.

The present invention further relates to the host cell according to the invention, wherein the antigen presenting cell is a dendritic cell.

The present invention further relates to a method of producing a peptide according to the invention, the method comprising culturing the host cell described and isolating the peptide from the host cell or its culture medium.

The present invention further relates to an in vitro method for producing activated cytotoxic T lymphocytes (CTL), the method comprising contacting in vitro CTL with antigen loaded human class I or II MHC molecules expressed on the surface of a suitable antigen-presenting cell for a period of time sufficient to activate said CTL in an antigen specific manner, wherein said antigen is any peptide according to the invention.

The present invention further relates to the method as described, wherein said antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 325, SEQ ID NO: 326 to SEQ ID NO: 447 or SEQ ID NO: 448 to SEQ ID NO: 605 or said variant amino acid sequence.

The present invention further relates to activated cytotoxic T lymphocytes (CTL), produced by the method according to the invention, which selectively recognize a cell which aberrantly expresses a polypeptide comprising an amino acid sequence described.

The present invention further relates to a method of killing target cells in a patient which target cells aberrantly express a polypeptide comprising any amino acid sequence according to the invention, the method comprising administering to the patient an effective number of cytotoxic T lymphocytes (CTL) according to the invention.

The present invention further relates to the use of any peptide according to the invention, a nucleic acid according to the invention, an expression vector according to the invention, a cell according to the invention, or an activated cytotoxic T lymphocyte according to the invention as a medicament or in the manufacture of a medicament.

The present invention further relates to a use according to the invention, wherein the medicament is a vaccine.

The present invention further relates to a use according to the invention, wherein the medicament is active against cancer.

The present invention further relates to a use according to the invention, wherein said cancer cells are AML cells or other non-solid tumor cells.

The present invention further relates to particular marker proteins and biomarkers that can be used in the prognosis of lung cancer.

Further, the present invention relates to the use of the novel targets as described in accordance with the present invention for cancer treatment.

The term "antibody" or "antibodies" is used herein in a broad sense and includes both polyclonal and monoclonal antibodies. In addition to intact or "full" immunoglobulin molecules, also included in the term "antibodies" are fragments or polymers of those immunoglobulin molecules and humanized versions of immunoglobulin molecules, so long as they exhibit any of the desired properties (e.g., specific binding of an lung cancer marker polypeptide, delivery of a toxin to an lung cancer cell expressing a lung cancer marker gene at an increased level, and/or inhibiting the activity of a lung cancer marker polypeptide) according to the invention.

Whenever possible, the antibodies of the invention may be purchased from commercial sources. The antibodies of the invention may also be generated using well-known methods. The skilled artisan will understand that either full length lung cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 325, SEQ ID NO: 326 to SEQ ID NO: 447 or SEQ ID NO: 448 to SEQ ID NO: 605 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the lung cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Harlow and Lane, Antibodies: A Laboratory Manual, Cold Spring Harbor Laboratory Press, Cold Spring Harbor, N.Y., 1988, new $2^{nd}$ edition 2013). For example, the antibodies may be tested in ELISA assays, Western blots, immunohistochemical staining of formalin-fixed lung cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a $F(ab')_2$ fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5.

Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody for treating lung cancer, the efficacy of the therapeutic antibody can be assessed in various ways well known to the skilled practitioner. For instance, the size, number, and/or distribution of lung cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of lung cancer.

Because the peptides as mentioned in Tables 2 and 5 (specifically the ones associated with AML) of the invention and thus their underlying polypeptides are highly expressed in AML, and are expressed at rather to extremely low levels in normal cells, inhibition of ABCA13 and/or MMP12 expression or polypeptide activity may be preferably integrated into a therapeutic strategy for treating or preventing AML.

The principle of antisense therapy is based on the hypothesis that sequence-specific suppression of gene expression (via transcription or translation) may be achieved by intracellular hybridization between genomic DNA or mRNA and a complementary antisense species. The formation of such a hybrid nucleic acid duplex interferes with transcription of the target tumor antigen-encoding genomic DNA, or processing/transport/translation and/or stability of the target tumor antigen mRNA.

Antisense nucleic acids can be delivered by a variety of approaches. For example, antisense oligonucleotides or antisense RNA can be directly administered (e.g., by intravenous injection) to a subject in a form that allows uptake into tumor cells. Alternatively, viral or plasmid vectors that encode antisense RNA (or RNA fragments) can be introduced into cells in vivo. Antisense effects can also be induced by sense sequences; however, the extent of phenotypic changes is highly variable. Phenotypic changes induced by effective antisense therapy are assessed according to changes in, e.g., target mRNA levels, target protein levels, and/or target protein activity levels.

In a specific example, inhibition of lung tumor marker function by antisense gene therapy may be accomplished by direct administration of antisense lung tumor marker RNA to a subject. The antisense tumor marker RNA may be produced and isolated by any standard technique, but is most readily produced by in vitro transcription using an antisense tumor marker cDNA under the control of a high efficiency promoter (e.g., the T7 promoter). Administration of antisense tumor marker RNA to cells can be carried out by any of the methods for direct nucleic acid administration described below.

An alternative strategy for inhibiting ABCA13 and MMP12 function using gene therapy involves intracellular expression of an anti-ABCA13, -MMP12 antibody or a portion of an anti-ABCA13, -MMP12 antibody. For example, the gene (or gene fragment) encoding a monoclonal antibody that specifically binds to an ABCA13, MMP12 polypeptide and inhibits its biological activity is placed under the transcriptional control of a specific (e.g., tissue- or tumor-specific) gene regulatory sequence, within a nucleic acid expression vector. The vector is then administered to the subject such that it is taken up by lung cancer cells or other cells, which then secrete the anti-ABCA13, -MMP12 antibody and thereby block biological activity of the ABCA13, MMP12 polypeptide. Preferably, the ABCA13, MMP12 polypeptides are present at the extracellular surface of AML cancer cells.

In the methods described above, which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for inhibition of AML tumor marker protein expression. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis., US), as well as other liposomes developed according to procedures standard in the art. In addition, the nucleic acid or vector of this invention can be delivered in vivo by electroporation, the technology for which is available from Genetronics, Inc. (San Diego, US) as well as by means of a SONOPORATION machine (ImaRx Pharmaceutical Corp., Tucson, Ariz., US).

As one example, vector delivery can be via a viral system, such as a retroviral vector system that can package a recombinant retroviral genome. The recombinant retrovirus can then be used to infect and thereby deliver to the infected cells antisense nucleic acid that inhibits expression of ABCA13 and/or MMP12. The exact method of introducing the altered nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors. Physical transduction techniques can also be used, such as liposome delivery and receptor-mediated and other endocytosis mechanisms. This invention can be used in conjunction with any of these or other commonly used gene transfer methods.

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more ABCA13 and MMP12 targets and the affinity value (Kd) is less than $1\times10$ μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the ABCA13 and/or MMP12 proteins express in situ.

The present invention thus provides a peptide comprising a sequence that is selected from the group of consisting of SEQ ID NO: 1 to SEQ ID NO: 325, SEQ ID NO: 326 to SEQ ID NO: 447 or SEQ ID NO: 448 to SEQ ID NO: 605 or a variant thereof which is 90% homologous to SEQ ID NO: 1 to SEQ ID NO: 325, SEQ ID NO: 326 to SEQ ID NO: 447 or SEQ ID NO: 448 to SEQ ID NO: 605 or a variant thereof that will induce T cells cross-reacting with said peptide.

The peptides of the invention have the ability to bind to a molecule of the human major histocompatibility complex (MHC) class-I and/or class II.

In the present invention, the term "homologous" refers to the degree of identity (see Percent Identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other analysis tools are provided by public databases.

A person skilled in the art will be able to assess, whether T cells induced by a variant of a specific peptide will be able to cross-react with the peptide itself (Fong L, et al. Altered peptide ligand vaccination with Flt3 ligand expanded dendritic cells for tumor immunotherapy. Proc Natl Acad Sci USA. 2001 Jul. 17; 98(15):8809-14; Zaremba S, et al. Identification of an enhancer agonist cytotoxic T lymphocyte peptide from human carcinoembryonic antigen. Cancer Res. 1997 Oct. 15; 57(20):4570-7; Colombetti S, et al. Impact of orthologous melan-A peptide immunizations on the anti-self melan-A/HLA-A2 T cell cross-reactivity. J Immunol. 2006 Jun. 1; 176(11):6560-7; Appay V, et al. Decreased specific CD8+ T cell cross-reactivity of antigen recognition following vaccination with Melan-A peptide. Eur J Immunol. 2006 July; 36(7):1805-14).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 325, SEQ ID NO: 326 to SEQ ID NO: 447 or SEQ ID NO: 448 to SEQ ID NO: 605. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated CTL.

These CTL can subsequently cross-react with cells and kill cells that express a polypeptide that contains the natural amino acid sequence of the cognate peptide as defined in the aspects of the invention. As can be derived from the scientific literature (Godkin A, et al. Use of eluted peptide sequence data to identify the binding characteristics of peptides to the insulin-dependent diabetes susceptibility allele HLA-DQ8 (DQ 3.2). Int Immunol. 1997 June; 9(6): 905-11) and databases (Rammensee H. et al. SYFPEITHI: database for MHC ligands and peptide motifs. Immunogenetics. 1999 November; 50(3-4):213-9), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus one skilled in the art would be able to modify the amino acid sequences set forth in SEQ ID NO: 1 to SEQ ID NO: 325, SEQ ID NO: 326 to SEQ ID NO: 447 or SEQ ID NO: 448 to SEQ ID NO: 605, by maintaining the known anchor residues, and would be able to determine whether such variants maintain the ability to bind MHC class I or II molecules. The variants of the present invention retain the ability to bind to the TCR of activated CTL, which can subsequently cross-react with and kill cells that express a polypeptide containing the natural amino acid sequence of the peptide according to the present invention.

Those amino acid residues that do not substantially contribute to interactions with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

Longer peptides may also be suitable. It is also possible, that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

Accordingly, the present invention also provides peptides and variants of MHC class I epitopes wherein the peptide or variant has an overall length of between 8 and 100, preferably between 8 and 30, and most preferred between 8 and 14, namely 8, 9, 10, 11, 12, 13, 14 amino acids, in case of the class II binding peptides the length can also be 15, 16, 17, 18, 19, 20, 21 or 23 amino acids.

Of course, the peptide or variant according to the present invention will have the ability to bind to a molecule of the human major histocompatibility complex (MHC) class I. Binding of a peptide or a variant to a MHC complex may be tested by methods known in the art.

In a particularly preferred embodiment of the invention the peptide consists or consists essentially of an amino acid sequence according to SEQ ID NO: 1 to SEQ ID NO: 325, SEQ ID NO: 326: to SEQ ID NO: 447 or SEQ ID NO: 448 to SEQ ID NO: 605.

"Consisting essentially of" shall mean that a peptide according to the present invention, in addition to the sequence according to any of SEQ ID NO: 1 to SEQ ID NO: 325, SEQ ID NO: 326: to SEQ ID NO: 447 or SEQ ID NO: 448 to SEQ ID NO: 605 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes but is not limited to, modification by acylation, amidation, pyridoxylation of lysine, reductive alkylation, trinitrobenzylation of amino groups with 2,4,6-trinitrobenzene sulphonic acid (TNBS), amide modification of carboxyl groups and sulphydryl modification by performing acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals.

Woodward's Reagent K may be used to modify specific glutamic acid residues. N-β-(dimethylamino)propyl)-N'-ethylcarbodiimide can be used to form intra-molecular crosslinks between a lysine residue and a glutamic acid residue.

For example, diethylpyrocarbonate is a reagent for the modification of histidyl residues in proteins. Histidine can also be modified using 4-hydroxy-2-nonenal.

The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins.

Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Solid-phase peptide synthesis under continuous-flow conditions. Proc Natl Acad Sci USA. May 1981; 78(5): 2791-2795) and references therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethandithiol, phenol, anisole and water, the exact choice depending on the constituent amino acids of the peptide being synthesized. Also a combination of solid phase and solution phase methodologies for the synthesis of peptides is possible (see, for example, Bruckdorfer T, et al.

From production of peptides in milligram amounts for research to multi-tons quantities for drugs of the future. Curr Pharm Biotechnol. 2004 February; 5(1):29-43. Review, and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (UK) Ltd, Nottingham NG7 2QJ, UK.

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Diagnosis of sickle cell anemia and beta-thalassemia with enzymatically amplified DNA and nonradioactive allele-specific oligonucleotide probes. N Engl J Med. 1988 Sep. 1; 319(9):537-41). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example E. coli and Bacillus subtilis), yeasts (for example Saccharomyces cerevisiae), filamentous fungi (for example Aspergillus spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the preprotrypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al. (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Small E J, et al. Placebo-controlled phase III trial of immunologic therapy with sipuleucel-T (APC8015) in patients with metastatic, asymptomatic hormone refractory prostate cancer. J Clin Oncol. 2006 Jul. 1; 24(19):3089-94. Rini et al. Combination immunotherapy with prostatic acid phosphatase pulsed antigen-presenting cells (provenge) plus bevacizumab in patients with serologic progression of prostate cancer after definitive local therapy. Cancer. 2006 Jul. 1; 107(1):67-74).

A further aspect of the invention then provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., Nature Medicine 18, 1254-1261 (2012)).

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Karre et al 1985 (Ljunggren, H.-G., and K. Karre. 1985. J. Exp. Med. 162:1745).

Preferably, the host cell before transfection expresses substantially no MHC class I molecules. It is also preferred that the stimulator cell expresses a molecule important for providing a co-stimulatory signal for T-cells, such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive CTLs.

If an antigen-presenting cell is transfected to express such an epitope, preferably the cell comprises an expression vector capable of expressing a peptide containing SEQ ID NO: 1 to SEQ ID NO: 325, SEQ ID NO: 326 to SEQ ID NO: 447 or SEQ ID NO: 448 to SEQ ID NO: 605, or a variant amino acid sequence thereof as described herein.

A number of other methods may be used for generating CTL in vitro. For example, autologous tumor-infiltrating lymphocytes can be used in the generation of CTL. Plebanski et al (1995) (Induction of peptide-specific primary cytotoxic T lymphocyte responses from human peripheral blood. Eur J Immunol. 1995 June; 25(6):1783-7) make use of autologous peripheral blood lymphocytes (PLBs) in the preparation of CTL. Furthermore, the production of autologous CTL by pulsing dendritic cells with peptide or polypeptide, or via infection with recombinant virus is possible. Also, B cells can be used in the production of autologous CTL. In addition, macrophages pulsed with peptide or polypeptide, or infected with recombinant virus, may be used in the preparation of autologous CTL. S. Walter et al. 2003 (Cutting edge: predetermined avidity of human CD8 T cells expanded on calibrated MHC/anti-CD28-coated microspheres. J Immunol. 2003 Nov. 15; 171(10):4974-8) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, vaccinia-infected target cells. In addition plant viruses may be used (see, for example, Porta et al (1994) Development of cowpea mosaic virus as a high-yielding system for the presentation of foreign peptides. Virology. 1994 Aug. 1; 202(2):949-55) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO: 325, SEQ ID NO: 326 to SEQ ID NO: 447 or SEQ ID NO: 448 to SEQ ID NO: 605.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)). The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattinoni L, et al. Adoptive immunotherapy for cancer: building on success. Nat Rev Immunol. 2006 May; 6(5):383-93. Review. and Morgan R A, et al. Cancer regression in patients after transfer of genetically engineered lymphocytes. Science. 2006 Oct. 6; 314(5796):126-9).

Any molecule of the invention, i.e. the peptide, nucleic acid, antibody, expression vector, cell, activated CTL, T-cell receptor or the nucleic acid encoding it is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

Preferably, the medicament of the present invention is a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker, 1993). The peptide may also be tagged, may be a fusion protein, or may be a hybrid molecule. The peptides whose sequence is given in the present invention are expected to stimulate CD4 or CD8 T cells. However, stimulation of CD8 CTLs is more efficient in the presence of help provided by CD4 T-helper cells. Thus, for MHC Class I epitopes that stimulate CD8 CTL the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID NO: 1 to SEQ ID NO: 605 and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

In another aspect, the vaccine comprises at least one peptide having the amino acid sequence set forth in SEQ ID NO: 1 to SEQ ID NO: 325, SEQ ID NO: 326 to SEQ ID NO: 447 or SEQ ID NO: 448 to SEQ ID NO: 605, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

The polynucleotide may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. (Pascolo et al., 2005 Human peripheral blood mononuclear cells transfected with messenger RNA stimulate antigen-specific cytotoxic T-lymphocytes in vitro. Cell Mol Life Sci. 2005 August; 62(15):1755-62). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e g, immune responses mediated by CTLs and helper-T ($T_H$) cells to an antigen, and would thus be considered useful in the medicament of the present invention. Suitable adjuvants include, but are not limited to, 1018 ISS, aluminum salts, AMPLIVAX®, AS15, BCG, CP-870,893, CpG7909, CyaA, dSLIM, flagellin or TLRS ligands derived from flagellin, FLT3 ligand, GM-CSF, IC30, IC31, Imiquimod (AL-DARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995 The Yin and Yang of T cell costimulation. Science. 1995 Nov. 10; 270(5238):932-3. Review). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich, 1996 Production of vascular endothelial growth factor by human tumors inhibits the functional maturation of dendritic cells Nat Med. 1996 October; 2(10):1096-103).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T cell help. The $T_{H1}$ bias induced by TLR9 stimulation is maintained even in the presence of vaccine adjuvants such as alum or incomplete Freund's adjuvant (IFA) that normally promote a $T_{H2}$ bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivatives thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod.

In a preferred embodiment of the pharmaceutical composition according to the invention, the adjuvant is cyclophosphamide, imiquimod or resiquimod.

Even more preferred adjuvants are Montanide IMS 1312, Montanide ISA 206, Montanide ISA 50V, Montanide ISA-51, poly-ICLC (Hiltonol®) and anti-CD40 mAB or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, $3^{rd}$ Ed., 2000, American Pharmaceutical Association and pharmaceutical press. The composition can be used for a prevention, prophylaxis and/or therapy of adenomateous or cancerous diseases. Exemplary formulations can be found in, for example, EP2113253.

Nevertheless depending on the number and the physico-chemical characteristics of the peptides of the invention further research is needed to provide formulations for specific combinations of peptides, especially combinations with more than 20 peptides that are stable for more than 12 to 18 months.

The present invention provides a medicament that useful in treating cancer, in particular AML, Chronic lymphatic leukemia (CLL) and other hematological malignancies.

The present invention is further directed at a kit comprising:

(a) a container containing a pharmaceutical composition as described above, in solution or in lyophilized form;

(b) optionally a second container containing a diluent or reconstituting solution for the lyophilized formulation; and (c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 μg) and preferably not more than 3 mg/mL/peptide (=1500 μg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably the administration is s.c., and most preferably i.d. Administration may be by infusion pump.

Since the peptides of the invention were isolated from tumor tissue related to AML, the medicament of the invention is preferably used to treat AML. In a preferred embodiment, the peptides of the invention derived from ABCA13 and MMP12 were isolated from AML, the medicament of the invention is preferably used to treat AML overexpressing these polypeptides.

The present invention further includes a method for producing a personalized pharmaceutical for an individual patient comprising manufacturing a pharmaceutical composition comprising at least one peptide selected from a warehouse (database) of pre-screened TUMAPs, wherein the at least one peptide used in the pharmaceutical composition is selected for suitability in the individual patient. Preferably, the pharmaceutical composition is a vaccine. The method could also be adapted to produce T cell clones for down-stream applications such as TCR isolations.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group of peptides that have been pre-screened for immunogenicity and over-presentation in a particular tumor type, e.g. in the form of a database or an actual storage unit. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored.

The warehouse (e.g. in the form of a database or actual storage unit) is composed of tumor-associated peptides which were highly overexpressed in the tumor tissue of several HLA-A, HLA-B and HLA-C positive AML patients analyzed (see tables 1 to 3). It contains MHC class I and MHC class II peptides. In addition to the tumor associated peptides collected from several GBM tissues, the warehouse may contain an HLA-A*02 and an HLA-A*24 marker peptide. These peptides allow comparison of the magnitude of T-cell immunity induced by TUMAPS in a quantitative manner and hence allow important conclusion to be drawn on the capacity of the vaccine to elicit anti-tumor responses. Secondly, it functions as an important positive control peptide derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient population.

HLA class I and II TUMAPs for the warehouse (e.g. in the form of a database or actual storage unit) are identified by using an integrated functional genomics approach combining gene expression analysis, mass spectrometry, and T-cell immunology. The approach assures that only TUMAPs truly present on a high percentage of tumors but not or only minimally expressed on normal tissue, are chosen for further analysis. For peptide selection, AML samples from patients and blood from healthy donors were analyzed in a stepwise approach:

1. HLA ligands from the malignant material were identified by mass spectrometry
2. Genome-wide messenger ribonucleic acid (mRNA) expression analysis by microarrays was used to identify genes over-expressed in the malignant tissue (AML) compared with a range of normal organs and tissues
3. Identified HLA ligands were compared to gene expression data. Peptides encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues
6. To assess whether an induction of in vivo T-cell responses by the selected peptides may be feasible, in vitro immunogenicity assays were performed using human T cells from healthy donors as well as from AML patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on a method according to the present invention as herein and as follows.

The HLA phenotype, transcriptomic and peptidomic data will be gathered from the patient's tumor material and blood samples to identify the most suitable peptides for each patient containing warehouse (database) and patient-unique (i.e. mutated) TUMAPs. Those peptides will be chosen, which are selectively or over-expressed in the patients tumor and, where possible, showed strong in vitro immunogenicity if tested with the patients individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing model, TUMAPs may be identified in the patient de novo and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germ line DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina) Additionally, tumor mRNA is sequenced for direct quantification of gene expression and validation that mutated genes are expressed in the patients' tumors. The resultant millions of sequence reads are processed through software algorithms The output list contains mutations and gene expression. Tumor-specific somatic mutations are determined by comparison with the PBMC-derived germline variations and prioritized. The de novo identified peptides may then be tested for immunogenicity as described above for the warehouse (database), and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the methods described above; (b) comparing the peptides identified in a) with a warehouse (database) of peptides that have been prescreened for immunogenicity and overpresentation in tumors as compared to corresponding normal tissue; (c) selecting at least one peptide from the warehouse (database) that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides are selected, the vaccine is manufactured.

The vaccine preferably is a liquid formulation consisting of the individual peptides dissolved in 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

The final bulk solution is filled into vials and stored at −20° C. until use. One vial contains 700 µL solution containing 0.578 mg of each peptide. Thereof 500 µL (approx. 400 µg per peptide) will be applied for intradermal injection.

The present invention will now be described in the following examples with reference to the accompanying figures that describe preferred embodiments thereof, nevertheless, without being limited thereto. For the purposes of the present invention all references as cited herein are incorporated by reference in their entireties.

EXAMPLES

Example 1

Figure 1:
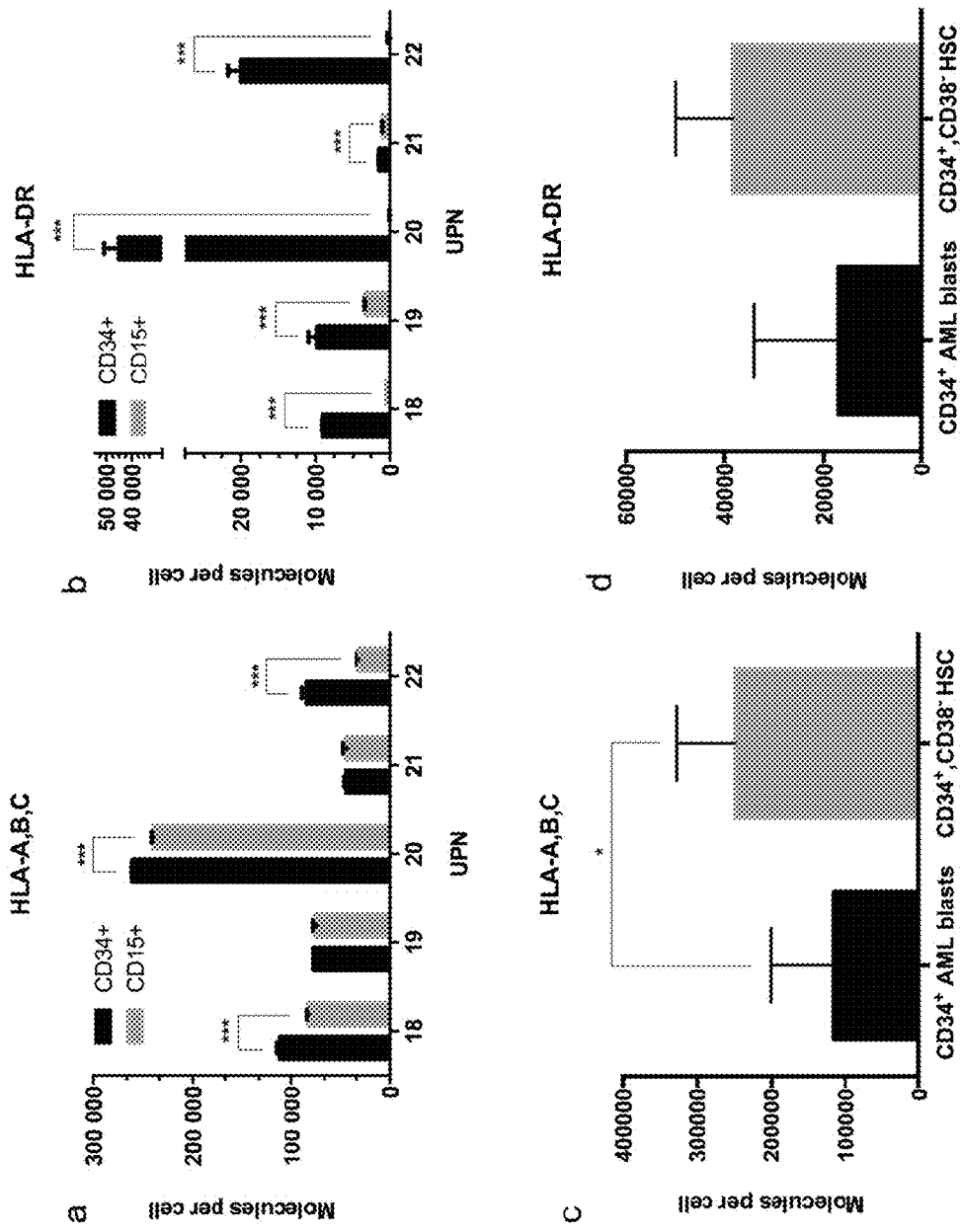
FIG. 1 shows the HLA surface expression of primary AML samples and healthy donor HSCs. Quantification was performed ex vivo using QIFIKIT (Dako). (a) HLA class I (W6/32 mAb) expression of CD34+ AML blasts compared to autologous CD15+ normal monocytes. (b) HLA-DR (L243 mAb) expression of CD34+ AML blasts compared to autologous CD15+ normal monocytes. (c) HLA class I (W6/32 mAb) expression of CD34+ AML blasts (n=5) and CD34+CD38− hematopoietic stem cells (n=5) derived from healthy donors. (d) HLA-DR (L243 mAb) expression of CD34+ AML blasts (n=5) and CD34+CD38− hematopoietic stem cells (n=5) derived from healthy donors. * P<0.05, *** P<0.001, unpaired t test. Abbreviations: UPN, uniform patient number
Figure 2:
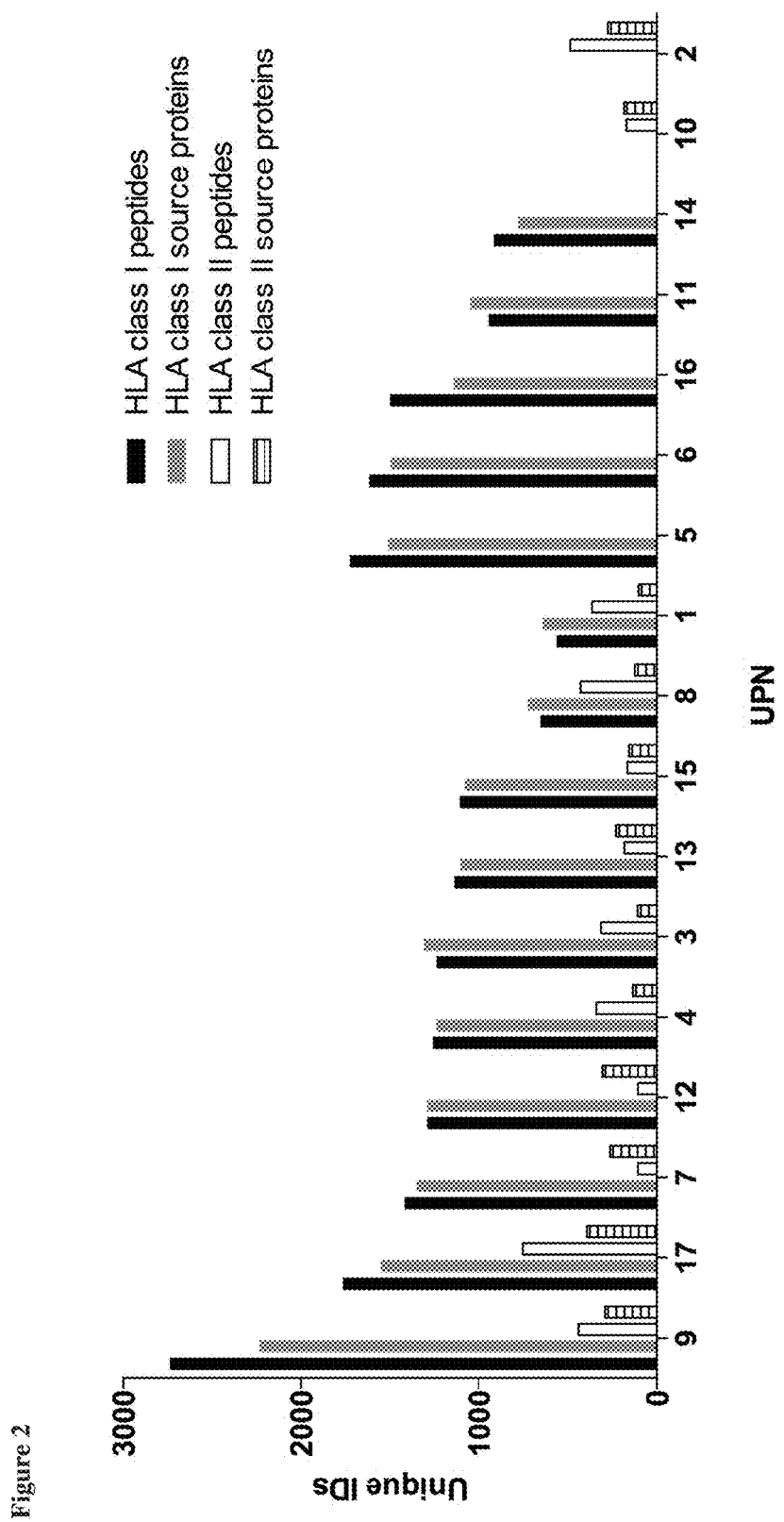
FIG. 2 shows the number of HLA ligand and source protein identifications from primary AML samples. Unique IDs (peptide sequences and corresponding source proteins) identified by LC-MS/MS for HLA class I (W6/32 mAb, n=15) and HLA class II (Tü139 mAb, n=12) in primary AML samples. Only samples fulfilling the threshold of ≥500 (HLA class I) and ≥100 (HLA class II) unique ligand identifications per sample were included in this study. Abbreviations: ID, identification; UPN, uniform patient number

Identification and Quantitation of Tumor Associated Peptides Presented on the Surface of the Cell Tissue Samples Patients' tumor samples were provided by University of Tübingen, Tübingen, Germany Written informed consents of all patients had been given. The samples were shock-frozen in liquid nitrogen immediately after surgery and stored until isolation of TUMAPs at −80° C. For ligandome analysis, PBMC from AML patients at time of diagnosis or at relapse prior to therapy (>80% AML blast count in blood), as well as PBMC and BMNC of healthy donors were isolated by density gradient centrifugation Isolation of HLA Peptides from Tissue Samples HLA class I and II molecules were isolated employing standard immunoaffinity purification as described previously. In brief, snap-frozen cell pellets were lysed in 10 mM CHAPS/PBS (AppliChem, St. Louis, Mo., USA/Gibco, Carlsbad, Calif., USA) containing 1× protease inhibitor (Complete, Roche, Basel, Switzerland). HLA molecules were single-step purified using the pan-HLA class I specific mAb W6/32 and the pan-HLA class II specific mAb Tü39 respectively, covalently linked to CNBr-activated sepharose (GE Healthcare, Chalfont St Giles, UK). HLA:peptide complexes were eluted by repeated addition of 0.2% trifluoroacetic acid (TFA, Merck, Whitehouse Station, N.J., USA). Elution fractions E1-E8 were pooled and free HLA ligands were isolated by ultrafiltration using centrifugal filter units (Amicon, Millipore, Billerica, Mass., USA). HLA ligands were extracted and desalted from the filtrate using ZipTip C18 pipette tips (Millipore). Extracted peptides were eluted in 35 μl of 80% acetonitrile (ACN, Merck)/0.2% TFA, centrifuged to complete dryness and resuspended in 25 μl of 1% ACN/0.05% TFA. Samples were stored at −20° C. until analysis by LC-MS/MS.

Analysis of HLA Ligands by LC-MS/MS

Peptide samples were separated by reversed-phase liquid chromatography (nanoUHPLC, UltiMate 3000 RSLCnano, ThermoFisher, Waltham, Mass., USA) and subsequently analyzed in an on-line coupled LTQ Orbitrap XL hybrid mass spectrometer (ThermoFisher). Samples were analyzed in 5 technical replicates. Sample volumes of 5 μl (sample shares of 20%) were injected onto a 75 μm×2 cm trapping column (Acclaim PepMap RSLC, ThermoFisher) at 4 μl/min for 5.75 min Peptide separation was subsequently performed at 50° C. and a flow rate of 175 nl/min on a 50 μm×50 cm separation column (Acclaim PepMap RSLC, ThermoFisher) applying a gradient ranging from 2.4 to 32.0% of ACN over the course of 140 min. Eluting peptides were ionized by nanospray ionization and analyzed in the mass spectrometer implementing a top 5 CID (collision induced dissociation) method generating fragment spectra for the 5 most abundant precursor ions in the survey scans. Resolution was set to 60,000. For HLA class I ligands, the mass range was limited to 400-650 m/z with charge states 2 and 3 permitted for fragmentation. For HLA class II, a mass range of 300-1,500 m/z was analyzed with charge states ≥2 allowed for fragmentation.

Figure 3:
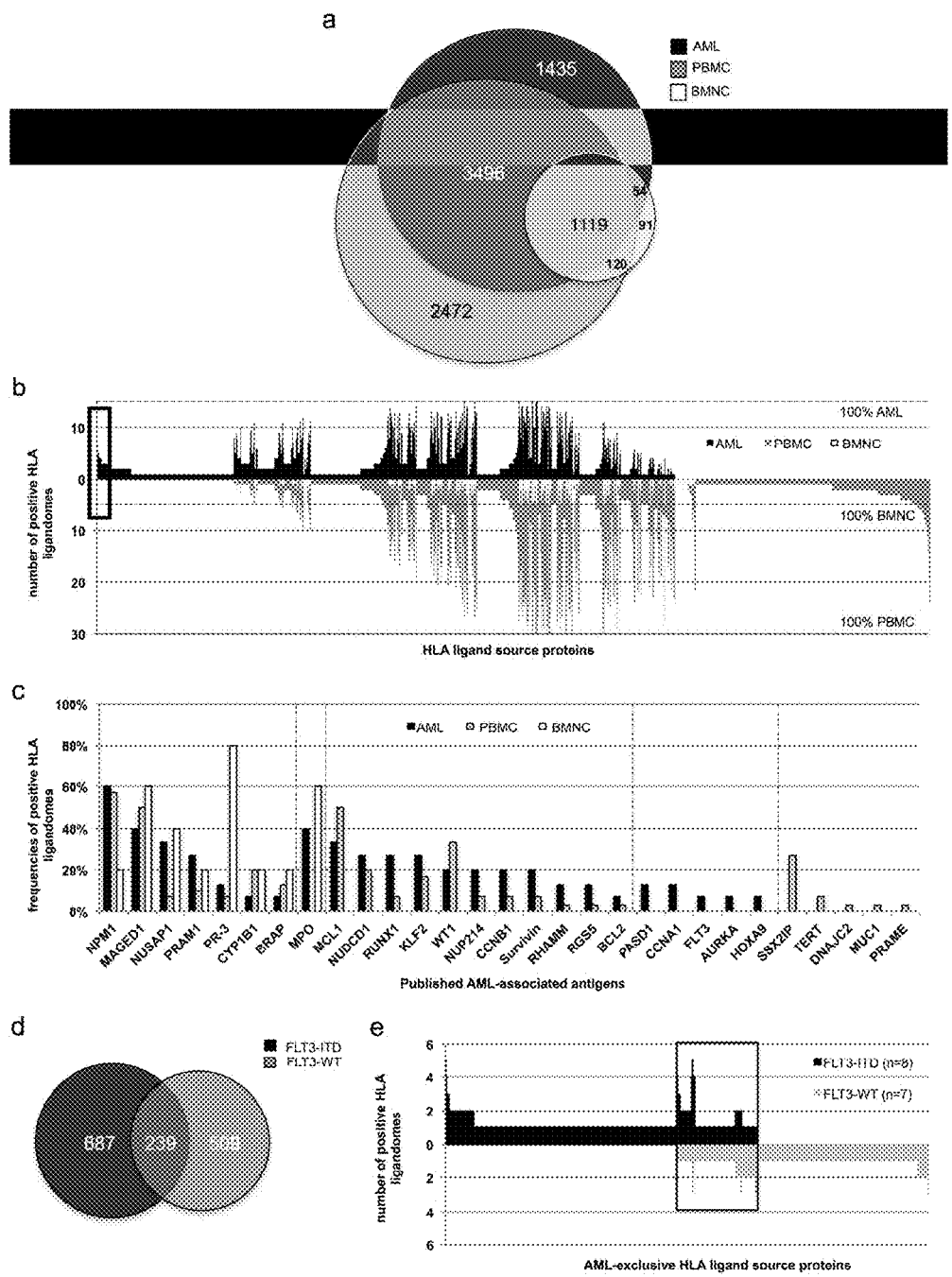
FIG. 3 shows the identification of peptide vaccine targets based on the characterization of the HLA class I ligandomes/source proteomes of AML (n=15), PBMC (n=30) and BMNC (n=5) (a) Overlaps of the HLA class I ligand source proteins of AML, PBMC and BMNC. (b) Comparative profiling of HLA class I ligand source proteins based on the frequency of HLA restricted representation in AML, PBMC and BMNC. Absolute numbers of patients/donors positive for HLA restricted presentation of the respective source protein (x-axis) are indicated on the y-axis. Dashed lines indicate 100% representation for each respective cohort. The box on the left-hand side highlights the subset of source proteins showing AML-exclusive representation with frequencies >20% (LiTAAs: ligandome-derived tumor-associated antigens). (c) Representation analysis of published AML-associated antigens in HLA class I ligandomes. Bars indicate relative representation of respective antigens by HLA class I ligands in AML, PBMC and BMNC. (d) Subset-specific analysis of FLT3-ITD mutated (n=8) versus FLT3-WT (n=7) AML HLA class I ligandomes. Overlap analysis of AML-exclusive source proteins (as defined in (b)) for FLT3-ITD and FLT3-WT AML. (e) Comparative profiling of AML-exclusive HLA class I ligand source proteins based on the frequency of HLA restricted representation in FLT3-ITD and FLT3-WT AML. The box in the middle highlights the subset of shared source proteins, which includes 91.3% of the here defined LiTAAs.

Presentation profiles of exemplary over-presented peptides are shown in FIG. 3.

Amplification of Peptide-Specific T Cells

PBMC from AML patients and healthy volunteers were cultured in RPMI1640 medium (Gibco) supplemented with 10% pooled human serum (PHS, produced in-house), 100 mM β-mercaptoethanol (Roth, Karlsruhe, Germany) and 1% penicillin/streptomycin (GE). For CD8$^+$ T cell stimulation, PBMC were thawed and pulsed with 1 μg/ml per peptide. Peptide-pulsed PBMC (5-6×10$^6$ cells/ml) were cultured at 37° C. and 5% CO$_2$ for 12 days. On day 0 and day 1, 5 ng/ml IL-4 (R&D Systems, Minneapolis, Minn., USA) and 5 ng/ml IL-7 (Promokine, Heidelberg, Germany) were added to the culture medium. On days 3, 5, 7 and 9, 2 ng/ml IL-2 (R&D Systems) were added to the culture medium. Peptide-stimulated PBMC were functionally characterized by ELISPOT assays on day 12 and by intracellular cytokine staining on day 13 respectively. For CD4$^+$ T-cell stimulation, culture was performed as described for CD8$^+$ T cells with 2 modifications: pulsing was carried out with 10 μg/ml of HLA class II peptide and no IL-4 and IL-7 was added.

IFN-γ ELISPOT Assay

IFN-γ ELISPOT assays were carried out as described previously (Widenmeyer M, Griesemann H, Stevanovic S, Feyerabend S, Klein R, Attig S, et al. Promiscuous survivin peptide induces robust CD4+ T-cell responses in the majority of vaccinated cancer patients. Int J Cancer. 2012 Jul. 1; 131(1):140-9). In brief, 96-well nitrocellulose plates (Millipore) were coated with 1 mg/ml IFN-γ mAb (Mabtech, Cincinnati, Ohio, USA) and incubated over night at 4° C. Plates were blocked with 10% PHS for 2 h at 37° C. 5×10$^5$ cells/well of pre-stimulated PBMC were pulsed with 1 μg/ml (HLA class I) or 2.5 μg/ml (HLA class II) peptide and incubated for 24-26 h. Readout was performed according to manufacturer's instructions. Spots were counted using an ImmunoSpot S5 analyzer (CTL, Shaker Heights, Ohio, USA). T cell responses were considered to be positive when >15 spots/well were counted and the mean spot count per well was at least 3-fold higher than the mean number of spots in the negative control wells (according to the cancer immunoguiding program (CIP) guidelines).

Intracellular IFN-γ and TNF-α Staining

The frequency and functionality of peptide-specific CD8$^+$ T cells was analyzed by intracellular IFN-γ and TNF-α staining. PBMC were pulsed with 1 μg/ml of individual peptide and incubated in the presence of 10 μg/ml Brefeldin A (Sigma, St. Louis, Mo., USA) and 10 μg/ml GolgiStop (BD) for 6-8 h. Cells were labeled using Cytofix/Cytoperm (BD), CD8-PECy7 (Beckman Coulter, Fullerton, Calif., USA), CD4-APC (BD Bioscience), TNF-α-PE (Beckman Coulter) and IFN-γ-FITC (BD). Samples were analyzed on a FACS Canto II.

Quantification of HLA Surface Expression

To allow for comparison with healthy monocytes, quantification of HLA surface expression was performed in additional patient samples containing CD15$^−$ AML blasts and at least 5% normal CD15$^+$ monocytes as defined by immunophenotyping. HLA surface expression was analyzed using the QIFIKIT® quantitative flow cytometric assay kit (Dako, Glostrup, Denmark) according to manufacturer's instructions. In brief, triplicates of each sample were stained with the pan-HLA class I specific monoclonal antibody (mAb) W6/32, HLA-DR specific mAb L243 (both produced in house) or IgG isotype control (BioLegend, San Diego, Calif., USA) respectively. Secondary staining with FITC-conjugated rabbit-anti-mouse F(ab')$_2$ fragments (Dako) was subsequently carried out on PBMC, BMNC as well as QIFIKIT® quantification beads. Surface marker staining was carried out with directly labeled CD34 (BD, Franklin Lakes, N.J., USA), CD15 (BD), CD45 (BD) and CD38 (BD). 7AAD (BioLegend) was added as viability marker immediately prior to flow cytometric analysis on a LSR Fortessa cell analyzer (BD).

Results
Primary AML Samples Display No Loss or Down-Regulation of HLA Expression Compared to Autologous Benign Leukocytes The HLA expression levels on AML blasts compared to corresponding benign leukocytes were determined. To this end HLA surface levels were quantified by flow cytometry in a panel of 5 patients with CD15− AML and 5 healthy BMNC donors. AML blasts were gated as $CD34^+$, $CD45^{med}$ viable cells, and their HLA expression was compared to autologous $CD15^+$ normal granulocytes and monocytes. HLA levels were found to be heterogeneous with total HLA class I molecule counts ranging from 45,189-261,647 molecules/cell on AML blasts and 75,344-239,496 molecules/cell on $CD15^+$ cells. Patient individual analysis of HLA surface expression in triplicates revealed slight, albeit significant overexpression in 3/5 patients (unpaired t test, P≤0.001). HLA-DR expression ranged from 1,476-45,150 molecules/cell on AML blasts and 0-3,252 on $CD15^+$ cells and was significantly higher on AML blasts in all analyzed patients (P≤0.001). For reference, HLA surface molecule counts on hematopoietic stem cells (HSC, $CD34^+CD38^-$) of 5 healthy BMNC donors were analyzed. Comprehensive statistical analysis of HLA surface expression on AML compared to normal monocytes revealed no significant differences in mean HLA class I and II expression. Mean HLA class I count on normal HSC (248,587±35,351 molecules/cell) was found to be significantly higher than that on AML blasts (116,445±37,855 molecules/cell, P=0.034, FIG. 1c). Mean HLA class II count on normal HSC (38,373±5,159 molecules/cell) showed no significantly elevated level compared to AML blasts (17,103±7,604 molecules/cell, P=0.053).

LC-MS/MS Identifies a Vast Array of Naturally Presented HLA Class I and II Ligands Mapping the HLA class I ligandomes of 15 AML patients (Table 1) a total of 13,238 different peptides representing 6,104 source proteins was identified. The numbers of identified (cancer) unique peptides per patient ranged from 563-2,733 (mean 1,299 peptides). In the healthy cohort (30 PBMC donors, 5 BMNC donors), a total of 17,940 unique peptides were identified (17,322 peptides/7,207 source proteins on PBMC; 1,738 peptides/1,384 source proteins on BMNC, supplementary). Analysis of HLA class II ligandomes in 12 AML patients yielded a total of 2,816 unique peptides (range 104-753 peptides/patient, mean 332 peptides) representing 885 source proteins. The HLA class II healthy control cohort (13 PBMC, 2 BMNC donors) yielded 2,202 different peptides (2,046 peptides/756 source proteins on PBMC, 317 peptides/164 source proteins on BMNC). No correlation of analyzed cell numbers and number of peptide identifications was found neither for HLA class I (Spearman r=0.27, P=0.33), nor for HLA class II (r=0.31, P=0.33).

Comparative Profiling of HLA Class I Ligandomes Reveals a Multitude of AML-Associated Antigens To identify novel targets for peptide vaccination in AML, the HLA ligand source proteins of the AML, PBMC and BMNC cohorts were comparatively mapped. Overlap analysis of HLA source proteins revealed 1,435 proteins (23.6% of the mapped AML source proteome) to be exclusively represented in the HLA ligandomes of AML patients. AML was found to share 75.5% (4,588 proteins) of its HLA source proteins with PBMC and 19.3% (1,173 proteins) with BMNC. HLA ligand source proteins of BMNC showed 89.9% (1,173 proteins) overlap with the source proteome of PBMC. Out of this vast array of potential targets we aimed to select the most relevant and broadly applicable candidates for off-the-shelf vaccine design. Accordingly, we defined AML-exclusivity and high frequency of representation in AML ligandomes as paramount criteria for antigen selection on our platform. Ranking of HLA ligand source proteins according to these criteria identified a subset of 132 proteins (2.2% of the AML source proteome) exclusively represented in ≥20% of AML ligandomes. Within these LiTAAs (ligandome-derived tumor-associated antigens) defined by these two criteria, we identified as highest ranking the FAS associated factor 1 (FAF1), which was detected in 8/15 (53.3%) of patient ligandomes and was represented by 6 different HLA ligands (AEQFRLEQI (SEQ ID NO: 1) (B*44), FTAEFSSRY (SEQ ID NO: 2) (A*03), HHDESVLTNVF (SEQ ID NO: 3) (B*38:01), REQDEAYRL (SEQ ID NO: 4) (B*44:25), RPVMPSRQI (SEQ ID NO: 5) (B*07), VQREYNLNF (SEQ ID NO: 6) (B*15). An overview of the top 15 LiTAAs which showed representation in ≥33% of AML ligandomes is shown in Table 2. In summary, the top 132 most frequent LiTAAs alone provide a panel of 341 different naturally presented HLA ligands (LiTAPs, ligandome-derived tumor-associated peptides) of more than 25 different HLA restrictions, suited for the development of broadly applicable AML-specific peptide vaccines. In addition, the further 1,389 AML-exclusive source proteins with representation frequencies <20% represented by 1,727 different HLA ligands may serve as repositories for more individualized vaccine design approaches.

Identification of Naturally Presented HLA Class I Ligands Derived from Established AML-Associated Antigens A secondary data mining approach focused on the identification and ranking of established AML-associated antigens (as summarized in Anguille S, Van Tendeloo V F, Berneman Z N. Leukemia-associated antigens and their relevance to the immunotherapy of acute myeloid leukemia. Leukemia. 2012 October; 26(10):2186-96) in the dataset of naturally presented HLA ligands. 122 different HLA ligands representing 29 of these published antigens were identified. Strikingly, it was found >80% (24/29) of these antigens also to be represented on benign PBMC and/or BMNC and thus not to be AML-specific.

AML-exclusivity with regard to HLA presentation was found for FLT3 (SELKMMTQL, B*40) (SEQ ID NO: 338), PASD1 (LLGHLPAEI, C*01:02) (SEQ ID NO: 447), HOXA9 (DAADELSVGRY, A*26:01) (SEQ ID NO: 437), AURKA (REVEIQSHL, B*49:01) (SEQ ID NO: 400) and CCNA1 (LEADPFLKY, B*18:01 (SEQ ID NO: 402); EPPAVLLL, B*51:01 (SEQ ID NO: 401)). For myeloperoxidase (MPO), a total of 19 different HLA ligands were identified and detected representation in 6/15 (40%) of AML and 0/30 PBMC ligandomes. However, analysis of normal BMNC revealed representation in 3/5 (60%) of ligandomes underlining the relevance of employing both, PBMC and BMNC for target identification. In summary, our analysis revealed that a large proportion of established AML-associated antigens do not meet the requirement of tumor-exclusive HLA-restricted representation.

Figure 6:
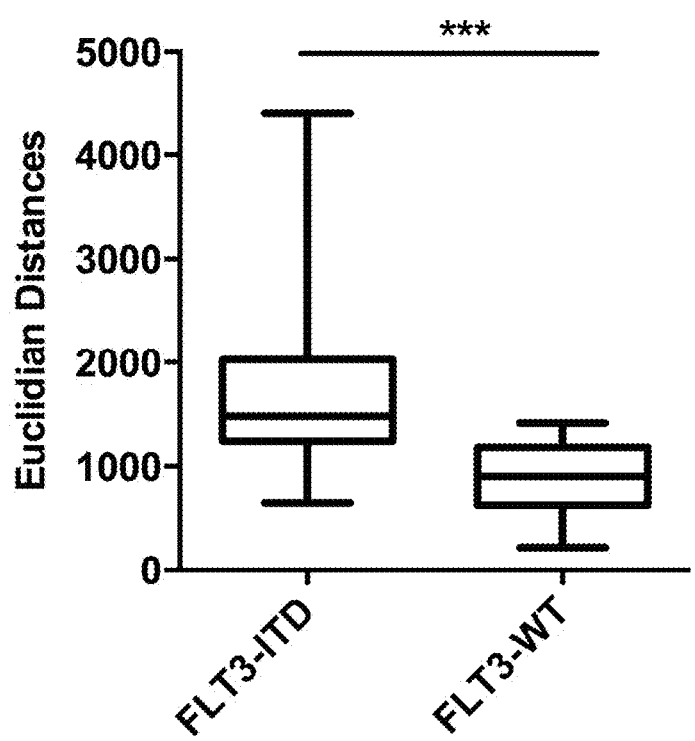
FIG. 6 shows the results of an experiment in order to evaluate the internal heterogeneity of HLA class I ligandomes in the FLT3-ITD (n=8) versus the FLT3-WT (n=7) subsets. The inventors performed semi-quantitative similarity indexing. To enable comparison of ligandomes of different HLA types, the inventors performed the analysis on the level of HLA ligand source proteins. Semi-quantitative information was derived from analyzing spectral counts (PSMs) of representing HLA ligands. Euclidean distances were analyzed as a measure for sample-pair similarity/dissimilarity, with low values indicating high similarities and high values indicating high dissimilarities. Euclidean distances were calculated for every possible sample pair within each subset utilizing an in-house Python script (Python v 3.3.3, Python Software Foundation). In brief, total PSM counts in each sample pair were normalized to the respective higher counting sample. The source protein lists were combined and the absolute values of differences in PSM counts representing the respective source proteins were summed up to yield the Euclidean distance. *** P<0.001, unpaired t test.

Subset-Specific Analysis of FLT3-ITD Mutated Versus FLT3-WT AML HLA Class I Ligandomes Identifies Shared LiTAAs in Spite of Significant Ligandome Dissimilarity To assess the applicability of our novel targets across different subsets of AML, the representation of LiTAAs in FMS-like tyrosine kinase 3 internal tandem duplication (FLT3-ITD, n=8) and FLT3 wild type (FLT3-WT, n=7) patient subsets was characterized. Similarity indexing of HLA class I ligandomes revealed that the FLT3-WT subset displayed significantly lower internal heterogeneity (mean 916.2±70.6, n=21) than the FLT3-TID subset (mean 1687.0±156.5, n=21, P<0.0001, FIG. 6). Overlap analysis of AML-exclusive HLA source proteins (FLT3-WT: 748 proteins, FLT3-ITD: 926 proteins) revealed overlaps of 32.0% (FLT3-WT/FLT3-ITD) and 25.6% (FLT3-ITD/FLT3-WT) respectively (FIG. 3d). Of note, 42/46 (91.3%) of the high ranking LiTAAs were found to be represented in both subsets (FIG. 3e). The three HLA ligand source proteins SKP1 (5/8), C16orf13 (5/8) and ERLIN1 (4/8), which were identified exclusively in the FLT3-ITD subset, reached representation frequencies of ≥50%. The FLT3-WT specific LiTAA MUL1 was represented in 4/7 (57.1%) of FLT3-WT ligandomes. Taken together, these data support the devised strategy of cohort-comprising analysis of HLA ligandomes for target selection while pointing out a small fraction of highly frequent, subset-specific targets.

Functional Characterization of LiTAPs Reveals AML-Associated Immunoreactivity

In order to evaluate the immunogenicity and specificity of our HLA-A*03 LiTAPs, the inventors next performed 12-day recall IFN-γ ELISPOT assays. PBMC obtained from 6 AML patients as well as 8 healthy individuals were stimulated with different pools ($P^I_1$ and $P^I_2$) of top ranking HLA-A*03 LiTAPs. Significant IFN-γ secretion was observed with both employed peptide pools in 2/6 AML samples (FIG. 4a). In order to confirm these findings, intracellular cytokine staining and flow cytometry for IFN-γ and TNF-α was carried out using 12-day pre-stimulated PBMC (FIG. 4b). it was confirmed $P^I_1$ and $P^I_2$-specific CD8$^+$ T cell responses functionally characterized by IFN-γ ($P^I_1$: 1.6%, $P^I_2$: 1.7% of CD8$^+$ T cells) and TNF-α ($P^I_1$: 2.6%, $P^I_2$: 2.4% of CD8$^+$ T cells) secretion. Cross-checking ELISPOT assays using A*03 positive healthy donor PBMC stimulated with $P^I_1$ and $P^I_2$ showed no significant secretion of IFN-γ (0/8, FIG. 4c). These initial characterizations demonstrate the here defined LiTAPs to potentially function as AML-specific T cell epitopes.

HLA Class II Ligandome Analysis Provides Additional Targets and Pinpoints Potentially Synergistic Embedded Ligands Overlap analysis of HLA class II source proteomes identified 396 proteins (44.7%) represented by 1,079 different HLA ligands to be exclusively represented in the HLA ligandome of AML. AML was found to share 53.3% (472 proteins) and 15.1% (134 proteins) of its source proteome with PBMC and BMNC, respectively. BMNC showed 88.2% (127 proteins) source proteome overlap with PBMC. Performing comparative HLA source proteome profiling as described above for HLA class I, the inventors were able to identify 36 LiTAAs (represented by 152 different HLA class II ligands) with representation frequencies ≥20%. The highest ranking class II LiTAA (A1BG) was identified on 6/12 (50%) patients represented by 5 different ligands. In order to identify LiTAAs presented in both, the HLA class I and class II ligandomes, the inventors subsequently compared the respective AML-exclusive source proteomes. This revealed a panel of only 43 shared source proteins (3.0%/10.4% of the HLA class I/HLA class II source proteome, respectively). Mapping of the respective class I against class II ligands identified 3 HLA class II peptides containing complete embedded HLA class I ligands.

Figure 5:
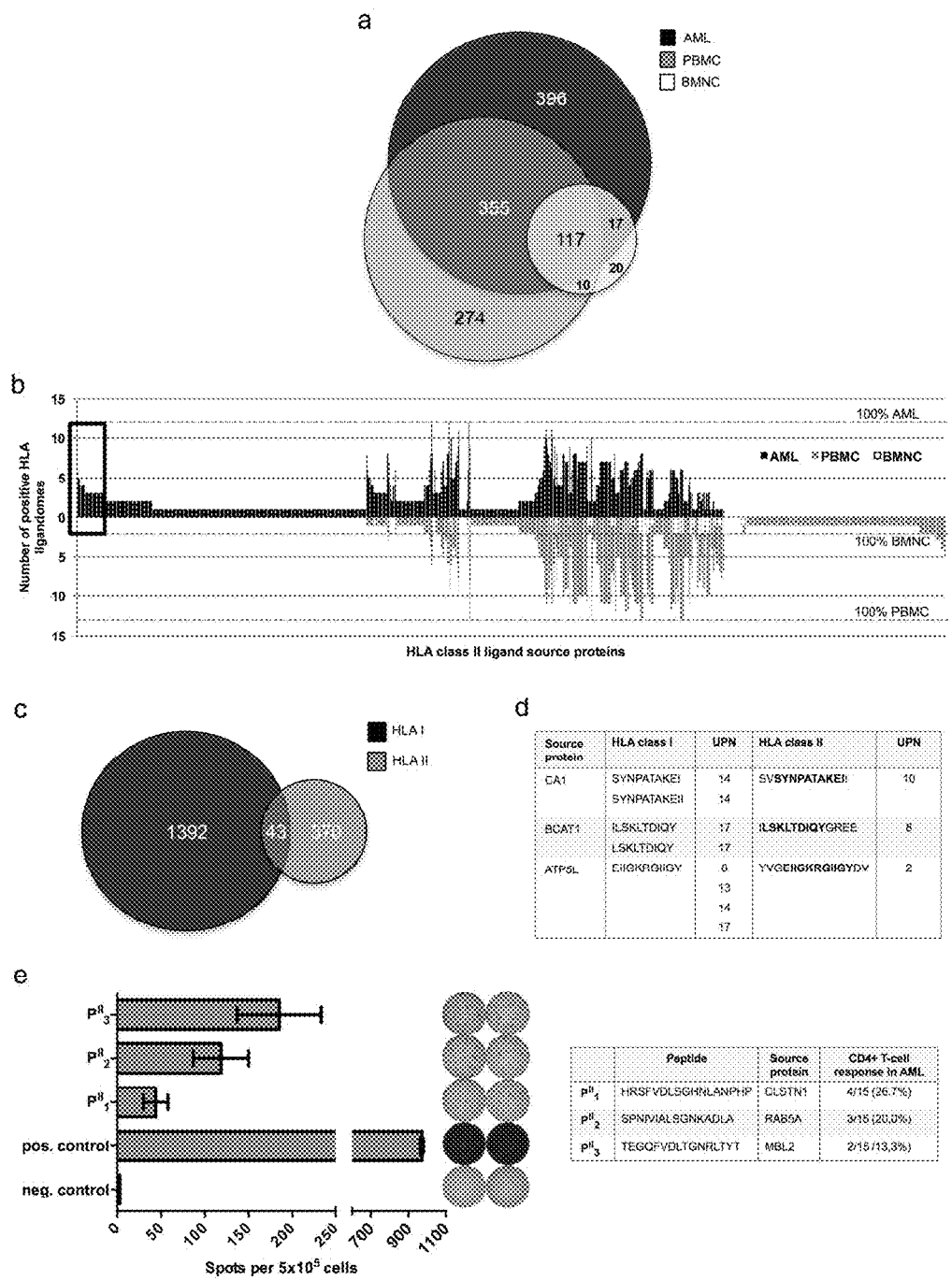
FIG. 5 shows the identification of additional/synergistic peptide vaccine targets based on the characterization of the AML HLA class II ligandome. (a) Overlap analysis of the HLA class II ligand source proteomes of AML (n=12), PBMC (n=13) and BMNC (n=2). (b) Comparative profiling of HLA class II ligand source proteins based on the frequency of HLA restricted representation in AML, PBMC and BMNC. Absolute numbers of patients/donors positive for HLA restricted presentation of the respective source protein (x-axis) are indicated on the y-axis. Dashed lines indicate 100% representation for each respective cohort. The box on the left-hand side highlights the subset of source proteins showing AML-exclusive representation with frequencies >20%. (c) Overlap analysis of HLA class I and HLA class II AML-exclusive source proteins. (d) Of the 43 shared AML-exclusive source proteins a subset of 3 was identified to contain complete HLA class I ligands (SYNPATAKEI (SEQ ID NO: 608), SYNPATAKEII (SEQ ID NO: 609), ILSKLTDIQY (SEQ ID NO: 610), LSKLTDIQY (SEQ ID NO: 611), and EIIGKRGIIGY (SEQ ID NO: 18)) embedded in HLA class II peptides (SVSYNPATAKEII (SEQ ID NO: 612), ILSKLTDIQYGREE (SEQ ID NO: 613), and YVGEIIGKRGIIGYDV (SEQ ID NO: 614)). The embedded sequences are depicted in bold. (e) IFN-γ ELISPOT assay of AML patient PBMC after stimulation with different HLA class II AML LiTAPs ($P^{II}_1$ (HRSFVDLSGHNLANPHP (SEQ ID NO: 478)), $P^{II}_2$ (SPNIVIALSGNKADLA (SEQ ID NO: 558)) and $P^{II}_3$ (TEGQFVDLTGNRLTYT (SEQ ID NO: 544)). PHA served as positive control, stimulation with FLNA$_{1669-1683}$ HLA-DR peptide as negative control. For $P^{II}_1$, $P^{II}_2$ and $P^{II}_3$ a significant increase in IFN-γ production was observed in multiple patients. Abbreviations: UPN, uniform patient number.

In order to functionally characterize the HLA class II LiTAPs, the inventors performed 12-day recall IFN-γ ELISPOT assays. For 3/7 of the top ranking LiTAPs significant secretion of IFN-γ was detected in AML patients. T cell responses were detected for the peptide $P^{II}_1$ (CL-STN1$_{836-852}$) in 4/15 (26.7%), for $P^{II}_2$ (LAB5A$_{123-138}$) in 3/15 (20.0%) and for $P^{II}_3$ (MBL2$_{191-206}$) in 2/15 (13.3%) of AML patients. FIG. 5e shows an example of the frequency of specific T cells for peptides $P^{II}_1$, $P^{II}_2$ and $P^{II}_3$ in an AML patient. Cross-checking ELISPOT assays using healthy donor PBMC stimulated with $P^{II}_1$, $P^{II}_2$ and $P^{II}_3$ showed no significant secretion of IFN-γ (0/8). Thus, the here defined AML-specific HLA class II epitopes have the potential to complement a HLA class I peptide vaccine.

Example 2

Expression Profiling of Genes Encoding the Peptides of the Invention

Not all peptides identified AML as being presented on the surface of tumor cells by MHC molecules are suitable for immunotherapy, because the majority of these peptides are derived from normal cellular proteins expressed by many cell types. Only few of these peptides are tumor-associated and likely able to induce T cells with a high specificity of recognition for the tumor from which they were derived. In order to identify such peptides and minimize the risk for autoimmunity induced by vaccination the inventors focused on those peptides that are derived from proteins that are over-expressed on tumor cells compared to the majority of normal tissues.

The ideal peptide will be derived from a protein that is unique to the tumor and not present in any other tissue. To identify peptides that are derived from genes with an expression profile similar to the ideal one the identified peptides were assigned to the proteins and genes, respectively, from which they were derived and expression profiles of these genes were generated.

RNA Sources and Preparation

Surgically removed tissue specimens were provided by University of Heidelberg, Heidelberg, Germany (see Example 1) after written informed consent had been obtained from each patient. Tumor tissue specimens were snap-frozen in liquid nitrogen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal kidney sample was arbitrarily set to 1.0.

Exemplary expression profiles of source genes of the present invention that are highly over-expressed or exclusively expressed in AML are shown in FIG. 3.

Example 3

In Vitro Immunogenicity for AML MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for 9 HLA-A*0201 restricted TUMAPs of the invention so far, demonstrating that these peptides are T-cell epitopes against which CD8+ precursor T cells exist in humans.

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the Transfusion Medicine Tuebingen, Germany, after informed consent.

Isolated CD8+ lymphocytes or PBMCs were incubated until use in T-cell medium (TCM) consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (Promo Cell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

All pMHC complexes used for aAPC loading and cytometric readout were derived from UV-induced MHC ligand exchange (Rodenko B, et al. Generation of peptide-MHC class I complexes through UV-mediated ligand exchange. Nat Protoc. 2006; 1(3):1120-32) with minor modifications. In order to determine the amount of pMHC monomer obtained by exchange, the inventors performed streptavidin-based sandwich ELISAs according to Rodenko B, et al., 2006.

The purified co-stimulatory mouse IgG2a anti human CD28 Ab 9.3 (Jung G, et al. Induction of cytotoxicity in resting human T lymphocytes bound to tumor cells by antibody heteroconjugates. Proc Natl Acad Sci USA. 1987 July; 84(13):4611-5) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO: 606) from modified Melan-A/MART-1) and A*0201/DDX5-001 (YLLPAIVHI from DDX5 (SEQ ID NO: 607)), respectively.

800.000 beads/200 µl were coated in 96-well plates in the presence of 4×12.5 ng different biotin-pMHC, washed and 600 ng biotin anti-CD28 were added subsequently in a volume of 200 Stimulations were initiated in 96-well plates by co-incubating $1 \times 10^6$ CD8+ T cells with $2 \times 10^5$ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. This stimulation cycle was performed for a total of three times. For the pMHC multimer readout using 8 different pMHC molecules per condition, a two-dimensional combinatorial coding approach was used as previously described (Andersen et al., 2012 Parallel detection of antigen-specific T cell responses by combinatorial encoding of MHC multimers. Nat Protoc. 2012 Apr. 12; 7(5):891-902.) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+ CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for AML Peptides

Figure 4:
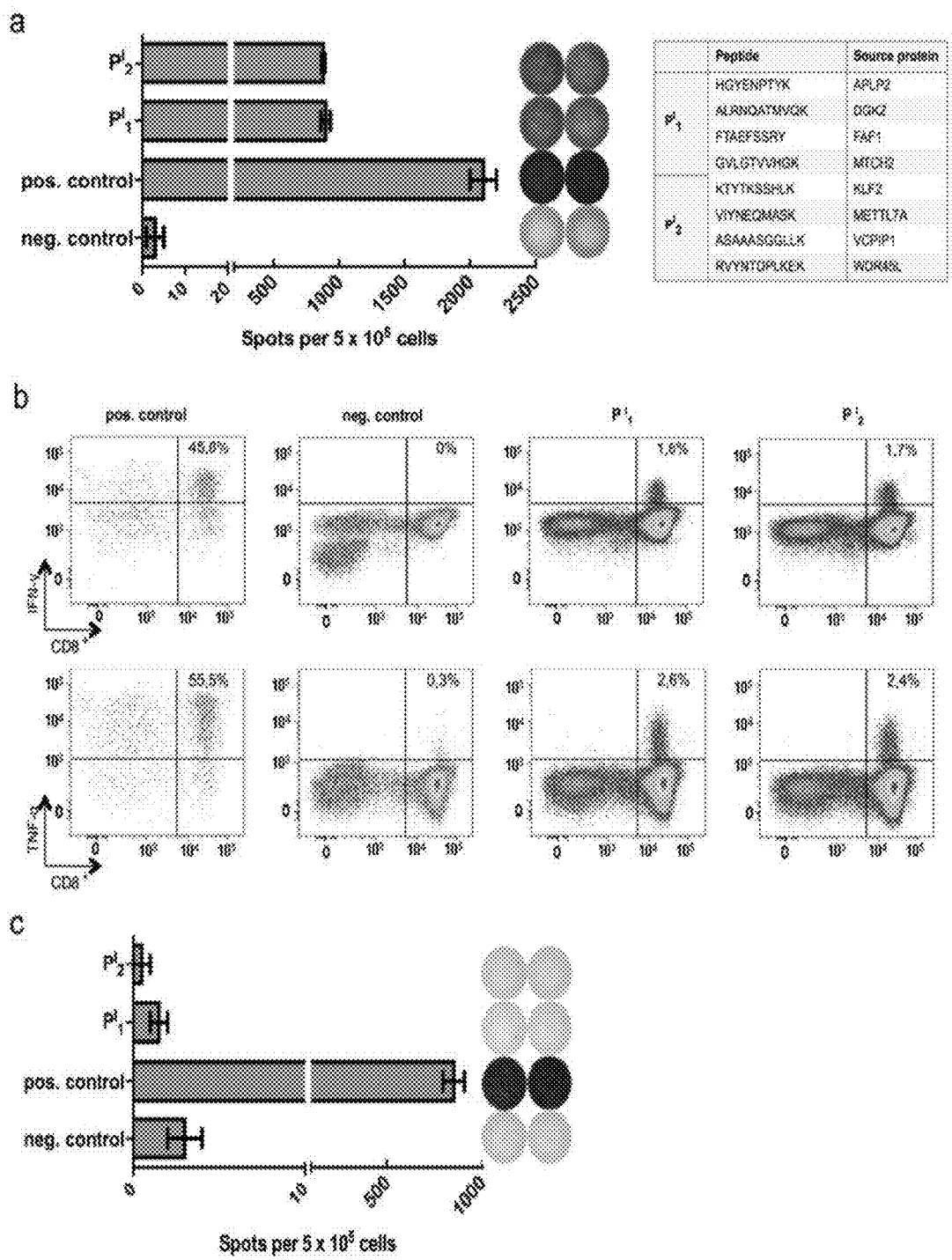
FIG. 4 shows the functional characterization of HLA class I AML-LiTAPs. (a) IFN-γ ELISPOT assay of AML patient PBMC after stimulation with 2 different A*03 restricted AML LiTAP (ligandome-derived tumor-associated peptide) pools ($P^I_1$ fHGYENPTYK (SEQ ID NO: 35), ALRNQATMVQK (SEQ ID NO: 47), FTAEFSSRY (SEQ ID NO: 2), and GVLGTVVHGK (SEQ ID NO: 49)) and $P^I_2$ (KTYTKSSHLK (SEQ ID NO: 89), VIYNEQMASK (SEQ ID NO: 296), ASAAASGGLLK (SEQ ID NO: 99), and RVYNTDPLKEK (SEQ ID NO: 67)). PHA served as positive control, stimulation with HIV GAG$_{18-26}$ A*03 peptide as negative control. For $P^I_1$ and $P^I_2$ a significant IFN-γ production was observed. (b) Intracellular staining for IFN-γ and TNF-α of $P^I_1$ and $P^I_2$ stimulated AML patient PBMC (same as in (a)). PMA/Ionomycin served as positive control, HIV GAG$_{18-26}$ A*03 peptide as negative control. (c) Cross-checking IFN-γ ELISPOT assay of healthy donor PBMC after stimulation with A*03 restricted AML LiTAP pools $P^I_1$ and $P^I_2$, revealed no significant IFN-γ production.

For tested HLA class I peptides, in vitro immunogenicity can be demonstrated by generation of peptide specific T-cell lines. Exemplary flow cytometry results after TUMAP-specific multimer staining for two peptides of the invention are shown in FIG. 4 together with corresponding negative controls.

Example 4

Synthesis of Peptides

All peptides were synthesized using standard and well-established solid phase peptide synthesis using the Fmoc-strategy. After purification by preparative RP-HPLC, ion-exchange procedure was performed to incorporate physiological compatible counter ions (for example trifluoro-acetate, acetate, ammonium or chloride).

Identity and purity of each individual peptide have been determined by mass spectrometry and analytical RP-HPLC. After ion-exchange procedure the peptides were obtained as white to off-white lyophilizates in purities of 90% to 99.7%.

All TUMAPs are preferably administered as trifluoro-acetate salts or acetate salts, other suitable salt-forms are also possible. For the measurements of example 3, trifluoroacetate salts of the peptides were used.

Example 5

MHC Binding Assays—MHC Class I

Candidate peptides for T cell based therapies according to the present invention were further tested for their MHC binding capacity (affinity). The individual peptide-MHC complexes were produced by exchange with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko, B. et al., Nat Protoc. 1 (2006): 1120-1132).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*0201/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 μg/ml HRP conjugated anti-β2m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

MHC class I binding scores for the peptides as tested were; <20%=+; 20%-49%=++; 50%-75%=+++; >= 75%=++++

| Seq ID NO. | sequence | Peptide exchange |
|---|---|---|
| 54 | AVIEAEKIAQV | ++++ |
| 266 | KLQEQLAQL | ++++ |
| 36 | SLLYKVPYV | ++++ |
| 251 | VLGGKAFLEHL | ++++ |

Example 6

MHC Binding Assays—MHC Class II

HLA class II proteins are divided into three major isotypes HLA-DR, -DP, DQ which are encoded by numerous haplotypes. The combination of various α- and β-chains increases the diversity of the HLA class II proteins found in an arbitrary population. Thus, the selected HLA class II TUMAPs have to bind to several different HLA-DR molecules (i.e. show promiscuous binding ability) in order to be able to contribute to an effective T-cell response in a significant percentage of patients.

The promiscuous binding of GALNT7-001 and ERGIC1-001 to various HLA-DR haplotypes and the stability of the formed complexes was assessed in an in vitro binding assay.

The peptides as tested were:

| Sequence ID No | Peptide ID | Sequence | length |
|---|---|---|---|
| 597 | GALNT7-001 | GNQLFRINEANQLMQ | 15 |
| 604 | ERGIC1-001 | FEGQFSINKVPGNFHVS | 17 |

The seven investigated HLA-DR haplotypes are selected according to their frequencies in HLA-A*02- and HLA-A*24-positive North American populations. Data are derived from the analysis of 1.35 million HLA-typed volunteers registered in the National Marrow Donor Program (Mori M, Beatty P G, Graves M, Boucher K M, Milford E L (1997). HLA gene and haplotype frequencies in the North American population: the National Marrow Donor Program Donor Registry. Transplantation 64, 1017-1027). The analyzed population was subdivided in the following ethnic groups: Caucasian Americans (N=997,193), African Americans (N=110,057), Asian Americans (N=81,139), Latin Americans (N=100,128), and Native Americans (N=19, 203).

The MHC-peptide binding assay as used determined the ability of each candidate peptide to bind to the selected HLA class II haplotype and stabilize the HLA-peptide complex. For this, the candidate peptides are assembled in vitro with a particular HLA class II protein.

The binding capacity of a candidate peptide to a particular HLA molecule is compared to a reference peptide with known very strong binding properties (positive control) for each HLA haplotype. Experimental standard errors derive from binding experiments of triplicated positive controls.

Besides the affinity of a peptide to a particular HLA molecule, the enduring stability of the formed HLA-peptide complex is crucial for the occurrence of an immune response. For this reason the presence of the formed HLA-peptide complex is measured after its incubation for 24 h at 37° C. The stability of the formed MHC-peptide complex is calculated as a ratio of the binding scores at 24 h and the binding scores which are received right after the refolding (accordingly at time 0) in percent.

The analysis of GALNT7-001 and ERGIC1-001 in REVEAL® MHC-peptide binding assay showed that both peptides bind to various HLA haplotypes. Both peptides were shown to form a complex with five of seven investigated HLA haplotypes (HLA-DR1, -DR2, -DR4, -DR5, and -DR7). The detected binding scores were in the range of 0.02 to about 78.5% compared to the positive control and clearly above scores of non-binding peptides. GALNT7-001 showed promiscuous strong binding (i.e. with the binding score over 15%, the value which based on experience of the service provider is considered to reflect the strong binding) to four of seven investigated HLA haplotypes (HLA-DR1, -DR2, -DR4, -DR7). For ERGIC-001, the binding scores of two investigated HLA haplotypes were about or over 15% (HLA-DR4, -DR5). Both peptides did not bind to HLA-DR3 and HLA-DR6.

The stability analysis of the formed HLA-GALNT7-001 and HLA-ERGIC1-001 complexes revealed that 4 of 7 investigated HLA-peptide complexes were stable after 24 h at 37° C. (HLA-DR1, -DR4, -DR5, -DR7).

The analysis of binding capacity of GALNT7-001 and ERGIC1-001 to the most frequent HLA-DR haplotypes using the in vitro binding assay revealed the promiscuous binding ability for both peptides. Both peptides formed complexes with 5 of 7 investigated HLA-DR haplotypes. Thus, the analysis showed considerable binding capacity of GALNT7-001 to at least 4 and of ERGIC1-001 to at least 2

HLA-DR haplotypes. Furthermore, 4 of 5 formed HLA-peptide complexes for each investigated peptide were stable for at least 24 h. Thus, the analysis showed that both peptides should be capable to contribute to an effective T-cell response in a significant percentage of patients.

REFERENCE LIST

Babbio, F. et al., Cell Cycle 3 (2004): 486-490
Bidkhori, G. et al., PLoS. One. 8 (2013): e67552
Enesa, K. et al., Adv. Exp. Med. Biol. 809 (2014): 33-48
Greiner, J. et al., Int. J Cancer 106 (2003): 224-231
Huang, A. et al., Cancer Res. 65 (2005): 5607-5619
Isaksson, H. S. et al., Oncotarget. 5 (2014): 4040-4049
Kuznetsova, E. B. et al., Mol. Biol. (Mosk) 41 (2007): 624-633
Liu, D. et al., Int. J Oncol. 45 (2014): 1232-1240
McLellan, J. et al., Mol. Biol. Cell 20 (2009): 5306-5313
Oh, Y. et al., J Biol. Chem 287 (2012): 17517-17529
Price, J. C. et al., PLoS. One. 8 (2014): e63313
Rao, W. et al., Carcinogenesis 35 (2014a): 1573-1581
Rao, W. et al., PLoS. One. 9 (2014b): e85705
RefSeq, The NCBI handbook [Internet], Chapter 18 (2002)
Sand, M. et al., Mol. Carcinog. 51 (2012): 916-922
Scanlan, M. J. et al., Cancer Immun. 1 (2001): 4
Soupene, E. et al., J Lipid Res. 49 (2008): 1103-1112
Tian, Y. et al., Int. J Oncol. 43 (2013): 2082-2090
Uchiyama, K. et al., J Cell Biol. 159 (2002): 855-866
Vanneste, D. et al., Curr. Biol. 19 (2009): 1712-1717
Yotov, W. V. et al., Genes Chromosomes. Cancer 26 (1999): 62-69
Zhang, J. et al., J Allergy Clin. Immunol. 115 (2005): 548-554
Zhou, B. et al., Cancer Biol. Ther 13 (2012a): 871-879
Zhou, B. et al., Cancer Lett. 322 (2012b): 195-203

The invention claimed is:

1. A method of eliciting an immune response in an acute myeloid leukemia patient, comprising administering to the patient a population of activated T cells that kill the cancer cells, which present a peptide consisting of the amino acid sequence of AEQFRLEQI (SEQ ID NO: 1), wherein the peptide is in a complex with an MHC class I molecule.

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the activated T cells are expanded in vitro.

6. The method of claim 1, wherein the MHC molecule is a class I or II MHC molecule.

7. The method of claim 1, wherein the activated T cells are produced by contacting T cells with the peptide loaded human class I or II MHC molecules expressed on the surface of an antigen-presenting cell for a period of time sufficient to activate the T cells.

8. The method of claim 7, wherein the antigen presenting cell is infected with a recombinant virus expressing the peptide.

9. The method of claim 8, wherein the antigen presenting cell is a dendritic cell or a macrophage.

10. The method of claim 5, wherein the expansion is in the presence of an anti-CD28 antibody and IL-12.

11. The method of claim 1, wherein the population of activated T cells comprises CD8-positive cells.

12. The method of claim 1, wherein the population of activated T cells are administered in the form of a composition.

13. The method of claim 12, wherein the composition comprises at least one adjuvant.

14. The method of claim 13, wherein the at least one adjuvant is selected from the group consisting of anti-CD40 antibody, imiquimod, resiquimod, GM-CSF, cyclophosphamide, sunitinib, bevacizumab, interferon-alpha, interferon-beta, CpG oligonucleotides and derivates, poly-(I:C) and derivates, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

15. The method of claim 1, wherein the immune response is capable of killing cancer cells that present a peptide consisting of the amino acid sequence of AEQFRLEQI (SEQ ID NO: 1).

16. The method of claim 15, wherein the immune response comprises a cytotoxic T cell response.

17. A method of treating an acute myeloid leukemia patient, comprising administering to the patient a population of activated T cells that kill the cancer cells, which present a peptide consisting of the amino acid sequence of AEQFRLEQI (SEQ ID NO: 1), wherein the peptide is in a complex with an MHC class I molecule.

* * * * *